US011788055B2

(12) United States Patent
Foster et al.

(10) Patent No.: US 11,788,055 B2
(45) Date of Patent: Oct. 17, 2023

(54) MATERIALS AND METHODS FOR CONTROLLING OXIDATION AND REDUCTION IN BIOSYNTHETIC PATHWAYS OF SPECIES OF THE GENERA RALSTONIA AND CUPRIAVIDUS AND ORGANISMS RELATED THERETO

(71) Applicant: INV NYLON CHEMICALS AMERICAS, LLC, Wilmington, DE (US)

(72) Inventors: Alexander Brett Foster, Redcar (GB); Jonathan Paul Combe, Redcar (GB); Arghya Barman, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

(21) Appl. No.: 16/398,351

(22) Filed: Apr. 30, 2019

(65) Prior Publication Data
US 2019/0338375 A1  Nov. 7, 2019

Related U.S. Application Data

(60) Provisional application No. 62/665,814, filed on May 2, 2018.

(51) Int. Cl.
| C12N 1/20 | (2006.01) |
| C12N 9/14 | (2006.01) |
| C12N 15/78 | (2006.01) |
| C12P 7/16 | (2006.01) |
| C12P 7/18 | (2006.01) |
| C12P 7/54 | (2006.01) |
| C12R 1/38 | (2006.01) |

(52) U.S. Cl.
CPC ............ *C12N 1/205* (2021.05); *C12N 9/14* (2013.01); *C12N 15/78* (2013.01); *C12P 7/16* (2013.01); *C12P 7/18* (2013.01); *C12P 7/54* (2013.01); *C12R 2001/38* (2021.05); *C12Y 101/01* (2013.01); *C12Y 203/01* (2013.01)

(58) Field of Classification Search
None
See application file for complete search history.

(56) References Cited

U.S. PATENT DOCUMENTS

| 3,809,027 | A  | 5/1974  | Morgan et al. | |
| 7,384,783 | B2 | 6/2008  | Kunas et al. | |
| 8,986,960 | B2 | 3/2015  | Sichwart | |
| 9,580,733 | B2 | 2/2017  | Botes et al. | ............ C12P 13 02 |
| 9,637,764 | B2 | 5/2017  | Botes et al. | ........... C12P 13 001 |
| 9,862,973 | B2 | 1/2018  | Botes et al. | ............ C12P 5 007 |
| 9,920,339 | B2 | 3/2018  | Kadi et al. | ................ C12P 7 62 |
| 10,072,150 | B2 | 9/2018  | Conradie et al. | ........ C08L 77 12 |
| 10,196,657 | B2 | 2/2019  | Pearlman et al. | .... C12P 13 001 |
| 2011/0171702 | A1* | 7/2011  | Reinecke | ................. C12P 7/42 435/243 |
| 2012/0003706 | A1 | 1/2012  | Hickey | |
| 2012/0064622 | A1 | 3/2012  | Fischer et al. | |
| 2013/0034884 | A1 | 2/2013  | Burgard et al. | |
| 2013/0065285 | A1 | 3/2013  | Sefton | |
| 2013/0323714 | A1 | 12/2013 | Cheng et al. | |
| 2015/0315599 | A1 | 11/2015 | Shetty et al. | |
| 2017/0218406 | A1 | 8/2017  | Conradie et al. | |
| 2018/0023103 | A1 | 1/2018  | Foster et al. | |
| 2018/0023104 | A1 | 1/2018  | Cartman et al. | |
| 2018/0100160 | A1 | 4/2018  | Bawdon et al. | ....... C12N 15 74 |
| 2019/0124947 | A1 | 5/2019  | Pearlman et al. | |
| 2019/0300838 | A1 | 10/2019 | Smith et al. | |
| 2019/0300839 | A1 | 10/2019 | Smith et al. | |
| 2019/0316072 | A1 | 10/2019 | Smith et al. | |
| 2019/0338320 | A1 | 11/2019 | Foster et al. | |

FOREIGN PATENT DOCUMENTS

| EP | 0995490 A2 | 4/2000 |
| EP | 1728853 A1 | 12/2006 |
| EP | 1938892 A1 | 7/2008 |
| EP | 3399015 A1 | 11/2018 |
| JP | 2009225662 A | 10/2009 |
| JP | 2013179909 A | 9/2013 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2017115855 A1 | 7/2014 |
| WO | 2015117019 A1 | 8/2015 |

(Continued)

OTHER PUBLICATIONS

Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostablity. 2018. Structure. 26, 1474-1485. (Year: 2018).*
Kizer L et al. Application of Functional Genomics to Pathway Optimization for Increased Isoprenoid Production. Applied and Environmental Microbiology. 2008. Vol. 74, No. 10. p. 3229-3241. (Year: 2008).*
Prather KLJ et al. De novo biosynthetic pathways: Rational design of microbial chemical factories. Current Opinion in Biotechnology. 2008. 19:468-474 (Year: 2008).*
Cavalheiro JMBT et al. Poly(3-hydroxybutyrate) production by Cupriavidus necator using waste glycerol. 2009. Process Biochemistry. 44:509-515.*

(Continued)

*Primary Examiner* — Paul J Holland

(57) ABSTRACT

Methods for increasing carbon-based chemical product yield in an organism by perturbing redox balance in an organism as well as nonnaturally occurring organisms with perturbed redox balance and methods for their use in producing carbon-based chemical products are provided.

8 Claims, 3 Drawing Sheets

Specification includes a Sequence Listing.

(56) References Cited

FOREIGN PATENT DOCUMENTS

| WO | 2015195654 A1 | 12/2015 |
| WO | 2017165244 A1 | 9/2017 |
| WO | 2018005 //0 A2 | 1/2018 |
| WO | 2018022595 A1 | 2/2018 |
| WO | 2018022633 A1 | 2/2018 |
| WO | 2018106549 A1 | 6/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

KEGG Enzyme 1.6.1.1. Retrieved Feb. 22, 2022. p. 1-2 (Year: 2022).*
KEGG Enzyme 1.6.1.2. Retrieved Feb. 22, 2022. p. 1-2 (Year: 2022).*
KEGG Enzyme 7.1.1.1. Retrieved Feb. 22, 2022. p. 1-2 (Year: 2022).*
Alagesan, S., et al., "13C-assisted metabolic flux analysis to investigate heterotrophic and mixotrophic metabolism n Cupriavidus necator H16", Metabolomics, 2018, vol. 14, Issue 9, p. 9.
Alagesan, S., et al., "Functional genetic elements for controlling gene expression in Cupriavidus necator H16", Applied and Environmental Microbiology,vol. 84, Oct. 2018 (Aug. 2018), pp. 1-17.
Anderson, A.J., et al., "Occurrence, metabolism, metabolic role, and industrial uses of bacterial polyhydroxyalkanoates". Microbiology Review, 1990, vol. 54, pp. 450-472.
Atlic et al., "Continuous Production of Poly([R]-3-Hydroxybutyrate) by Cupriavidus Necator in a Multistage Bioreactor Cascade", Appl Microbial Biotechnology, vol. 91, 2011, pp. 295-304.
Bramer, C.O., "The malate dehydrogenase of Ralstonia eutropha and functionality of the C(3)/C(4) metabolism in a Tn5-induced mdh mutant", FEMS Microbiol Letters, Jul. 2, 2002, vol. 212, Issue 2, pp. 159-164.
Brandt, U., et al., "Elevated poly(3-hydroxybutyrate) synthesis in mutants of Ralstonia eutropha HI6 defective in ipopolysaccharide biosynthesis" Applied Microbiology and Biotechnology, 2012, vol. 95, pp. 471-483.
Brown, D.R., et al., "Nitrogen stress response and stringent response are coupled in *Escherichia coli*", Nature Communications, 2014, vol. 5, 4115, pp. 8.
Bruland et al., "Unravelling the C3/C4 carbonmetabolism in Ralstonia eutropha H16", Journal of Applied Microbiology, 2010, vol. 109, pp. 79-90.
Chae, T.U., et al., "Metabolic engineering of Escherichia colifor the production of four-, five- and six-carbon lactams Metabolic Engineering", Academic Press, US, vol. 41 ,Apr. 5, 2017, pp. 82-91.
Chakravarty, J., et al., "Solvent production by engineered Ralstonia eutropha: channeling carbon to biofuel", Applied Microbiology and Biotechnology, vol. 102, Apr. 29, 2018 (Apr. 29, 2018), pp. 5021-5031.
Darani, K.K., et al., "Simulation of bioreactors for poly(3-hydroxybutyrate) production from natural gas", Iranian Journal of Chemistry and Chemical Engineering, vol. 39, 2018, pp. 1-24.
Ding, H., et al., "Glycerol utilization by Rhizobium leguminosarum requires an ABC transporter and affects competition for nodulation", Microbiology, 2012, vol. 158, pp. 1369-1378.
Doberstein, C., et al., "Polythioester synthesis in Ralstonia eutropha H16: novel insights into 3,3'- thiodipropionic acid and 3,3'-dithiodipropionic acid catabolism" Journal of Biotechnology, 2014, vol. 184, pp. 187-198.
Du et al., "Effects of Environmental Conditions on Cell Growth and Poly-B-Hydroxybutyrate Accumulation in Alcaligenes Eutrophus", World Journal of Microbiology & Biotechnology, vol. 16, 2000, pp. 9-13.
Eggers et al., "Impact of Ralstonia Eutropha's Poly(3-Hydroxybutyrate) (PHB) Depolymerases and Phasins on PHB Storage in Recombinant *Escherichia Coli*", Applied and Environmental Microbiology, vol. 80, No. 24,Dec. 2014, pp. 7702-7709.
Frng, Y., et al., "Tuning of acyl-ACP thioesterase activity directed for tailored fatty acid synthesis", Applied Microbiology And Biotechnology, Springer, De, vol. 102, No. 7 ,Feb. 22, 2018, pp. 3173-3182.
Gao, C., et al. "Lactate utilization is regulated by the FadR-type regulator LldR in Pseudomonas aeruginosa", Journal of Bacteriology, 2012, vol. 194, pp. 2687-2692.
Girdhar, A., et al., "Process Parameters for Influencing Polyhyroxyalkanoate Producing Bacterial Factories: An Overview", Petroleum & Environmental Biotechnology, 2013, vol. 4, Issue 5, pp. 9.
Gyaneshwar et al., "Sulfur and Nitrogen Limitation in *Escherichia Coli* K-12: Specific Homeostatic Responses", Journal of Bacteriology, vol. 187, No. 3, Feb. 2005, pp. 1074-1090.
Hanko, E.K.R., et al., "Characterisation of a 3-hydroxypropionic acid-inducible system from Pseudomonas putida for orthogonal gene expression control in *Escherichia coli* and Cupriavidus necator", Scientific Reports, vol. 7, 2017, pp. 1-12.
Hauryliuk, V., et al. "Recent functional insights into the role of (p)ppGpp in bacterial physiology", Nature Reviews Microbiology, 2015, vol. 13, pp. 298-309.
Haushalter, R.W., et al., "Production of Odd-Carbon Dicarboxylic Acids in *Escherichia coli* Using an Engineered Biotin-Fatty Acid Biosynthetic Pathway" Journal of the American Chemical Society, vol. 139, No. 13 ,Mar. 21, 2017, pp. 4615-4618.
Horvat et al., "Mathematical Modelling and Process Optimization of a Continuous 5-Stage Bioreactor Cascade for11 Production of Poly[-(R)-3-Hydroxybutyrate] by Cupriavidus Necator", Bioprocess Biosyst Eng, vol. 36, 2013, pp. 1235-1250.
Hun-Suk Song et al., "Enhanced isobutanolproduction from acetate by combinatorialoverexpression of acetyl-CoA synthetaseand anaplerotic enzymes in engineered*Escherichia coli*", Biotechnology and Bioengineering,vol. 115, May 2, 2018 (May 2, 2018), pp. 1971-1978.
International Search Report and Written Opinion for International Application Serial No. PCT/US2019/025189, dated Jul. 2, 2019, pp. 12.
International Search Report and Written Opinion for International Application Serial No. PCT/US2019/025194, dated Aug. 22, 2019, pp. 24.
International Search Report and Written Opinion for International Application Serial No. PCT/US2019/025202, dated Jul. 30, 2019, pp. 15.
International Search Report and Written Opinion for International Application Serial No. PCT/US2019/025211, dated Jul. 29, 2019, pp. 16.
International Search Report and Written Opinion for International Application Serial No. PCT/US2019/025218, dated Sep. 5, 2019, pp. 17.
International Search Report and Written Opinion for International Application Serial No. PCT/US2019/029973 dated Jul. 23, 2019, Jul. 23, 2019, 5 pgs.
International Search Report and Written Opinion in PCT/US2019/029798 dated Sep. 12, 2019, p. 19.
International Search Report and Written Opinion in PCT/US2019/029817 dated Sep. 23, 2019.
International Search Report and Written Opinion in PCT/US2019/029827 dated Sep. 23, 2019.
International Search Report and Written Opinion in PCT/US2019/029956 dated Aug. 13, 2019.
Invitation to Pay Additional Fees and, Where Applicable, Protest Fee in PCT/082019/029798 dated Jul. 22, 2019.
Invitation to Pay Additional Fees and, Where Applicable, Protest Fee in PCT/US2019/029817, dated Aug. 1, 2019.
Invitation to Pay Additional Fees and, WhereApplicable, Protest Fee in PCT/US2019/029827, dated Jul. 23, 2019.
Jhonson, A., et al., "An engineered constitutive promoter set with broad activity range for Cupriavidus necator H16", ACS Synthetic Biology, vol. 7, Jun. 27, 2018 (Jun. 27, 2018), pp. 1918-1928.

(56) References Cited

OTHER PUBLICATIONS

Joris, Beld, et al., "Evolution of acyl-ACP thioesterases and [beta]-ketoacyl-ACP synthases revealed by protein-protein nteractions", Journal of Applied Phycology, vol. 26, No. 4 ,Nov. 22, 2013, pp. 1619-1629.

Juengert, J.R, et al., "Absence of ppGpp Leads to Increased Mobilization of Intermediately Accumulated Poly(3-Hydroxybutyrate) in Ralstonia eutropha HI6" Applied and Environmental Microbiology, 2017, vol. 83, Issue 13, pp. e00755-17.

Justyna Mozejko-Ciesielska et al.: "Bacterial polyhydroxyalkanoates: Still fabulous ?", Microbiological Research, vol. 192, 2016, pp. 271-282.

Kaddor, C., et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbiol., 2011, vol. 77, pp. 3582-3590.

Kaddor, C., et al., "Implications of various phosphoenolpyruvate-carbohydrate phosphotransferase system mutations on glycerol utilization and poly(3-hydroxybutyrate) accumulation in Ralstonia eutropha H16", AMB Express, 2011, vol. 1, pp. 16.

Karstens, K., et al., "Phosphotransferase protein EIIANtr interacts with SpoT, a key enzyme of the stringent response, in Ralstonia eutropha HI6", Microbiology, 2014, vol. 160, pp. 711-722.

Katalin Kovacs et al.: Metabolic engineering of Cupriavidus necator H16 for the sustainable production of C3 and 35 monomers and polymers, Clnet Conference 4, Jan. 20-23, 2019 Conference paper (Abstract), 2019, p. 26.

Kazakov, A.E., et al., "Comparative genomics of regulation of fatty acid and branched-chain amino acid utilization in proteobacteria". Journal of Bacteriology, 2009, vol. 191, pp. 52-64.

Kim et al. "Effect of overexpression of Actinobacillus succinogenes phosphoenolpyruvate carboxykinase on succinate production in *Escherichia coli*" Applied and Environmental Microbiology, 2004, vol. 70, Issue 2, pp. 1238-1241.

Kluge, J., et al., "Inducible promoters and functional genomic approaches for the genetic engineering of filamentous fungi", Applied Microbiology and Iotechnology, vol. 102, Jun. 2, 2018 (Jun. 2, 2018), pp. 6357-6372.

Koller et al., "Potential and Prospects of Continuous Polyhydroxyalkanoate (PHA) Production", Bioengineering,May 29, 2015, pp. 94-121.

Koller, M., "A review on established and emerging fermentation schemes for microbial production of polyhydroxyalkanoate (PHA) biopolyesters", Fermentation,vol. 4, Apr. 23, 2018 (Apr. 23, 2018), pp. 1-30.

Brigham et al. "Whole-genome microarray and gene deletion studies reveal regulation of the polyhydroxyalkanoate production cycle by the stringent response in Ralstonia eutropha H16" Appl Environ Microbiol. 2012 78(22):8033-44.

Brigham et al. "Correction for Whole-genome microarray and gene deletion studies reveal regulation of the polyhydroxyalkanoate production cycle by the stringent response in Ralstonia eutropha H16" Appl Environ Microbiol. 2017 83(15):1-2.

Byrd et al. "Bacterial control of Agromyces ramosus in soil" Can J Microbiol 1985 31:1157-1163.

Chen et al. "A highly active decarboxylating dehydrogenase with rationally inverted coenzyme specificity" PNAS 1996 92 (25):11666-11670.

Chen et al. "Redesigning secondary structure to invert coenzyme specificity in isopropylmalate dehydrogenase" PNAS 1996 93:12171-12176.

Choi et al. "Modulation of 3-hydroxyvalerate molar fraction in poly(3-hydroxybutyrate-3-hydroxyvalerate) using Ralstonia eutropha transformant co-amplifying phbC and NADPH generation-related zwf genes" Enzyme and Microbial Technology 2003 32(1):178-185).

Cramm, R. J. "Genomic view of energy metabolism in Ralstonia eutropha H16" Mol. Microbiol. Biotechnol. 2009 16(1-2):38-52.

Grousseau et al. "Isopropanol production with engineered Cupriavidus necator as bioproduction platform" Appl Microbiol Biotechnol. 2014 98(9):4277-90.

Ienczak et al. "High cell density strategy for poly(3-hydroxybutyrate) production by Cupriavidus necator" Brazilian Journal of Chemical Engineering 2011 28(4):585-596.

Inoue et al. "Biochemical and molecular characterization of the NAD(+)-dependent isocitrate dehydrogenase from the chemolithotroph Acidithiobacillus thiooxidans" FEMS Microbiol Lett 2002 214(1):127-32.

Lee et al. "Regulation of poly-β-hydroxybutyrate biosynthesis by nicotinamide nucleotide in Alcaligene eutrophus" FEMS Microbiological letters 1995 131:35-39.

Lee et al. "Metabolic Engineering of Pentose Phosphate Pathway in Ralsonia eutropha for Enhanced Biosynthesis of Poly-β-hydroxybutyrate" Biotechnology Progress 2003 19(5):1444-49.

Li et al. "Overexpression of NAD kinase in recombinant *Escherichia coli* harboring the phbCAB operon improves poly(3-hydroxybutyrate) production" Appl Microbiol Biotechnol. 2009 83(5):939-47.

Lu et al. "Studies on the production of branched-chain alcohols in engineered Ralsonia eutropha" Appl. Microbiol. Biotechnol. 2012 96:283-297.

Makkar, N.S. & Casida, L.E. "Cupriavidus necator gen. nov., sp. nov.: a Nonobligate Bacterial Predator of Bacteria in Soil" Int. J. of Systematic Bacteriology 1987 37(4): 323-326.

McKinlay and Harwood "Carbon dioxide fixation as a central redox cofactor recycling mechanism in bacteria" PNAS 2010 107 (26) 11669-11675.

Pryzbylski et al. "Synthesis of the building block 2-hydroxyisobutyrate from fructose and butyrate by Cupriavidus necator H16" Appl. Microbiol. Biotechnol. 2013 97(20):8875-85.

Qi et al. "Model-driven redox pathway manipulation for improved isobutanol production in *Bacillus subtilis* complemented with experimental validation and metabolic profiling analysis" PLoS ONE 2014 9(4):e93815.

Raberg et al. "A closer look on the polyhydroxybutyrate- (PHB-) negative phenotype of Ralstonia eutropha PHB-4" PLoS ONE 2014 9(5):1-11.

Sanchez et al. "Effect of overexpression of a soluble pyridine nucleotide transhydrogenase (UdhA) on the production of poly(3-hydroxybutyrate) in *Escherichia coli*" Biotechnol Prog. 2006 22(2):420-5.

Schlegel & Vollbrecht "Formation of the Dehydroganses for Lactate, Ethanol and Butanediol in the Strictly Aerobi Bacterium Alcaligene eutrophus" Microbiology 1980 117:475-481.

Sekar et al. "Co-production of hydrogen and ethanol from glucose in *Escherichia coli* by activation of pentose-phosphate pathway through deletion of phosphoglucose isomerase (*pgi*) and overexpression of glucose-6-phosphate dehydrogenase (*zwf*) and 6-phosphogluconate dehydrogenase (*gnd*)" Biotechnol. Biofuels 2017 10:85.

Sillman, C. E. & Casida, L. E. "Isolation of nonobligate bacterial predators of bacteria from soil" Can J Microbiol 1986 32:760-762.

Stokke et al. "Biochemical characterization of isocitrate dehydrogenase from Methylococcus capsulatus reveals a unique NAD+-dependent homotetrameric enzyme" Arch Microbiol. 2007 187(5):361-70.

Vollbrecht and Schlegel "Excretion of Metabolites by hydrogen Bacteria III. D(−)-3-hydroxybutanoate" European J. Appl. Microbiol. Biotechnol. 1979 7:259-266.

Wang and Lee "Poly(3-Hydroxybutyrate) Production with High Productivity and High Polymer Content by a Fed-Bath Culture of Alcaligene latus under Nitrogen Limitation" Applied and Environmental Microbiology 1997 370-376.

Wang et al. "Isocitrate dehydrogenase from *Streptococcus mutans*: biochemical properties and evaluation of a putative phosphorylation site at Ser102" PLoS One. 2013 8(3):e58918.

Wu et al. "A Novel Type II NAD+-Specific Isocitrate Dehydrogenase from the Marine Bacterium Congregibacter litoralis KT71" PLoS One. 2015 10(5):1-17.

Zeph, L.E. & Casida, L.E. "Gram-negative versus gram-positive (actinomycete) nonobligate bacterial predators of bacteria on soil" Applied and Environmental Microbiology 1986 52(4):819-823.

International Search Report and Written Opinion on PCT/US2019/029795 dated Jul. 11, 2019.

International Preliminary Report on Patentability in PCT/US2019/029795 dated Nov. 3, 2020.

(56) References Cited

OTHER PUBLICATIONS

Devos et al., "Practical Limits of Function Prediction", PROTEINS: Structure, Function and Genetics, vol. 41, pp. 98-107 (2000).
International Preliminary Report on Patentability in PCT/US2019/029817 dated Nov. 3, 2020, 14 pages.
International Preliminary Report on Patentability received for PCT application No. PCT/US2019/029798 dated Nov. 3, 2020, 13 pages.
International Preliminary Report on Patentability received for PCT application No. PCT/US2019/029827, dated Nov. 3, 2020, 13 pages.
Kisselev, "Polypeptide Release Factors in Prokaryotes and Eukaryotes: Same Function, Different Structure", Structure, vol. 10, pp. 8-9 (2002).
Non-Final office action received for U.S. Appl. No. 16/398,384, dated Oct. 23, 2020, 13 pages.
Whisstock et al., "Prediction of protein function from protein sequence and structure", Quarterly Reviews of BioPhysics, vol. 36, Issue 3, pp. 307-340 (2003).
Witkowski et al., "Conversion of β-Ketoacyl Synthase to a Malonyl Decarboxylase by Replacement of the Active-Site Cysteine with Glutamine", Biochemistry, vol. 38, pp. 11643-11650 (1999).
Youngquist et al., "Functional Genomics Analysis of Free Fatty Acid Production under Continuous PhosphateLimiting Conditions", J Ind. Microbial. Biotechnol., vol. 44, May 2017, pp. 759-772.
Zhu, J., et al., "Factors for promoting polyhydroxyalkanoate (PHA) synthesis in bio-nutrient-removal and recovery system", 4th International Conference on nvironmental Systems Research (ICESR 2017) Conference paper, 2018, pp. 1-4.
Ziesack, M., et al., "Chimeric Fatty Acyl-Acyl Carrier Protein Thioesterases Provide Mechanistic Insight into Enzyme Specificity and Expression", Applied And Environmental Microbiology, vol. 84, No. 10,Mar. 16, 2018, pp. 12.
Koller, M., et al., "Continuous production mode as a viable process-engineering tool for efficient poly (hydroxyalkanoate) (PHA) bio-production", Chemical and Biochemical Product Engineering, vol. 28, Issue 1, 2014, pp. 35-77.
Krausse et al., "Essential role of the hprK gene inRalstonia eutropha H16", J Mol Microbiol Biotechnol, 2009, vol. 17, pp. 146-152.
Kunasundari et al., "Revisiting the Single Cell Protein Application of Cupriavidus Necator H16 and Recovering Bioplastic Granules Simultaneously", Plos One, vol. 8, No. 10, Oct. 2013, 15 pages.
Lardi, M., et al., "o54-Dependent Response to Nitrogen Limitation and Virulence in Burkholderia cenocepacia Strain H111" Appl. Environ. Microbiol., 2015, vol. 81, Issue 12, pp. 4077-4089.
Lee, et al., "Microbial Production of Ethanol from Acetate by Engineered Ralstonia Eutropha", Biotechnology and Bioprocess Engineering, vol. 21, 2016, pp. 402-407.
Leyn et al., "Control of proteobacterial centralcarbon metabolism by the HexR transcriptionalregulator: a case study in Shewanella oneidensis", Journal of Biological Chemistry, 2011, vol. 286, Issue 41, pp. 35782-35794.
Leyn, S.A., et al. "Comparative genomics and evolution of transcriptional regulons in Proteobacteria", Microbial Genomics, 2016, pp. 1-15.
Liu, X., et al., "Comparative analysis of genes frequently regulated by drugs based on connectivity map transcriptome data" PLoS One, 2017, vol. 12, Issue 6, e0179037.
Marc, J., et al., "Over expression of GroESL in Cupriavidus necator for heterotrophic and autotrophic isopropanol production", Metabolic Engineering,vol. 42, 2017, pp. 74-84.
March, J.C., et al., "Expression of an anaplerotic enzyme, pyruvate carboxylase, improves recombinant protein production in *Escherichia coli*" Applied and Environmental Microbiology, 2002, vol. 68, Issue 11, pp. 5620-5624.
Martin, Koller, et al., "Continuous production mode as a viable process-engineering tool for efficient poly (hydroxyalkanoate) (PHA) bio-production", Chemical and Biochemical Engineering Quarterly, vol. 28, XP002792820 ,2014, pp. 65-77.

Meng, J., et al. "High-yield anaerobic succinate production by strategically regulating multiple metabolic pathways based on stoichiometric maximumin *Escherichia coli*", Microbial Cell Factories, vol. 15, 2016, pp. 13.
Montiel-Jarillo, G., et al., "Enrichment of a mixed microbial culture for polyhydroxyalkanoates production: Effect of pH and N and P concentrations", Science of the Total Environment, vol. 583, 2017, pp. 300-307.
Nguyen, C., et al., "Trapping the dynamic acyl carrier protein in fatty acid biosynthesis", Nature, vol. 505, No. 7483 ,Dec. 22, 2013, pp. 427-431.
Obruca, S., et al. "Application of random mutagenesis to enhance the production of polyhydroxyalkanoates by Cupriavidus necator H16 on waste frying oil". World J Microbiol Biotechnol, 2013, vol. 29, pp. 2417-2428.
Olaya-Abril et al., "Poly(3-hydroxybutyrate) hyperproduction by a global nitrogen regulator NtrB mutant strain of Paracoccus denitrificans PD1222", FEMS Microbiology Letters, 2008, vol. 365:fnx251, pp. 8.
Orita, L., et al., "Identification of mutation points in Cupriavidus necator NCIMB 11599 and genetic reconstitution of glucose-utilization ability in wild strain H16 for polyhydroxyalkanoate production" Journal of Bioscience and Bioengineering, 2012, vol. 113, Issue 1, pp. 63-69.
Papagiani, M., "Recent advances in engineering the central carbon metabolism of industrially important bacteria", Microbial Cell Factories, 2012, vol. 11, pp. 13.
Park, J-S., et al., "Metabolic Characteristics of Isocitrate Dehydrogenase Leaky Mutant of Alcaligene eutrophus and Its Utilization for Poly-Hydroxybutyrate Production" Journal of Fermentation and Bioengineering, 1996, vol. 81, Issue 3, pp. 197-205.
Park, S., et al., "Oxaloacetate and malate production in engineered *Escherichia coli* by expression of codon-optimized phosphoenolpyruvate carboxylase2 gene from Dunaliella salina", Bioprocess Biosyst Eng., 2013, vol. 36, Issue 1, pp. 127-131.
Persuhn, D.C., et al. "The transcriptional activator NtrC controls the expression and activity of glutamine synthetase in Herbaspirillum seropedicae", FEMS Microbiology Letters, 2000, vol. 192, pp. 217-221.
Pohlmann, A., et al., "Genome sequence of the bioplastic-producing "Knallgas" bacterium Ralsonia eutropha H16" Nature Biotechnology, 2007, vol. 24, No. 10, pp. 1257-1262.
Raberg, M., "Ralstoni a eutropha H16 in progress: applications beside PHAs and establishment as production platform by advanced genetic tools", Critical Reviews in Biotechnology, vol. 38, Dec. 12, 2017 (Dec. 12, 2017), pp. 494-510.
Raberg, M., et al., "A closer look on the polyhydroxybutyrate-(PHB-) negative phenotype of Ralstonia eutropha PHB-4" PLoS One, 2014, vol. 9, Issue 5, pp. 11.
Rosa, L.T., et al., "Tripartite ATP-lndependent Periplasmic (TRAP) Transporters and Tripartite Tricarboxylate Transporters (TTT): From Uptake to Pathogenicity", Frontiers in Microbiology, 2018, vol. 8, pp. 16.
Russell, J.B., "The Energy Spilling Reactions of Bacteria and Other Organisms", Journal of Molecular Microbiology Biotechnology, vol. 13, No. 1, 2007, pp. 1-11.
Sacamboio, E.N.M., et al. "The transcriptional regulator NtrC controls glucose-6-phosphate dehydrogenase expression and polyhydroxybutyrate synthesis through NADPH availability in Herbaspirillum seropedicae" Scientific Reports, 2017, vol. 7, Article No. 13546, pp. 1-12.
Saur, U., et al.,"The PEP-pyruvate-oxaloacetate node as the switch point for carbon flux distribution in bacteria", FEMS Microbiology Reviews, 2005, vol. 29, Issue 4, pp. 765-794.
Schlegel, H.G., et al., "Formation of the Dehydrogenases for Lactate, Ethanol and Butanediol in the Strictly Aerobic Bacterium Alcaligenes eutrophus" Microbiology, 1980, vol. 117, pp. 475-481.
Schobert, P., et al., "Unusual C3 and C4 metabolism in the chemo-autotroph Alcaligenes eutrophus" Journal of Bacterialogy, 1984, vol. 159, Issue 1, pp. 167-172.
Schramke, h., et al., "Revisiting Regulation of Potassium Homeostasis in *Escherichia Coli*: The Connection toPhosphate Limitation", Wiley Microbiologyopen, vol. 6, No. 3, 2017, pp. 1-16.

(56) References Cited

OTHER PUBLICATIONS

Schwartz, E., et al., "A proteomic view of the facultatively chemolithoautotrophic lifestyle of Ralstonia eutropha HI6" Proteomics, 2009, vol. 9, Issue 22, pp. 5132-5142.
Segura, D., et al., "Inactivation of pycA, encoding pyruvate carboxylase activity, increases polybeta-hydroxybutyrate accumulation in Azotobacter vinelandii on solid medium" Appl Microbial Biotechnol, 2004, pp. 65, Issue 4, pp. 414-418.
Shang et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-1419.
Shively, J.M., et al., "Something From Almost Nothing: Carbon Dioxide Fixation In Chemoautotrophs", Annu. Rev. Microbiol., vol. 52, 1998, pp. 191-230.
Silva, F., et al., "Impact of nitrogen feeding regulation on polyhydroxyalkanoates production by mixed microbial cultures", New Biotechnology, vol. 37, 2017, pp. 90-98.
Steinbuchel, A., et al., "A multifunctional fermentative alcohol dehydrogenase from the strict aerobe Alcaligenes eutrophus: purification and properties" Eur J Biochem, 1984, vol. 141, Issue 3, pp. 555-564.
Sun, J., et al., "Involvement of glnB, glnZ, and glnD genes in the regulation of poly-3-hydroxybutyrate biosynthesis by ammonia in Azospirillum brasilense Sp7", Appl. Environ. Microbiol, 2002, vol. 68, Issue 2, pp. 985-988.
Sun, J., et al., "The ntrB and ntrC genes are involved in the regulation of poly-3-hydroxybutyrate biosynthesis by ammonia in Azospirillum brasilense Sp7", Appl Environ. Microbiol., 2000, vol. 66, Issue 1, pp. 113-117.
Tan, Z., et al. "Activating phosphoenolpyruvate carboxylase and phosphoenolpyruvate carboxykinase in combination tor improvement of succinate production" Appl. Environ. Microbiol, 2013, vol. 79, Issue 16, pp. 4838-4844.
Tanaka, K, et al., Production Of Poly (D-3-HydrOxybutyrate) From CO2, H2, and O2 By High Cell Density Autotropic Cultivation of Alcaligenes Eutrophus Biotechnology and Bioengineering, Wiley, vol. 45, No. 3, (Feb. 5, 1995), XP000489583 ,Feb. 5, 1995, 268-275.
Valderrama, J.A., et al., "AccR is a master regulator involved in carbon catabolite repression of the anaerobic catabolism of aromatic compounds in Azoarcus sp. CIB" Journal of Biological Chemistry, 2014, vol. 289, Issue 4, pp. 1892-1904.
Vemuri, G.N., et al., "Physiological response of central metabolism in *Escherichia coli* to deletion of pyruvate oxidase and introduction of heterologous pyruvate carboxylase" Biotechnology and Bioengineering, 2005, vol. 90, Issue 1 pp. 64-76.
Vollbrecht, D., et al., "Excretion of Metabolites by Hydrogen Bacteria II. Influence of Aeration, pH, Temperature, and Age of Cells", European Journal of Applied Microbiology and Biotechnology, 1978, vol. 6, Issue 2, pp. 157-166.
Vollbrecht, D., et al., "Excretion of Metabolites by hydrogen Bacteria III. D(−)-3-hydroxybutanoate", European J. Appl. Microbiol. Biotechnol., 1979, vol. 7, pp. 259-266.
Vollbrecht, D., et al., "Excretion of Metabolites by Hydrogen Bacteria IV. Respiration Rate- Dependent Formation of Primary Metabolites and of Poly-3-hydroxybutanoate", Eropean Journal of Applied Microbiology and Biotechnology, 1979, vol. 7, Issue 3, pp. 267-276.
Volodina, E., et al., "Characterization of propionate CoA-transferase from Ralstonia eutropha HI6", Appl Microbial Biotechnol., 2014, vol. 98, Issue 8, pp. 3579-3589.
Weiden et al., "Cation Transport in *Escherichia Coli* Vii. Potassium Requirement for Phosphate Uptake", The Journal of General Physiology, vol. 50, No. 6, 1967, pp. 1641-1661.
Weinberg, Z., et al. "Identification of 22 candidate structured RNAs in bacteria using the Cmfinder comparative genomics pipeline" Nucleic Acids Research, 2007, vol. 35, pp. 4809-4819.
Winnen, B., et al., "The tripartite tricarboxylate transporter (TTT) family" Res. Microbial., 2003, vol. 154, Issue 7, pp. 457-465.
Non-final office action received for U.S. Appl. No. 16/399,145, dated Aug. 12, 2020, 16 pages.
Non-Final Office Action received for U.S. Appl. No. 16/398,365, dated Jan. 25, 2021, 10 Pages.
Non-final Office Action received for U.S. Appl. No. 16/398,401, dated Feb. 16, 2021, 29 Pages.
Uniprot database, entry A0A0U2WHG0, Mar. 2016.
Pohlmann A. et al.,"Phosphoenolpyruvate carboxykinase Cupriavidus necator H16", Gen Bank Q0K5F4, Retrieved from Internet URL: https://www.ncbi.nlm.nih.gov/protein/123133475?sat=35&satkey=13483043, Nov. 28, 2006, 01 page.
Pohlmann A. et al.,"Phosphoenolpyruvate carboxylase Cupriavidus necator H16",Gen Bank Q0K7M4, Retrieved from Internet URL: https://www.ncbi.nlm.nih.gov/protein/123133692?sat=35&satkey=13483220, Nov. 28, 2006, 01 page.
Pohlmann A. et al. "Pyruvate carboxylase Cupriavidus necator H16", Gen Bank Q0KC80, Retrieved from Internet URL: https://www.ncbi.nlm.nih.gov/protein/Q0KC80, Nov. 28, 2006, 02 pages.
Bramer,C.O. et al. "Putative lyase protein", Gen Bank Q2Z1A9, Retrieved from Internet URL: https://www.ncbi.nlm.nih.gov/protein/122559031?sat=35&satkey=13062155, Oct. 31, 2006, 01 page.
Inui M et al. "Metabolic Engineering of Corynebacterium glutamicum for Fuel Ethanol Production under Oxygen Deprivation Conditions", J. Mol. Microbial. Biotechnol. 8, 2004, pp. 243-254.
Non-Final Rejection received for U.S. Appl. No. 16/398,401, dated Nov. 9, 2021, 38 Pages.
Office Action received for U.S. Appl. No. 16/398,401, dated Sep. 1, 2022, 32 pages.
Ogawa et al.,"Role of Phosphoenolpyruvate in the NADP-lsocitrate Dehydrogenase and Isocitrate Lyase Reaction in *Escherichia coli*", Journal of Bacteriology, vol. 189, No. 3, Feb. 2007, pp. 1176-1178.
Final office action received for U.S. Appl. No. 16/398,401, dated Feb. 6, 2023, 25 pages.
GenBank A6VKV4 GenBank 2012 p. 1-4.
GenBank Q0K4C1, GenBank, 2006; p. 1.
GenBank Q0K790, GenBank, 2006; p. 1.
GenBank Q46WX6, GenBank, 2006; p. 1-2.
GenBank Q474V2, GenBank, 2006; p. 1-2.
GenBank CAQ69169.1, 2015, pp. 1-2.
GenBank Q8XWW2.1, 2015, pp. 1-2.
Lu et al., "Studies on the production of branched-chain alcohols in engineered Ralstonia eutropha", Appl Microbiology Biotechnology, vol. 96, pp. 283-297 (2012).
Non-Final Rejection received for U.S. Appl. No. 16/398,401, dated Jun. 22, 2023, 18 pages.
Non-Final Rejection received for U.S. Appl. No. 16/399,145, dated Jul. 27, 2023, 29 pages.
PTO STIC search in GenEmbl datase run on Jun. 27, 2022, pp. 1-6.

\* cited by examiner

MATERIALS AND METHODS FOR CONTROLLING OXIDATION AND REDUCTION IN BIOSYNTHETIC PATHWAYS OF SPECIES OF THE GENERA RALSTONIA AND CUPRIAVIDUS AND ORGANISMS RELATED THERETO

This patent application claims the benefit of priority from U.S. Provisional Patent Application Ser. No. 62/665,814 filed May 2, 2018, teachings of which are herein incorporated by reference in their entirety.

FIELD

The present invention relates to methods for increasing carbon-based chemical product yield in an organism by perturbing redox balance within the organism, nonnaturally occurring organisms having increased carbon-based chemical product yield, and methods for production of these organisms by modulating activity of one or more polypeptides functioning as a transhydrogenase, reductase, dehydrogenase or hydrogenase enzyme in the organisms.

BACKGROUND

When organisms, such as *Cupriavidus necator*, are grown under conditions in which there is a relative excess of a carbon source and a limitation of other nutrients (e.g. phosphorous, nitrogen and/or oxygen), excess carbon is sunk intracellularly into the storage carbohydrate polyhydroxybutyrate (PHB). PHB has a key role in intracellular carbon and energy storage.

Importantly, PHB is used as a mechanism for redox balancing to enable cell survival during periods of starvation and other stress conditions.

The enzymes citrate synthase and isocitrate dehydrogenase are known to be significantly inhibited by NADH and NADPH and therefore, the redox balance is considered a major regulatory factor for diverting carbon flux from either the TCA cycle or PHB biosynthetic pathway (Lee et al. FEMS Microbiological letters 1995 131:35-39).

It is known that PHB production rate increases with increased ratio of intracellular NADH/NAD and NADPH/NADP, which are highly dependent on the limiting nutrient (Wang and Lee Applied and Environmental Microbiology 1997 370-376; Pryzbylski et al. Appl. Microbiol. Biotechnol. 2013 97(20):8875-85). Under normal conditions the conversion of NADPH to NADP by acetoacetyl-CoA reductase (PhaB) reduces this effect, alleviating the inhibitory effect upon TCA cycle enzymes. However, when the PHB pathway is absent, the NADPH/NADP ratio continues to limit entry to the TCA pathway leading to the overflow of carbon to pyruvate (Lee et al. FEMS Microbiological letters 1995 131:35-39; Grousseau et al. Appl Microbiol Biotechnol. 2014 98(9):4277-90).

Under conditions of oxygen limitation in the absence of terminal electron acceptors, *Cupriavidus* generates a variety of NAD-linked dehydrogenases. These enzymes prevent 'over-reduction' of the cytoplasm, along with reversible cytoplasmic soluble hydrogenases by regenerating $NAD^+$ (Cramm, R. J. Mol. Microbiol. Biotechnol. 2009 16(1-2): 38-52). The consequence is partial fermentation products as observed by Schlegel & Vollbrecht (Microbiology 1980 117:475-481), reporting the accumulation of ethanol, succinate, formate, acetate, and 2-oxoglutarate.

Within biotechnology, the approach of redirecting carbon flux to a desired product utilizing nutrient limitation is well-established. With *Cupriavidus*, it is the principle methodology for obtaining high PHI titres, as it exploits the organism's natural mechanism of intracellular storage of carbon and energy. To utilize *Cupriavidus* or *Ralstonia* to generating other chemicals however, this natural mechanism is detrimental for obtaining high productivity and/or yields. Attenuation or elimination of PHA synthesis is therefore required, in order to maximize the efficiency of generating the desired product.

An unintended consequence of such an approach is that there is a cascade of effects upon metabolism due to high amounts of reducing equivalents and build-up of key central metabolites including pyruvate and acetyl-CoA. These manifestations include, among others, metabolic bottlenecks, heightened generation of overflow metabolites and a redox imbalance.

Replacement of traditional chemical production processes relying on, for example fossil fuels and/or potentially toxic chemicals, with environmentally friendly and/or sustainable solutions is being considered, including work to identify suitable building blocks and biosynthetic systems for use in the manufacturing of a range of products.

SUMMARY

Methods for increasing product yield of organisms and organisms capable of increased product yield are provided.

An aspect of the present invention relates to methods for increasing carbon-based chemical product yield in an organism. These methods comprise perturbing redox balance in an organism selected from a species of *Cupriavidus* or *Ralstonia* with diminished polyhydroxybutyrate synthesis or an organism with properties similar thereto by modulating activity of one or more polypeptides functioning as a transhydrogenase, reductase, dehydrogenase or hydrogenase enzyme or functional fragment thereof.

In one nonlimiting embodiment, modulating the activity of one or more polypeptides comprises overexpressing an endogenous or exogenous nucleic acid sequence in the organism.

In another nonlimiting embodiment, modulating the activity of one or more polypeptides comprises downregulating, deleting or mutating an endogenous or exogenous nucleic acid sequence in the organism.

In one nonlimiting embodiment, the perturbation in redox balance increases yield of a carbon-based chemical product derived from a NADPH dependent dehydrogenase or reductase enzyme pathway.

In one nonlimiting embodiment, the perturbation in redox balance increases yield of a carbon-based chemical product derived from a NADH dependent dehydrogenase or reductase enzyme pathway.

In one nonlimiting embodiment, the organism expresses a native or exogenous transhydrogenase or functional fragment thereof.

Another aspect of the present invention relates to nonnaturally occurring organisms capable of yielding a carbon-based chemical product. These nonnaturally occurring organisms comprise a species of *Cupriavidus* or *Ralstonia* with diminished polyhydroxybutyrate synthesis or an organism with properties similar thereto modified to perturb redox balance by modulating activity of one or more polypeptides functioning as a transhydrogenase, reductase, dehydrogenase or hydrogenase enzyme or functional fragment thereof.

In one nonlimiting embodiment, the nonnaturally occurring organism exhibits increased carbon-based chemical product yield as compared to an organism without modulated polypeptide activity.

In one nonlimiting embodiment, the nonnaturally occurring organism exhibits increased yield of a carbon-based chemical product derived from a NADPH dependent dehydrogenase or reductase enzyme pathway.

In one nonlimiting embodiment, the nonnaturally occurring organism exhibits increased yield of a carbon-based chemical product derived from a NADH dependent dehydrogenase or reductase enzyme pathway.

In one nonlimiting embodiment, the organism expresses a native or exogenous transhydrogenase or functional fragment thereof.

Yet another aspect of the present invention relates to methods for producing a carbon-based chemical product. In these methods, a nonnaturally occurring organism of the present invention is fermented with a carbon source.

In one nonlimiting embodiment, the carbon source is derived from a biological or nonbiological feedstock.

In one nonlimiting embodiment, feedstock fed to the fermentation process comprises a gaseous or liquid stream.

DETAILED DESCRIPTION

Figure 1:
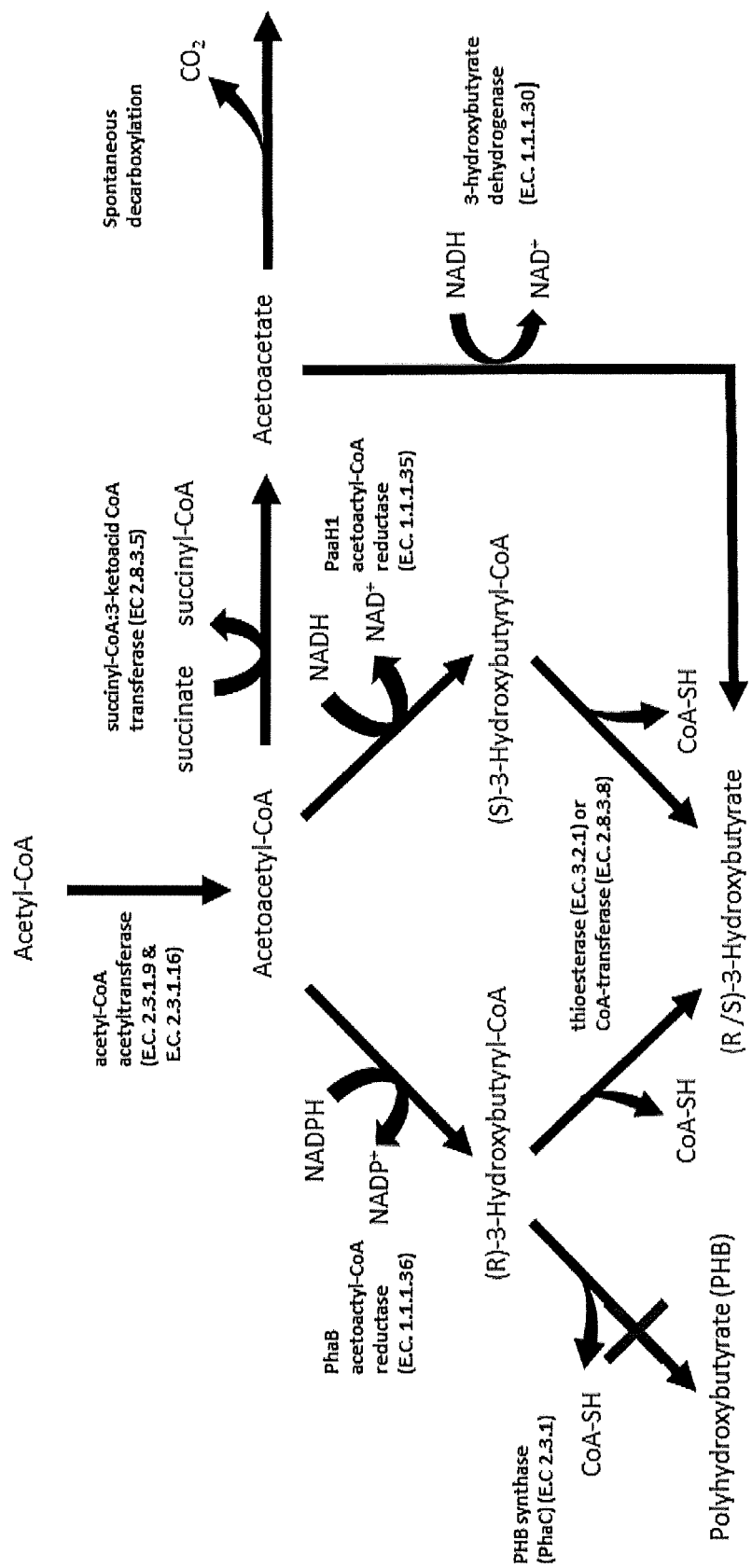
FIG. 1 shows alternative pathways for the fermentative production of 3-hydroxybutyrate in *C. necator*.

PHB has a key role in intracellular carbon and energy storage. Importantly, PHB is also used as a mechanism for redox balancing to enable cell survival during periods of starvation and other stress conditions. Upon formation of PHB, $NADP^+$ is generated. When the PHB pathway is perturbed or deleted, $NADP^+$ is no longer generated and there is consequently an $NADP^+$ imbalance referred to as a redox imbalance. With $NADP^+$ formation blocked as a result of the absence of PHB synthesis, the cell is forced to utilize other mechanisms to balance $NADPH/NADP^+$.

The present invention relates to further manipulation of these mechanisms to increase or decrease the $NADPH/NADH$ to $NADP^+/NAD^+$ ratios within an organism, in order to increase product yield in the organism.

In the present invention carbon-based chemical product yield is increased in an organism via perturbing redox balance within the organism by modulating the activity of one or more polypeptides functioning as a transhydrogenase, reductase, dehydrogenase, or hydrogenase enzyme or functional fragment thereof in the organism.

In one nonlimiting embodiment, the activity of one or more polypeptides functioning as a transhydrogenase, reductase, dehydrogenase, or hydrogenase enzyme or functional fragment is genetically modulated to have one or more different characteristic properties relative to those of the corresponding unmodified wild type organism. In certain aspects, the organism is modified by altering, engineering, or introducing one or more nucleic acid sequences within the organism. The altering of modifying of the nucleic acid sequences can be, for example and without limitation, via genetic engineering, by adaptive mutation, or by selective isolation of naturally occurring mutant strains.

In some nonlimiting embodiments, one or more enzymes or nucleic acids of the organism are modified via non-direct or rational enzyme design approaches with aims of improving activity, improving specificity, reducing feedback inhibition, reducing repression, improving enzyme solubility, changing stereo-specificity, or changing cofactor specificity. In some embodiments, the enzymes in the pathways outlined herein can be gene dosed (i.e., overexpressed by having a plurality of copies of the gene in the host organism), into the resulting genetically modified organism via episomal or chromosomal integration approaches.

In some nonlimiting embodiments, genome-scale system biology techniques such as Flux Balance Analysis can be utilized to devise genome scale attenuation or knockout strategies for directing carbon flux. Attenuation strategies include, but are not limited to, the use of transposons, homologous recombination (double cross-over approach), mutagenesis, enzyme inhibitors, and RNA interference (RNAi). In some embodiments, fluxomic, metabolomic and transcriptomal data can be utilized to inform or support genome-scale system biology techniques, thereby devising genome-scale attenuation or knockout strategies in directing carbon flux. In some embodiments, the tolerance of the host microorganism to high concentrations of the extracellular product can be improved through continuous cultivation in a selective environment.

The modified nucleic acid sequences of the organism can include, for example, one or more enzymes, one or more promoters, one or more transcription factors, or combinations thereof. The modifications can be to nucleic acids encoding polypeptides functioning as a transhydrogenase, reductase, dehydrogenase, or hydrogenase enzyme or functional fragments thereof. The modifications can be to nucleic acids not directly involved in encoding polypeptides functioning as a transhydrogenase, reductase, dehydrogenase, or hydrogenase enzyme or functional fragments thereof, but indirectly affecting the polypeptides through the interconnected metabolic network and metabolic control strategy of the organism. The modification of the nucleic acid sequences can include one or more deletions, one or more substitutions, one or more insertions, or combinations thereof.

Enzymes with substitutions will generally have not more than 50 (e.g., not more than 1, not more than 2, not more than 3, not more than 4, not more than 5, not more than 6, not more than 7, not more than 8, not more than 9, not more than 10, not more than 12, not more than 15, not more than 20, not more than 25, not more than 30, not more than 35, not more than 40, or not more than 50) amino acid substitutions (e.g., conservative or non-conservative substitutions). This applies to any of the enzymes described herein and functional fragments thereof. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic, or acidic groups by another member of the same group can be deemed a conservative substitution. In contrast, a non-conservative substitution is a substitution of one amino acid for another with dissimilar characteristics.

Deletion variants can, for example, lack 1, 2, 3, 4, 5, 6, 7, 8, 9, 10, 11, 12, 13, 14, 15, 16, 17, 18, 19, or 20 amino acid segments (of two or more amino acids) or non-contiguous single amino acids.

In one nonlimiting embodiment, modification of the organism is carried out by allele exchange. In this embodiment, genome edits are made in a *Cupriavidus* or *Ralstonia* organism with perturbed PHB synthesis or an organism with properties similar thereto by allele exchange (also referred to as allelic exchange). In one nonlimiting embodiment, the organism is a ΔphaCAB H16 *C. necator* strain generated using allele exchange.

The term 'allele' is often used interchangeably with the term 'gene' more generally, and refers to a defined genomic locus. In allele exchange, a specific run of DNA sequence (i.e., the native allele) in a genome of an organism is literally exchanged for a recombinant, mutant, or synthetic run of DNA sequence (i.e., the recombinant allele). Depending on the nature of the recombinant allele, this allele exchange can result in a gene deletion, a gene substitution, or a gene insertion.

In one nonlimiting embodiment, recombinant/synthetic alleles can be constructed via gene synthesis and/or standard molecular biology techniques. These alleles are then cloned into a plasmid vector for transfer into the organism and execution of the allele exchange procedure.

In some nonlimiting embodiments, the organism is modified to include one or more exogenous nucleic acid sequences.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In certain aspects, the organism is modified to include one or more functional fragments of enzymes, other polypeptides, or nucleic acids. The phrase "functional fragment" as used herein refers to a peptide fragment of a polypeptide or a nucleic acid sequence fragment encoding a peptide fragment of a polypeptide that has at least 25%, e.g., at least 30%, at least 40%, at least 50%, at least 60%, at least 70%, at least 75%, at least 80%, at least 85%, at least 90%, at least 95%, at least 98%, at least 99%, or at least 100% of the activity of the corresponding mature, full-length, polypeptide. The functional fragment can generally, but not always, be comprised of a continuous region of the polypeptide, wherein the region has functional activity.

Nonlimiting examples of enzymes in the NADPH dependent dehydrogenase or reductase enzyme pathway which may be altered in redox balance in accordance with this disclosure include aldehyde reductases or alcohol dehydrogenases for alcohol synthesis, 3-ketoacyl-ACP reductases, enoyl-ACP reductases for fatty acid derived products, HMG-CoA reductases or 4-hydroxy-3-methylbut-2-enyl diphosphate reductases for isoprene or isoprenoid-derived products, alcohol dehydrogenases for isopropanol synthesis, aspartate dehydrogenases for aspartate synthesis-derived products and oxoglutarate dehydrogenases for glutarate-derived products.

Nonlimiting examples of enzymes in the NADH dependent dehydrogenase or reductase enzyme pathway which may be altered in redox balance in accordance with this disclosure include alcohol dehydrogenases, 3-hydroxybutyryl-CoA dehydrogenases, or aldehyde dehydrogenases for butanol synthesis; lactate dehydrogenases for lactate synthesis; methylglyoxal dehydrogenases or alcohol dehydrogenases for propanol, 1,2 propandiol, or 1,3 propandiol synthesis; alcohol dehydrogenases for ethanol synthesis; and butanediol dehydrogenases for 2,3, butandiol, 1,3 butandiol and butadiene synthesis.

In one nonlimiting embodiment, genetic modulation comprises deleting/reducing the expression of terminal oxidases to increase the NAD(P)H/NAD(P)$^+$ ratio by limiting the organism's capacity to use oxygen as a terminal electron acceptor for the regeneration of NAD$^+$. In one nonlimiting embodiment, genetic modulation comprises targeting hydrogenases (EC 1.12.1.2 and EC 1.12.5.1) that can release or take up hydrogen, including the overexpression of a soluble, oxygen tolerant NiFe hydrogenase (SH, encoded by hoxFUYH in *C. necator* H16) to either increase NADH production under lithotrophic or mixotrophic cultivation with molecular hydrogen or increase the rate of NAD+ recycling in heterotrophically grown cultures when the intracellular redox state is over-reduced by high NAD(P)H levels (e.g. microaerobic or anaerobic fermentations). Further genetic modulation of the hydrogenases may include changing the ratio of the soluble (SH) and membrane-bound (MBH, EC 1.12.5.1 encoded by hoxKGZ in *C. necator*) hydrogenase enzymes to alter the ratio of ATP and NADH molecules produced from the oxidation of molecular hydrogen. In one nonlimiting embodiment, genetic modulation comprises targeting transhydrogenase (EC 1.6.1.1, EC 1.6.1.2, or EC 7.1.1.1)) genes which shuttle hydrogen between NADP (H) and NAD(H). Modulations of the transhydrogenase genes include the deletion, reduced expression or overexpression of either subunit encoding transhydrogenases PntA1, PntA2, PntA3, PntA4 in *C. necator* H16 in order to alter the ratio of NADPH to NADH. In one nonlimiting embodiment, genetic modulation comprises deleting or mutating one or more NAD(P)$^+$ alcohol dehydrogenases. In one nonlimiting embodiment, genetic modulation comprises deleting or mutating NAD(P)$^+$ Lactate dehydrogenase enzymes (EC 1.1.1.27 and EC 1.1.1.28). In one nonlimiting embodiment, genetic modulation comprises deleting or mutating NAD$^+$-dependent formate dehydrogenase enzymes (EC 1.2.1.2). In one nonlimiting embodiment, genetic modulation comprises exchange of NADPH with various NADH enzyme equivalents. In one nonlimiting embodiment, genetic modulation comprises oxygen limitation. In one nonlimiting embodiment, genetic modulation comprises using a defined oxygen respiration rate. In one nonlimiting embodiment, genetic modulation comprises exchanging or augmenting native NAD$^+$ dependent enzymes with equivalent enzymes able to perform similar reactions. In one nonlimiting embodiment, genetic modulation comprises deleting or mutating terminal oxidases thereby hindering the capacity to use oxygen as a terminal electron acceptor. Nonlimiting examples of terminal oxidases which can be deleted include coxMNOP, ctaABCDE, cyoABC, cyo123, and ccoNOPQ. In one nonlimiting embodiment, genetic modulation comprises deletion or mutation of reversible cytoplasmic soluble hydrogenases (EC 1.12) including, but not limited to, HoxH, HoxY, HoxF and Hox. In one nonlimiting embodiment, genetic modulation comprises overexpressing, mutating or deleting one or more NADP (EC 1.6.1.2 and EC 1.6.1.1) genes which shuttle hydrogen between NADP (H) and NAD(H). Nonlimiting examples of transhydrogenase genes include PntA1, namely H16_A0850, H16_A0851, and H16_A0852, PntA2, namely H16_A1264, H16_A1265 and H16_A1266, PntA3, namely H16_A3128, H16_A3130 and H16_A3131 and PntA4, namely H16_B1714 and H16_B1715. In one nonlimiting embodiment, further manipulation comprises the overexpression of triosephosphate isomerase (EC 5.3.1.1, H16_A1047). In one nonlimiting embodiment, genetic modulation comprises replacement of isocitrate dehydrogenase with an NAD$^+$ dependent version from such as those found in *Methylophilus methylotrophus*, *Acidithiobacillus thiooxidans* (Inoue et al. FEMS Microbiol Lett 2002 214 (1):127-32), *Methylococcus capsulatus* (Stokke et al. Arch Microbiol. 2007 187(5):361-70), and *Streptococcus mutans* (Wang et al. PLoS One. 2013 8(3):e58918). In one nonlimiting embodiment, genetic modulation comprises deleting or mutating one or more NAD(P) alcohol dehydrogenases (EC 1.1.1.1 and EC 1.1.1.2). Nonlimiting examples include H16_A0171, H16_A0602, H16_A0757, H16_A0849, H16_A0861, H16_A0931, H16_A1168, H16_A1591, H16_A3330, H16_B0517, H16_B0663, H16_B0713, H16_B0831, H16_B1417, H16_B1433, H16_B1699, H16 81745, H16_B1834, H16_B1960, H16_B2470 and PHG229. In one nonlimiting embodiment, genetic modulation comprises deleting or mutating a NAD(P) lactate dehydrogenase (EC 1.1.1.27 and EC 1.1.1.28) enzymes. Nonlimiting examples include H16_A0666, H16_B0460, H16_B1817, H16_A1681 and H16_A1682. In one nonlimiting embodiment, genetic modulation comprises overexpression of heterologous Zwf from *Zymomonas mobilis* or *Leuconostoc mesenteroides* to prevent NADPH feedback inhibition on glycolysis. In one nonlimiting embodiment, genetic modulation comprises overexpression of Gnd from *Gluconobacter oxydans* or *Corynebacterium glutamicum* to prevent NADPH feedback inhibition on glycolysis. In one nonlimiting embodiment, genetic modulation comprises molecular hydrogen production via the reverse reaction of the membrane bound and soluble NiFe hydrogenases (EC 1.12.1.2 and EC 1.12.5.1).

In one nonlimiting embodiment of the present invention, at least one exogenous nucleic acid excluding Gnd, tktA and zwf of *E. coli* is introduced into the organism.

Additional redox balancing strategies which can be preturbed in accordance with the present invention are set forth herein in the Examples and Table A.

In some nonlimiting embodiments, the methods for increasing product yield further comprise reducing NADPH/NADP ratio under limiting conditions such as phosphate, carbon, nitrogen, and/or oxygen by increasing activity or introducing select NADPH dependent enzymes. It is important dissipate excess reducing potential so that the reactions are not subject to inhibition and carbon flux can be maintained.

In one nonlimiting embodiment, this is achieved via overexpression or mutation of an alcohol dehydrogenase, EC 1.1.1.2, or aldehyde reductase, EC 1.1.1.21, to generate NADP from NADPH by converting either formaldehyde to methanol, propionaldehyde to propanol, 3-hydroxypropanal to 1-3 propanediol, butyraldehyde to butanol, isobutanal to isobutanol, glucose to sorbitol, C5 to C18 fatty aldehydes to corresponding C5 to C18 fatty alcohols, succinate semialdehyde to 4-hydroxybutanoate, oxaloacetate to L-aspartate, 2-oxoglutaric acid to glutamate, L-lactaldehyde to propane-1,2-diol, C4-C18 enoyl-ACP to a corresponding C4-C18 acyl-ACP, C4-C18 enoyl-CoA to a corresponding C4-C18 acyl-CoA, C6-C18 acyl-ACP to a corresponding C6-C18 fatty aldehyde, C6-C18 acyl-CoA to corresponding C6-C18 fatty aldehyde, 4-hydroxybenzoate to protocatechuate, phenol to catechol, acetaldehyde to ethanol, acetone to 2-propanol, pyruvate to 2-hydroxypropanoic acid, D-glyceraldehyde to glycerol or acetoin to butanediol.

In one nonlimiting embodiment, this is achieved by diverting carbon flux enzymes such as EC 1.1.1.61, EC 1.1.1.79, EC 1.1.1.2 or EC 1.1.1.21 to convert succinate semialdehyde to 4-hydroxybutanoate.

In one nonlimiting embodiment, this is achieved via overexpression of aspartate dehydrogenase or glutamate dehydrogenase to convert oxaloacetate to L-aspartate or 2-oxoglutaric acid to glutamate.

In one nonlimiting embodiment, this is achieved via conversion of malonyl-CoA by EC 1.2.1.18 to malonate-semialdehyde and/or subsequently 3-hydroxypropionate by EC 1.1.1.298.

In one nonlimiting embodiment, this is achieved via conversion of L-lactaldehyde to propane-1,2-diol by EC 1.1.1.55.

In one nonlimiting embodiment, this is achieved via introduction of EC 1.1.1.36, EC 1.3.1.38 and/or EC 1.1.1.100 to convert C4-C18 enoyl-ACP to a corresponding C4-C18 acyl-ACP or to convert C4-C18 enoyl-CoA to a corresponding C4-C18 acyl-CoA.

In one nonlimiting embodiment, this is achieved via introduction of EC 1.2.1.80 to convert C6-C18 acyl-ACP to a corresponding C6-C18 fatty aldehyde or to convert C6-C18. Acyl-CoA to a corresponding C6-C18 fatty aldehyde.

In one nonlimiting embodiment, this is achieved via introduction of an enzyme belonging to EC 1.14.13.X which converts 4-hydroxybenzoate to protocatechuate or phenol to catechol.

Additional NADPH balancing strategies which can be used in accordance with the present invention are set forth herein in the Examples.

By "carbon-based chemical product" as used herein, it is meant to include C3 to C12 alkenes, alcohols, diols, monoacids, diacids, hydroxyacids, amino acids and diamines. In one nonlimiting embodiment, the carbon-based chemical product may be any C6-C12 difunctional aliphatic fatty acid or derivative thereof including, but not limited to, C6-C12 amino acids, C6-C12 diamines, C6-C12 hydroxyacids, C6-C12 diols, and C6-C12 diacids. Nonlimiting examples of carbon-based chemical products produced in accordance with this disclosure include 1,3-propanediol, 1,2-propanediol, methionine, threonine, lysine, glutamic acid, tryptophan, aspartic acid, leucine, isoleucine, valine, citric acid, maleic acid, succinic acid, isoprene, linalool, limonene, 3-hydroxypropanoic acid, malonic acid, lactic acid, n-butanol, 2-butanone, butadiene, 2-3 butanediol, 1-3 butanediol, benzoic acid, 1,4-benzenediamine, benzeneamine, pyridine, vanillin, hydroquinone, 1,4-diaminobutane, 2-hydroxyisobutyric acid, itaconic acid, 3-hydroxybutyrate and nylon intermediates.

In some nonlimiting embodiments, the organism has been modified to exhibit an increased synthesis of the extracellular product relative to that of the corresponding wild type organism.

In some nonlimiting embodiments, the carbon-based chemical product includes pimelic acid, 7-aminoheptanoate, 7-hydroxyheptanoate, heptamethylenediamine, 1,7-heptanediol, or a combination thereof. Additional descriptions of the synthesis of these carbon-based chemical products with *Ralstonia, Cupriavidus*, or an organism similar thereto can be found in U.S. Pat. No. 10,196,657, the disclosure of which is incorporated by reference herein in its entirety for all purposes.

In some nonlimiting embodiments, the carbon-based chemical product includes 1,4-butanediol, putrescine, 4-hydroxybutyrate, 4-aminobutyrate, or a combination thereof. Additional descriptions of the synthesis of these carbon-based chemical products with *Ralstonia, Cupriavidus*, or an organism related thereto can be found in U.S. Pat. Nos. 10,072,150 and 9,637,764, the disclosures of which are incorporated by reference herein in their entirety for all purposes.

In some nonlimiting embodiments, the carbon-based chemical product includes glutaric acid, 5-aminopentanoic acid, cadaverine (also known as 1,5 pentanediamine), 5-hydroxypentanoic acid, 1,5-pentanediol, glutarate semialdehyde (also known as 5-oxopentanoate), or a combination thereof. Additional descriptions of the synthesis of these carbon-based chemical products with *Ralstonia, Cupriavidus*, or an organism related thereto can be found in U.S. Pat. No. 9,920,339, the disclosure of which is incorporated by reference herein in its entirety for all purposes.

In some nonlimiting embodiments, the carbon-based chemical product includes isoprene. Additional descriptions of the synthesis of this carbon-based chemical product with *Ralstonia, Cupriavidus*, or an organism related thereto can be found in U.S. Pat. No. 9,862,973, the disclosure of which is incorporated by reference herein in its entirety for all purposes.

In some nonlimiting embodiments, the carbon-based chemical product includes adipic acid, 6-aminohexanoic acid, hexamethylenediamine, caprolactam, 1,6-hexanediol, or a combination thereof. Additional descriptions of the synthesis of these carbon-based chemical products with *Ralstonia, Cupriavidus*, or an organism related thereto can be found in U.S. Pat. No. 9,580,733, the disclosure of which is incorporated by reference herein in its entirety for all purposes.

For products of the present invention containing carboxylic acid groups such as organic monoacids, hydroxyacids, aminoacids and dicarboxylic acids, these products may be formed or converted to their ionic salt form when an acidic proton present in the parent product either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia and the like. The salt can be isolated as is from the system as the salt or converted to the free acid by reducing the pH to below the lowest pKa through addition of acid or treatment with an acidic ion exchange resin.

For products of the present invention containing amine groups such as but not limited to organic amines, amino acids and diamine, these products may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. The salt can be isolated as is from the system as a salt or converted to the free amine by raising the pH to above the lowest pKa through addition of base or treatment with a basic ion exchange resin. Acceptable inorganic bases are known in the art and include aluminum hydroxide, calcium hydroxide, potassium hydroxide, sodium carbonate and/or bicarbonate, ammonia, sodium hydroxide, and the like.

For products of the present invention containing both amine groups and carboxylic acid groups such as but not limited to amino acids, these products may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases include aluminum hydroxide, calcium hydroxide, potassium hydroxide, sodium carbonate, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate and/or bicarbonate, ammonia, sodium hydroxide, and the like. The salt can be isolated as is from the system or converted to the free acid by reducing the pH to below the lowest pKa through addition of acid or treatment with an acidic ion exchange resin.

Nonnaturally occurring organisms produced and used in accordance with the present invention are selected from a species of *Cupriavidus* or *Ralstonia* with diminished polyhydroxybutyrate synthesis or an organism with properties similar thereto.

For purposes of the present invention, by "diminishing" or "diminished" polyhydroxybutyrate synthesis, it is meant that the organism is altered to synthesize less polyhydroxybutyrate as compared to an unaltered wild-type organism of the same species. Organisms used in this disclosure can exhibit at least 20%, 25%, 30%, 40%, 50% or even greater decreased polyhydroxybutyrate synthesis as compared to an unperturbed wild-type organism of the same species.

Nonlimiting examples of species of *Cupriavidus* or *Ralstonia* useful in accordance with this disclosure include *Cupriavidus necator, Cupriavidus metallidurans, Cupriavidus taiwanensis, Cupriavidus pinatubonensis, Cupriavidus basilensis* and *Ralstonia pickettii*.

*C. necator* (also referred to as *Hydrogenomonas eutrophus, Alcaligenes eutropha, Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar, N. S. & Casida, L. E. Int. J. of Systematic Bacteriology 1987 37(4): 323-326), bacterial predation (Byrd et al. Can J Microbiol 1985 31:1157-1163; Sillman, C. E. & Casida, L. E. Can J Microbiol 1986 32:760-762; Zeph, L. E. & Casida, L. E. Applied and Environmental Microbiology 1986 52(4):819-823) and polyhydroxybutyrate (PHB) synthesis. In addition, the cells have been reported to be capable of either aerobic or nitrate dependent anaerobic growth. A nonlimiting example of a *C. necator* organism useful in the present invention is a *C. necator* of the H16 strain. In one nonlimiting embodiment, a *C. necator* host of the H16 strain with at least a portion of the phaC1AB1 gene locus knocked out (ΔphaCAB) is used. In one nonlimiting embodiment, the organism is further modified to eliminate phaCAB, involved in PHBs production and/or H16-A0006-9 encoding endonucleases thereby improving transformation efficiency as described in U.S. patent application Ser. No. 15/717,216, teachings of which are incorporated herein by reference.

By "an organism with properties similar thereto" it is meant an organism having one or more of the above-mentioned properties of *C. necator*.

In the process described herein, a fermentation strategy can be used that entails anaerobic, micro-aerobic or aerobic cultivation coupled with nutrient limitation such as iron, sulphate, nitrogen, potassium, oxygen, phosphorus, carbon and/or or NADP limitations, gradients thereof and any combinations thereof.

A cell retention strategy using a ceramic hollow fiber membrane can also be employed to achieve and maintain a high cell density during fermentation.

The principal carbon source fed to the fermentation can derive from a biological or non-biological feedstock. In one nonlimiting embodiment, the feedstock is fed to the fermentation as a gaseous or liquid stream.

Accordingly, feedstocks for fermentation may be gases such as carbon dioxide or hydrogen; sugars such as glucose, xylose or fructose; sugar acids such as gluconate; fatty acids or fats/oils, carboxylic acids such as propionic acid, lactic acid, and formic acid; amino acids, aromatics such as phenol and benzoic acid and/or alcohols such as glycerol.

The feedstocks may be carbon sources derived from by-product or waste streams such as brewing, dairy, plant oil, ethanol, corn, soy, fish, or sugar industries or any other food or agricultural waste such as used cooking oil.

The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles or waste streams from the food processing or dairy industries municipal waste such as fruit peel/pulp or whey. The non-biological feedstock can be, or can derive from, natural gas, syngas, $CO_2/H_2$, CO, $H_2$, $O_2$, methanol, ethanol, waste streams from processes to produce monomers for the Nylon-6,6 and Nylon-6 industries such as but not limited to non-volatile residues (NVRs) and caustic wash waste streams from the cyclohexane oxidation process used to manufacture adipic acid or caprolactam or waste stream from other chemical industry processes such as, but not limited to a carbon black industry or a hydrogen-refining industry, or petrochemical industry, a nonlimiting example being a PTA-waste stream.

In one nonlimiting embodiment, at least one of the enzymatic conversions of the production method comprises gas fermentation within the modulated *Ralstonia* or *Cupriavidus* organism or other organism with properties similar thereto. In this embodiment, the gas fermentation may comprise at least one of natural gas, syngas, CO, $H_2$, $O_2$, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO_2/H_2$.

The methods of the present invention may further comprise recovering produced product from the organism. Once produced, any suitable method can be used to isolate these products or derivatives or compounds related thereto.

The present invention also provides nonnaturally occurring organisms and methods for producing the nonnaturally occurring organisms with the redox balance perturbed to increase product yield as compared to product yield in the same organism without the redox balance perturbed. The nonnaturally occurring organisms are selected from a species of *Cupriavidus* or *Ralstonia* with diminished polyhydroxybutyrate synthesis or an organism with properties similar thereto. Redox balance is perturbed in the organism by modulating activity of one or more polypeptides having the activity of any one of a transhydrogenase, reductase, dehydrogenase, or hydrogenase enzyme or a functional fragment thereof.

In some embodiments, the organism is modulated by increasing activity or introducing select NADPH dependent enzymes. These nonnaturally occurring organisms exhibit increased product yield as compared to product yield in the same organism without pertubation of the redox balance and/or increasing activity or introducing select NADPH dependent enzymes.

Nonlimiting examples of species of *Cupriavidus* or *Ralstonia* useful in accordance with this disclosure include *Cupriavidus necator*, *Cupriavidus metallidurans*, *Cupriavidus taiwanensis*, *Cupriavidus pinatubonensis*, *Cupriavidus basilensis* and *Ralstonia pickettii*.

In one nonlimiting embodiment of the nonnaturally occurring organisms of the present invention, at least one exogenous nucleic acid excluding gnd, tktA and zwf of *E. coli* is introduced.

In one nonlimiting embodiment, the present invention relates to a substantially pure culture of the nonnaturally occurring organism with a redox balance perturbed to increase product yield.

As used herein, a "substantially pure culture" of an altered organism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the altered microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of nonnaturally occurring microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In addition, the present invention provides bio-derived, bio-based, or fermentation-derived products produced using the methods and/or nonnaturally occurring organisms disclosed herein. Examples of such products include, but are not limited to, compositions comprising at least one bio-derived, bio-based, or fermentation-derived compound or any combination thereof, as well as molded substances, formulations and semi-solid or non-semi-solid streams comprising one or more of the bio-derived, bio-based, or fermentation-derived compounds or compositions, combinations or products thereof.

While the invention has been described in detail, in some instances making reference to a specific aspect thereof, it is apparent to one of skill in the art that various changes and modifications can be made thereto without departing from its spirit and scope. The following section provides further illustration of the methods and materials of the present invention. These Examples are illustrative only and are not intended to limit the scope of the invention in any way.

EXAMPLES

Redox Rebalancing Strategies

Example 1: Recycle NADH to NAD by Overexpressing the CBB Cycle

For each $CO_2$ molecule fixed, 1 molecule of NADH is oxidized to $NAD^+$ by the GAPDH (EC 1.2.1.12)-mediated reduction of 1,3 biphosphoglycerate to glyceradehyde-3-phosphate. In *C. necator*, the two CBB cycle operons (on chromosome 2 and plasmid pHG1) are induced by nitrogen limitation (Brigham et al. Appl Environ Microbiol. 2012 78(22):8033-44; Brigham et al. Appl Environ Microbiol. 2017 83(15):1-2), suggesting that the rate of $CO_2$ fixation is limited by the intrinsic activity of the CBB pathway enzymes and not $CO_2$ availability. Under certain growth conditions it may be possible to regenerate more $NAD^+$ molecules, and rebalance the cellular redox state, by overexpressing the CBB pathway enzymes. In support of this notion, the $CO_2$ fixation pathway has been shown to have a central redox cofactor recycling role in *Rhodopseudomonas palustris* when cultured under photoheterotrophic growth conditions (McKinlay and Harwood PNAS 2010 107 (26) 11669-11675).

Example 2: Regenerate $NAD^+$ by Increasing the Rate Oxidative Phosphorylation

Under conditions where molecular oxygen is not limiting the rate of NADH oxidation, the $NAD^+$ to NADH ratio can be increased by the overexpression of components of the respiratory electron transport chain that limit the rate of electron transfer between NADH and oxygen. The core *C. necator* respiratory chain consists of an NADH dehydrogenase complex, succinate dehydrogenase, a $bc_1$ complex, and at least three terminal oxidases that either receive electrons directly from ubiquinone Q8/menaquinone electron carriers or cytochrome C. In a comparative proteomic study, two isoforms (menG2 and menG3) of demethylmenaquinone methytfererase, an enzyme involved in ubiquinone/menaquinone biosynthesis, were shown to be induced to higher levels under nitrogen limitation in a PHB-deficient strain, PHB-4, than wildtype H16 (Raberg et al. PLoS ONE 2014 9(5):1-11). This is consistent with an adaptive response to increased NADH production as a result of more carbon flux entering the TCA cycle, rather than polyhydroxyalkanoate synthesis, and suggests that a component of the respiratory electron transport chain can limit the rate of NADH to NAD⁺ recycling under certain conditions.

Example 3: Regenerate NAD⁺ and/or NADP⁺ by Partial Fermentation of Organic Substrates Under conditions where the rate of NAD⁺ regeneration is limited by the aerobic respiratory chain, *C. necator* has the capacity to use organic substrates (as well as molecular oxygen) as final electron acceptors, by expressing a variety of NAD(P)-linked dehydrogenases to produce partial fermentation products such as ethanol, malate, citrate, isocitrate, lactate, succinate, formate, acetate, 2-oxoglutarate, cis-aconitate and 3-Hydroxybutyrate. Table 1 contains a list of NAD(P)-dependent dehydrogenases that can be overexpressed/heterologously expressed in *C. necator* to rebalance the redox state of *C. necator* strains and increase the production of specific overflow metabolites.

TABLE 1

| Enzyme Name/EC Number | Reaction | Potential fermentation products |
|---|---|---|
| Alcohol dehydrogenase, iron containing 1.1.1.1 | aldehyde + NADH <=> primary alcohol + NAD(+) or ketone + NADH <=> secondary alcohol + NAD(+) | aldehyde to primary alcohol, ketone to secondary alcohol |
| Alcohol dehydrogenase [NADP] 1.1.1.2 | aldehyde + NADPH <=> primary alcohol + NADP(+) or ketone + NADH <=> secondary alcohol + NADP(+) | aldehyde to primary alcohol, ketone to secondary alcohol |
| (R,R)-butanediol dehydrogenase 1.1.1.4 | (R)-acetoin + NADH <=> (R,R)-butane-2,3-diol + NAD(+) | (2S)-acetoin to butane-2,3-diol, (R,S)-3-hydroxy-2-pentanone to 2,3-pentanediol, 1-hydroxy-2-propanone to propane-1,2-diol, 2-pentanone to (S)-2-pentanol, 2-butanone to 2-butanol, acetaldehyde to ethanol, acetone to propan-2-ol |
| Glycerol dehydrogenase 1.1.1.6 | glycerone + NADH <=> Glycerol + NAD(+) | 3-hydroxypropionaldehyde to propan-1,3-diol, acetaldehyde to ethanol, acetoin to 2,3-butanediol, DL-glyceraldehyde to glycerol, N-butyraldehydeto 1-butanol |
| Glycerol-3-phosphate dehydrogenase 1.1.1.8 (NAD(+)) | glycerone phosphate + NADH <=> sn-glycerol 3-phosphate + NAD(+) | dihydroxyacetone phosphate to glycerol-3-phosphate, |
| Aldehyde reductase 1.1.1.21 | aldose + NAD(P)H <=> Alditol + NAD(P)(+) | Succinate semialdehyde to 4-hydroxybutyrate, 1-decanal to 1-decanol 1-butanal to 1-butanol, 1-hexanal to hexanol , 1-propanal to propanol, acetaldehyde to ethanol, DL-glyceraldehyde to glycerol, glucose to sorbitol, D-xylulose to D-xylitol, D-mannose to mannitol |
| Glyoxylate reductase 1.1.1.26 | glyoxylate + NADH <=> Glycolate + NAD(+) | glyoxylate to glycolate, 2-oxobutyrate to isovalerate, hydroxypyruvate to D-glycerate, phenylpyruvate to phenyllactate, succinic semialdehyde to 4-hydroxybutyrate |
| L-lactate dehydrogenase 1.1.1.27 | pyruvate + NADH <=> (L)-lactate + NAD(+) | Pyruvate to (L)-Lactic acid |
| D-lactate dehydrogenase 1.1.1.28 | pyruvate + NADH <=> (D)-lactate + NAD(+) | Pyruvate to (D)-Lactic acid |
| glycerate dehydrogenase 1.1.1.29 | hydroxypyruvate + NADH <=> D-glycerate + NAD(+) | glyoxylate to glocolate, hydroxypyruvate to D-glycerate |
| D-beta-hydroxy-butyrate dehydrogenase 1.1.1.30 | acetoacetate + NADH <=> (R)-3-hydroxybutyrate + NAD(+) | acetoacetate to (R)-3-hydroxybutyrate |

TABLE 1-continued

| Enzyme Name/EC Number | Reaction | Potential fermentation products |
|---|---|---|
| 3-hydroxy-isobutyrate dehydrogenase 1.1.1.31 | 2-methyl-3-oxopropanoate + NADH <=> 3-hydroxyisobutyrate + NAD(+) | 2-methyl-3-oxopropanoate to 3-hydroxyisobutyrate |
| Hydroxymethyl-glutaryl-CoA reductase (NADPH) 1.1.1.34 | (S)-3-hydroxy-3-methylglutaryl-CoA + 2 NADPH <=> (R)-mevalonate + CoA + 2 NADP(+) | (S)-3-hydroxy-3-methylglutaryl-CoA to mevalonate (when coexpressed with HMG-CoA synthase,) |
| 3-hydroxyacyl-CoA dehydrogenase 1.1.1.35 | 3-oxoacyl-CoA + NADH <=> (S)-3-hydroxyacyl-CoA + NAD(+) | 3-acetoacetyl-CoA to (S)-3-hydroxybutyryl-CoA ((S)-3-hydroxybutyrate), 3-oxohexadecanoyl-CoA to NADH + (S)-3-hydroxhexadecanoyl-CoA |
| Acetoacetyl-CoA reductase 1.1.1.36 | acetoacetyl-CoA + NADPH <=> 3-hydroxyisobutyrate-CoA+ NADP(+) | (R/S)-3-hydroxybutyrate |
| Malate dehydrogenase 1.1.1.37 | oxaloacetate + NADH <=> (S)-malate + NAD(+) | alpha-ketoisovalerate to 2-hydroxyisovalerate, 2-oxoglutarate to 2-hydroxybutyrate |
| Malate dehydrogenase (oxaloacetate-decarboxylating) 1.1.1.38 | pyruvate + CO(2) + NADH <=> (S)-malate + NAD(+) | pyruvate to (S)-malate, |
| Malate dehydrogenase(de-carboxylating) 1.1.1.39 | pyruvate + CO(2) + NADH <=> (S)-malate + NAD(+) | pyruvate to (S)-malate |
| Bifunctional malic enzyme oxidoreductase/ Phosphotrans-acetylase 1.1.1.40/2.3.1.8 | pyruvate + CO(2) + NADPH <=> (S)-malate + NADP(+) | pyruvate to (S)-malate |
| L-gulonate 3-dehydrogenase 1.1.1.45 | 3-dehydro-L-gulonate + NADH <=> L-gulonate + NAD(+) | L-3-hydroxybutanoate to acetoacetate (decarboxylates to acetone) |
| 2-hydroxy-3-oxopropionate reductase 1.1.1.61 | succinate semialdehyde + NADH <=> 4-hydroxybutyrate + NAD(+) | Succinate semialdehyde to 4-hydroxybutyrate |
| mannitol 2-dehydrogenase 1.1.1.67 | D-fructose + NADH <=> D-mannitol + NAD(+) | D-fructose to mannitol |
| Glyoxylate/ hydroxypyruvate reductase 1.1.1.79/1.1.1.81 | glyoxylate + NADPH <=> Glycolate + NADP(+) | Succinate semialdehyde to 4-hydroxybutanoate |
| 3-oxoacyl-[ACP] reductase 1.1.1.100 | 3-oxoacyl-[acyl-carrier-protein] + NADPH <=> (3R)-3-hydroxyacyl-[acyl-carrier-protein] + NADP(+) | Convert C4-C18 enoyl-ACP to corresponding C4-C18 Acyl-ACP |
| 3-hydroxybutyryl-CoA dehydrogenase 1.1.1.157 | 3-acetoacetyl-CoA + NADPH <=> (S)-3-hydroxybutyryl-CoA + NADP(+) | 3-acetoacetyl-CoA to (S)-3-hydroxybutanoyl-CoA (coverted to (S)-3-hydroxybutyrate with either CoA transferease or an esterase) |
| 2-dehydropantoate 2-reductase 1.1.1.169 | 2-dehydropantoate + NADPH + H+ <=> (R)-pantoate + NADP+ | (R)-4-dehydropantoate to (R)-pantoate, 2-oxoisovalerate to 2-hydroxyvalerate |
| 1,3-propanediol dehydrogenase 1.1.1.202 | 3-hydroxypropanal + NADH <=> Propane-1,3-diol + NAD(+) | 3-hydroxypropanal to Propane-1,3-diol |
| 3-hydroxy-propionate dehydrogenase (NADP+) 1.1.1.298 | 3-oxopropanoate + NADPH <=> 3-hydroxypropanoate + NADP(+) | malonate semialdehyde to 3-hydroxypropanoate |

TABLE 1-continued

| Enzyme Name/EC Number | Reaction | Potential fermentation products |
|---|---|---|
| Malonate-semialdehyde dehydrogenase (acetylating) 1.2.1.18 | acetyl-CoA + CO(2) + NAD(P)H <=> 3-oxopropanoate + CoA + NAD(P)(+) | malonyl-CoA to malonate-semialdehyde (coverted to 3-hydroxypropanoate by EC1.1.1.298) |
| Long-chain acyl-[acyl-carrier-protein] reductase 1.2.1.80 | a long-chain acyl-[acyl-carrier-protein] + NAD(P)H <=> A long-chain aldehyde + an [acyl-carrier protein] + NAD(P)(+) | Convert C6-C18 Acyl-ACP to corresponding C6-C18 fatty aldehyde |
| 2-oxoglutarate + NH(3) + NADPH <=> L-glutamate + H(2)O + NADP(+) 1.4.1.4 | 2-oxoglutarate + NH3 + NADPH + H+ <=> L-glutamate + H2O + NADP+ | oxaloacetate to L-glutamate |
| Aspartate dehydrogenase 1.4.1.21 | oxaloacetate + NH3 + NAD(P)H+ <=> L-aspartate + H2O + NAD(P)+ | oxaloacetate to L-aspartate |

One such partial fermentation product is 3-hydroxybutyrate, which has been shown to accumulate in PHB-deficient strains, especially under nitrogen and oxygen limitation (Vollbrecht and Schlegel European J. Appl. Microbiol. Biotechnol. 1979 7:259-266). In the absence of polyhydroxyalkanoate synthase activity, the overflow metabolism of the PHB pathway can be channeled towards the (R)-3-Hydroxybutyrate production by the co-expression of an (R)-3-hydroxybutyryl-CoA dehydrogenase (E.C. 1.1.1.36, encoded by phaB1, phaB2 or phaB3), with either a thioesterase (E.C. 3.2.1) or CoA-transferase (E.C. 2.8.3.8) that is able to remove the CoA moiety from the (R)-3-hydroxybutyryl-CoA intermediate (FIG. 1). As with the PHB pathway, 1 NADP$^+$ molecule is generated for each acetoacetyl-CoA molecule reduced.

Instead of NADP$^+$, 1 NAD$^+$ molecule can be generated for each acetoactetyl-CoA molecule reduced, by one of two alternative 3-hydroxybutyrate biosynthetic pathways (FIG. 1).

In the first NADH-dependent pathway, flux is channeled into the production of (S)-3-hydroxybutyrate by either deleting the (R)-3-hydroxybutyryl-CoA dehydrogenase activities encoded by phaB1, phaB2 and phaB3 and/or the expression of NADH-dependent (S)-3-hydroxybutyryl-CoA dehydrogenases, encoded by C. necator paaH1 (H16_A0281) or paaH2 (H16_A1103).

In the second NADH-dependent pathway, (R)-3-hydroxybutyrate is generated in two enzymatic steps involving first the removal of the CoA moiety from acetoacetyl-CoA by succinyl-CoA:3-ketoacid CoA transferase (E.C. 2.8.3.5) and then the reduction of the acetoacetate intermediate by (R)-3 hydroxybutyrate dehydrogenase (E.C. 1.1.1.30).

Succinyl-CoA:3-ketoacid CoA transferase contains 2 subunits encoded in C. necator H16 by H16_A1331 and H16_A1332. These ORFs are organized into a bicistronic operon, whose transcription is preferentially induced in the C. necator H16 ΔphaC1AB1 mutant, compared to wildtype H16, under nitrogen limitation conditions (see RNAseq data in Table 2).

TABLE 2

| | Normalized RNAseq counts | | | | | | | |
|---|---|---|---|---|---|---|---|---|
| | WT H16 | | | | H16 ΔphaC1AB1 | | | |
| ORF | C-Lim-1 | C-Lim-2 | N-Lim-1 | N-Lim-2 | C-Lim-1 | C-Lim-2 | N-Lim-1 | N-Lim-2 |
| H16_A1331 | 2407 | 3863 | 7971 | 9697 | 1596 | 2584 | 82412 | 41073 |
| H16_A1332 | 2969 | 4607 | 10516 | 12929 | 2411 | 3086 | 151374 | 76229 |

The gene product encoded by H16_A1331 has also been shown to be overexpressed in the PHB-negative strain, C. necator PHB$^-$4, compared to wild type H16 (Raberg et al. PLoS ONE 2014 9(5):1-11).

(R)-3 hydroxybutyrate dehydrogenase (E.C. 1.1.1.30), is a homotetrameric enzyme involved in the degradation of PHBs, by oxidizing depolymerized (R)-3 hydroxybutyrate monomers back to acetoacetate (see FIG. 1). Two (R)-3 hydroxybutyrate dehydrogenase enzymes appear to be present in the C. necator H16, encoded by H16_A1334 and H16_A1814.

Modifications of the TCA Cycle to Increase the NAD$^+$ to NADH and/or NADP$^+$ to NADPH Ratios Example 4: The Redirection of Flux into the Glyoxylate Pathway from Isocitrate, by Overexpressing Isocitrate Lyase (ICL, EC 4.1.3.1) or Knocking Out/Reducing Expression of Isocitrate Dehydrogenase (IDH, EC 1.1.1.42/EC 1.1.1.41)

The glyoxylate pathway produces 1 NADH molecule for each acetyl-CoA molecule, compared with 2 NADH molecules and 1 NADPH molecule with the complete oxidation of acetyl-CoA by the TCA cycle. Isocitrate lyase (ICL, EC 4.1.3.1) is a homotetramer with two gene copies encoded in the C. necator H16 genome, H16_A2211 (iclA) and H16_A2227 (iclB).

One of the two C. necator H16 isocitrate lyase genes, iclA (H16_A2211) is preferentially induced in the ΔphaC1AB1 genetic background compared to wild type H16, especially under nitrogen limitation (see Table 3).

produce itaconic acid and $CO_2$. By heterologously expressing this enzyme in C. necator, excess flux can be channeled out of the TCA cycle before reaching the oxidative enzymatic steps that produce 1 NADPH molecule and 2 NADH molecules per acetyl-CoA molecule oxidised.

Strategies for Increasing the NADPH Pool

TABLE 3

| | | Normalized RNAseq counts | | | | | | |
|---|---|---|---|---|---|---|---|---|
| | | WT H16 | | | | H16 ΔphaCAB | | |
| ID | Name | C-Lim-1 | C-Lim-2 | N-Lim-1 | N-Lim-2 | C-Lim-1 | C-Lim-2 | N-Lim-1 | N-Lim-2 |
| H16_A2211 | iclA | 1844 | 3041 | 2228 | 2517 | 7604 | 12467 | 29833 | 14939 |
| H16_A2227 | iclB | 15958 | 23733 | 11621 | 12547 | 7220 | 11675 | 25627 | 13396 |

Elevated ICL polypeptide levels have also been observed in a proteomic comparison of a similar PHB-negative strain, C. necator PHB⁻4, with wild type H16 (Raberg et al. PLoS ONE 2014 9(5):1-11). These observations suggest that C. necator compensates for the loss of $NADP^+$ recycling, via the PHB pathway, by redirecting flux through the glyoxylate pathway and away from some of the NAD(P)H generating steps of the TCA cycle.

Example 5: Delete/Reduce Expression of C. necator $NADP^+$-Dependent Isocitrate Dehydrogenases (IDH, EC:1.1.1.42), icd1 (H16_A3056) and icd2 (H16_B1931) and/or Overexpress/Heterologously Express an $NAD^+$-Dependent IDH (EC 1.1.1.41)

IDH catalyzes the decarboxylation of isocitrate to 2-oxoglutarate (α-ketoglutarate), with the release of $CO_2$ and either NADPH or NADH. Only an $NADP^+$-dependent IDH activity has been measured so far in C. necator cell-free extracts (Wang et al. PLoS One. 2013 8(3):e58918), although a putative $NAD^+$-dependent IDH is encoded by icd3. By switching the nucleotide specificity of the native C. necator IDH activity to $NAD^+$, 3 NADH molecules can be formed by the complete oxidation of acetyl-CoA, instead of 2 NADH molecules and 1 NADPH molecule. This has the net effect of increasing the NADH to $NAD^+$ ratio but reducing the NADPH to $NADP^+$ ratio.

$NAD^+$-dependent IDH enzymes putatively include C. necator icd3 (H16_B1016), and the IDH from Congregibacter litoralis KT71 ClIDH, EAQ96042 (Wu et al. PLoS One. 2015 10(5):1-17), Acidithiobacillus thiooxidans (Inoue et al., FEMS Microbiol Lett. 2002 214(1):127-32) and Streptococcus mutans (Wang et al. PLoS One. 2013 8(3): e58918).

A mutant version of the E. coli IDH (K44D/Y345I/V351A/Y391K/R395S) with an altered nucleotide specificity for NAD+ (Chen et al. PNAS 1996 92 (25):11666-11670) could also be used to replace the native C. necator $NADP^+$ dependent IDH enzyme activity.

Example 6: The Redirection of Flux into Itaconic Acid Production from Cis-Aconitate, by Expressing Aspergillus itaconicus Cis-Aconitate Decarboxylase (EC 4.1.1.6)

Aspergillus itaconicus cis-aconitate decarboxylase (EC 4.1.1.6) catalyzes the decarboxylation of cis-aconitate to Example 7: Engineered C. necator Strain with an Optimized Pentose Phosphate Pathway (oxPP)

In C. necator, the catabolism of fructose, glucose and gluconate proceeds by the Entner-Doudoroff (ED) pathway, where the oxidation of 1 mol of fructose/glucose to pyruvate yields 1 mol of NADPH and 1 mol of NADH. However, 2 mols of NADPH can theoretically be produced from each mol of fructose/glucose catabolized to pyruvate, by engineering a C. necator strain that utilizes the oxidative pentose phosphate (oxPP) pathway rather than the ED pathway. The C. necator H16 genome encodes all the enzymes of the oxPP pathway, with the exception of 6-phosphogluconate dehydrogenase (6PGDH, EC 1.1.1.44 and EC 1.1.1.351) which performs an essential oxidative decarboxylation step to convert 6-phospho-D-gluconate to D-ribose 5-phosphate. The preparatory phase of the Embden-Meyerhoff-Parnas (EMP) pathway, for the conversion of one hexose sugar molecule into two glyceraldehyde 3-phosphate (GAP) molecules, also appears to be not functional in C. necator, as a result of there being no gene coding for phosphofructokinase (EC 2.7.1.11). Lee et al. (Biotechnology Progress 2003 19(5):1444-49) has exemplified the basic principle of using the oxPP pathway to increase the NADPH to NADH ratio in C. necator, by heterologously expressing the E. coli gnd and tktA genes encoding 6PGDH and the oxPP transketolase (TK), respectively. Measurable increases in NADPH levels were observed for the expression of E. coli gnd and tktA. However, the expression of E. coli gnd led to reduced cell growth and lower PHB titers. Although Lee et al. 2003 putatively detected endogenous 6-phosphogluconate dehydrogenase activity from C. necator cell free extracts, the subsequent publication of the whole C. necator H16 genome sequence revealed that C. necator is unlikely to possesses a 6PGDH enzyme. The performance of the oxPP pathway for increasing the NADPH pool in C. necator may be improved by:

(1) the overexpression of glucose-6-phosphate dehydrogenase (G6PDH, EC 1.1.1.49) with 6PGDH to overcome feedback inhibition by NADPH. The activities of both G6PDH and 6PGDH are sensitive to feedback inhibition by NADPH (Sekar et al. Biotechnol. Biofuels 2017 10:85). In the case of G6PDH, this can lead to flux through both the ED and oxPP pathways being negatively affected. However, the overexpression of G6PDH has been shown to increase the flux through ED and oxPP pathways, resulting in higher NADPH production rates. The E. coli zwf gene encoding G6PDH has been expressed in C. necator, resulting in an altered molar ratio of 3-hydroxyvalerate to 3-hydroxybutyrate in biopolymers and increased NADPH levels (Choi et al. Enzyme and Microbial Technology 2003 32(1):178-185);

(2) eliminating futile cycles between the Calvin Benson Bassham and oxPP pathways by removing or attenuating one or more enzymatic steps that are unique to the CBB cycle. The oxidative pentose phosphate pathway and the Calvin Benson Bassham (CBB) $CO_2$ fixation pathway share some of the same enzymatic steps that operate in opposing directions (see FIG. 2). This may lead to formation of futile cycles when flux is going through both pathways, resulting in energy being dissipated as heat. By deleting or attenuating the phosphoribulokinase (EC 2.7.1.19) activity of the CBB cycle, potential futile cycles between the CBB cycle and the non-oxidative phase of the oxPP pathway can be minimized; and (3) co-expressing phosphofructokinase with 6PGDH to create a *C. necator* strain with complete EMP, ED and oxPP pathways. The EMP, ED and oxPP pathways produce different ratios of NADH, NADPH and ATP molecules for each hexose sugar oxidized (see Table 4). This enables the fine turning of the molecular stoichiometry between NADH, NADPH and ATP for optimal NADPH and biomass production, by manipulating the relative fluxes through these competing pathways.

Estimated molar ratios of NADPH, NADH and ATP produced from the oxidation of 1 mol of glucose, gluconate and fructose to pyruvate by either the Embden-Meyerhoff-Parnas (EMP), Entner-Doudoroff (ED) or oxidative pentose phosphate (oxPP) pathways, and 1 mol of glycerol by either the aerobic or fermentative glycerol utilization pathways are shown in Table 4.

of glycerol oxidized to pyruvate by exclusively using $NADP^+$-dependent dehydrogenases for the production of DHAP. This can be achieved in *C. necator* by deleting genes H16_A2509 and H16_B1198 encoding the membrane-bound glycerol-3-phosphate dehydrogenases (EC 1.1.5.3), and/or overexpressing an $NADP^+$-dependent glycerol-3-phosphate dehydrogenase (EC 1.1.1.94, encoded by H16_A0336 in *C. necator* H16). The alternative 'fermentative' glycerol utilization pathway could also be used to produce 1 to 1 molar ratio of NADPH to glycerol, by co-expressing an $NADP^+$-dependent glycerol dehydrogenase (EC 1.1.1.156) with dihydroxyacetone kinase (EC 2.7.1.29), in a *C. necator* H16 strain with the genes encoding glycerol kinase (H16_A2507 and H16_B1199) and/or membrane bound glycerol-3-phosphate dehydrogenase (H16_A2508 and H16_B1198) deleted.

Example 9: Manipulation of Glycerol Utilization Pathways in *C. necator* to Maximize NADH Synthesis from a Glycerol-Containing Feedstock The glycerol-utilization pathway can be optimized for the production of NADH by a similar strategy used to optimize NADPH production. 2 mols NADH can be produced for each mol of glycerol oxidized to pyruvate by expressing the 'fermentative' glycerol utilization pathway consisting of an $NAD^+$-dependent glycerol dehydrogenase (EC 1.1.1.6) and dihydroxyacetone kinase (EC 2.7.1.29), in a *C. necator* strain deficient in glycerol kinase (EC 2.7.1.30) activity (e.g. *C. necator* ΔH16A2507 and ΔH16B1199).

TABLE 4

|  | Glucose | | | Gluconate | | | Fructose | | | Glycerol Glycerol/Gly3P dehydrogenase | | |
|---|---|---|---|---|---|---|---|---|---|---|---|---|
| Cofactor | EMP | ED | oxPP | EMP | ED | oxPP | EMP | ED | oxPP | EC 1116/156 | EC 1115.3 | EC 11194 |
| NADPH | 0 | 1 | 2 | 0 | 0 | 1 | 0 | 1 | 2 | 0 | 0 | 1 |
| NADH | 2 | 1 | 1.67 | 2 | 1 | 1.67 | 2 | 1 | 1.67 | 2 | 1 | 1 |
| ATP | 2 | 1 | 1.67 | 2 | 1 | 1.67 | 2 | 1 | 1.67 | 1 | 1 | 1 |

Figure 2:
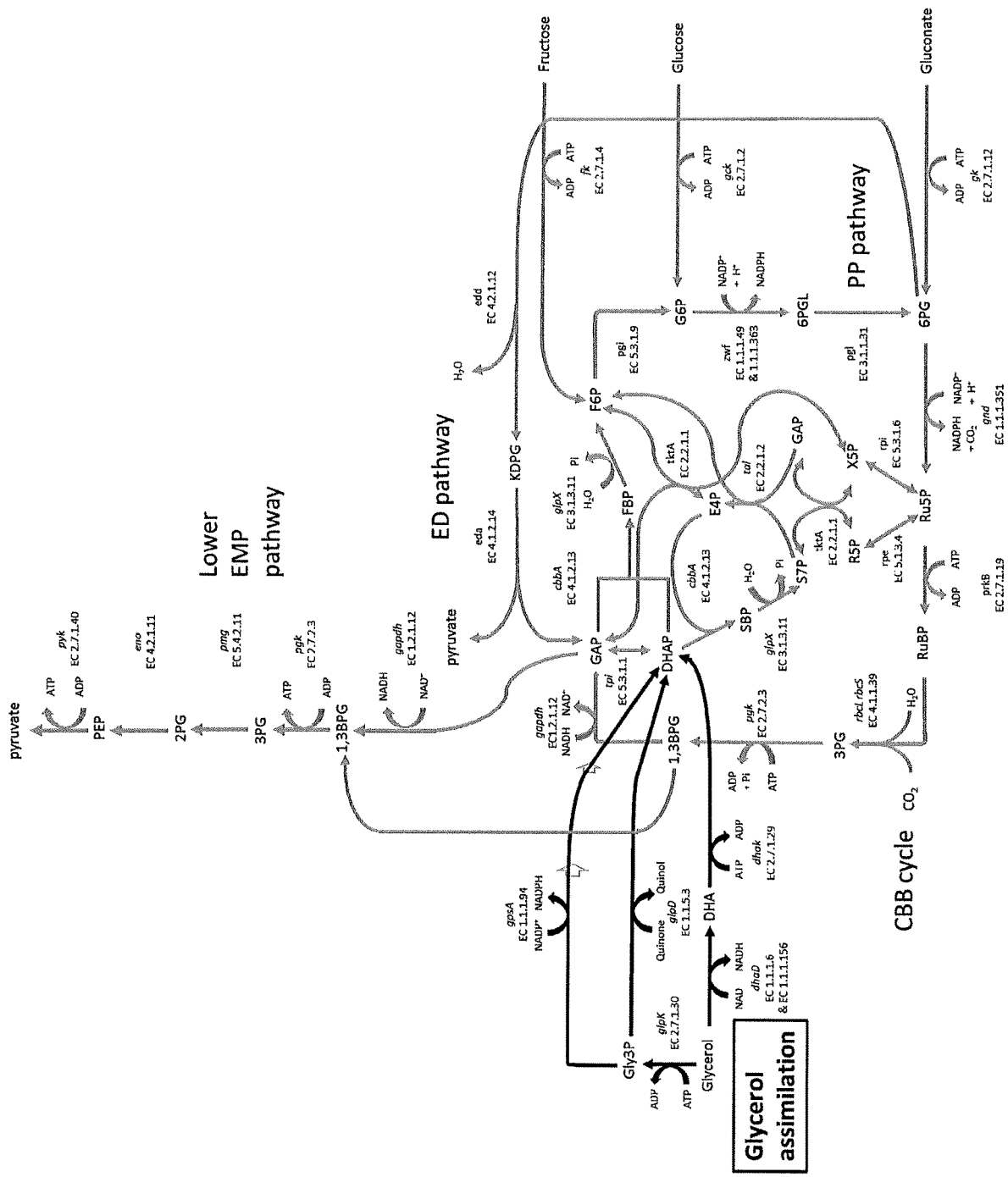
FIG. 2 shows the pathways for the oxidation of hexose sugars and glycerol to pyruvate and the assimilation of $CO_2$ by the Calvin-Benson-Bassham cycle (CBB). Abbreviations are as follows: PP, pentose phosphate pathway; ED, Entner-Doudoroff pathway; EMP, Embden-Meyerhof-Parnas pathway; F6P, fructose 6-phosphate; G6P, glucose 6-phosphate; 6PGL, 6-phosphogluconolactonase; 6PG, 6-phosphogluconate; Ru5P, ribulose 5-phosphate; X5P, xylulose 5-phosphate; R5P, ribose 5-phosphate; S7P, sedoheptulose-7-phosphate; E4P, erythrose 4-phosphate; GAP, glyceraldehyde 3-phosphate; SBP, sedoheptulose 1,7-biphosphate; DHAP, DHAP, dihydroxyacetone phosphate; FBP, fructose 1,6-bisphosphatase; RuBP, ribulose 1,5-biphosphate; 2PH, 2-phosphoglycerate; 3PG, 3-phosphoglycerate; 1,3BPG, 1,3-bisphosphoglycerate; Gly3P, glycerol 3-phosphate; DHA, dihydroxyacetone; PEP, phosphoenolpyruvate; and KDPG, 2-dehydro-3-deoxy-D-gluconate 6-phosphate.

Example 8: Manipulation of the Glycerol Utilisation Pathway in *C. necator* to Maximize NADPH Synthesis Glycerol catabolism proceeds by one of two routes to dihydroxyacetone-phosphate (DHAP), which is then isomerized to glyceraldehyde 3-phosphate and converted to pyruvate by the lower EMP pathway (FIG. 2). In *C. necator*, glycerol is first phosphorylated to glycerol 3-phosphate (Gly3P) by glycerol kinase (EC 2.7.1.30) and then oxidized to DHAP by either a membrane-bound glycerol-3-phosphate dehydrogenase (EC 1.1.5.3 encoded by H16_A2508 and H16_B1198 in *C. necator* H16) that directly transfers electrons from glycerol to the respiratory chain, or an $NADP^+$-dependent glycerol-3-phosphate dehydrogenase (EC 1.1.1.94, encoded by H16_A0336). An alternative, fermentative, glycerol utilization pathway also exists in other microorganisms that first oxidizes glycerol to glycerone (DHA), with either an $NAD^+$ (EC 1.1.1.6) or $NADP^+$ (EC 1.1.1.156)-linked glycerol dehydrogenase, followed by a phosphorylation reaction by dihydroxyacetone kinase (EC 2.7.1.29) to produce DHAP. These glycerol utilization pathways can be manipulated to produce 1 mol NADPH per mol Example 10: Manipulation of the Lower EMP Pathway to Maximize NADPH Synthesis by Changing the Nucleotide Specificity of Glyceraldehyde 3-Phosphate Dehydrogenase (GAPDH) to $NADP^+$ For each mol of pyruvate produced, the classical lower EMP pathway generates 1 mol of NADH from the oxidation of glyceraldehyde 3-phosphate (GAP) to 1,3 biphosphoglycerate by an $NAD^+$-dependent glyceraldehyde 3-phosphate dehydrogenase (GAPDH, EC 1.2.1.12). By deleting the native $NAD^+$-dependent GAPDH activity in *C. necator* (H16_A3146, H16_B1386 and PHG418) and recombinantly expressing a $NADP^+$-dependent GAPDH enzyme (EC 1.2.1.13), 1 mol of NADPH can instead be synthesized from the lower EMP pathway. When combined with measures to maximize NADPH production from the upstream glycerol utilization pathway, a maximum of 2 mols of NADPH, and no NADH, can be synthesized from the oxidation of 1 mol of glycerol to pyruvate. Depending on whether the ED, EMP or oxPP pathways are utilized, a maximum of 2 to 3.67 mols of NADPH can be produced from hexose sugars using an $NADP^+$-dependent GAPDH enzyme.

Example 11: Maximize Net NADH/NADPH Production from GAPDH by Attenuating or Blocking the CBB Cycle In the CBB cycle, GAPDH catalyzes the reverse reaction to the lower EMP pathway by reducing 1,3 biphosphoglycerate to glyceraldehyde 3-phosphate, with the result that 1 NAD(P)H molecule is consumed for every $CO_2$ molecule fixed. The flux through this NAD(P)H-consuming reaction can be minimized either by redirecting 1,3 biphosphoglycerate from the CBB cycle into the lower EMP pathway through the overexpression of phosphoglycerate kinase (EC 2.7.2.3), or by deleting/attenuating the activity of an upstream CBB enzyme, such as phosphoribulokinase (EC 2.7.1.19), to limit the carbon flux entering the CBB cycle. Modifications of the TCA Cycle to Increase the NADPH Synthesis Example 12: Redirection of Flux into the Oxidative TCA Cycle from the Glyoxylate Pathway, by Knocking Out Isocitrate Lyase (ICL, EC 4.1.3.1) and or the Overexpression of Isocitrate Dehydrogenase (IDH, EC 1.1.1.42/EC 1.1.1.41)

A maximum of 1 mol of NADPH is generated from 1 mol of acetyl-CoA entering the citric acid cycle. However, the enzyme performing this NADPH-generating reaction, isocitrate dehydrogenase (EC 1.1.1.42), resides at a branch point in the TCA cycle where flux can either enter the glyoxylate pathway, for the conversion of acetyl CoA into succinate or malate via isocitrate lyase (ICL, EC 4.1.3.1), or remain in the TCA cycle for the complete oxidation of 1 mol of acetyl-CoA to 2 mols of NADH and 1 mol of NADPH. The TCA cycle can be manipulated to achieve the maximum theoretical yield of NADPH, by deleting the *C. necator* genes coding for isocitrate lyase (iclA, H16_A2211 and iclB, H16_A2227) and/or the overexpression of a $NADP^+$-dependent isocitrate dehydrogenase.

Example 12: Manipulation of the Anaplerotic Reactions of the TCA Cycle

Figure 3:
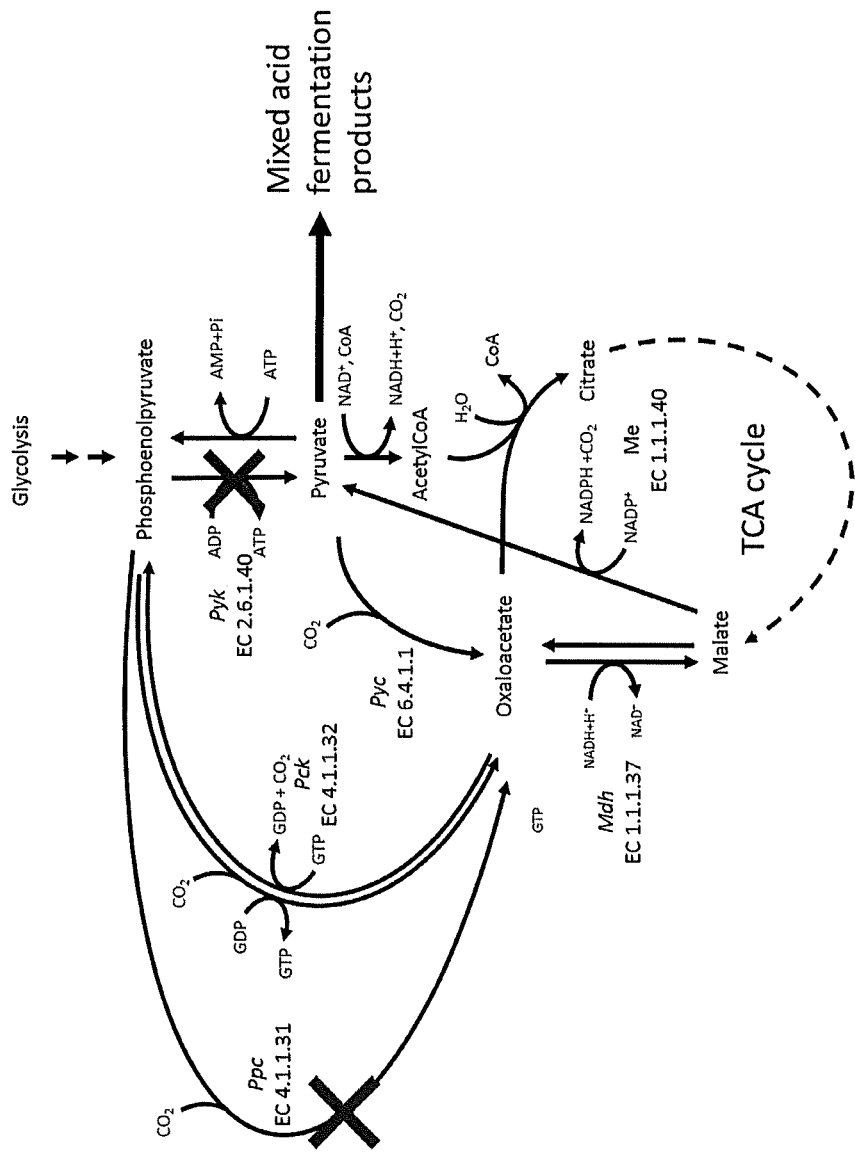
FIG. 3 shows a strategy for the conversion of NADH to NADPH by re-routing pyruvate synthesis via oxaloacetate and malate. Mdh, malate dehydrogenase (EC 1.1.1.37); Me, malic enzyme (EC 1.1.1.40); Ppc, phosphoenolpyruvate carboxylase (EC 4.1.1.31); Pck, phosphoenolpyruvate carboxykinase (EC 4.1.1.32); Pyk, phosphoenolpyruvate kinase (EC 2.6.1.40); Pyc, pyruvate carboxylase (EC 6.4.1.1).

The anaplerotic node of the TCA cycle mediates the interconversion between C3 and C4 molecules for the maintenance of TCA cycle intermediates and metabolism of C3/C4 substrates. For instance, the C3 molecule phosphoenolpyruvate is converted by either phosphoenolpyruvate carboxylase (PEPC, EC 4.1.1.31) or phosphoenolpyruvate carboxykinase (PEPCK, EC 4.1.1.32) to the C4 molecule oxaloacetate. In a similar carboxylation reaction, pyruvate is converted to oxaloacetate by pyruvate carboxylase (PC, EC 6.4.1.1). Under microaerobic or anaerobic conditions, oxaloacetate can be recycled back to pyruvate by malic enzyme (ME, EC1.1.1.40), which catalyzes the $NADP^+$-dependent oxidative decarboxylation of malate to pyruvate (see FIG. 3). The recycling of oxaloacetate to pyruvate via $NAD^+$-dependent malate dehydrogenase (MDH, EC 1.1.1.37) and $NADP^+$-dependent malic enzyme has the net effect of converting 1 NADH molecule to 1 NADPH molecule. Flux through this NADPH generation pathway can be increased by channeling pyruvate production via oxaloacetate. This can be achieved by re-routing glycolysis through the EMP or oxPP pathways, instead of the ED pathway, and the knock-out or knock-down of the *C. necator* genes (pyk1-H16_A0567 pyk2-H16_A3602 and pyk3-H16_B0961) encoding pyruvate kinase (EC 2.7.1.40). In order to ensure the same number of ATP molecules (or equivalent) are generated from the oxaloacetate-dependent conversion of PEP to pyruvate, the carboxylation of PEP to oxaloacetate can be channeled through phosphoenolpyruvate carboxykinase (PEPCK, EC 4.1.1.32), by knocking out the *C. necator* gene (H16_A2921) encoding phosphoenolpyruvate carboxylase (PEPC, EC 4.1.1.31). As a result, 1 mol of GTP is generated from the carboxylation of 1 mol of phosphoenopyruvate to oxaloacetate, which can be readily converted to ATP by nucleoside-diphosphate kinase (EC 2.7.4.6).

Example 13: Manipulation of Transhydrogenase Activity

The pyridine nucleotide transhydrogenases (EC 1.6.1.1 EC 1.6.1.2, and EC 7.1.1.1) catalyze the reversible hydride transfer between NAD(H) and NADP(H). These enzymes can be divided into two groups, energy-independent soluble transhydrogenases (STH, EC 1.6.1.1) and the energy-dependent, proton-translocating, membrane-bound transhydrogenases ($H^+$-TH, EC 1.6.1.2, EC 7.1.1). Although both isoforms theoretically catalyze reversible hydride exchange between NAD(H) and NADP(H). The membrane-bound transhydrogenases couple electron transfer between pyridine nucleotides with proton import from the periplasmic space into the cytosol, with the result that the transfer of electrons between NADH and $NADP^+$ is strongly favored thermodynamically. The *C. necator* H16 genome codes for four putative transhydrogenases composed of two alpha-beta subunits, PntA1, PntA2, PntA3 and PntA4. The overexpression of a transhydrogenase may directly increase the NADPH pool in *C. necator*. In some circumstances, the overexpression of a soluble transhydrogenase can actually increase productive yields of NADPH-dependent biosynthetic pathways. For instance, the overexpression of STH increased NADPH-dependent poly(3-hydroxybutyrate) production by 82% in a recombinant *E. coli* strain (Sanchez et al. Biotechnol Prog. 2006 22(2):420-5).

Example 14: Manipulation of $NAD^+$ Kinase Activity $NAD^+$ kinase (NADK, EC 2.7.1.23) plays an essential role in de novo $NADP^+$ biosynthesis, by catalyzing the conversion of $NAD^+$ to $NADP^+$. Most NADKs can also phosphorylate NADH to directly produce NADPH, but the enzymes generally have a substrate preference for $NAD^+$. The overexpression of NADKs have been shown to increase the production yields of a number of NADPH-dependent pathways, including a recombinant polyhydroxyalkanoate pathway expressed in *E. coli*. (Li et al. Appl Microbiol Biotechnol. 2009 83(5):939-47). Higher NADPH yields may be achieved in *C. necator* by combining the overexpression of NADK with strategies to increase the NADH pool, such as limiting the capacity of the respiratory electron transport chain to oxidize NADH under aerobic conditions or the ability of oxidoreductases to use organic substrates as terminal electron acceptors under oxygen-limited culture conditions.

Example 15: Controlled NADH Synthesis by Mixotrophic Cultivation of *C. necator* with an Organic Carbon Source and Molecular Hydrogen In addition to heterotrophic and lithotrophic modes of growth, *C. necator* is capable of adopting a mixotrophic lifestyle by simultaneously deriving carbon and energy from organic and inorganic substrates, such as fructose and $CO_2$/

$H_2$. A mixotrophic cultivation strategy can provide a means to independently manipulate biomass accumulation and ATP/NAD(P)H production, allowing a greater degree of in-process control of the intracellular NADH/NAD$^+$ ratio during fermentations. One example of a mixotrophic fermentation strategy able to control NADH levels consists of an organic carbon source supplying all the carbon and most of the energy requirements, supplemented with molecular hydrogen for additional NADH/ATP synthesis. The redox state of a fermentation can be monitored in real time by measuring the $CO_2$ evolution rate and $H_2/O_2$ uptake rates, allowing the intracellular NADH pool to be maintained at constant level by adjusting the hydrogen supply.

TABLE A

List of terminal oxidases and fermentation products derived from the Brenda enzyme database (https://with the extension brenda-enzymes.org/of the world wide web)

| Enzyme Name/EC number | Reaction | Potential fermentation products |
|---|---|---|
| Alcohol dehydrogenase, iron containing/ 1.1.1.1 | aldehyde + NADH <=> primary alcohol + NAD(+) or ketone + NADH <=> secondary alcohol + NAD(+) | Aldehydes to primary alcohols Ketones to secondary alcohols |
| alcohol dehydrogenase [NADP]/1.1.1.2 | aldehyde + NADPH <=> alcohol + NADP(+) | Aldehydes to primary alcohols Ketones to secondary alcohols |
| homoserine dehydrogenase/ 1.1.1.3 | L-aspartate 4-semialdehyde + NAD(P)H <=> L-homoserine + NAD(P)(+) | L-aspartate 4-semialdehyde to L-homoserine |
| (R,R)-butanediol dehydrogenase/1.1.1.4 | (R)-acetoin + NADH <=> (R,R)-butane-2,3-diol + NAD(+) | (2S)-acetoin to butane-2,3-diol,(R,S)-3-hydroxy-2-pentanone to 2,3-pentanediol, 1-hydroxy-2-propanone to propane-1,2-diol,2-pentanone to (S)-2-pentanol, 2-butanone to 2-butanol, acetaldehyde to ethanol, acetone to propan-2-ol |
| Glycerol dehydrogenase/ 1.1.1.6 | glycerone + NADH <=> Glycerol + NAD(+) | 3-hydroxypropionaldehyde to propan-1,3-diol, acetaldehyde to ethanol, acetoin to 2,3-butanediol, DL-glyceraldehyde to glycerol, N-butyraldehyde to 1-butanol |
| Propanediol-phosphate Dehydrogenase/ 1.1.1.7 | Propane-1,2-diol 1-phosphate <=> Propane-1,2-diol 1-phosphate + NAD(+) | hydroxyacetone phosphate to propane-1,2-diol-1-phosphate |
| Glycerol-3-phosphate dehydrogenase (NAD(+))/ 1.1.1.8 | glycerone phosphate + NADH <=> sn-glycerol 3-phosphate + NAD(+) | glycolaldehyde to ethane-1,2-diol |
| Glucuronolactone reductase/ 1.1.1.20 | D-glucurono-3,6-lactone + NADPH <=> L-gulono-1,4-lactone + NADP(+) | D-glucuronic acid to L-gulonic acid, D-glucurono-3,6-lactone to D-gulono-1,4-lactone |
| Aldehyde reductase/ 1.1.1.21 | aldose + NAD(P)H <=> Alditol + NAD(P)(+) | Succinate semialdehyde to 4-hydroxybutyrate, 1-decanal to 1-decanol 1-butanal to 1-butanol, 1-hexanal to hexanol, 1-propanal to propanol, acetaldehyde to ethanol, DL-glyceraldehyde to glycerol, glucose to sorbitol, D-xylulose to D-xylitol, D-mannose to mannitol |
| Quinate dehydrogenase/ 1.1.1.24 | 3-dehydroquinate + NADH <=> Quinate + NAD(+) | 3-dehydroquinate to Quinate |
| shikimate dehydrogenase/ 1.1.1.25 | 3-dehydroshikimate + NADPH <=> Shikimate + NADP(+) | 3-dehydroquinate to 3-dehydroshikimate, 3-dehydroshikimate to shikimate, |
| Glyoxylate reductase/ 1.1.1.26 | glyoxylate + NADH <=> Glycolate + NAD(+) | glyoxylate to glycolate, 2-oxobutyrate to isovalerate, hydroxypyruvate to D-glycerate, phenylpyruvate to phenyllactate, succinic semialdehyde to 4-hydroxybutyrate |

TABLE A-continued

List of terminal oxidases and fermentation products derived from the Brenda enzyme database (https://with the extension brenda-enzymes.org/of the world wide web)

| Enzyme Name/EC number | Reaction | Potential fermentation products |
|---|---|---|
| L-lactate dehydrogenase/ 1.1.1.27 | pyruvate + NADH <=> (L)-lactate + NAD(+) | Pyruvate to (L)-lactate, 2-oxobutyrate to 2-hydroxybutyrate, 2-oxoglutarate to 2-hydroxyglutarate, 2-oxopentanoate to 2-hydroxypentanoate, 2-oxovalerate to 2-hydroxyvalerate, phenylpyruvate to phenyllactate, pyruvate ethyl ester to 2-hydroxypropanoate ethyl ester |
| D-lactate dehydrogenase/ 1.1.1.28 | pyruvate + NADH <=> (D)-lactate + NAD(+) | pyruvate to (D)-Lactic acid, 2-ketocaproate to 2-hydroxycaproate, 2-ketoisocaproate to 2-hydroxyisocaproate, 2-ketoisovalerate to 2-hydroxyisovalerate, 2-ketovalerate to 2-hydroxyvalerate, 2-oxobutyrate to 2-hydroxybutyrate, glyoxylate to hydroxyacetic acid, hydroxypyruvate to glycerate, oxaloacetate to malate |
| glycerate dehydrogenase/ 1.1.1.29 | hydroxypyruvate + NADH <=> D-glycerate + NAD(+) | glyoxylate to glocolate, hydroxypyruvate to D-glycerate |
| D-beta-hydroxybutyrate dehydrogenase/1.1.1.30 | acetoacetate + NADH <=> (R)-3-hydroxybutyrate + NAD(+) | (R)-3-hydroxybutyrate |
| 3-hydroxyisobutyrate dehydrogenase/1.1.1.31 | 2-methyl-3-oxopropanoate + NADH <=> 3-hydroxyisobutyrate + NAD(+) | 3-hydroxyisobutyrate |
| Hydroxymethylglutaryl-CoA reductase (NADPH)/ 1.1.1.34 | (S)-3-hydroxy-3-methylglutaryl-CoA + 2 NADPH <=> (R)-mevalonate + CoA + 2 NADP(+) | (S)-3-hydroxy-3-methylglutaryl-CoA to mevalonate (when coexpressed with HMG-CoA synthase) |
| 3-hydroxyacyl-CoA dehydrogenase/1.1.1.35 | 3-oxoacyl-CoA + NADH <=> (S)-3-hydroxyacyl-CoA + NAD(+) | 3-acetoacetyl-CoA to (S)-3-hydroxybutyryl-CoA ((S)-3-hydroxybutyrate), 3-oxohexadecanoyl-CoA to NADH + (S)-3-hydroxhexadecanoyl-CoA |
| acetoacetyl-CoA reductase/ 1.1.1.36 | acetoacetyl-CoA + NADPH <=> 3-hydroxyisobutyrate-CoA + NADP(+) | acetoacetyl-CoA to (R/S)-3-hydroxybutyrate |
| malate dehydrogenase/ 1.1.1.37 | oxaloacetate + NADH <=> (S)-malate + NAD(+) | alpha-ketoisovalerate to 2-hydroxyisovalerate, 2-oxoglutarate to 2-hydroxybutyrate |
| malate dehydrogenase (oxaloacetate-decarboxylating)/1.1.1.38 | pyruvate + CO(2) + NADH <=> (S)-malate + NAD(+) | pyruvate to (S)-malate, |
| Malate dehydrogenase (decarboxylating)/ 1.1.1.39 | pyruvate + CO(2) + NADH <=> (S)-malate + NAD(+) | pyruvate to (S)-malate |
| bifunctional malic enzyme oxidoreductase/ phosphotransacetylase/ 1.1.1.40/2.3.1.8 | pyruvate + CO(2) + NADPH <=> (S)-malate + NAD(+) | pyruvate to (S)-malate |
| Phosphogluconate dehydrogenase (NADP(+)-dependent, decarboxylating)/ 1.1.1.44 | D-ribulose 5-phosphate + CO(2) + NADPH <=> 6-phospho-D-gluconate + NADP(+) | 3-oxo-2-deoxy-6-phosphogluconate to 2-deoxy-6-phosphogluconate |
| L-gulonate 3-dehydrogenase/ 1.1.1.45 | 3-dehydro-L-gulonate + NADH <=> L-gulonate + NAD(+) | L-3-hydroxybutanoate to acetoacetate (decarboxylates to acetone) |

TABLE A-continued

List of terminal oxidases and fermentation products derived from the Brenda enzyme database (https://with the extension brenda-enzymes.org/of the world wide web)

| Enzyme Name/EC number | Reaction | Potential fermentation products |
|---|---|---|
| 2-hydroxy-3-oxopropionate reductase/1.1.1.60 | 2-hydroxy-3-oxopropanoate + NAD(P)H <=> D-glycerate + NAD(P)(+) | D-glycerate |
| 2-hydroxy-3-oxopropionate reductase/1.1.1.61 | succinate semialdehyde + NADH <=> 4-hydroxybutyrate + NAD(+) | Succinate semialdehyde to 4-hydroxybutyratate |
| mannitol 2-dehydrogenase/ 1.1.1.67 | D-fructose + NADH <=> D-mannitol + NAD(+) | D-fructose to mannitol |
| gluconate 5-dehydrogenase/ 1.1.1.69 | 5-Dehydro-D-gluconate + NADPH <=> D-Gluconic acid + NADP+ | 5-dehydro-D-gluconate to D-Gluconic acid |
| glyoxylate/hydroxypyruvate reductase/1.1.1.79/1.1.1.81 | glyoxylate + NADPH <=> Glycolate + NADP(+) | 2-oxoglutarate to 2-hydroxyglutarate, 2-oxoisocaproate to 2-hydroxy-4-methylpentanoate, acetaldehyde to ethanol, glyoxylate to glycolate, hydroxypyruvate to glycerate, oxaloacetate to malate, succinic semialdehyde to 4-hydroxybutyrate, |
| hydroxypyruvate reductase/ 1.1.1.81/1.1.1.29 | hydroxypyruvate + NAD(P)H <=> D-glycerate + NAD(P)(+) | 2,3-butandione to butan-2-ol-3-one, glyoxylate to glycolate, hydroxypyruvate D-glycerate, oxaloacetate to malate |
| ketol-acid reductoisomerase/ 1.1.1.86 | (2S)-2-hydroxy-2-methyl-3-oxobutanoate + NADPH <=> (2R)-2,3-dihydroxy-3-methylbutanoate + NADP(+) | (S)-2-acetolactate to (R)-2,3-dihydroxyisovalerate, 2-aceto-2-hydroxybutyrate to 2,3-dihydroxy-3-methylvalerate, 2-acetolactate to 2,3-dihydroxy-3-methylbutanoate, 2-hydroxy-2-ethyl-3-oxobutanoate to 2,3-dihydroxy-2-ethyl-butanoate, 2-hydroxy-2-methyl-3-oxobutanoate to 2,3-dihydroxy-2-methyl-butanoate, 2-methylacetoacetate to 3-hydroxy-2-methylbutanoate, 3-hydroxy-3-ethyl-2-oxobutanoate to 2,3-dihydroxy-3-ethyl-butanoate |
| tartrate dehydrogenase/ decarboxylase/ 1.1.1.93/1.1.1.83/4.1.1.73 | oxaloglycolate + NADH <=> tartrate + NAD(+) | Oxaloglycolate to tartrate |
| 3-oxoacyl-[ACP] reductase/ 1.1.1.100 | 3-oxoacyl-[acyl-carrier-protein] + NADPH <=> (3R)-3-hydroxyacyl-[acyl-carrier-protein] + NADP(+) | Convert C4-C18 enoyl-ACP to corresponding C4-C18 Acyl-ACP |
| dTDP-4-dehydrorhamnose reductase/ 1.1.1.133 | dTDP-4-dehydro-beta-L-rhamnose + NADPH <=> dTDP-beta-L-rhamnose + NADP(+) | dTDP-4-dehydro-6-deoxy-D-glucose to dTDP-L-rhamnose, dTDP-6-deoxy-L-mannose to dTDP-4-dehydro-6-deoxy-L-mannose, UDP-4-keto-6-deoxy-D-glucose to UDP-L-rhamnose |
| 3-hydroxybutyryl-CoA dehydrogenase/ 1.1.1.157 | 3-acetoacetyl-CoA + NADPH <=> (S)-3-hydroxybutyryl-CoA + NADP(+) | 3-acetoacetyl-CoA to (S)-3-hydroxybutanoyl-CoA (coverted to (S)-3-hydroxybutyrate with either CoA transferease or an esterase) |

TABLE A-continued

List of terminal oxidases and fermentation products derived from the Brenda enzyme
database (https://with the extension brenda-enzymes.org/of the world wide web)

| Enzyme Name/EC number | Reaction | Potential fermentation products |
| --- | --- | --- |
| 2-dehydropantoate 2-reductase/ 1.1.1.169 | 2-dehydropantoate + NADPH + H+ <=> (R)-pantoate + NADP+ | (R)-4-dehydropantoate to (R)-pantoate, 2-oxoisovalerate to 2-hydroxyvalerate |
| 1,3-propanediol dehydrogenase/ 1.1.1.202 | 3-hydroxypropanal + NADH <=> Propane-1,3-diol + NAD(+) | 3-hydroxypropanal to Propane-1,3-diol |
| hydroxyphenylpyruvate reductase/ 1.1.1.237/1.1.1.222 | 3-(4-hydroxyphenyl)pyruvate + NADH <=> 3-(4-hydroxyphenyl)lactate + NAD(+) | Hydroxypyruvate to D-glycerate, 3,4-dihydroxyphenylpyruvate to 3-(3,4-dihydroxyphenyl)lactate, glyoxylate to glycolate |
| 1-deoxy-D-xylulose 5P reductoisomerase/ 1.1.1.267 | 1-deoxy-D-xylulose 5-phosphate + NADPH <=> 2-C-methyl-D-erythritol 4-phosphate + NADP(+) | 1-deoxy-D-xylulose 5-phosphate to 2-C-methyl-D-erythritol 4-phosphate |
| formaldehyde dehydrogenase, glutathione-dependent/ 1.1.1.284 | S-formylglutathione + NAD(P)H <=> S-(hydroxymethyl)glutathione + NAD(P)(+) | S-formylglutathione to S-formylglutathione |
| S-(hydroxymethyl)glutathione dehydrogenase/ 1.1.1.284/1.1.1.1 | S-formylglutathione + NAD(P) <=> S-(hydroxymethyl)glutathione + NAD(P)(+) | S-formylglutathione to formaldehyde and glutathione, S-nitrosoglutathione to S-amino-L-glutathione |
| erythronate-4-phosphate dehydrogenase/ 1.1.1.290 | (3R)-3-hydroxy-2-oxo-4-phosphonooxybutanoate + NADH <=> 4-phospho-D-erythronate + NAD(+) | 2-oxoglutarate to L-2-hydroxyglutarate |
| 3-hydroxypropionate dehydrogenase (NADP+)/ 1.1.1.298 | 3-oxopropanoate + NADPH <=> 3-hydroxypropanoate + NADP(+) | malonate semialdehyde to 3-hydroxypropanoate |
| 2,5-didehydrogluconate reductase/ 1.1.1.346 | 2,5-didehydro-D-gluconate + NADPH <=> 2-dehydro-L-gulonate | 2,5-didehydro-D-gluconate to 2-dehydro-L-gulonate, 2-dehydro-D-gluconate to D-gluconate, 2-dehydro-L-gulonate to L-idonate, ethyl 2-acetylpent-4-enoate to ethyl (2R)-2-[(1S)-1-hydroxyethyl] pent-4-enoate, ethyl 2-ethyl-3-oxobutanoate to ethyl (2R,3S)-2-ethyl-3-hydroxybutanoate, ethyl 2-methylacetoacetate to ethyl (2R)-methyl-(3S)-hydroxybutanoate, ethyl acetoacetate to ethyl (3S)-3-hydroxybutanoate |
| Malonate-semialdehyde dehydrogenase (acetylating)/ 1.2.1.18 | acetyl-CoA + CO(2) + NAD(P)H <=> 3-oxopropanoate + CoA + NAD(P)(+) | malonyl-CoA to malonate-semialdehyde (converted to 3-hydroxypropanoate by EC1.1.1.298) |
| Long-chain acyl-[acyl-carrier-protein] reductase/ 1.2.1.80 | a long-chain acyl-[acyl-carrier protein] + NAD(P)H <=> A long-chain aldehyde + an [acyl-carrier protein] + NAD(P)(+) | Convert C6-C18 Acyl-ACP to corresponding C6-C18 fatty aldehyde |
| 2-oxoglutarate + NH(3) + NADPH <=> L-glutamate + H(2)O + NADP(+)/ 1.4.1.4 | 2-oxoglutarate + NH3 + NADPH + H+ <=> L-glutamate + H2O + NADP+ | oxaloacetate to L-glutamate |
| aspartate dehydrogenase/ 1.4.1.21 | oxaloacetate + NH3 + NAD(P)H+ <=> L-aspartate + H2O + NAD(P)+ | oxaloacetate to L-aspartate |

TABLE B

PROTEIN AND NUCLEOTIDE SEQUENCES

*Cupriavidus necator* H16 NAD(P)⁺ oxidoreductases

| EC Number | Gene name | Protein Sequence | Nucleotide Sequence |
|---|---|---|---|
| 1.1.1.1 | H16_A0757 | SEQ ID NO: 1 | SEQ ID NO: 2 |
| | H16_A3330 | SEQ ID NO: 3 | SEQ ID NO: 4 |
| | H16_B0517 | SEQ ID NO: 5 | SEQ ID NO: 6 |
| | H16_B1433 | SEQ ID NO: 7 | SEQ ID NO: 8 |
| | H16_B1699 | SEQ ID NO: 9 | SEQ ID NO: 10 |
| | H16_B1745 | SEQ ID NO: 11 | SEQ ID NO: 12 |
| | H16_B1834 | SEQ ID NO: 13 | SEQ ID NO: 14 |
| | H16_B2470 | SEQ ID NO: 15 | SEQ ID NO: 16 |
| 1.1.1.21 | H16_A3186 | SEQ ID NO: 17 | SEQ ID NO: 18 |
| | H16_B2162 | SEQ ID NO: 19 | SEQ ID NO: 20 |
| 1.1.1.27 | H16_A0666 | SEQ ID NO: 21 | SEQ ID NO: 22 |
| 1.1.1.28 | H16_A1681 | SEQ ID NO: 23 | SEQ ID NO: 24 |
| 1.1.1.29 | H16_B0611 | SEQ ID NO: 25 | SEQ ID NO: 26 |
| 1.1.1.30 | H16_A1334 | SEQ ID NO: 27 | SEQ ID NO: 28 |
| | H16_A1814 | SEQ ID NO: 29 | SEQ ID NO: 30 |
| 1.1.1.31 | H16_A1239 | SEQ ID NO: 31 | SEQ ID NO: 32 |
| | H16_A3004 | SEQ ID NO: 33 | SEQ ID NO: 34 |
| | H16_B1190 | SEQ ID NO: 35 | SEQ ID NO: 36 |
| | H16_B1657 | SEQ ID NO: 37 | SEQ ID NO: 38 |
| | H16_B1750 | SEQ ID NO: 39 | SEQ ID NO: 40 |
| | H16_B2317 | SEQ ID NO: 41 | SEQ ID NO: 42 |
| 1.1.1.35 | H16_A0282 | SEQ ID NO: 43 | SEQ ID NO: 44 |
| | H16_A1102 | SEQ ID NO: 45 | SEQ ID NO: 46 |
| | H16_B0388 | SEQ ID NO: 47 | SEQ ID NO: 48 |
| | H16_B1652 | SEQ ID NO: 49 | SEQ ID NO: 50 |
| 1.1.1.36 | H16_A1439 | SEQ ID NO: 51 | SEQ ID NO: 52 |
| | H16_A2002 | SEQ ID NO: 53 | SEQ ID NO: 54 |
| | H16_A2171 | SEQ ID NO: 55 | SEQ ID NO: 56 |
| 1.1.1.37 | H16_A2634 | SEQ ID NO: 57 | SEQ ID NO: 58 |
| | H16_B0334 | SEQ ID NO: 59 | SEQ ID NO: 60 |
| 1.1.1.38 | H16_A3153 | SEQ ID NO: 61 | SEQ ID NO: 62 |
| 1.1.1.40 | H16_A1002 | SEQ ID NO: 63 | SEQ ID NO: 64 |
| 1.1.1.61 | H16_A1553 | SEQ ID NO: 65 | SEQ ID NO: 66 |
| 1.1.1.81 | H16_A2132 | SEQ ID NO: 67 | SEQ ID NO: 68 |
| | H16_A3601 | SEQ ID NO: 69 | SEQ ID NO: 70 |
| 1.1.1.100 | H16_A1287 | SEQ ID NO: 71 | SEQ ID NO: 72 |
| | H16_A2567 | SEQ ID NO: 73 | SEQ ID NO: 74 |
| | H16_B0361 | SEQ ID NO: 75 | SEQ ID NO: 76 |
| | H16_B0385 | SEQ ID NO: 77 | SEQ ID NO: 78 |
| | H16_B1075 | SEQ ID NO: 79 | SEQ ID NO: 80 |
| | H16_B1669 | SEQ ID NO: 81 | SEQ ID NO: 82 |
| | H16_B1904 | SEQ ID NO: 83 | SEQ ID NO: 84 |
| | H16_B2496 | SEQ ID NO: 85 | SEQ ID NO: 86 |
| | H16_B2510 | SEQ ID NO: 87 | SEQ ID NO: 88 |
| 1.1.1.169 | H16_A1715 | SEQ ID NO: 89 | SEQ ID NO: 90 |
| | H16_B1719 | SEQ ID NO: 91 | SEQ ID NO: 92 |
| | H16_B1769 | SEQ ID NO: 93 | SEQ ID NO: 94 |
| 1.1.1.284 | H16_B1195 | SEQ ID NO: 95 | SEQ ID NO: 96 |
| 1.4.1.4 | H16_B1945 | SEQ ID NO: 97 | SEQ ID NO: 98 |
| 2.3.1.8 | H16_B1631 | SEQ ID NO: 99 | SEQ ID NO: 100 |
| | H16_B1871 | SEQ ID NO: 101 | SEQ ID NO: 102 |

Other NAD(P)⁺ oxidoreductases

| EC Number | Organism/gene name/accession number | Protein Sequence | Nucleotide Sequence |
|---|---|---|---|
| 1.1.1.2 | *Escherichia coli* YqhD | SEQ ID NO: 103 | SEQ ID NO: 104 |
| 1.1.1.4 | *Saccharomyces cerevisiae* | SEQ ID NO: 105 | SEQ ID NO: 106 |
| 1.1.1.6 | *Escherichia coli* | SEQ ID NO: 107 | SEQ ID NO: 108 |
| 1.1.1.8 | *Homo sapiens* | SEQ ID NO: 109 | SEQ ID NO: 110 |
| 1.1.1.26 | *Saccharomyces cerevisiae* | SEQ ID NO: 111 | SEQ ID NO: 112 |
| 1.1.1.27 | *Homo sapiens* | SEQ ID NO: 113 | SEQ ID NO: 114 |
| 1.1.1.34 | *Saccharomyces cerevisiae* | SEQ ID NO: 115 | SEQ ID NO: 116 |
| 1.1.1.39 | *Monoraphidium neglectum* 25729514 | SEQ ID NO: 117 | SEQ ID NO: 118 |
| 1.1.1.45 | *Homo sapiens* NP_057058 | SEQ ID NO: 119 | SEQ ID NO: 120 |
| 1.1.1.67 | *Saccharomyces cerevisiae* (NP_010844) | SEQ ID NO: 121 | SEQ ID NO: 122 |
| 1.1.1.157 | *Escherichia coli* paaH | SEQ ID NO: 123 | SEQ ID NO: 124 |
| 1.1.1.202 | *Aquifex aeolicus* dhaT(NP_213782) | SEQ ID NO: 125 | SEQ ID NO: 126 |
| 1.1.1.298 | *Sulfolobus acidocaldarius* N8AGE71536 | SEQ ID NO: 127 | SEQ ID NO: 128 |
| 1.2.1.18 | *Homo sapiens* ALDH6A1 (NP_005580) | SEQ ID NO: 129 | SEQ ID NO: 130 |
| 1.2.1.80 | *Crinalium epipsammum* AFZ15198 | SEQ ID NO: 131 | SEQ ID NO: 132 |
| 1.4.1.21 | *Pseudopedobacter saltans* ADY50896 | SEQ ID NO: 133 | SEQ ID NO: 134 |

What is claimed is:

1. A method for increasing yield of 3-hydroxybutyrate in a *Cupriavidus* or *Ralstonia* organism, said method consisting of perturbing redox balance in said *Cupriavidus* or *Ralstonia* organism by knocking out at least a portion of its phaC1AB1 gene locus to diminish polyhydroxybutyrate synthesis as compared to an unperturbed wild-type *Cupriavidus* or *Ralstonia* organism and by modifying the organism to overexpress an endogenous or to express an exogenous nucleic acid sequence encoding a transhydrogenase enzyme selected from EC 1.6.1.1, EC 1.6.1.2, or EC 7.1.1.1 and/or deleting a dehydrogenase, culturing said *Cupriavidus* or *Ralstonia* organism under conditions to produce 3-hydroxybutyrate, and recovering 3-hydroxybutyrate from the organism, thereby increasing 3-hydroxybutyrate yield as compared to *Cupriavidus* or *Ralstonia* organism without the modifications.

2. The method of claim 1 wherein the organism overexpresses a native or expresses an exogenous transhydrogenase enzyme selected from EC 1.6.1.1, EC 1.6.1.2, or EC 7.1.1.1.

3. The method of claim 1 wherein phosphate, carbon, nitrogen, and/or oxygen are limited.

4. A method for producing 3-hydroxybutyrate in an organism, said method consisting of fermenting a non-naturally occurring organism selected from a species of *Cupriavidus* or *Ralstonia* with at least a portion of its phaC1AB1 gene locus knocked out to diminish polyhydroxybutyrate synthesis as compared to an unperturbed wild-type *Cupriavidus* or *Ralstonia* organism and modified to perturb redox balance by modifying the organism to overexpress an endogenous or to express an exogenous nucleic acid sequence encoding a transhydrogenase enzyme selected from EC 1.6.1.1, EC 1.6.1.2, or EC 7.1.1.1 and/or deleting a dehydrogenase enzyme with a carbon source; culturing said *Cupriavidus* or *Ralstonia* under conditions to produce 3-hydroxybutyrate and recovering 3-hydroxybutyrate from the organism.

5. The method of claim 4 wherein perturbing redox balance in the organism increases 3-hydroxybutyrate yield in the organism as compared to an organism without the modifications.

6. The method of claim 4 wherein the nonnaturally occurring organism overexpresses a native or expresses an exogenous transhydrogenase enzyme_selected from EC 1.6.1.1, EC 1.6.1.2, or EC 7.1.1.1.

7. The method of claim 4 wherein the carbon source is derived from a biological or nonbiological feedstock.

8. The method of claim 7 wherein feedstock fed to the fermentation process comprises a gaseous or liquid stream.

* * * * *

SEQUENCE LISTING

<160> NUMBER OF SEQ ID NOS: 134

<210> SEQ ID NO 1
<211> LENGTH: 366
<212> TYPE: PRT
<213> ORGANISM: C. necator

<400> SEQUENCE: 1

Met Thr Ala Met Met Lys Ala Ala Val Phe Val Glu Pro Gly Arg Ile
1               5                   10                  15

Glu Leu Ala Asp Lys Pro Ile Pro Asp Ile Gly Pro Asn Asp Ala Leu
            20                  25                  30

Val Arg Ile Thr Thr Thr Thr Ile Cys Gly Thr Asp Val His Ile Leu
        35                  40                  45

Lys Gly Glu Tyr Pro Val Ala Lys Gly Leu Thr Val Gly His Glu Pro
    50                  55                  60

Val Gly Ile Ile Glu Lys Leu Gly Ser Ala Val Thr Gly Tyr Arg Glu
65                  70                  75                  80

Gly Gln Arg Val Ile Ala Gly Ile Cys Pro Asn Phe Asn Ser Tyr
                85                  90                  95

Ala Ala Gln Asp Gly Val Ala Ser Gln Asp Gly Ser Tyr Leu Met Ala
            100                 105                 110

Ser Gly Gln Cys Gly Cys His Gly Tyr Lys Ala Thr Ala Gly Trp Arg
        115                 120                 125

Phe Gly Asn Met Ile Asp Gly Thr Gln Ala Glu Tyr Val Leu Val Pro
130                 135                 140

Asp Ala Gln Ala Asn Leu Thr Pro Ile Pro Asp Gly Leu Thr Asp Glu
145                 150                 155                 160

Gln Val Leu Met Cys Pro Asp Ile Met Ser Thr Gly Phe Lys Gly Ala
                165                 170                 175

Glu Asn Ala Asn Ile Arg Ile Gly Asp Thr Val Ala Val Phe Ala Gln
            180                 185                 190

Gly Pro Ile Gly Leu Cys Ala Thr Ala Gly Ala Arg Leu Cys Gly Ala
        195                 200                 205

Thr Thr Ile Ile Ala Ile Asp Gly Asn Asp His Arg Leu Glu Ile Ala
210                 215                 220

Arg Lys Met Gly Ala Asp Val Val Leu Asn Phe Arg Asn Cys Asp Val
225                 230                 235                 240

Val Asp Glu Val Met Lys Leu Thr Gly Gly Arg Gly Val Asp Ala Ser
                245                 250                 255

Ile Glu Ala Leu Gly Thr Gln Ala Thr Phe Glu Gln Ser Leu Arg Val
            260                 265                 270

Leu Lys Pro Gly Gly Thr Leu Ser Ser Leu Gly Val Tyr Ser Ser Asp
        275                 280                 285

Leu Thr Ile Pro Leu Ser Ala Phe Ala Ala Gly Leu Gly Asp His Lys
290                 295                 300

Ile Asn Thr Ala Leu Cys Pro Gly Gly Lys Glu Arg Met Arg Arg Leu
305                 310                 315                 320

Ile Asn Val Ile Glu Ser Gly Arg Val Asp Leu Gly Ala Leu Val Thr
                325                 330                 335

His Gln Tyr Arg Leu Asp Asp Ile Val Ala Ala Tyr Asp Leu Phe Ala
            340                 345                 350

Asn Gln Arg Asp Gly Val Leu Lys Ile Ala Ile Lys Pro His
        355                 360                 365

<210> SEQ ID NO 2
<211> LENGTH: 1101
<212> TYPE: DNA
<213> ORGANISM: C. necator

<400> SEQUENCE: 2
atgaccgcaa tgatgaaagc cgccgttttt gtcgagcctg gccggatcga actggcagac    60
aagccgatcc cggatatcgg ccccaacgat gccctggtgc gtatcaccac caccaccatc   120
tgcggcaccg acgtgcacat cctcaagggt gagtacccgg tggcgaaggg cctgaccgtg   180
ggccatgagc ccgtcggcat cattgaaaag ctcggcagcg cggtgacggg ataccgcgaa   240
ggccagcgcg tgatcgccgg cgcaatctgc ccaacttca actcctacgc ggcgcaggac   300
ggcgtggcct cgcaggatgg cagctacctg atgccagcg ccagtgcgg ctgccacggc   360 tacaaggcga ccgcgggctg gcgcttcggc aacatgatcg acggtaccca ggcggaatac   420

-continued

```
gtgctggtgc ccgacgccca ggccaacctg acgccaatcc ccgatggcct caccgacgag    480
caggtgctga tgtgccccga catcatgtcc accggcttca agggcgcgga aaacgccaat    540
atccgcatcg gcgacaccgt ggccgtgttc gcgcagggcc cgatcgggct atgcgcgacc    600
gccggcgcgc ggctgtgcgg cgccaccacc atcatcgcca tcgacggcaa cgaccaccgg    660
ctggagatcg cgcgcaagat gggcgcggac gtggtcctga acttccgcaa ctgcgacgtg    720
gtggacgagg tcatgaagct gaccggcggg cgcggcgtgg atgcctcgat cgaggcgctg    780
ggcacgcagg caaccttcga gcagtcgctg cgcgtgctca gcccggcgg cacgctgtcc    840
agcctggggg tctattcaag cgacctgacc attccgctgt cggctttcgc cgcggggctg    900
ggcgaccaca agatcaacac cgcgctgtgc cccgcggca aggaacgcat gcggcggctg    960
atcaatgtga tcgagtcggg gcgggtcgac ctgggagcgc tggtgacgca ccagtacagg   1020
ctggacgaca tcgtcgcggc ctacgacctg ttcgccaacc agcgcgacgg cgtgctgaag   1080
atcgccatca agccgcactg a                                             1101
```

<210> SEQ ID NO 3
<211> LENGTH: 334
<212> TYPE: PRT
<213> ORGANISM: C. necator

<400> SEQUENCE: 3

```
Met Thr Phe Gln Ala Leu Leu Leu Thr Gln Ala Asp Gly Ala Thr Gln
1               5                   10                  15

Ala Ser Ile Ala Thr Leu Asp Asp Ala Gln Leu Pro Ala Asp Gly Asp
            20                  25                  30

Val Leu Val Ala Val Asp Tyr Ser Thr Ile Asn Phe Lys Asp Gly Leu
        35                  40                  45

Ala Ile Thr Gly Arg Ser Pro Val Val Arg Lys Trp Pro Met Val Ala
    50                  55                  60

Gly Ile Asp Gly Ala Gly Thr Val Leu Glu Ser Ala His Pro Arg Trp
65                  70                  75                  80

Lys Ala Gly Asp Lys Val Val Leu Asn Gly Tyr Gly Val Gly Glu Thr
                85                  90                  95

His Trp Gly Cys Leu Ala Gln Arg Ala Arg Leu Lys Gly Asp Trp Leu
            100                 105                 110

Val Arg Leu Pro Asp Ala Phe Thr Thr Arg Gln Ala Met Ala Ile Gly
        115                 120                 125

Thr Ala Gly Tyr Thr Ala Met Leu Ser Val Leu Ala Leu Glu Arg Gly
    130                 135                 140

Gly Val Asp Gly Pro Val Arg Pro Gly Asp Gly Glu Val Leu Val Thr
145                 150                 155                 160

Gly Ala Ser Gly Gly Val Gly Thr Val Ala Ile Ser Leu Leu Ser Lys
                165                 170                 175

Leu Gly Tyr Lys Val Val Ala Ser Thr Gly Lys Thr Arg Glu Ala Asp
            180                 185                 190

Phe Leu Lys Ala Leu Gly Ala Asp Asp Val Ile Asp Arg Ala Glu Leu
        195                 200                 205

Gly Val Pro Gly Lys Pro Leu Gln Lys Glu Arg Trp Ala Ala Val
    210                 215                 220

Asp Ser Val Gly Ser His Thr Leu Val Asn Ala Cys Ala Gln Val Arg
225                 230                 235                 240

Tyr Gly Gly Val Val Thr Ala Cys Gly Leu Ala Gln Gly Leu Asp Phe
                245                 250                 255
```

Pro Gly Ser Val Ala Pro Phe Ile Leu Arg Gly Ile Thr Leu His Gly
            260                 265                 270

Ile Asp Ser Val Met Ala Ala Met Pro Leu Arg Glu Gln Ala Trp Gln
        275                 280                 285

Arg Leu Ala Gly Asp Leu Glu Pro Asp Arg Leu Asn Ala Leu Thr Arg
    290                 295                 300

Glu Ile Gly Leu Gly Asp Ala Ile Glu Ala Gly Arg Lys Ile Met Glu
305                 310                 315                 320

Gly Gly Met Arg Gly Arg Val Val Asp Val Asn Arg Gly
                325                 330

<210> SEQ ID NO 4
<211> LENGTH: 1005
<212> TYPE: DNA
<213> ORGANISM: C. necator

<400> SEQUENCE: 4

```
atgaccttcc aggcattgct gctgacccag gccgacggcg ccacccaggc cagtatcgcc      60
acgctcgacg acgcgcagct gcccgccgac ggcgacgtgc tggttgccgt cgactactcc     120
accatcaact tcaaggacgg gctggcgatc acgggccgct cgccggtggt gcgcaagtgg     180
ccgatggtgg cgggcatcga cggcgccggc acggtgctgg aatccgcgca cccgcgctgg     240
aaggcaggcg acaaggtagt gctcaacggc tacggcgtgg cgagacgca ttggggctgc     300
cttgcgcagc gcgcgcgcct gaagggcgac tggctggtgc cctgcccga cgccttcacc     360
acgcgccagg ccatggcgat cggcaccgcg ggctataccg cgatgctgtc ggtgctggcg     420
ctggagcgcg cggcgtcga cggcccggtg cgccccggcg atggcgaggt gctggtgacc     480
ggcgcctccg gtggggtggg gacggtggcg atctcgctgc tgagcaagct tggctacaag     540
gtggtggcct cgaccggcaa gacccgggag gcggatttcc tgaaggcgct gggcgccgat     600
gacgtgatcg accgtgctga gctgggcgta cccggcaagc gctgcaaaa ggagcgctgg     660
gccgcggtgg tcgactcggt cggctcgcac acgctggtca atgcctgcgc ccaggtgcgc     720
tacgcgggcg tggtgacggc gtgcgggctg gcgcagggcc ttgacttccc ggggtcggtg     780
gcgccgttca tcctgcgcgg catcaccttg cacggcatcg acagtgtgat ggcggcgatg     840
ccgctgcgcg agcaggcctg gcagcgcctg gccggcgacc tggagccgga ccggctcaat     900
gcgctgacgc gcgagatcgg cctgggcgac gcgatcgagg cgggccgcaa gatcatggaa     960
ggcggcatgc gcgggcgcgt ggtggtggat gtgaatcgcg gctga                    1005
```

<210> SEQ ID NO 5
<211> LENGTH: 357
<212> TYPE: PRT
<213> ORGANISM: C. necator

<400> SEQUENCE: 5

Met Ala Leu Ala Gly Asn Gln Tyr Ser Gly Phe Thr Val Phe Asn Arg
1               5                   10                  15

Pro Glu Tyr Pro Met Thr Ser Ser Met Gln Arg Trp Gln Leu Ser Ala
            20                  25                  30

Phe Gly Arg Asn Asn Leu Arg Arg Val Asp Ala Pro Ile Pro Val Pro
        35                  40                  45

Gly Pro Gly Glu Val Leu Val Arg Val His Ala Val Ala Leu Asn Tyr
    50                  55                  60

Arg Asp Leu Leu Ile Ile Gln Asp Gly Met Gly Met Pro Val Gln Pro

```
                65                  70                  75                  80
        Pro Leu Val Leu Gly Ser Asp Met Arg Gly Glu Val Val Ala Ser Gly
                        85                  90                  95
        Asp Gly Val Ala Asp Phe Ala Pro Gly Asp Ala Val Ile Ser Thr Phe
                        100                 105                 110
        Phe Thr Gly Trp Leu Asp Gly Val Gln Pro His Arg Ser Met Pro Leu
                        115                 120                 125
        Gly Val Pro Gly Pro Gly Met Leu Ser Glu Tyr Val Val Leu Ala Glu
                        130                 135                 140
        Asp Ser Leu Val Ser Ala Pro Arg Thr Leu Asp Ala Ala Gln Ala Ser
        145                 150                 155                 160
        Thr Leu Thr Cys Ala Gly Leu Thr Ala Trp Gln Ala Leu Ala Glu Ala
                        165                 170                 175
        Thr Val Thr Arg Pro Gly Asp Thr Val Val Ile Gly Thr Gly Gly
                        180                 185                 190
        Val Ala Leu Phe Ala Val Gln Ile Ala Arg Ala Gln Gly Ala Arg Val
                        195                 200                 205
        Ile Val Val Ser Gly Ser Asp Asp Lys Leu Ala Arg Val Gln Glu Leu
                        210                 215                 220
        Gly Ala Ala His Gly Val His Arg Gly Arg Thr Ala Asp Trp Pro Ala
        225                 230                 235                 240
        Ala Val Arg Glu Leu Thr Gly Gly Arg Gly Ala Asp His Val Leu Glu
                        245                 250                 255
        Leu Ala Gly Gly Asp Asn Phe Gly Arg Ser Leu Ala Ala Leu Ala Gln
                        260                 265                 270
        Gly Gly Arg Ile Ser Val Ile Gly Asn Leu Gln Gly Asp Glu Leu Arg
                        275                 280                 285
        Ala Ser Val Tyr Pro Val Leu His Gly Arg Val Thr Val Gln Gly Ile
                        290                 295                 300
        Gly Val Ser His Arg Arg Ala Leu Gln Asp Leu Val Arg Ala Val Asp
        305                 310                 315                 320
        Trp Leu Gly Leu Arg Pro Val Ile Glu Ser Glu Tyr Gly Phe Gly Asp
                        325                 330                 335
        Leu Pro Ala Ala Leu Asp His Leu Glu Arg Gly Ala Phe Gly Lys Val
                        340                 345                 350
        Val Val Arg Leu Arg
                        355

<210> SEQ ID NO 6
<211> LENGTH: 1074
<212> TYPE: DNA
<213> ORGANISM: C. necator

<400> SEQUENCE: 6
atggcgctgg cagggaatca gtatagtggg ttcaccgttt tcaacagacc ggagtacccc      60
atgacttcct ccatgcagcg ctggcaactg tccgctttcg gccgcaacaa cctgcgtcgc     120
gtcgacgcgc ccattcccgt gcccggtccc ggcgaggtgc tggtgcgggt ccatgccgtg     180
gccttgaact accgcgacct gctgatcatc aggacggca tgggcatgcc cgtgcagccg     240
ccgctggttc tcgggtcgga catgcgcggc gaggtggtgg cgagtggcga tggtgtagcc     300
gactttgccc tggcgacgc cgtgatcagc accttcttca ccggctggct cgatggcgtg     360
cagccgcacc gcagcatgcc gctgggcgtg ccgggtcccg gcatgctgtc ggagtacgtg     420
gtattggcag aggactcgct ggtgtcggcc ccgcgcacgc tggacgccgc gcaggccagc     480
```

```
acgctgacct gcgccggcct gacggcctgg caagccctgg ctgaagcgac ggtgacgcgg    540
cccggcgaca ccgtcgtggt gatcggcacc ggcggagtgg ccctgtttgc ggtgcagatc    600
gcccgcgcac agggggcgcg cgtgatcgtg gtgtcaggca gcgacgacaa gctggcgcgc    660
gtgcaggagc tgggcgcggc gcatggcgtc atcgcggcc gcaccgctga ctggccggct    720
gccgtgcgcg agctgaccgg aggccgcggt gccgaccatg tgctggaact ggctggcgga    780
gacaacttcg gccggtcgct tgccgcgctg gcgcagggcg ccggatctc ggtgatcggc    840 aaccttcagg gggatgagct gcgcgccagc gtctatccgg tgctgcatgg ccgcgtgacc    900
gtgcagggga tcggcgtgtc gcaccggcgc gcgctgcagg acctggtgcg tgccgtggac    960
tggttggggc tgcgcccggt gatcgagagc gagtacgggt tcggggactt gcccgcggcg   1020
ctcgaccacc tggaacgcgg ggccttcggc aaggtggtgg tgcggctgcg ctga          1074
```

<210> SEQ ID NO 7
<211> LENGTH: 337
<212> TYPE: PRT
<213> ORGANISM: C. necator

<400> SEQUENCE: 7

```
Met Pro His Gln Thr Met Arg Ala Met Val Phe Glu Gly Ala Gly Leu
1               5                   10                  15

Pro Leu Arg Leu His His Leu Pro Val Ala Glu Pro Gly Pro Gly Glu
            20                  25                  30

Leu Arg Ile Ala Val Gly Ala Cys Gly Val Cys Arg Thr Asp Leu His
        35                  40                  45

Ile Ala Asp Gly Asp Leu Arg His Pro Lys Pro Val Leu Ile Pro Gly
    50                  55                  60

His Glu Ile Val Gly Gln Val Asp Ser Cys Gly Ala Gly Val Thr Val
65                  70                  75                  80

Phe Lys Pro Gly Asp Arg Val Gly Val Pro Trp Leu Gly His Ser Cys
                85                  90                  95

Gly His Cys Arg Tyr Cys Leu Arg His His Glu Asn Leu Cys Asp Ala
            100                 105                 110

Pro Leu Phe Thr Gly Tyr Thr Arg Asp Gly Gly Tyr Ala Glu Tyr Val
        115                 120                 125

Val Ala Asp Ser Gly Tyr Cys Phe Arg Ile Pro Pro Gly Tyr Asp Asp
    130                 135                 140

Glu His Ala Ala Pro Leu Leu Cys Ala Gly Leu Ile Gly Tyr Arg Thr
145                 150                 155                 160

Leu Arg Met Ala Gly Ala Ala Ser His Ala Gln Arg Val Gly Ile Tyr
                165                 170                 175

Gly Phe Gly Ala Ala His Leu Val Thr Gln Ile Ala Val Ala Gln
            180                 185                 190

Gly Arg Glu Val Tyr Ala Phe Thr Arg Thr Gly Asp Ala Gly Ala Gln
        195                 200                 205

Gln Leu Ala Tyr Gln Ser Gly Ala Cys Trp Ala Gly Ser Ser Glu Leu
    210                 215                 220

Glu Ser Pro Val Pro Leu Asp Ala Ala Leu Ile Phe Ala Pro Val Gly
225                 230                 235                 240

Ala Leu Val Pro Lys Ala Leu Arg Ala Val Asp Lys Gly Gly Ile Val
                245                 250                 255

Val Cys Gly Gly Ile His Met Ser Asp Ile Pro Ser Met Pro Tyr Gln
            260                 265                 270
```

```
Leu Leu Trp Glu Glu Arg Arg Leu Cys Ser Val Ala Asn Leu Thr Arg
        275                 280                 285

Ala Asp Gly Ile Ala Leu Met Asp Ile Ala Ala Arg Thr Pro Leu His
    290                 295                 300

Thr His Thr Thr Ala Tyr Pro Leu Glu Gln Ala Asn Glu Ala Leu Ala
305                 310                 315                 320

Asp Leu Arg Glu Gly Arg Leu Thr Gly Ala Ala Val Leu Lys Val Arg
                325                 330                 335

Gln
```

<210> SEQ ID NO 8
<211> LENGTH: 1014
<212> TYPE: DNA
<213> ORGANISM: C. necator

<400> SEQUENCE: 8

```
atgcccacc aaaccatgcg tgcaatggtc ttcgagggcg caggcctgcc gctgcgcctc      60
caccacttgc cggttgccga accggggccc ggcgaacttc gcattgccgt gggagcttgc    120
ggggtgtgcc ggaccgacct gcatatcgcc gacggcgacc tgcgccatcc caagccggtg    180
ctcatcccgg acatgaaat cgtcggacag gtggattcgt gcggcgccgg tgtcaccgtc    240
ttcaagccgg ggaccgcgt cggtgtgccc tggctcggac atagctgtgg ccattgtcgc    300
tactgcctgc gtcatcacga gaatctttgc gacgcaccgc tgttcactgg ctatacccgc    360
gatggcggct atgcggagta cgttgttgcc gacagcggct attgcttccg gattccgccc    420
ggctacgatg acgaacacgc cgcgccacta ctctgcgcgg gcctgatcgg ctaccggacg    480
ctgcgcatgg cgggcgcagc cagccatgcg cagcgcgtcg gcatctacgg cttcggcgcc    540
gccgcccacc tggtgacgca gatcgcggtg gcgcaaggcc gcgaagtcta cgccttcacc    600
cgcacgggcg acgcaggcgc ccagcaactc gcctaccaat ccggtgcgtg ctgggccggc    660
tcgagcgagc tcgagtcgcc cgtgccgctg gacgccgcgc tgattttcgc cccggtgggc    720
gcgctggtgc ccaaggcgct cgcgccgtg acaagggtg catcgtggt ctgtggcgga    780
attcatatga gcgatatccc aagcatgcct taccagctgc tttgggaaga aaggcgcctg    840
tgttccgtag ccaacctcac gcgtgccgac ggcatcgcgc tgatggatat cgccgcccgg    900
acgccgctgc atacgcacac caccgcgtat ccgctggagc aggccaacga agcactggcc    960
gacctgcgcg agggccggct taccggcgcc gccgtcctga agtccgtca atag          1014
```

<210> SEQ ID NO 9
<211> LENGTH: 338
<212> TYPE: PRT
<213> ORGANISM: C. necator

<400> SEQUENCE: 9

```
Met Lys Ala Ile Gly Leu Thr Gln Tyr Leu Pro Ile Ser Asp Pro Arg
1                5                  10                  15

Ser Leu Gln Asp Val Glu Ile Asp Met Pro Ser Pro Gly Gly Arg Asp
                20                  25                  30

Leu Leu Val Lys Val Glu Ala Val Ser Val Asn Pro Val Asp Thr Lys
            35                  40                  45

Val Arg Ala Pro Lys Ala Gln Val Glu Pro Ala Pro Arg Val Leu Gly
        50                  55                  60

Trp Asp Ala Ala Gly Thr Val Ala Ala Val Gly Pro Glu Val Thr Leu
65                  70                  75                  80
```

```
Phe Lys Val Gly Asp Pro Val Tyr Tyr Ala Gly Ser Ile Thr Arg Ser
                 85                  90                  95
Gly Ser Asn Ala Glu Phe His Leu Val Asp Glu Arg Ile Val Gly His
            100                 105                 110
Lys Pro Ala Ser Leu Asp Phe Ala Asn Ala Ala Leu Pro Leu Thr
        115                 120                 125
Ala Ile Thr Ala Trp Glu Ala Leu Phe Asp Arg Leu Gly Ile Ser Pro
130                 135                 140
Asn Gly Asp His Ala Gly Arg Pro Val Leu Ile Ile Gly Gly Ala Gly
145                 150                 155                 160
Gly Val Gly Ser Ile Gly Ile Gln Leu Ala Lys Val Leu Ala Gly Leu
                165                 170                 175
Thr Val Ile Ala Thr Ala Ser Arg Pro Glu Ser Gln Glu Trp Cys Arg
            180                 185                 190
Arg Leu Gly Ala Asp His Thr Val Asp His Arg Gly Asp Leu Pro Ala
        195                 200                 205
Gln Leu Lys Ala Leu Gly Phe Ala Glu Val Asp Tyr Ile Leu Cys Phe
    210                 215                 220
Asn Asp Ile Asp Gly His Phe Pro Ala Met Ala Glu Val Val Ala Pro
225                 230                 235                 240
Gln Gly Lys Ile Cys Thr Ile Val Ala Asn Thr Arg Pro Leu Pro Val
                245                 250                 255
Glu Leu Leu Lys Asn Lys Ser Ala Thr Phe Val Trp Glu Phe Met Phe
            260                 265                 270
Thr Arg Ala Met Tyr Ser Thr Pro Asp Met Val Ala Gln His Arg Leu
        275                 280                 285
Leu Asn Glu Val Thr Arg Leu Val Asp Ala Gly Arg Leu Gln Thr Thr
    290                 295                 300
Leu Gly Glu Asn Leu Gly Arg Ile Asn Ala Glu Asn Leu Arg Arg Ala
305                 310                 315                 320
His Ala Met Leu Glu Gly Gly Arg Thr Ile Gly Lys Leu Val Leu Glu
                325                 330                 335
Gly Phe

<210> SEQ ID NO 10
<211> LENGTH: 1017
<212> TYPE: DNA
<213> ORGANISM: C. necator

<400> SEQUENCE: 10
atgaaagcca tcggcctgac ccagtacctg cccatctccg accgcgttc gctgcaagac        60
gtggagatcg acatgcccag ccccggcggc cgcgacctgc tggtgaaggt tgaggccgtc      120
tcggtcaacc cggtcgacac caaggtgcgc gcgcccaagg cgcaggtaga gcccgcgccg      180
cgcgtgctgg gctgggacgc ggccggcacg gtggccgccg tggggccgga ggtgaccctg      240
ttcaaggtcg gcgacccggt ctactacgcg ggcagcatca ctcggtccgg ctccaacgcc      300
gagttccacc tggtcgatga gcgcatcgtc ggccacaagc ctgcctcgct ggatttcgcc      360
aacgcggcgc gcctgccgct gacggcgatc accgcctggg aggctctgtt cgaccggctg      420
ggcatttcgc caatgggga tcacgccggg cgcccggtgc tgatcatcgg cggcgcgggc       480
ggcgtgggct cgatcggcat ccagctggcc aaggtgctgg ccgggctgac cgtgatcgcc      540
accgcgtcgc ggcccgagtc gcaggaatgg tgccgccgcc ttggcgccga ccatacggtt      600
```

```
gaccatcgtg gcgatctgcc ggcgcagctg aaggcgctgg gatttgccga ggtcgactac    660
atcctctgct tcaacgacat cgacgggcat ttcccggcga tggctgaagt ggtcgccccg    720
cagggcaaga tctgcacgat cgtcgcaaat acgcggccgt tgccggtgga attgctcaag    780
aacaagagcg ccaccttcgt ctgggaattc atgttcacgc gcgccatgta cagcacgccc    840
gacatggtcg cgcagcatcg tctgcttaac gaggtcacgc ggctggtcga tgccgggcgc    900
ctgcagacca cgctgggcga aacctgggg cgcatcaatg cggagaacct gcggcgcgcg    960
cacgccatgc tggaaggcgg gcgcactatc ggcaagctgg tgctggaagg gttctga     1017
```

<210> SEQ ID NO 11
<211> LENGTH: 368
<212> TYPE: PRT
<213> ORGANISM: C. necator

<400> SEQUENCE: 11

```
Met Arg Thr Lys Val Gln Ala Ala Val Met Val Lys Ala Arg Glu Leu
 1               5                  10                  15

Gln Val Glu Leu Leu Asp Leu Asp Glu Pro His Asp Asn Glu Val Met
            20                  25                  30

Val Glu Ile Ala Ala Thr Gly Val Cys His Ser Asp Leu Ser Val Tyr
        35                  40                  45

Gln Ala Val Leu Pro Thr Pro Leu Pro Val Ile Leu Gly His Glu Ser
    50                  55                  60

Ala Gly Val Val Gly Leu Gly Ser Gln Val Ser Gly Leu Ala Leu
65                  70                  75                  80

Gly Asp Arg Val Val Leu Ser Leu Leu Ala Gln Cys Gly Asn Cys Phe
                85                  90                  95

Tyr Cys Asn His Gly Gln Pro Val Leu Cys Glu Ser Gly Gln Pro Ser
            100                 105                 110

Met Leu Gln Gly Thr Met Ala Asp Gly Thr Thr Arg Phe Thr Trp Asn
        115                 120                 125

Gly Ala Pro Val Phe Gln Met Ala Gly Leu Gly Thr Leu Ala Gln Arg
    130                 135                 140

Val Val Val Pro Ala Thr Ser Val Pro Ile Pro Asp Ser Leu Pro
145                 150                 155                 160

Leu Glu Gln Ala Ala Leu Leu Gly Cys Gly Val Met Thr Gly Trp Gly
                165                 170                 175

Ala Ala Val Asn Thr Ala Arg Val Glu Val Gly Glu Ala Val Ala Ile
            180                 185                 190

Leu Gly Cys Gly Gly Val Gly Leu His Ala Ile Gln Gly Ala Arg Thr
        195                 200                 205

Ser Gly Ala Ser Met Ile Ile Ala Ile Asp Pro Arg Thr Asp Arg Leu
    210                 215                 220

Glu Leu Ala Arg Ser Leu Gly Ala Thr His Gln Leu Gln Pro Gly Thr
225                 230                 235                 240

Gly Leu Val Glu Lys Val Arg Ala Leu Thr Gly Arg Gly Val Glu
                245                 250                 255

Val Ala Leu Glu Val Ala Gly Arg Gln Gln Ser Ile Asp Asp Ala Ile
            260                 265                 270

Arg Met Thr Arg Arg Gly Gly Arg Ala Val Ile Val Ser Ala Pro Gly
        275                 280                 285

Lys Asp Val Val Asn Ile Ser Ala Phe Gly Gly Leu Val Leu Thr
    290                 295                 300
```

```
Glu Lys Thr Ile Arg Gly Ser Leu Tyr Gly Ser Ala His Val Arg Arg
305                 310                 315                 320

Asp Ile Ala Arg Leu Val Asp Leu His Gly Ala Gly Lys Leu Gln Leu
            325                 330                 335

Asp Asn Leu Ala Ser Val Ile Tyr Ser Leu Asp Gln Val Asn Glu Ala
            340                 345                 350

Met Ala His Cys Ala Thr Glu Ala Gly Gly Arg Ala Ile Val Arg Pro
            355                 360                 365
```

<210> SEQ ID NO 12
<211> LENGTH: 1107
<212> TYPE: DNA
<213> ORGANISM: C. necator

<400> SEQUENCE: 12

```
atgcgaacaa aggtgcaggc tgccgtgatg gtgaaggccc gcgaactcca ggtggagttg      60
ctggacctgg atgaaccgca cgataacgaa gtgatggtgg agattgccgc gacaggcgtg     120
tgccattcgg aacctgtcggt gtaccaagca gtgctgccga caccgctgcc agtgatactg     180
gggcacgaaa gcgcgggtgt cgtcgtgggc ctgggatctc aggtgtcggg cctggcgctc     240
ggcgaccgcg tggtgctcag cctgctggcc cagtgtggca actgcttcta ttgcaaccac     300
ggccagccgg tgttgtgcga gtcggggcag ccatcgatgc tgcagggcac catggcagat     360
ggcacgacgc gatttacatg gaatggcgca ccggtgttcc agatgccgg tctgggaacg     420
cttgcacagc gggttgtcgt accggctaca tcggtcgttc ccatcccgga ctctctgccg     480
ctggagcagg cggcattgct cggctgcggg gtcatgacgg gctggggcgc agcggtcaac     540
acggcccggg tcgaagtcgg cgaagcggtg gccatcctcg gttgcggcgg tgtcggcctg     600
catgcgatcc agggcgcgcg taccagcggt gccagcatga tcatcgcaat cgatccccgt     660
acggatcgcc tggagctggc gcggtcgctg gtgcgacccc atcagctgca gcccgggacc     720
ggactggtgg aaaaggtacg cgcgctcacc ggtgggcgcg cgtcgaggt cgcgctggaa     780
gtcgccgggc gccagcaatc catcgatgac gccatacgga tgacccgacg aggcggccgt     840
gccgtcattg tcagtgcgcc gggtaaggac gtggtggtga acatctccgc gttcggcggg     900
ctggtgctca cagagaagac catccgcggc tccctctatg gttccgctca cgtgcgccgc     960
gacattgcgc ggctggtaga cctccacggg gcgggcaagc tgcaactgga caacctcgcg    1020
tcagtcatct attcgctgga ccaggtcaat gaggccatgg cgcattgcgc cacggaggcg    1080
ggcggtcggg ccatcgtgcg cccatga                                        1107
```

<210> SEQ ID NO 13
<211> LENGTH: 250
<212> TYPE: PRT
<213> ORGANISM: C. necator

<400> SEQUENCE: 13

```
Met Ser Glu Leu Ser Asp Gln Val Ala Ile Val Thr Gly Ala Gly Ser
1               5                   10                  15

Gly Phe Gly Ala Ala Ile Ala Arg Ala Phe Ile Gln Ala Gly Ala Lys
            20                  25                  30

Val Val Leu Ala Asp Ile Asp Arg Asp Ala Val Gln Arg Leu Ala Asp
        35                  40                  45

Glu Leu Gly Pro Asn Ala Ser Ala Ala Pro Cys Asp Val Thr Ser Pro
    50                  55                  60

Ala Gln Ile Asn Ala Ala Val Gln His Cys Cys Asp His Phe Gly Glu
```

```
Pro Asp Val Val Asn Asn Ala Gly Thr Thr His Arg Asn Gln Ser
             85                  90                  95

Met Leu Glu Val Asp Glu Ala Val Phe Asp Arg Val Phe Ala Val Asn
            100                 105                 110

Val Lys Ser Ile Tyr His Met Ala Arg Ala Val Val Pro Leu Met Lys
        115                 120                 125

Gln Arg Gly Lys Gly Val Ile Leu Asn Ile Gly Ser Val Gly Ser His
130                 135                 140

Arg Pro Arg Pro Gly Leu Thr Trp Tyr Asn Ser Ser Lys Gly Ala Val
145                 150                 155                 160

Ser Val Met Ser Lys Ser Met Ala Val Glu Leu Ala Ala His Gly Ile
                165                 170                 175

Arg Val Asn Leu Ile Ser Pro Val Met Ala Ala Thr Gly Leu Leu Gln
            180                 185                 190

Asp Phe Met Gly Val Ala Asp Thr Ala Glu Asn Arg Ala Arg Phe Val
        195                 200                 205

Ala Thr Ile Pro Leu Gly Arg Met Cys Glu Pro Ala Asp Val Ala Asn
210                 215                 220

Ala Ala Val Phe Leu Ala Ser Pro Gly Ala Arg Phe Leu Thr Gly Ile
225                 230                 235                 240

Asp Met Pro Val Asp Gly Gly Arg Ala Ile
                245                 250
```

<210> SEQ ID NO 14
<211> LENGTH: 753
<212> TYPE: DNA
<213> ORGANISM: C. necator

<400> SEQUENCE: 14

```
atgtcggagc tatcagacca ggttgccatt gtcacgggcg caggcagtgg ctttggcgcc    60
gcgattgcgc gggccttat ccaggcggga gcgaaggtcg tgctggccga tatcgatcgc    120
gatgccgtgc agagactggc ggacgagttg gggccgaatg ccagtgcggc tccgtgcgac    180
gtcaccagcc cggcgcagat caacgccgcg gtgcagcact gctgcgacca tttcggcgag    240
ccggacgtgg tcgtcaacaa tgccggcacc acgcatcgga atcagtcgat gctggaagtc    300
gacgaagcgg tcttcgaccg cgtcttcgcc gtcaacgtca agtcgatcta ccacatggca    360
cgcgcggtcg tgccgctgat gaagcagcgc ggcaaaggcg tgatcctcaa tatcggctcg    420
gtcggcagcc accggccgcg cccggggctg acctggtaca acagctcgaa gggcgcggtg    480
agcgtgatgt cgaaatcgat ggctgttgaa ctggccgcgc acgggatccg ggtcaacctg    540
atctcgcccg tgatggcggc gaccgggctg ctgcaggact tcatggggt tgccgacacc    600
gccgagaacc gcgcccgctt tgttgccacc ataccgctgg ggcgaatgtg cgagccggcc    660
gacgtggcca atgccgcggt cttcctggca agcccgggtg cccgcttcct taccggcatc    720
gacatgcccg ttgacggagg ccgggccatc tga                                 753
```

<210> SEQ ID NO 15
<211> LENGTH: 361
<212> TYPE: PRT
<213> ORGANISM: C. necator

<400> SEQUENCE: 15

```
Met Lys Ala Ala Val Leu Tyr Gln Pro Lys Thr Pro Leu Ile Ile Glu
1               5                   10                  15
```

Asp Val Ala Ile Gly Lys Pro Gly Pro Arg Glu Val Leu Val Arg Thr
    20                  25                  30

Ala Ala Val Gly Val Cys His Ser Asp Leu His Phe Leu Asp Gly Ala
        35                  40                  45

Tyr Pro Tyr Pro Met Pro Ala Ile Leu Gly His Glu Ala Ala Gly Val
    50                  55                  60

Val Glu Gln Val Gly Ala Glu Val Arg Thr Val Lys Pro Gly Asp His
65                  70                  75                  80

Val Ile Thr Cys Leu Ser Ala Tyr Cys Gly His Cys Glu His Cys Leu
                85                  90                  95

Thr Gly Arg Leu Ser Leu Cys Ile Glu Pro Asp Thr Arg Arg Glu
            100                 105                 110

Gly Glu Glu Pro Arg Leu Met Ala Arg Gln Gly Gly Pro Met Asn Gln
            115                 120                 125

Phe Leu Asn Leu Ser Ala Phe Ala Glu Gln Met Leu Ile His Glu His
    130                 135                 140

Ala Leu Val Ala Ile Arg Arg Asp Met Pro Leu Asp Arg Ala Ala Leu
145                 150                 155                 160

Ile Gly Cys Ala Val Thr Thr Gly Met Gly Ala Val Ile His Thr Ala
                165                 170                 175

Lys Val Gln Pro Gly Glu Thr Val Ala Val Ile Gly Cys Gly Gly Ile
            180                 185                 190

Gly Leu Ala Thr Val Asn Ser Ala Ala Ile Ala Gly Ala Gly Arg Ile
        195                 200                 205

Ile Ala Ile Asp Arg Val Pro Ala Lys Leu Glu Leu Ala Arg Arg Phe
    210                 215                 220

Gly Ala Thr Asp Val Ile Asp Ala Gly Asn Ala Asp Val Leu Asp Ala
225                 230                 235                 240

Val Arg Thr Leu Thr Gly Gly Val His His Ala Phe Glu Ala Ile
                245                 250                 255

Gly Leu Lys Gln Thr Thr Glu Gln Ala Phe Ala Met Leu Arg Arg Gly
            260                 265                 270

Gly Thr Ala Thr Val Ile Gly Met Ile Ala Pro Gly Val Lys Ile Glu
        275                 280                 285

Leu Lys Gly Ser Asp Phe Leu Gly Glu Lys Arg Ile Gln Gly Ser Leu
    290                 295                 300

Met Gly Ser Asn Arg Phe Pro Val Asp Met Pro Arg Met Val Asp Phe
305                 310                 315                 320

Tyr Met Ala Gly Arg Leu His Leu Asp Glu Leu Ile Ala Gln Arg Leu
                325                 330                 335

Pro Leu Glu Arg Ile Asn Asp Ala Phe Asp Gln Leu Arg Arg Gly Glu
            340                 345                 350

Leu Ala Arg Ser Val Ile Leu Phe Asp
        355                 360

<210> SEQ ID NO 16
<211> LENGTH: 1086
<212> TYPE: DNA
<213> ORGANISM: C. necator

<400> SEQUENCE: 16
atgaaggccg ctgtcctgta tcaacccaag accccgctga ttatcgaaga cgttgccatc    60
ggcaagcccg gcccgcgcga ggtgctggtg cgcaccgccg ccgtgggcgt gtgccactcg   120

```
gacctgcatt tcctggacgg tgcctacccg tacccgatgc cggcaatcct gggccacgag       180
gccgcgggtg tggtcgagca ggtcggcgcc gaagtgcgca cggtcaagcc cggtgaccac       240
gtgatcacct gcctgtcggc ctactgcggc cattgcgaac actgcctgac cggccgcctg       300
tcgctgtgca ttgagcccga tacccgccgc gcgaaggcg aagagccgcg cctgatggcc        360
cgccagggcg ggcccatgaa ccagttcctg aacctgtcgg cgttcgccga gcagatgctg       420
atccatgagc acgcgctggt ggcaatacgg cgcgacatgc cgctggaccg cgccgcgctg       480
atcggctgcg cggtcaccac cggcatgggc gcggtgatcc ataccgcgaa ggtgcagccg       540
ggcgagaccg ttgccgtgat cggctgcggc ggcatcgggc tggccacggt caacagcgcc       600
gccatcgccg gtgccgggcg catcatcgcc atcgaccgcg tgccggccaa gctggagctg       660
gcgcgcaggt tcggcgcgac cgacgtgatc gacgccggca atgccgatgt gctggatgcc       720
gtgcgcaccc tcaccggcgg cggcgtgcac catgccttcg aggccatcgg cctgaagcag       780
accaccgagc aggcctttgc catgctgcgc cggggcggca ccgccacggt catcggcatg       840
atcgcgccgg gcgtcaagat tgaactgaag gcagcgatt tcctgggcga aagcgcatc        900 cagggctcgc tgatgggctc caaccgcttc ccggtggaca tgccgcgcat ggtggacttc       960 tatatgccg ccgccctgca cctggacgaa ctgatcgcgc agcgcctgcc gctggagcgc       1020
atcaacgatg ccttcgacca actgcgccgc ggcgagctgg cgcgctcggt gatcctgttc       1080
gattaa                                                                 1086
```

<210> SEQ ID NO 17
<211> LENGTH: 277
<212> TYPE: PRT
<213> ORGANISM: C. necator

<400> SEQUENCE: 17

```
Met Lys Gln Val Thr Leu Pro Asp Gly Glu Arg Ile Pro Ala Leu Gly
1               5                   10                  15

Met Gly Thr Trp Asn Met Gly Glu Ser Arg Ala Ala Arg Ala Glu Glu
            20                  25                  30

Ile Ala Thr Leu Arg Leu Gly Leu Asp Leu Gly Leu Arg Leu Ile Asp
        35                  40                  45

Thr Ala Glu Met Tyr Gly Glu Gly Gln Ser Glu Glu Met Ile Gly Glu
    50                  55                  60

Ala Ile Ala Gly Arg Arg Asp Glu Ala Phe Leu Val Ser Lys Val Tyr
65                  70                  75                  80

Pro Phe Asn Ala Ser Arg Arg Gly Thr Val Gln Ala Cys Glu Arg Ser
                85                  90                  95

Leu Lys Arg Leu Arg Thr Asp Arg Ile Asp Leu Tyr Leu Leu His Trp
            100                 105                 110

Arg Gly Gly Val Pro Leu Glu Glu Thr Val Gln Ala Met Glu Ala Leu
        115                 120                 125

Gln Arg Asp Gly Lys Ile Arg Arg Trp Gly Val Ser Asn Leu Asp Leu
    130                 135                 140

Ser Asp Met Gln Glu Leu Trp Asp Ala Pro Gly Gly Asp Arg Leu Ala
145                 150                 155                 160

Ile Asn Gln Leu Leu Tyr Asn Leu Gly Arg Arg Gly Ile Glu Trp Asp
                165                 170                 175

Leu Leu Pro Trp Leu Arg Gln Arg Gly Val Pro Val Met Ala Tyr Ser
            180                 185                 190

Pro Ile Glu Gln Ser Arg Leu Leu Gly Asn Pro Gly Leu Lys Arg Phe
```

Ala Arg Asp His Gly Met Thr Ala Ala Gln Ala Ala Leu Ala Trp Leu
        210                 215                 220

Leu Ala Gln Asp Gly Val Ile Ala Ile Pro Lys Thr Ser Arg Arg Glu
225                 230                 235                 240

Arg Leu Leu Glu Asn Leu Gly Ala Leu Ser His Thr Leu Ser Ala Ala
                245                 250                 255

Gln Leu Ala Glu Leu Asp Arg Ile Phe Pro Pro Pro Asp Gly Pro Gly
        260                 265                 270

Pro Leu Glu Met Leu
        275

<210> SEQ ID NO 18
<211> LENGTH: 834
<212> TYPE: DNA
<213> ORGANISM: C. necator

<400> SEQUENCE: 18
atgaagcaag tcaccctgcc cgacggcgag cgcatcccgg cgctcggcat gggaacgtgg      60
aatatgggcg agtcgcgcgc cgcgcgcgcc gaagaaatcg ccacgctgcg cctgggcctg     120
gaccttggcc tgcggctgat cgataccgcc gagatgtatg gcgagggcca gtccgaggag     180
atgatcggcg aggccatcgc cgggcgccgc gacgaggcct tcctcgtcag caaggtctat     240
cccttcaacg ccagccggcg cggcaccgtg caagcctgcg agcgcagcct gaagcggctg     300
cgcaccgacc gcatcgacct ctatttattg cactggcgcg cggcgtgcc gctggaagag     360 accgtgcagg ccatggaggc gctgcagcgc gacggcaaga tccgccgctg gggcgtgagc     420
aacctggacc tgtccgatat gcaggagttg tgggacgcac cggcggcga ccggctggcc     480 atcaaccagt tgctgtacaa cctgggccgg cgcggcatcg aatgggacct gctgccgtgg     540
ctgcgccagc gcggcgtgcc ggtgatggcc tattcgccga tcgagcagtc acgcctgctg     600
ggcaaccccg gtctgaagcg ctttgcgcgc gaccacggca tgacggcggc acaggcggcg     660
ctggcctggc tgctggcgca ggacggcgtc atcgccatcc caagaccag ccggcgcgag     720 cgcctgctgg agaacctggg cgcgctgtcg catacgctgt cggccgccca gctggccgag     780
ctcgaccgca tcttcccgcc gcccgacggc ccgggcccgc tggaaatgct ttga          834

<210> SEQ ID NO 19
<211> LENGTH: 267
<212> TYPE: PRT
<213> ORGANISM: C. necator

<400> SEQUENCE: 19

Met Ser Val Pro Ser Phe Gly Val Gly Thr Phe Arg Leu Thr Gly Gln
1               5                   10                  15

Ala Val Ile Asp Ser Val Arg Asn Ala Leu Asp Leu Gly Tyr Arg Ala
            20                  25                  30

Val Asp Thr Ala Gln Ile Tyr Gly Asn Glu Ala Asp Val Gly Gln Ala
        35                  40                  45

Ile Ala Lys Ala Gly Val Lys Arg Asp Glu Leu Phe Val Thr Thr Lys
    50                  55                  60

Ile Trp Thr Ala Asn Tyr Ala Ala Gly Lys Leu Val Pro Ser Leu Arg
65                  70                  75                  80

Glu Ser Leu Asp Lys Leu Arg Thr Asp Tyr Val Asp Leu Thr Leu Ile
                85                  90                  95

```
His Trp Pro Ala Pro Gly Asn Gly Val Ala Leu Pro Glu Tyr Met Ala
            100                 105                 110

Ala Leu Ala Glu Ala Lys Ala Leu Gly Leu Thr Arg Gln Ile Gly Val
        115                 120                 125

Ser Asn Phe Asn Ile Ala Leu Thr Lys Gln Ala Leu Asp Ala Val Gly
    130                 135                 140

Lys Gly Glu Ile Ala Thr Asn Gln Ile Glu Leu Ser Pro Tyr Leu Gln
145                 150                 155                 160

Asn His Lys Leu Ala Ala Phe Leu Lys Glu Gln Gly Ile Ala Val Thr
                165                 170                 175

Ser Tyr Met Thr Leu Ala Tyr Gly Lys Val Leu Lys Asp Pro Val Leu
            180                 185                 190

Ala Gln Ile Ala Asn Lys His Arg Ala Thr Val Ala Gln Val Ala Leu
        195                 200                 205

Ala Trp Ala Leu Gln Leu Gly Tyr Ala Val Ile Pro Ser Ser Thr Arg
    210                 215                 220

Arg Glu Asn Leu Ala Ser Asn Leu Leu Ala Arg Asp Leu Lys Leu Asp
225                 230                 235                 240

Ala Asp Asp Met Ala Gln Ile Ala Ala Leu Glu Arg Asn Gly Arg Glu
                245                 250                 255

Val Ser Pro Glu Gly Leu Ala Pro Ala Trp Asp
            260                 265

<210> SEQ ID NO 20
<211> LENGTH: 804
<212> TYPE: DNA
<213> ORGANISM: C. necator

<400> SEQUENCE: 20
atgagcgttc cttcatttgg tgtcgggact ttccgcctga ccggccaggc cgtgatcgat      60
tcggtgcgca acgcgctgga cctgggctat cgcgccgtcg atacggcaca gatctacggc     120
aacgaggccg acgtcggcca ggctatcgcc aaggccggcg tgaagcgcga tgaactgttt     180
gtgaccacca agatctggac ggcgaactac gccgccggca agcttgtgcc gagcctgcgc     240
gaaagcctgg acaagctgcg caccgactac gtcgacctga ccctgatcca ctggccggcg     300
ccgggcaatg gcgtggcgct gcccgaatac atggcggcgc tggccgaagc caaggcgctg     360
ggcctgacgc ggcagattgg tgtttccaac ttcaatatcg cactgacgaa gcaggcgctc     420
gatgcggttg gcaagggcga aatcgccacc aaccagatcg aactgagccc ctatctgcag     480
aaccacaagc tcgccgcgtt cctgaaggag cagggcatcg ccgtgacgtc gtacatgacg     540
ctggcctacg gcaaggtgct gaaggacccg gtgctggcgc agatcgcgaa caagcaccgc     600
gccaccgtcg cgcaggttgc gctggcatgg gcgctgcaac tcggctatgc ggtgattcca     660
tcgtcgacca ggcgcgagaa cctggccagc aacctgctgg cgcgcgacct gaagctcgac     720
gccgacgaca tggcccagat cgccgcgctg gagcgcaacg gccgcgaggt cagccccgag     780
ggcctggccc cggcctggga ctga                                            804

<210> SEQ ID NO 21
<211> LENGTH: 349
<212> TYPE: PRT
<213> ORGANISM: C. necator

<400> SEQUENCE: 21

Met Lys Ile Ser Leu Thr Ser Ala Arg Gln Leu Ala Arg Asp Ile Leu
1               5                   10                  15
```

Ala Ala Gln Gln Val Pro Ala Asp Ile Ala Asp Val Ala Glu His
                 20                  25                  30

Leu Val Glu Ser Asp Arg Cys Gly Tyr Ile Ser His Gly Leu Ser Ile
             35                  40                  45

Leu Pro Asn Tyr Arg Thr Ala Leu Asp Gly His Ser Val Asn Pro Gln
 50                  55                  60

Gly Arg Ala Lys Cys Val Leu Asp Gln Gly Thr Leu Met Val Phe Asp
 65                  70                  75                  80

Gly Asp Gly Gly Phe Gly Gln His Val Gly Lys Ser Val Met Gln Ala
                 85                  90                  95

Ala Ile Glu Arg Val Arg Gln His Gly His Cys Ile Val Thr Leu Arg
            100                 105                 110

Arg Ser His His Leu Gly Arg Met Gly His Tyr Gly Glu Met Ala Ala
            115                 120                 125

Ala Ala Gly Phe Val Leu Leu Ser Phe Thr Asn Val Ile Asn Arg Ala
130                 135                 140

Pro Val Val Ala Pro Phe Gly Gly Arg Val Ala Arg Leu Thr Thr Asn
145                 150                 155                 160

Pro Leu Cys Phe Ala Gly Pro Met Pro Asn Gly Arg Pro Leu Val
                165                 170                 175

Val Asp Ile Ala Thr Ser Ala Ile Ala Ile Asn Lys Ala Arg Val Leu
            180                 185                 190

Ala Glu Lys Gly Glu Pro Ala Pro Glu Gly Ser Ile Ile Gly Ala Asp
            195                 200                 205

Gly Asn Pro Thr Thr Asp Ala Ser Thr Met Phe Gly Glu His Pro Gly
210                 215                 220

Ala Leu Leu Pro Phe Gly Gly His Lys Gly Tyr Ala Leu Gly Val Val
225                 230                 235                 240

Ala Glu Leu Leu Ala Gly Val Leu Ser Gly Gly Thr Ile Gln Pro
                245                 250                 255

Asp Asn Pro Arg Gly Gly Val Ala Thr Asn Asn Leu Phe Ala Val Leu
            260                 265                 270

Leu Asn Pro Ala Leu Asp Leu Gly Leu Asp Trp Gln Ser Ala Glu Val
            275                 280                 285

Glu Ala Phe Val Arg Tyr Leu His Asp Thr Pro Pro Ala Pro Gly Val
290                 295                 300

Asp Arg Val Gln Tyr Pro Gly Glu Tyr Glu Ala Ala Asn Arg Ala Gln
305                 310                 315                 320

Ala Ser Asp Thr Leu Asn Ile Asn Pro Ala Ile Trp Arg Asn Leu Glu
                325                 330                 335

Arg Leu Ala Gln Ser Leu Asn Val Ala Val Pro Thr Ala
            340                 345

<210> SEQ ID NO 22
<211> LENGTH: 1050
<212> TYPE: DNA
<213> ORGANISM: C. necator

<400> SEQUENCE: 22
atgaagatct ccctcaccag cgcccgccag cttgcccgcg acatcctcgc cgcgcagcag      60
gtgcccgccg acatcgctga cgacgtggcc gagcacctgg tcgaatccga ccgctgcggc     120
tatatcagcc acggcctgtc gatcctgccc aactaccgca ccgccctcga cggccacagc     180
gtcaacccgc aaggccgcgc caaatgcgtg ctggaccagg gcacgctgat ggtgttcgac     240

```
ggcgacggcg gcttcggcca gcacgtgggc aagtccgtga tgcaagcagc gatcgagcgc        300
gtgcgccagc atggccactg catcgtcact ctgcgccgct cgcaccatct cggccgcatg        360
ggccactacg gcgagatggc ggccgccgcc ggctttgtgc tgctgagctt caccaacgtg        420
atcaaccgcg cgccggtggt ggcgccgttc ggcggccgcg tggcgcggct caccaccaac        480
ccgctgtgtt cgccggcccc gatgcccaac gggcggccgc ctctggtggt ggacatcgcc        540
accagcgcga ttgccatcaa caaggcccgt gtgctggccg agaaaggcga gccggcgccc        600
gaaggcagca tcatcggcgc cgacggcaac cccaccaccg acgcgtcaac catgttcggc        660
gaacaccccg cgcgctgct gcccttggc ggccacaagg gctacgcact gggcgttgtg         720
gccgagctgc tggcgggcgt gctgtccggc ggcggtacca tccagccaga caatccgcgc        780
ggcggcgtgg ccaccaacaa cctgttcgcg gtgctgctca atcccgcgct ggacctgggc        840
ctggactggc agagcgccga ggtcgaggcg ttcgtgcgct acctgcacga cacaccgccg        900
gcgccgggcg tcgaccgcgt gcagtacccc ggcgagtacg aggccgccaa ccgggcgcag        960
gccagcgaca cgctaaacat caacccggcc atctggcgca atcttgagcg cctggcgcag       1020
tcgctcaacg tggccgtccc cacggcctga                                        1050
```

<210> SEQ ID NO 23
<211> LENGTH: 331
<212> TYPE: PRT
<213> ORGANISM: C. necator

<400> SEQUENCE: 23

```
Met Glu Ile Ala Val Phe Ser Ala Lys Ser Tyr Asp Arg Gln His Leu
1               5                   10                  15

Asp Ala Ala Asn Ala Ala Glu Gly His Gln Leu Lys Tyr Phe Glu Val
                20                  25                  30

Pro Leu Asp Asn Glu Thr Val Gly Leu Ala Ala Gly His Gly Ala Val
            35                  40                  45

Cys Ile Phe Val Asn Asp Arg Ala Asp Ala Thr Val Leu Glu Ala Leu
        50                  55                  60

Gly Arg Gly Gly Thr Lys Leu Val Ala Leu Arg Cys Thr Gly Phe Asn
65                  70                  75                  80

Asn Val Asp Leu Lys Ala Ala Gln Ala Leu Gly Ile Lys Val Val Arg
                85                  90                  95

Val Val Asp Tyr Ser Pro Asn Ala Val Ala Glu His Ala Ala Ala Leu
            100                 105                 110

Leu Met Ala Val Asn Arg Lys Ile His Arg Ala Tyr Asn Arg Thr Arg
        115                 120                 125

Asp Phe Asn Phe Ser Leu Glu Gly Leu Met Gly Phe Asp Leu Cys Gly
    130                 135                 140

Lys Thr Val Ala Val Ile Gly Thr Gly Lys Ile Gly Arg Val Phe Ala
145                 150                 155                 160

Lys Ile Met Val Gly Phe Gly Cys Asn Val Ile Gly Tyr Asp Lys Tyr
                165                 170                 175

Pro Ser Pro Glu Phe Glu Ala Leu Gly Gly Arg Tyr Ala Asp Glu Gly
            180                 185                 190

Glu Ile Gly Ala Ser Ala Asp Cys Ile Ser Leu His Cys Pro Leu Thr
        195                 200                 205

Pro Glu Thr His His Ile Ile Asn Ala Glu Thr Leu Ser Arg Ala Lys
    210                 215                 220
```

Pro Gly Ala Leu Leu Ile Asn Thr Ser Arg Gly Leu Ile Asp Thr
225                 230                 235                 240

Glu Ala Val Ile Gly Ala Leu Arg Ser Gly Gln Leu Gly Gly Leu Ala
            245                 250                 255

Ile Asp Val Tyr Glu Gln Glu Ala Gly Leu Phe Phe Arg Asp Leu Ser
            260                 265                 270

Gly Ile Ile Val Asp Asp Ser Val Leu Gln Gln Leu Ile Thr Phe Pro
        275                 280                 285

Asn Val Ile Val Thr Gly His Gln Ala Phe Leu Thr Arg Glu Ala Val
        290                 295                 300

Thr Thr Ile Cys Glu Thr Thr Leu Arg Ser Val Thr Glu Phe Glu Ser
305                 310                 315                 320

Gly Lys Pro Leu Thr Asn Glu Val Gly Ala Gly
                325                 330

<210> SEQ ID NO 24
<211> LENGTH: 996
<212> TYPE: DNA
<213> ORGANISM: C. necator

<400> SEQUENCE: 24
atggaaatcg ccgtcttcag cgcaaagtcc tatgatcgtc aacatctcga tgccgcgaat      60
gcggccgaag ccatcagct caagtacttc gaagttccct ggacaatga acgtgtgggc      120
ctcgccgcgg ccacggcgc agtgtgcatc ttcgtcaatg accggccga tgcgaccgtg      180
ctggaagcgc tcggacgcgg cggcaccaag ctggtcgcgc tgcgctgcac ggggttcaac      240
aacgtcgacc tgaaagccgc gcaggcgctc gggatcaagg tggtgcgcgt tgtcgactac      300
tcgcccaacg cggtcgccga gcacgcggcg gccctgctga tggcggtcaa ccgcaagatc      360
caccgggcct acaatcgcac gcgggacttc aatttctcgc tcgaaggcct gatgggcttc      420
gacctgtgcg gcaagaccgt ggccgtgatc ggcaccggca agatcgggcg cgtgtttgcg      480
aaaatcatgg tcgggttcgg ttgcaacgtg atcggctacg acaagtaccc gtccccggaa      540
ttcgaggccc ttggtggacg ctacgcggac gagggagaaa tcggcgcaag cgcggactgc      600
atctcgctgc attgcccgct cacgcccgag acccatcaca tcatcaatgc cgaaacgctg      660
tcgcgcgcca agccggggggc cttgctcatc aacaccagcc gcggcgggct gatcgacacg      720
gaagcagtca tcggagcgct ccggagcggg caactcggcg gctggcgat cgacgtgtac      780
gagcaggagg cgggcctgtt cttccgcgac ctgtccggca tcatcgtcga cgactccgtg      840
ctgcagcagc taatcacgtt tcctaacgtg atcgtgaccg gcaccaagc cttcctcacg      900
cgtgaggccg tgacgaccat ttgcgaaaca accttgcgca gcgtgacgga gttcgaaagc      960
ggcaagccgc tcacgaacga agtcggtgcc ggttga                                996

<210> SEQ ID NO 25
<211> LENGTH: 318
<212> TYPE: PRT
<213> ORGANISM: C. necator

<400> SEQUENCE: 25

Met Lys Ile Val Phe Leu Asp Arg Ser Thr Ile Ser Pro Gln Val Thr
1               5                   10                  15

Leu Pro Ala Leu Pro Phe Pro His Glu Leu Gln Leu Tyr Gly Glu Thr
            20                  25                  30

Pro Asp Glu Asp Val Ala Ala Arg Ile Ala Ala Ala Asp Val Val Ile
        35                  40                  45

```
Thr Asn Lys Val Lys Leu Asp Ala Arg Gln Leu Glu Gln Ala Pro Asn
     50                  55                  60

Leu Lys Leu Ile Ala Ile Ala Ala Thr Gly Thr Asp Val Val Asp Leu
 65                  70                  75                  80

Gln Ala Cys Ala Ala Arg Gly Ile Val Val Ser Asn Ile Arg Asn Tyr
                 85                  90                  95

Ala Val His Thr Val Pro Glu His Thr Phe Ala Leu Ile Val Ala Leu
                100                 105                 110

Arg Arg Ser Leu Ala Ala Tyr His Asp Ala Val Arg Arg Gly Arg Trp
            115                 120                 125

Gln Glu Ser Gly Ser Phe Cys Phe Phe Asp Tyr Pro Ile Lys Asp Leu
        130                 135                 140

His Gly Ser Val Leu Gly Ile Ile Gly Asp Gly Val Leu Gly Gln Ser
145                 150                 155                 160

Val Ala Arg Met Ala Ser Ala Leu Gly Met Gln Pro Leu Phe Ala Ala
                165                 170                 175

His Lys Gly Arg Glu Gly Met Gly Pro Leu Tyr Thr Pro Phe Asp Glu
            180                 185                 190

Val Leu Arg Arg Ser Asp Ile Ile Thr Leu His Cys Pro Leu Val Ala
        195                 200                 205

Gln Thr Arg Asn Leu Ile Asp Thr Ala Glu Phe Ser Lys Met Glu Arg
    210                 215                 220

Arg Pro Leu Leu Ile Asn Thr Ala Arg Gly Gly Leu Val Asn Glu Ala
225                 230                 235                 240

Ala Leu Val Glu Ala Leu Gln Ser Gly Lys Val Ala Gly Ala Gly Phe
                245                 250                 255

Asp Val Ala Thr Gln Glu Pro Pro Gly Ala Glu His Pro Phe His Gln
            260                 265                 270

Leu Lys Asp Ala Pro Asn Phe Ile Leu Thr Pro His Val Ala Trp Ala
        275                 280                 285

Ser Asp Glu Ala Val Gln Gly Leu Ala Asp Gln Leu Ile Asp Asn Ile
    290                 295                 300

Cys Ala Phe Ala Gln Gly Ala Pro Arg Asn Val Val Ala Ala
305                 310                 315
```

<210> SEQ ID NO 26
<211> LENGTH: 957
<212> TYPE: DNA
<213> ORGANISM: C. necator

<400> SEQUENCE: 26

```
atgaagatcg tattcctgga ccgttccacc atctcgccgc aggtcacgct gccagcgctg    60
ccgttcccgc atgagctcca actctacggg aaacgcctg acgaggacgt cgccgcgcgc   120
atcgccgccg cggacgtggt catcaccaac aaggtgaagc tggatgcccg ccagcttgag   180
caggcaccga acctgaagct catcgccatt gcggcgaccg gcaccgatgt tgtcgacctg   240
caagcctgtg ccgcccgcgg catcgtcgtc tccaatatcc gcaactatgc cgtccatacg   300
gtgccggaac atacatttgc cctgatcgtc gcgctgcggc gaagcctggc cgcctaccac   360
gatgcggtcc ggcgcggccg ctggcaggaa tccggatcct tctgcttctt cgactacccg   420
atcaaggact tgcacgggtc ggtgcttggc atcatcggcg acggcgtgct cggccagtcg   480
gtggccagga tggcgagtgc gctgggcatg cagccgctgt ttgcggccca aagggacgc   540 gagggcatgg gcccgctcta cacgcctttc gacgaggtgc tgcgccgtag cgacatcatc   600
```

```
accttgcatt gcccgctggt ggcgcagaca cgcaacctga tcgacaccgc ggagttctcg    660
aagatggagc ggcgcccgtt gctgatcaac accgcccgag gcgggctggt caatgaagcg    720
gcgctggtgg aagcgctgca atccggaaag gtggccgggg ccggcttcga cgttgcgacg    780
caggagccgc ccggcgcgga cacccgttc catcagttga aggatgcgcc gaacttcatc     840
ctgaccccgc acgttgcatg ggccagcgac gaggccgtgc aaggcctggc cgaccagctt    900
atcgacaata tctgtgcctt cgcgcaaggc gcgcccagga cgtggtggc cgcatga       957
```

<210> SEQ ID NO 27
<211> LENGTH: 258
<212> TYPE: PRT
<213> ORGANISM: C. necator

<400> SEQUENCE: 27

```
Met Leu Asn Gly Lys Thr Ala Leu Val Thr Gly Ser Thr Ser Gly Ile
1               5                   10                  15

Gly Leu Gly Ile Ala Lys Ala Leu Ala Ala Gln Gly Ala Asn Ile Ile
            20                  25                  30

Val Asn Gly Phe Gly Asp Ala Asp Ala Ala Lys Ala Glu Ile Ala Gln
        35                  40                  45

Ala Gly Gln Gly Ile Arg Val Gly Tyr His Gly Ala Asp Met Ser Lys
    50                  55                  60

Ala Ala Glu Ile Glu Asp Met Met Arg Tyr Ala Gln Ser Asp Phe Gly
65                  70                  75                  80

Gly Ala Asp Ile Leu Val Asn Asn Ala Gly Ile Gln His Val Ala Ala
                85                  90                  95

Ile Glu Asp Phe Pro Pro Glu Arg Trp Asp Ala Ile Ile Ala Ile Asn
            100                 105                 110

Leu Thr Ser Ala Phe His Thr Thr Arg Leu Ala Leu Pro Gly Met Lys
        115                 120                 125

Gln Lys Asp Trp Gly Arg Ile Ile Asn Val Ala Ser Thr His Gly Leu
    130                 135                 140

Val Ala Ser Ala Gln Lys Ser Ala Tyr Val Ala Ala Lys His Gly Ile
145                 150                 155                 160

Val Gly Phe Thr Lys Val Thr Ala Leu Glu Thr Ala Gln Thr Gly Val
                165                 170                 175

Thr Ala Asn Ala Ile Cys Pro Gly Trp Val Leu Thr Pro Leu Val Gln
            180                 185                 190

Lys Gln Val Glu Ala Arg Ala Gln Lys Glu Gly Ile Pro Val Glu Gln
        195                 200                 205

Ala Lys Arg Glu Leu Val Leu Glu Lys Gln Pro Ser Gly Gln Phe Val
    210                 215                 220

Thr Pro Asp Glu Leu Gly Ala Leu Ala Val Phe Leu Ser Ser Glu Ala
225                 230                 235                 240

Ala Arg Gln Val Arg Gly Ala Ile Trp Asn Met Asp Gly Gly Trp Val
                245                 250                 255

Ala Gln
```

<210> SEQ ID NO 28
<211> LENGTH: 777
<212> TYPE: DNA
<213> ORGANISM: C. necator

<400> SEQUENCE: 28

```
atgctcaacg gcaagaccgc actggtgact ggctcgacca gcggcatcgg gctcggcatc    60
gcgaaagcgc tggcggccca gggcgccaac atcatcgtca acggctttgg tgacgcggac   120
gccgcaaagg cagaaatcgc gcaggccggc caggggatcc gggtcggcta ccacggcgcc   180
gacatgagca aggcggccga gatcgaagac atgatgcgct acgcgcagtc cgacttcggc   240
ggcgccgaca tcctggtcaa caacgccggc atccagcacg tggccgcgat cgaggatttc   300
ccgcccgagc gctgggacgc gatcatcgcc atcaacctga cctcggcctt ccacaccacg   360
cgcctggcgc tgcccggcat gaagcagaag gactggggcc gcatcatcaa tgtcgcctcc   420
acccacgggc tggtggcctc ggcgcagaag tccgcctacg tggcggccaa gcacggcatc   480
gtcggcttca ccaaggtgac cgcgctggaa accgcgcaga ccggcgtcac cgccaacgcg   540
atctgcccgg gctgggtgct gacgccactg gtgcagaagc aggtcgaagc ccgcgcgcag   600
aaggaaggca ttccggtgga acaggccaag cgcgagctgg tgctggagaa caaccctcg   660
ggacagttcg tcacgcccga tgagctgggc gcgctggccg tgttcctgtc gtccgaagcg   720
gcccgccagg tccgcggcgc gatctggaac atggacggcg ctgggtggc gcagtaa      777
```

<210> SEQ ID NO 29
<211> LENGTH: 260
<212> TYPE: PRT
<213> ORGANISM: C. necator

<400> SEQUENCE: 29

```
Met Leu Glu Gly Lys Ser Ala Ile Val Thr Gly Ser Ser Gly Ile
1               5                   10                  15

Gly Leu Gly Ile Ala Arg Ala Phe Ala Ala His Gly Ala Asp Val Leu
            20                  25                  30

Leu Asn Gly Phe Gly Asp Ala Glu Gln Ile Glu Ala Thr Arg Ala Gly
        35                  40                  45

Leu Glu Gly Glu Tyr Gly Val Arg Val Arg Tyr Ser Pro Ala Asp Met
    50                  55                  60

Ser Gln Pro Cys Gln Val Arg Glu Met Ala Glu Phe Ala Ala Ser Glu
65                  70                  75                  80

Phe Gly Lys Val Asp Val Ile Val Asn Asn Ala Gly Ile Gln His Val
                85                  90                  95

Ala Pro Thr Glu Glu Met Pro Asp Asp Lys Trp Asp Ala Ile Val Ala
            100                 105                 110

Ile Asn Leu Ser Ser Ala Phe His Leu Ile Lys Ala Val Leu Pro Gly
        115                 120                 125

Met Lys Ala Arg Arg Trp Gly Arg Ile Ile Asn Ile Ala Ser Ala His
    130                 135                 140

Gly Leu Val Ala Ser Pro Phe Lys Ala Pro Tyr Val Ala Ala Lys His
145                 150                 155                 160

Gly Leu Ile Gly Leu Ser Lys Ala Val Ala Leu Glu Thr Ala Glu Phe
                165                 170                 175

Gly Ile Thr Ser Asn Thr Ile Cys Pro Gly Tyr Val Lys Thr Pro Leu
            180                 185                 190

Val Glu Gln Gln Ile Ala Asp Gln Ala Arg Ala His Arg Ile Ser Pro
        195                 200                 205

Ala Asp Val Val Arg Asp Val Leu Leu Val His Gln Ala Arg Lys Glu
    210                 215                 220

Phe Val Arg Ile Asp Glu Leu Ala Val Leu Ala Leu Phe Leu Ala Ser
225                 230                 235                 240
```

-continued

Asp Asn Ser Ala Ser Met Thr Ala Thr Ala Leu Ala Met Asp Gly Gly
                245                 250                 255

Trp Thr Gln His
        260

<210> SEQ ID NO 30
<211> LENGTH: 783
<212> TYPE: DNA
<213> ORGANISM: C. necator

<400> SEQUENCE: 30

| | | |
|---|---|---|
| atgcttgaag gaaaatcagc catcgttacc ggctccagca gcggtatcgg gcttggcatt | 60 |
| gcgcgcgcct ttgccgccca tggcgccgat gtactgctga acggcttcgg cgatgccgag | 120 |
| caaattgaag ccacgcgtgc agggctggag ggcgagtatg gcgtgcgcgt gcgctattcg | 180 |
| ccggcggata tgagccaacc ttgccaggtt cgcgaaatgg ccgaatttgc tgcatccgag | 240 |
| ttcggcaagg ttgacgtcat cgtgaataac gcgggcatcc agcatgttgc cccgaccgaa | 300 |
| gagatgccgg acgacaagtg ggacgccatc gttgccatca acctgtcctc ggcgttccac | 360 |
| ctgatcaagg ccgtcctgcc cggcatgaag gccaggcgct ggggccgcat catcaatatc | 420 |
| gcctccgccc atggcctggt ggcttcgccg ttcaaggcgc cctatgtcgc cgccaagcac | 480 |
| gggctgatcg gcctgtccaa ggctgtggcg ctggagacgg ccgagtttgg cattaccagc | 540 |
| aatacgatct gccccggcta tgtcaagacg ccgctggtgg aacagcagat cgccgaccag | 600 |
| gcgcgcgcgc accggatctc gcccgccgac gtcgtgcgcg atgtcctgct ggtgcaccag | 660 |
| gcgcgcaagg agttcgtgcg gattgacgaa cttgctgtcc tggccctgtt cttggcctcg | 720 |
| gacaattcag cctcgatgac cgccactgcg ctcgcaatgg atggtggctg gacccagcac | 780 |
| tga | 783 |

<210> SEQ ID NO 31
<211> LENGTH: 305
<212> TYPE: PRT
<213> ORGANISM: C. necator

<400> SEQUENCE: 31

Met Ile Asn Thr Ser Asn Ala His Ala Val Gln Ser Pro Arg Leu Gly
1               5                   10                  15

Trp Ile Gly Val Gly Ala Met Gly Arg Pro Met Cys Leu Asn Leu Leu
            20                  25                  30

Lys Ala Gly Tyr Arg Leu Thr Val Phe Asp Arg Val Pro Ala Gln Cys
        35                  40                  45

Glu Ala Val Ala Ala Gly Ala Ala Val Ala Pro Ala Ala Gln Ala
    50                  55                  60

Leu Val Ala Asp Ser Asp Val Val Phe Ser Thr Ile Phe Asp Asp Gly
65                  70                  75                  80

Gly Leu Arg Asp Leu Phe Leu Ala Ser Gly Val Ala Gly Ala Ala
                85                  90                  95

Thr Ala Asp Lys Val Phe Val Asp Met Ser Thr Val Ser Pro Asp Ala
            100                 105                 110

Ser Ala Glu Val Ala Ala Leu Ala Arg Arg Gly Ala Ala Phe Leu
        115                 120                 125

Arg Ala Pro Val Ser Gly Thr Val Ser Leu Ala Ala Ser Ala Gln Leu
    130                 135                 140

Ser Cys Phe Val Ser Gly Pro Arg Pro Ala Phe Asp Ala Val Gln Pro
145                 150                 155                 160

Val Leu Ala Cys Leu Thr Ala Arg Gln Ser Tyr Val Gly Gly Ala Asp
              165                 170                 175

Glu Ala Arg Val Ile Lys Leu Met Ile Asn Met Met Val Phe Met Ser
        180                 185                 190

Thr Ala Val Ile Gly Glu Gly Leu Ala Phe Gly Ala Arg Ala Gly Leu
    195                 200                 205

Asn Arg Ala Leu Met Val Asp Ala Ile Asn Asp Ser Ile Val Gly Ser
210                 215                 220

Ala His Tyr Arg Thr Lys Ala Glu Gln Leu Lys Gln Arg Asp Tyr Ala
225                 230                 235                 240

Ala Val Gly Pro Ile Ser Leu Val Val Lys Asp Leu Asp Leu Ala Leu
                245                 250                 255

Ala Val Ala Arg Asp Asn Ala Val Ala Leu Pro Met Ser Ser Leu Val
            260                 265                 270

Arg Gln Tyr Leu Ala Leu Met Gln Gln Arg Arg Gln Gly His Leu Asp
        275                 280                 285

Ile Ala Ala Leu Ala Asp Val Leu Glu Trp Ala Gly Val Pro Gly Ala
    290                 295                 300

Val
305

<210> SEQ ID NO 32
<211> LENGTH: 918
<212> TYPE: DNA
<213> ORGANISM: C. necator

<400> SEQUENCE: 32
atgatcaaca caagcaacgc gcacgcggtg caatcaccgc ggcttggatg gatcggcgtt      60
ggtgccatgg gccgaccgat gtgcctgaac ctgctgaaag ccggctaccg gctcacggtc     120
tttgaccgcg tgccggcgca gtgcgaggcg gtggccgccg caggggcggc agtggcgcct     180
gccgcgcagg cactggtggc ggactcggat gtggtgttct caacgatctt tgacgatggc     240
gggctgcgcg acctgttcct ggcctccggc ggcgttgccg gcgccgcgac ggcggacaag     300
gtctttgtcg acatgagcac ggtctcgccc gatgcctcgg cagaggtggc tgccgcgctc     360
gcgcggcgcg cgccgctttt tctgcgcgcg ccggtgtcgg gtacggtatc gctggcggcg     420
agcgcgcagc tgagctgttt cgtatccggg ccgcggccgg ccttcgacgc ggtgcagccc     480
gtcctcgcgt gcctgaccgc cgccagtca tacgtgggcg gcgcggacga ggcccgcgtc     540
atcaagctga tgatcaacat gatggtgttc atgagcaccg cggtgatcgg cgaagggctg     600
gccttcggcg cgcgcgccgg gctgaaccgc gcgctgatgg tcgatgcgat caacgacagc     660
atcgtcggca cgcccactac cgcaccaag gcagagcagc tcaagcagcg cgactacgcc     720
gccgtcggcc cgatctcgct ggtggtgaag gacctcgacc tggcattggc ggtggcccgc     780
gacaacgcgg tcgcgctgcc gatgtcgtcg ctggtgcgca aatacctggc gctgatgcag     840
cagcgccggc agggccatct cgacatcgcc gcgctggccg atgtgctcga gtgggcaggc     900
gtgcccggcg cagtgtaa                                                  918

<210> SEQ ID NO 33
<211> LENGTH: 293
<212> TYPE: PRT
<213> ORGANISM: C. necator

<400> SEQUENCE: 33

```
Met Ser Thr Thr Leu Thr Pro Thr Val Ala Phe Ile Gly Leu Gly
1               5                   10                  15

Ala Met Gly Ser His Met Val Arg His Leu Ala Ala Gly His Thr
            20                  25                  30

Val Arg Ala Phe Val Arg Arg Pro Glu Ala Ala Glu Ala Ala Arg Ala
            35                  40                  45

Leu Gly Ala Glu Pro Phe Phe Thr Pro Ala Glu Ala Ala Arg Gly Ala
    50                  55                  60

Ser Val Val Phe Thr Asn Val Thr Ser Ser Glu Asp Val Arg Glu Val
65                  70                  75                  80

Leu Leu Gly Glu Gln Gly Val Ile His Gly Ala Ala Pro Gly Thr Ile
                85                  90                  95

Cys Val Asp His Ser Thr Ile Ser Pro Ile Val Thr Arg Glu Ile Ala
                100                 105                 110

Ala Ala Leu Ala Ala Arg Gly Ile Glu Ala Leu Asp Cys Pro Val Ser
            115                 120                 125

Gly Gly Thr Met Gly Ala Glu Ala Gly Thr Leu Thr Ile Met Val Gly
    130                 135                 140

Gly Lys Pro Glu Met Leu Glu Arg Val Arg Pro Leu Leu Gln Gln Leu
145                 150                 155                 160

Gly Lys Thr Ile Thr His Ile Gly Asp His Gly Ala Gly Gln Val Ala
                165                 170                 175

Lys Leu Cys Asn Gln Ile Ala Gln Val Val Asn Ile Glu Gly Ile Ala
            180                 185                 190

Glu Ala Met Arg Phe Ala Ala Gln Asn Val Asp Thr Gly Arg Val
                195                 200                 205

Phe Glu Ala Met Ala Thr Gly Met Ala Gly Ser Arg Met Leu Asp Leu
    210                 215                 220

Met Gly Pro Lys Met Val Ala Arg Asn Phe Ala Ala Gly Ile Glu Ala
225                 230                 235                 240

Arg Leu His Asp Lys Asp Phe Gly Leu Ala Arg Asp Ile Ala Glu Glu
                245                 250                 255

Ile Gly Leu Asp Leu Pro Ala Met Gln Ala Thr Ser Ala Gln Leu Arg
            260                 265                 270

Thr Leu Met Ala Asn Gly Trp Gly Lys Asp Asp Thr Ser Ser Leu Leu
            275                 280                 285

Arg Val Leu Glu Gly
    290
```

<210> SEQ ID NO 34
<211> LENGTH: 882
<212> TYPE: DNA
<213> ORGANISM: C. necator

<400> SEQUENCE: 34

| | | | | | |
|---|---|---|---|---|---|
| atgagcacca | ctctcacccc | caccaccgtc | gccttcatcg | gcctgggcgc | catgggctcg | 60 |
| cacatggtcc | gccacctgct | ggccgccggc | cacaccgtgc | gcgccttcgt | gcgtcgcccg | 120 |
| gaagcggccg | aggccgcgcg | cgcgctgggg | gcggagccct | tcttcactcc | ggctgaagcg | 180 |
| gcgcgcggcg | ccagcgtcgt | cttcaccaac | gtgacctcgt | ccgaagacgt | gcgcgaagtg | 240 |
| ctgctgggcg | agcagggcgt | gatccacggc | gccgcgccgg | gcaccatctg | cgtggaccac | 300 |
| agcaccatct | cgccgatcgt | cacgcgcgag | atcgccgcgg | cgctggccgc | gcgcggcatc | 360 |
| gaggcgctgg | actgcccggt | ctcgggcggc | accatgggcg | ccgaggcggg | cacgctgacc | 420 |

-continued

```
atcatggtcg gcggcaagcc cgagatgctc gagcgcgtac gcccgctgct gcagcagctg    480
ggcaagacca tcacccatat cggcgaccac ggcgcgggcc aggttgccaa gctgtgcaac    540
cagatcgcgc aggtggtcaa tatcgaaggc attgccgagg ccatgcgttt tgccgccgcg    600
cagaacgtcg acaccggccg cgtgttcgaa gccatggcga ccggcatggc cggcagccgc    660
atgctcgacc tgatgggccc aagatggtg gcgcgcaact tgccgccgg catcgaggcg     720 cggctgcacg acaaggactt cgggctggcg cgcgatatcg ccgaagaaat cggcctggac    780
ctgcccgcga tgcaggccac ctcggcgcag ctgcgcacgc tgatggccaa cggctggggc    840
aaggacgaca cctcgtcgct gctgcgcgtg ctggagggct ga                       882
```

<210> SEQ ID NO 35
<211> LENGTH: 300
<212> TYPE: PRT
<213> ORGANISM: C. necator

<400> SEQUENCE: 35

```
Met His Ile Ala Phe Ile Gly Leu Gly Asn Met Gly Ala Pro Met Ala
1               5                   10                  15

Arg Asn Leu Leu Lys Ala Gly His Thr Leu Thr Val Phe Asp Leu Asn
            20                  25                  30

Ala Ala Ala Val Ala Ser Leu Cys Ala Glu Gly Ala Ala Thr Ala Asp
        35                  40                  45

Ser Ala Arg Lys Ala Val Ala Glu Asp Phe Val Ile Thr Met Leu
    50                  55                  60

Pro Ala Ala Ala His Val Arg Ser Ala Tyr Leu Gly Pro Glu Gly Val
65                  70                  75                  80

Leu Ala Gly Val Arg Pro Gly Val Pro Leu Val Asp Ser Ser Thr Ile
                85                  90                  95

Asp Pro Ala Thr Val Arg Glu Leu Ala Ala Ala Glu Ala His Gly
            100                 105                 110

Asn Ala Leu Ala Asp Ala Pro Val Ser Gly Gly Thr Val Gly Ala Gln
        115                 120                 125

Ala Gly Thr Leu Thr Phe Met Val Gly Ala Thr Glu Ala Leu Phe Ala
    130                 135                 140

Gln Val Arg Pro Val Leu Ala Gly Met Gly Arg Asn Leu Val His Cys
145                 150                 155                 160

Gly Gly Thr Gly Thr Gly Gln Val Ala Lys Ile Cys Asn Asn Leu Ile
                165                 170                 175

Leu Gly Ile Ser Met Ile Gly Val Ser Glu Ala Met Ala Leu Gly Val
            180                 185                 190

Lys Leu Gly Ile Asp Ala Asn Val Leu Ala Gly Ile Val Asn Thr Ser
        195                 200                 205

Thr Gly Arg Cys Trp Ala Ser Asp Thr Cys Asn Pro Trp Pro Gly Val
    210                 215                 220

Ile Glu Ala Ala Pro Ala Gly Arg Gly Tyr Thr Gly Gly Phe Gly Ala
225                 230                 235                 240

Asp Leu Met Leu Lys Asp Leu Gly Leu Ala Asn Asp Ala Ala Arg Ser
                245                 250                 255

Val Lys Gln Pro Leu Phe Leu Gly Leu Ala Gln Gly Val Tyr Gln
            260                 265                 270

Ala Val Ser His Ala Gly Asp Gly Gln Leu Asp Phe Ser Gly Val Ile
        275                 280                 285

Arg Gln Tyr Leu Ser Ala Ala Asp Lys Glu Gly Lys
```

<210> SEQ ID NO 36
<211> LENGTH: 906
<212> TYPE: DNA
<213> ORGANISM: C. necator

<400> SEQUENCE: 36

```
atgcatatcg ccttcatcgg cctcggcaac atgggcgcgc ccatggcgcg caacctgctc      60
aaggccggcc atacgctgac cgtattcgac ctgaacgccg cggcggtggc gtcgctgtgc     120
gccgagggcg ccgccaccgc ggattccgcc cgaaaggccg tggccgaagc agactttgtc     180
atcaccatgc tgcccgccgc tgcccatgtg cgcagcgcct acctgggccc ggaaggcgtg     240
ctggccggcg tgcgcccggg cgtgccgctg gtggattcca gcaccatcga ccccgccacc     300
gtgcgcgaac tggccgctgc cgccgaggcg cacggcaatg cgctggccga tgcaccggtc     360
tccggcggca ccgttggcgc ccaggccggc acgctgacct tcatggtcgg cgccaccgaa     420
gcactgttcg cccaggtgcg cccggtgctg gccggcatgg ggcgcaacct ggtccactgc     480
ggcggcaccg gcaccggcca ggtcgccaag atctgcaaca acctgatcct cggcatctcc     540
atgatcggcg tatccgaggc gatggcgctg gcgtcaagc tgggcatcga cgccaatgtg     600
ctggccggca tcgtcaatac ctccaccggc cgctgctggg cctcggatac ctgcaacccc     660
tggcccggcg tgatcgaggc cgcaccggcc gggcgcggct acaccggcgg ctttggcgcc     720
gacctgatgc tcaaggacct gggcctggcc aacgacgccg cgcgcagcgt gaagcagccg     780
ctgttcctgg gcgcgctggc gcagcaggtc taccaggccg tgagccatgc cggcgacggc     840
cagctcgact tctccggcgt gatccgccag tacctgtccg ccgccgacaa ggagggcaag     900
caatga                                                                906
```

<210> SEQ ID NO 37
<211> LENGTH: 292
<212> TYPE: PRT
<213> ORGANISM: C. necator

<400> SEQUENCE: 37

```
Met Arg Val Ala Phe Leu Gly Leu Gly Val Met Gly Phe His Met Ala
1               5                   10                  15

Gly His Leu Ala Thr Lys Gly His Glu Val Thr Val Tyr Asn Arg Thr
            20                  25                  30

Ala Ala Lys Ala Gln Ala Trp Val Gly Lys Phe Gly Gly Lys Ala Ala
        35                  40                  45

Pro Thr Pro Ala Gln Ala Val Arg Asp Ala Gln Val Val Cys Ser Cys
    50                  55                  60

Val Gly Asn Asp Asp Asp Leu Arg Ala Val Leu Thr Gly His Asp Gly
65                  70                  75                  80

Ala Phe Phe Ser Ala Pro Ser Gly Cys Ile Phe Val Asp His Thr Thr
                85                  90                  95

Ala Ser Ala Asn Val Ala Arg Glu Leu His Ala Ala Ala Arg Glu His
            100                 105                 110

Gly Leu His Phe Val Asp Gly Pro Val Ser Gly Gly Glu Val Gly Ala
        115                 120                 125

Glu Lys Gly Ile Leu Thr Ile Met Cys Gly Gly Asp Ala Asp Ala Tyr
    130                 135                 140

Ala Arg Ala Glu Pro Val Ile Ala Ala Tyr Ala Arg Ala Val Thr Arg
145                 150                 155                 160
```

Ile Gly Glu Ser Gly Ala Gly Gln Leu Ala Lys Met Val Asn Gln Ile
            165                 170                 175

Ser Ile Ala Gly Leu Ile Gln Gly Leu Ser Glu Ala Ile Ala Phe Gly
            180                 185                 190

Glu Arg Ala Gly Leu Asp Met Arg Leu Val Leu Asp Val Ile Ser Lys
            195                 200                 205

Gly Ala Ala Gly Ser Trp Gln Leu Glu Asn Arg Gly Pro Thr Met Ile
        210                 215                 220

Asp Asn Lys Phe Asp Phe Gly Phe Ala Val Asp Trp Met Arg Lys Asp
225                 230                 235                 240

Leu Gly Leu Cys Leu Asp Glu Ala Arg Arg Asn Gly Ala Gly Leu Pro
                245                 250                 255

Val Thr Ala Leu Val Asp Gln Phe Tyr Ala Asp Leu Gln Gln Met Gly
            260                 265                 270

Cys Gly Arg Ala Asp Thr Ser Ser Leu Ile Lys Arg Leu Arg Gln His
        275                 280                 285

Ala Gly Val Ala
    290

<210> SEQ ID NO 38
<211> LENGTH: 879
<212> TYPE: DNA
<213> ORGANISM: C. necator

<400> SEQUENCE: 38

```
atgcgtgtcg catttctcgg actgggcgtc atgggtttcc acatggccgg ccacctcgcc    60
accaagggc acgaggtcac cgtgtacaac cgcaccgccg ccaaggcgca ggcctgggtc    120
gggaagttcg cggcaaagc ggctcccacg ccggcacagg ccgtgcgcga tgcgcaggtg    180
gtctgctcct cgtgggcaa tgacgacgac ctgcgcgcgg tgctgaccgg catgacggc    240
gccttcttca cgcgcccag cggctgcatt ttcgtggacc acaccaccgc cagcgccaac    300
gtggcgcgcg aactccacgc cgccgcgcgc gagcacggcc tgcactttgt cgacggcccg    360
gtctccggcg cgaagtcgg cgcggagaaa ggcatcctga ccatcatgtg cggcggcgat    420
gccgacgcct atgcgcgcgc cgaaccggtc attgccgcct acgcacgcgc cgtcacgcgc    480
atcggcgaat ccggcgccgg caactggcc aagatggtca accagatcag catcgccggg    540
ctgatccagg gcctgtccga ggccatcgcc tttggcgagc gcgccgggct ggacatgcgc    600
ctagtgctgg acgtcatcag caagggcgcg gccggctcat ggcagctcga aaccgcggc    660
cccaccatga tcgacaacaa gttcgacttc ggcttcgcgg tggactggat cgcaaggac    720
ctgggcctgt gcctggacga ggcgcgccgc aacggcgccg gcctgccggt gacggcgctg    780
gtcgaccagt tctatgccga cctgcagcag atgggctgcg gccgcgccga cacttcttcg    840
ctgatcaagc gcctgcgcca gcacgccggc gtcgcctga                          879
```

<210> SEQ ID NO 39
<211> LENGTH: 299
<212> TYPE: PRT
<213> ORGANISM: C. necator

<400> SEQUENCE: 39

Met Ser Arg Ile Ala Phe Ile Gly Leu Gly Asn Met Gly Met Pro Met
1               5                   10                  15

Ala Leu Asn Leu Val Arg Ala Gly His Asp Val Gln Gly Phe Asp Ile
            20                  25                  30

```
Ser Glu Ala Ala Leu Ala Gly Phe Ala Gly Gln Gly Gln Ser Gln
         35                  40                  45

Arg Ser Val Ala Ala Ala Val Asp Gly Ala Ser Ile Val Ile Ser Ile
 50                  55                  60

Val Arg Asn Ala Asp Asp Val Lys Asn Leu Tyr Cys Thr Ala Gly Gly
 65                  70                  75                  80

Val Leu Asp Val Ala Ala Pro Gly Ala Leu Leu Ile Glu Ser Ser Thr
                 85                  90                  95

Ile Gly Pro Ala Ala Ala Arg Ala Val Ala Ala Glu Ala Ala Gln Ala
            100                 105                 110

Gly Phe Ala Met Leu Asp Ala Pro Val Ala Gly Gln Ala Gly Ala
            115                 120                 125

Arg Glu Ala Arg Leu Thr Phe Met Val Gly Gly Ala Arg Thr Ala Phe
            130                 135                 140

Asp Arg Ala Glu Pro Val Leu Arg Gln Met Gly Ala Arg Ile Phe Tyr
145                 150                 155                 160

Ala Gly Ala Ser Gly Asn Gly Gln Ile Ala Lys Leu Cys Asn Asn Leu
                165                 170                 175

Ile Ala Cys Val Ser Ser Ala Val Val Ser Glu Ala Phe Ile Leu Gly
            180                 185                 190

Ser Lys Leu Gly Met Asp Tyr Gln Thr Met Tyr Asp Ile Ile Thr Gln
            195                 200                 205

Ser Thr Gly Gln Cys Trp Thr Leu Ser His Asn Cys Pro Val Pro Gly
            210                 215                 220

Pro Val Pro Ser Ser Pro Ala Ser Arg Asp Tyr Val Pro Gly Phe Ala
225                 230                 235                 240

Ala Asp Leu Met Leu Lys Asp Leu Ser Leu Val Ala Ser Ala Ala Ser
                245                 250                 255

Glu Val Gly Ala Ala Thr Pro Phe Gly Ala Arg Ala Ile Gln Leu Tyr
            260                 265                 270

Arg Gln Leu Ser Glu Ser Gly Leu Gly Ala Arg Asp Trp Thr Val Val
            275                 280                 285

Ala Arg Leu Ile Glu Asn Ser Ala Ser Leu Asn
            290                 295

<210> SEQ ID NO 40
<211> LENGTH: 900
<212> TYPE: DNA
<213> ORGANISM: C. necator

<400> SEQUENCE: 40
atgagcagaa ttgcattcat tggtcttggc aatatgggca tgcccatggc cctgaacctt      60
gtacgtgcgg ccacgacgt gcagggattc gatatctcgg aagccgcact ggccggcttc     120
gccggacagg gggggcaatc gcagcgcagc gtggcagcgg ctgtcgatgg cgcatcgatc     180
gtcatttcca tcgtgagaaa tgccgatgac gtgaagaacc tgtactgcac cgcaggcggt     240
gtcctggacg tcgccgcgcc gggagccctg ctgatcgaga gctcaaccat cggacccgcc     300
gccgcgcgtg ctgtcgccgc ggaagcggcg caagccggct tgcgatgtt ggatgctccc      360 gtggccggcg gccaggctgg cgcccgcgaa gcgcggctga cattcatggt cggcggcgcg     420
cgcacggcct tcgaccgcgc tgagccagtc ctgcgccaga tgggcgccag aatcttttat     480 gccgggcca gcgcaatgg ccagattgcc aagctgtgca caacctgat cgcctgcgtc       540 agcagcgcgg tcgtctcgga agccttcatc ctgggcagca agctcggcat ggactatcag     600
```

```
acgatgtacg acatcatcac acagtctacc ggccagtgct ggaccctctc gcacaactgc    660
ccggtgccgg gccccgtgcc gtcttcgccc gccagtcgcg attatgtccc tggatttgcg    720
gcggatctga tgctcaagga cctctccctc gtcgcgtctg ccgccagtga ggttggcgcc    780
gcgacaccgt ttggcgccag ggccatccag ctgtaccggc agctaagcga atctggcctt    840
ggcgcccgcg attggaccgt agttgccagg ttgatcgaaa acagcgcttc tctcaattaa    900
```

<210> SEQ ID NO 41
<211> LENGTH: 128
<212> TYPE: PRT
<213> ORGANISM: C. necator

<400> SEQUENCE: 41

```
Met Thr Tyr Ser Glu Thr Gly Leu Thr Ser Arg His Val Ala Ala Leu
1               5                   10                  15

Ala Pro Ile Glu Asp Tyr Leu Gln Gly His Ile Thr Gly Lys Ala Glu
            20                  25                  30

Phe Met Tyr Lys Ala Phe Ala Ala Asp Ala Arg Ile Val Ser Phe Arg
        35                  40                  45

Asp Gly Lys Leu His Ser Leu Thr Val Glu Glu Phe Ala Ser Ala Arg
    50                  55                  60

Cys Pro Gly His Pro Ala Ala Asp Glu Ala Gln Arg Lys Arg Phe Ile
65                  70                  75                  80

Thr Gln Phe Asp Val Val Gly Asn Ala Gly Val Ala Lys Val Val Leu
                85                  90                  95

Glu Tyr Pro Gly Val Thr Phe Thr Asp Tyr Met Thr Leu Leu Glu Ile
            100                 105                 110

Asp Gly Val Trp Lys Ile Val Asn Lys Thr Phe Ser Ala Ala Pro Arg
        115                 120                 125
```

<210> SEQ ID NO 42
<211> LENGTH: 387
<212> TYPE: DNA
<213> ORGANISM: C. necator

<400> SEQUENCE: 42

```
atgacgtatt cagaaacggg cctgacttcc cgccacgtgg ccgcgctcgc gccgatcgag     60
gattacctgc agggccatat caccggcaag gccgagttca tgtacaaggc gtttgccgcc    120
gacgcgcgca tcgtctcgtt ccgtgatggc aagctgcatt cgctgacggt cgaggaattc    180
gcctcggcgc gctgccccgg ccatcccgcg gcagacgagg cgcagcgcaa ggctttatc     240 acgcagttcg atgtggtggg caatgcgggc gtcgccaagg tggtgcttga atcccgggc     300 gtgaccttca ccgactacat gacgctgctg gagatcgacg gcgtctggaa gatcgtcaac    360
aagactttca gcgccgcacc cgcgctga                                       387
```

<210> SEQ ID NO 43
<211> LENGTH: 284
<212> TYPE: PRT
<213> ORGANISM: C. necator

<400> SEQUENCE: 43

```
Met Ser Ile Arg Thr Val Gly Ile Val Gly Ala Gly Thr Met Gly Asn
1               5                   10                  15

Gly Ile Ala Gln Ala Cys Ala Val Val Gly Leu Asn Val Met Val
            20                  25                  30
```

Asp Ile Ser Asp Ala Ala Val Gln Lys Gly Val Ala Thr Val Ala Ser
         35                  40                  45

Ser Leu Asp Arg Leu Ile Lys Lys Glu Lys Leu Thr Glu Ala Asp Lys
 50                  55                  60

Ala Ser Ala Leu Ala Arg Ile Lys Gly Ser Thr Ser Tyr Asp Asp Leu
 65                  70                  75                  80

Lys Ala Thr Asp Ile Val Ile Glu Ala Ala Thr Glu Asn Tyr Asp Leu
                 85                  90                  95

Lys Val Lys Ile Leu Lys Gln Ile Asp Gly Ile Val Gly Glu Asn Val
                100                 105                 110

Ile Ile Ala Ser Asn Thr Ser Ser Ile Ser Ile Thr Lys Leu Ala Ala
                115                 120                 125

Val Thr Ser Arg Ala Asp Arg Phe Ile Gly Met His Phe Phe Asn Pro
130                 135                 140

Val Pro Val Met Ala Leu Val Glu Leu Ile Arg Gly Leu Gln Thr Ser
145                 150                 155                 160

Asp Thr Thr His Ala Ala Val Glu Ala Leu Ser Lys Gln Leu Gly Lys
                165                 170                 175

Tyr Pro Ile Thr Val Lys Asn Ser Pro Gly Phe Val Val Asn Arg Ile
                180                 185                 190

Leu Cys Pro Met Ile Asn Glu Ala Phe Cys Val Leu Gly Glu Gly Leu
                195                 200                 205

Ala Ser Pro Glu Glu Ile Asp Glu Gly Met Lys Leu Gly Cys Asn His
                210                 215                 220

Pro Ile Gly Pro Leu Ala Leu Ala Asp Met Ile Gly Leu Asp Thr Met
225                 230                 235                 240

Leu Ala Val Met Glu Val Leu Tyr Thr Glu Phe Ala Asp Pro Lys Tyr
                245                 250                 255

Arg Pro Ala Met Leu Met Arg Glu Met Val Ala Ala Gly Tyr Leu Gly
                260                 265                 270

Arg Lys Thr Gly Arg Gly Val Tyr Val Tyr Ser Lys
                275                 280

<210> SEQ ID NO 44
<211> LENGTH: 855
<212> TYPE: DNA
<213> ORGANISM: C. necator

<400> SEQUENCE: 44
atgagcatca ggacagtggg catcgtcggt gccggcacca tgggcaatgg catcgcccag    60
gcctgcgcag tggtaggtct caacgtggtg atggtcgaca tcagcgatgc cgccgtgcag   120
aagggtgtcg ccaccgtggc aagcagcctg gaccgtctga tcaagaagga aaagctgacc   180
gaggccgaca aggccagcgc gctggcgcgc atcaagggca gcacctcgta tgacgatctc   240
aaggccaccg atatcgtgat cgaggccgcc accgagaact acgacctgaa ggtcaagatc   300
ctcaagcaga tcgacggcat cgtcggcgag aacgtgatca tcgcgtccaa cacctcgtcg   360
atctcgatca ccaagctggc tgccgtgacc tcgcgcgccg accgctttat cggcatgcac   420
ttcttcaacc cggtgccggt gatggcgctg gtggaactga tccgcggcct gcagaccagc   480
gacaccaccc acgccgccgt cgaggccctg tcgaagcagc tcggcaaata cccgatcacg   540
gtcaagaaca gccgggcttt cgtcgtcaac cgcatcctgt gcccgatgat caacgaggcc   600
ttctgcgtgc tgggcgaagg cctggcctcg ccggaagaga tcgacgaagg catgaagctg   660
ggctgcaacc acccgatcgg gccgctggcg ctggctgaca tgatcggcct ggacaccatg   720

```
ctggccgtga tggaagtgct gtacacggag tttgccgatc cgaagtaccg cccggcgatg    780
ctgatgcgcg adatggtcgc tgccggctac ctgggccgca agactggccg cggcgtgtac    840
gtctatagca agtaa                                                     855
```

<210> SEQ ID NO 45
<211> LENGTH: 507
<212> TYPE: PRT
<213> ORGANISM: C. necator

<400> SEQUENCE: 45

```
Met Ser Thr Phe Thr Ile Asp Thr Leu Gly Ile Val Gly Thr Gly Ala
1               5                   10                  15

Met Gly Arg Gly Ile Ala Gln Ile Ala Ala Gln Ala Gly Leu Thr Val
            20                  25                  30

Asn Leu Tyr Asp Ala Asn Pro Gln Ala Val Ala Ala Arg Gln Tyr
        35                  40                  45

Leu Gln Asp Thr Leu Ala Lys Leu Ala Asp Lys Gly Lys Ile Ser Ala
    50                  55                  60

Ala Asp Ala Glu Ala Thr Leu Ala Arg Val Lys Pro Cys Gly Thr Leu
65                  70                  75                  80

Glu Asp Leu Ala Gly Cys Asp Met Val Leu Glu Ala Ile Val Glu Lys
                85                  90                  95

Leu Glu Val Lys Arg Asp Leu Ile Ala Lys Leu Glu Ala Val Leu Arg
            100                 105                 110

Glu Asp Ala Val Ile Ala Ser Asn Thr Ser Ser Leu Ser Ile Thr Ala
        115                 120                 125

Ile Ala Val Gly Ser Arg His Pro Gly Arg Ile Ala Gly Tyr His Phe
    130                 135                 140

Phe Asn Pro Val Pro Leu Met Lys Val Val Glu Val Ile Asp Gly Leu
145                 150                 155                 160

Ser Gly Asn Pro Ala Val Gly Asp Ala Leu Met Ala Leu Ser Arg Arg
                165                 170                 175

Met Gly His Thr Pro Val Arg Cys Lys Asp Met Pro Gly Phe Ile Val
            180                 185                 190

Asn His Ala Gly Arg Gly Met Asn Ile Glu Gly Leu Lys Val Ala Gln
        195                 200                 205

Glu Gly Val Ala Gly Phe Ala Asp Ile Asp Asn Ile Met Arg Glu Gln
    210                 215                 220

Ala Gly Phe Arg Met Gly Pro Phe Glu Leu Met Asp Leu Thr Gly Leu
225                 230                 235                 240

Asp Val Ser His Pro Val Met Glu Ser Ile Tyr Asn Gln Phe Tyr Gln
                245                 250                 255

Glu Pro Arg Tyr Arg Pro Ser Pro Ile Thr Ala Ile Arg Ala Val Gly
            260                 265                 270

Gly Leu Ile Gly Arg Lys Ala Gly Ala Gly Phe Tyr Ser Tyr Ala Asp
        275                 280                 285

Gly Gln Lys Gln Val Pro Ala Ala Ala Val Pro Gly Ala Arg Pro
    290                 295                 300

Ser Ser Val Trp Val Ser His Ala Ser Glu Arg Gly His Ala Met Val
305                 310                 315                 320

Thr Lys Leu Leu Gly Ala Leu Gly Val Thr Pro Glu Gly Gly Asn Lys
                325                 330                 335

Pro Ser Ala Asp Ala Leu Ile Ile Val Thr Pro Leu Gly Leu Asp Ala
```

```
                        340                 345                 350
Thr Thr Ser Ala Leu Gln Gln Gly Leu Asp Pro Ala Arg Thr Val Ala
            355                 360                 365

Ile Asp Thr Leu Leu Pro Phe Glu Ala Thr Lys Arg Arg Thr Leu Met
    370                 375                 380

Thr Thr Pro Ala Thr Ser Ala Ala Arg Asp Ala Ala His Gly Leu
385                 390                 395                 400

Phe Ala Ser Asp Gly Val Pro Val Thr Val Ile Arg Asp Ser Ala Gly
                405                 410                 415

Phe Val Ala Gln Arg Val Leu Cys Cys Ile Ile Asn Ile Ala Ser Asp
            420                 425                 430

Ile Ala Gln Gln Arg Ile Ala Thr Pro Ser Asp Ile Asp Leu Ala Val
            435                 440                 445

Asn Leu Gly Leu Gly Tyr Pro Lys Gly Pro Leu Ala Leu Gly Asp Ala
        450                 455                 460

Val Gly Pro Gln Leu Val Leu Glu Thr Leu Arg Asn Met Glu Ala Leu
465                 470                 475                 480

Thr Gly Asp Met Arg Tyr Arg Pro Ser Pro Trp Leu Trp Arg Arg Ala
                485                 490                 495

Gly Leu Gly Leu Ser Leu Leu Ala Glu Glu Gln
            500                 505

<210> SEQ ID NO 46
<211> LENGTH: 1524
<212> TYPE: DNA
<213> ORGANISM: C. necator

<400> SEQUENCE: 46
atgagcactt tcaccatcga tacgctgggt atcgtcggca ccggcgccat gggccggggc    60
atcgcgcaga tcgccgcgca ggcgggcctg accgtcaacc tgtacgacgc caacccgcaa   120
gccgtggccg ccgcgcgcca gtacctgcag gacacgctgg ccaagctcgc cgacaagggc   180
aagatcagcg ccgccgacgc agaggccacg ctggcccgcg tcaagccctg cggcacgctg   240
gaagacctgg ccggctgcga catggtgctg aagccatcg tcgagaagct ggaggtcaag   300
cgcgacctga tcgccaagct cgaagcggtc ctgcgtgaag acgccgtcat tgcctccaac   360
acgtcgtcgc tgtcgatcac cgcgatcgcc gtgggttcaa ggcacccggg ccgcatcgcc   420
ggctaccact tcttcaaccc ggtgccgctg atgaaggtgg tcgaggtcat cgacggcctg   480
tcgggcaacc ccgcggtggg cgacgcgctg atggcgctgt cgcgccgcat gggccatacg   540
ccggtgcgct gcaaggacat gccaggcttt atcgtcaacc atgccggccg cggcatgaat   600
atcgaaggcc tgaaggtcgc gcaggaaggc gtggccggat tgccgacat cgacaacatc   660
atgcgcgagc aggccggctt ccgcatgggc ccgttcgagc tgatggacct gaccgggctg   720
gacgtgtcgc acccggtgat ggaatcgatc tacaaccagt tctaccagga accgcgctac   780
cgcccctcgc cgatcaccgc gatccgcgcg gtcgccgggg tgatcggccg caaggcgggt   840
gctggtttct attcgtatgc cgatggccag aagcaggtgc cggcagccgc cgcggtgccg   900
ggcgcacgtc cgtcgagcgt gtgggtcagc acgccagcg agcgcggcca cgccatggtg   960
accaagctgc tgggcgcgct gggcgtgacc ccggaaggcg gcaacaagcc gtcggccgac  1020
gcgctgatca tcgtcaccccc gctgggcctg gacgccacca ccagcgcgct gcaacagggc  1080
ctggaccccgg cccgcacggt tgccatcgac acgctgctgc cgttcgaggc caccaagcgc  1140
cgcacgctga tgaccacgcc ggccaccagc gccgccgccc gcgatgccgc gcacggcctg  1200
```

```
ttcgccagcg acggcgtgcc ggtcacggtg atccgtgatt cggccggctt cgtcgcgcag      1260
cgcgtgctct gctgcatcat caatatcgcc agcgatatcg cgcagcagcg catcgccacg      1320
ccgtcggaca tcgacctcgc cgtcaacctg gcctgggtt atcccaaggg cccgctggcg       1380
ctgggcgatg cggtcggccc gcaactggtg ctggagacgc tgcgcaacat ggaagcgctg      1440
accggcgaca tgcgctaccg cccgagcccg tggctgtggc gccgtgccgg cctgggcctg      1500
tcgctgctgg ccgaagagca gtaa                                            1524
```

<210> SEQ ID NO 47
<211> LENGTH: 251
<212> TYPE: PRT
<213> ORGANISM: C. necator

<400> SEQUENCE: 47

```
Met Asp Ile Arg Asp Asn Val Phe Leu Val Thr Gly Gly Ala Ser Gly
1               5                   10                  15

Leu Gly Glu Ala Thr Ala Arg Met Ile Ala Ala Gly Gly Lys Val
                20                  25                  30

Val Ile Ala Asp Ile Asn Pro Ala Gly Glu Ala Leu Ala Ala Glu Leu
            35                  40                  45

Gly Gly Arg Phe Val Arg Cys Asp Val Ser Ser Glu Ala Asp Gly Arg
        50                  55                  60

Ala Ala Val Asp Ala Ala Thr Ala Leu Gly Arg Leu Ala Gly Leu Val
65                  70                  75                  80

Asn Cys Ala Gly Val Ala Pro Ala Cys Lys Thr Val Gly Lys Asp Gly
                85                  90                  95

Pro His Pro Leu Asp Ala Phe Glu Arg Thr Val Arg Ile Asn Leu Ile
            100                 105                 110

Gly Thr Phe Asn Met Val Arg Leu Ala Ala Ala Ala Met Val Gly Asn
        115                 120                 125

Ala Pro Asp Ala Gly Gly Glu Arg Gly Val Ile Val Asn Thr Ala Ser
    130                 135                 140

Val Ala Ala Phe Glu Gly Gln Ile Gly Gln Ala Ala Tyr Ala Ala Ser
145                 150                 155                 160

Lys Gly Gly Val Ala Ser Met Thr Leu Ala Ile Ala Arg Asp Leu Ala
                165                 170                 175

Arg Asp Gly Val Arg Cys Val Thr Ile Ala Pro Gly Leu Phe Glu Thr
            180                 185                 190

Pro Met Leu Met Gly Leu Pro Glu Thr Val Arg Asp Ala Leu Gly Arg
        195                 200                 205

Met Val Pro Phe Pro Ser Arg Leu Gly Arg Pro Ala Glu Tyr Ala Arg
    210                 215                 220

Leu Val Glu Ala Val Val Gly Asn Pro Met Leu Asn Gly Glu Val Ile
225                 230                 235                 240

Arg Leu Asp Gly Ala Ile Arg Met Gln Pro Arg
                245                 250
```

<210> SEQ ID NO 48
<211> LENGTH: 756
<212> TYPE: DNA
<213> ORGANISM: C. necator

<400> SEQUENCE: 48

```
atggacatcc gcgacaacgt cttcctcgtt accggcggcg cctcgggcct cggcgaagcc       60
```

```
accgcccgca tgattgccgc cgccggcggc aagtcgtca tcgccgacat caaccccgcc    120
ggcgaggcgc tggctgccga actgggcggc cgcttcgtgc gctgcgacgt gagcagcgag    180
gccgacggcc gcgccgccgt cgacgccgcc accgcgctcg gccggctggc cggactggtg    240
aactgcgccg gcgtggcgcc cgcgtgcaag acgtcggta aggacggccc ccatccgctc     300
gacgccttcg agcgcaccgt gcgcatcaac ctgatcggca ccttcaacat ggtccgcctc    360
gccgccgcgg cgatggtggg caacgcgccc gatgccggcg cgagcgtgg cgtcatcgtc     420 aacaccgcgt cggtggcggc gttcgagggg cagatcgggc aggcggccta tgccgcgtcg    480
aagggcggcg tagcgtcgat gacgctggcc atcgcccgcg acctggcgcg cgacggcgtg    540
cgctgcgtga ccatcgcgcc gggcctttttc gaaacgccca tgctgatggg cttgcccgaa   600
accgtgcgcg acgcgctggg caggatggtg ccgttcccct cgcgcctcgg acggcccgcc    660
gagtatgcgc ggctggtgga agccgtggtc ggcaacccga tgctgaacgg cgaggtcatc    720
cgtctcgacg gggcgatccg gatgcagccc aggtaa                              756
```

<210> SEQ ID NO 49
<211> LENGTH: 322
<212> TYPE: PRT
<213> ORGANISM: C. necator

<400> SEQUENCE: 49

```
Met Pro Asn Pro Thr Ala Pro Val Ile Leu Ser Arg Pro Gly Ala Ala
1               5                   10                  15

His Ala Val Val Val Gly Gly Gly Thr Met Gly Ala Asp Val Ala Val
                20                  25                  30

Val Leu Thr Arg Ala Leu Cys Arg Thr Thr Val Val Glu Pro Asp Ala
            35                  40                  45

Gly Arg Ala Gly Ala Met Pro Gly Arg Val Arg Gly Asn Leu Ala Ala
        50                  55                  60

Ile Gly Arg Glu Gln Gly Ala Glu Arg Leu Ala Val Ala Ala Thr Leu
65                  70                  75                  80

Asp Ala Val Asp Trp Ser Thr Val Asp Leu Val Ile Glu Cys Ile Pro
                85                  90                  95

Glu Gln Leu Asp Leu Lys Gln Ala Leu Phe Ala Glu Leu Val Arg Arg
                100                 105                 110

Ala Arg Pro Asp Thr Val Leu Ala Ser Asn Ser Ser Phe Pro Ile
            115                 120                 125

Ser Ala Ile Gly Ala Gly Leu Asp Ser Arg Val Arg Met Leu Gly Leu
        130                 135                 140

His Phe Phe Met Pro Ala His Leu Val Pro Leu Val Glu Val Met
145                 150                 155                 160

Gly Asp Asp Ser Asp Glu Ala Cys Ala Asp Ala Leu Ile Ala Phe Met
                165                 170                 175

Arg Arg Cys Ala Met Val Pro Val Lys Val Arg Lys Asp Leu Pro Gly
            180                 185                 190

Phe Leu Ala Asn Arg Leu Gln His Ala Leu Ser Arg Glu Ala Phe Ser
        195                 200                 205

Leu Ile Asp Arg Gly Ile Ala Ser Pro Glu Asp Val Asp Ala Ala Val
    210                 215                 220

Arg Phe Gly Phe Gly Phe Arg Phe Leu Ala Ala Gly Pro Val Leu Gln
225                 230                 235                 240

Arg Asp His Ala Gly Ile Asp Val His Ala Ala Ala Gly Ala Thr Met
                245                 250                 255
```

Tyr Pro Thr Phe Cys Asn Asp Asp His Pro Ala Arg Cys Leu Ser Glu
                260                 265                 270

Arg Ala Ala Asp Gly Arg His Gly Met Lys Arg Gly Glu Gly Phe Tyr
            275                 280                 285

Gln Trp Thr Pro Glu Thr Ile Ala Ala Glu Arg Ala Arg Tyr Asp Ser
290                 295                 300

Leu Leu Arg Ala Gly Leu Ala Leu Ile Ala Pro Glu Leu Pro Glu Ile
305                 310                 315                 320

Glu Pro

<210> SEQ ID NO 50
<211> LENGTH: 969
<212> TYPE: DNA
<213> ORGANISM: C. necator

<400> SEQUENCE: 50
atgccgaacc cgaccgcacc ggtcatcctg agccgccccg cgccgcgcca tgcggtggtg      60
gtgggcggcg gcaccatggg cgccgatgtt gccgtggtgc tgacccgcgc gctgtgccgc     120
accaccgtgg tcgagcccga tgccggccgc gccggcgcca tgcccgggcg cgtgcgcggc     180
aacctggccg cgatcggccg tgaacaaggc gcggagcgcc tggcggtggc cgcgacgctg     240
gatgcggtgg actggtccac cgtggacctg gtgatcgagt gcatcccgga acagctggac     300
ctgaagcagg cgctctttgc cgagctggtg cggcgcgcgc ggcccgatac ggtgctggcc     360
agcaacagct ccagcttccc gatcagcgcc atcggcgcgg gactcgactc gcgtgtgcgc     420
atgctcggcc tgcacttctt catgccggcg cacctggtgc cgctggtgga agtggtgatg     480
ggcgatgaca cgacgaggc ctgtgccgac gcgctgatcg ccttcatgcg ccgctgcgcg     540
atggtgccgg tcaaggtgcg caaggacctg ccgggctttc ttgccaaccg gctgcagcat     600
gcgctgtcgc gcgaggcatt cagcctgatc gaccgcggca ttgcctcgcc cgaggatgtc     660
gatgcggcgg tgcgcttcgg cttttggcttt cgcttcctgg cggccgggcc ggtgctgcag     720
cgtgaccacg cgggcatcga cgtgcacgcg gccgccggcg ccaccatgta cccgaccttc     780
tgcaacgacg accatccggc gcgctgcctg tccagcgcg ccgccgacgg ccgccacggc     840
atgaagcgcg gcgaaggctt ctaccagtgg acccccgaaa ccattgccgc cgagcgcgca     900
cgctatgaca gcctgctgcg cgccggcctg gcgctgatcg cgcctgaact gcccgagatc     960
gagccatga                                                             969

<210> SEQ ID NO 51
<211> LENGTH: 246
<212> TYPE: PRT
<213> ORGANISM: C. necator

<400> SEQUENCE: 51

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
                20                  25                  30

Gly Cys Gly Pro Asn Ser Pro Arg Arg Glu Lys Trp Leu Glu Gln Gln
            35                  40                  45

Lys Ala Leu Gly Phe Asp Phe Ile Ala Ser Glu Gly Asn Val Ala Asp
        50                  55                  60

Trp Asp Ser Thr Lys Thr Ala Phe Asp Lys Val Lys Ser Glu Val Gly
65                  70                  75                  80

```
Glu Val Asp Val Leu Ile Asn Asn Ala Gly Ile Thr Arg Asp Val Val
                85                  90                  95
Phe Arg Lys Met Thr Arg Ala Asp Trp Asp Ala Val Ile Asp Thr Asn
            100                 105                 110
Leu Thr Ser Leu Phe Asn Val Thr Lys Gln Val Ile Asp Gly Met Ala
        115                 120                 125
Asp Arg Gly Trp Gly Arg Ile Val Asn Ile Ser Ser Val Asn Gly Gln
    130                 135                 140
Lys Gly Gln Phe Gly Gln Thr Asn Tyr Ser Thr Ala Lys Ala Gly Leu
145                 150                 155                 160
His Gly Phe Thr Met Ala Leu Ala Gln Glu Val Ala Thr Lys Gly Val
                165                 170                 175
Thr Val Asn Thr Val Ser Pro Gly Tyr Ile Ala Thr Asp Met Val Lys
            180                 185                 190
Ala Ile Arg Gln Asp Val Leu Asp Lys Ile Val Ala Thr Ile Pro Val
        195                 200                 205
Lys Arg Leu Gly Leu Pro Glu Glu Ile Ala Ser Ile Cys Ala Trp Leu
    210                 215                 220
Ser Ser Glu Glu Ser Gly Phe Ser Thr Gly Ala Asp Phe Ser Leu Asn
225                 230                 235                 240
Gly Gly Leu His Met Gly
                245

<210> SEQ ID NO 52
<211> LENGTH: 741
<212> TYPE: DNA
<213> ORGANISM: C. necator

<400> SEQUENCE: 52
atgactcagc gcattgcgta tgtgaccggc ggcatgggtg gtatcggaac cgccatttgc      60
cagcggctgg ccaaggatgg ctttcgtgtg gtggccggtt gcggccccaa ctcgccgcgc     120
cgcgaaaagt ggctggagca gcagaaggcc ctgggcttcg atttcattgc ctcggaaggc     180
aatgtggctg actgggactc gaccaagacc gcattcgaca aggtcaagtc cgaggtcggc     240
gaggttgatg tgctgatcaa caacgccggt atcacccgcg acgtggtgtt ccgcaagatg     300
acccgcgccg actgggatgc ggtgatcgac accaacctga cctcgctgtt caacgtcacc     360
aagcaggtga tcgacggcat ggccgaccgt ggctggggcc gcatcgtcaa catctcgtcg     420
gtgaacgggc agaagggcca gttcggccag accaactact ccaccgccaa ggccggcctg     480
catggcttca ccatggcact ggcgcaggaa gtggcgacca agggcgtgac cgtcaacacg     540
gtctctccgg gctatatcgc caccgacatg gtcaaggcga tccgccagga cgtgctcgac     600
aagatcgtcg cgacgatccc ggtcaagcgc ctgggcctgc cggaagagat cgcctcgatc     660
tgcgcctggt tgtcgtcgga ggagtccggt ttctcgaccg cgccgacttc ctcgctcaac     720
ggcggcctgc atatgggctg a                                              741

<210> SEQ ID NO 53
<211> LENGTH: 248
<212> TYPE: PRT
<213> ORGANISM: C. necator

<400> SEQUENCE: 53

Met Ala Gly Gln Arg Ile Ala Leu Val Thr Gly Gly Met Gly Gly Leu
1               5                   10                  15
```

Gly Glu Ala Ile Ala Val Arg Leu Leu Ala Asp Gly Ala Arg Val Val
             20                  25                  30

Val Thr His Ser Val His Asn Asp His Val Ala Gln Trp Leu Gly Thr
         35                  40                  45

Gln Arg Ser Ala Gly Arg Glu Phe Thr Ala Phe Pro Val Asp Val Thr
     50                  55                  60

Asp Phe Ala Ser Cys Gln Arg Cys Val Ser Gln Val Arg Ser Glu Leu
65                  70                  75                  80

Gly Asp Val Asp Ile Leu Ile Asn Asn Ala Gly Val Thr Arg Asp Arg
                 85                  90                  95

Thr Leu Arg Lys Met Asp Lys Ala Asp Trp Asp Phe Val Leu Arg Thr
            100                 105                 110

Asp Leu Asp Ser Leu Phe His Met Thr Arg Pro Leu Val Glu Pro Met
        115                 120                 125

Leu Ala Arg Gly Trp Gly Arg Ile Val Asn Ile Ser Ser Val Asn Ala
    130                 135                 140

Ser Arg Gly Ala Phe Gly Gln Thr Asn Tyr Ala Ala Ala Lys Ala Gly
145                 150                 155                 160

Val His Gly Phe Thr Lys Ala Leu Ala Leu Glu Leu Ala Arg Lys Gly
                165                 170                 175

Ile Thr Val Asn Thr Val Ser Pro Gly Tyr Leu Asp Thr His Met Val
            180                 185                 190

Thr Asp Met Pro Ala Glu Ile Leu Glu Arg Asp Val Leu Pro Thr Ile
        195                 200                 205

Pro Val Gly Arg Leu Gly Lys Pro Ala Glu Val Ala Ala Leu Ile Ser
    210                 215                 220

Tyr Leu Cys Ser Asp Asp Gly Ala Phe Val Thr Gly Ala Asn Phe Ala
225                 230                 235                 240

Ile Asn Gly Gly Gln His Leu Gln
                245

<210> SEQ ID NO 54
<211> LENGTH: 747
<212> TYPE: DNA
<213> ORGANISM: C. necator

<400> SEQUENCE: 54

```
atggccggac aacgcattgc cctggtaacg ggaggcatgg gcggcctcgg cgaagcgatt       60
gccgtgcggc tgctggccga cggcgcgcgc gtcgtggtga cgcactccgt acacaatgac      120
cacgtggccc agtggctcgg cacgcaacgc tccgccggcc gcgaattcac ggcgttcccg      180
gtcgacgtga cggacttcgc gtcctgccag cgctgcgtgt cgcaagtgcg cagcgagctc      240
ggcgacgtcg atattctgat caacaatgcc ggggtcacgc gcgaccggac cctgcgcaag      300
atggataagg ctgactggga cttcgtgctg cgcacggacc tcgactcgct ctttcatatg      360
acgcggccgc tggttgagcc gatgttggcg cgcggttggg gccggatcgt caatatttct      420
tcggtcaatg cctcgcgggg cgccttttggc cagaccaact atgccgccgc caaggcgggg      480
gtacatggct tcaccaaggc gctggcgctg gaactcgcac gcaaaggcat caccgtcaac      540
accgtttcgc cgggctacct ggatacgcac atggtgacgg acatgcccgc cgagatcctc      600
gagcgggacg tgttgccgac tatcccggtc ggccggctag gcaagccggc cgaggtcgcg      660
gcgctgatct cttacctgtg cagcgacgac ggggccttcg tcactggcgc gaattttgcc      720
atcaacggcg ggcaacacct gcaatga                                         747
```

<210> SEQ ID NO 55
<211> LENGTH: 236
<212> TYPE: PRT
<213> ORGANISM: C. necator

<400> SEQUENCE: 55

| Met | Gly | Gly | Leu | Gly | Glu | Ala | Ile | Ser | Ile | Lys | Leu | His | Asp | Ala | Gly |
|---|---|---|---|---|---|---|---|---|---|---|---|---|---|---|---|
| 1 | | | | 5 | | | | | 10 | | | | | 15 | |

Tyr Ala Val Val Thr His Ser Pro Gly Asn Ala Ala Ala Gln Asp
              20                  25                  30

Trp Leu Ala Ala Met Ala Ala Gly Gly Arg Glu Ile Arg Ala Tyr Glu
              35                  40                  45

Val Asp Val Ser Asp Tyr Asp Ala Cys Gln Ala Cys Ala Ala Gln Ile
 50                  55                  60

Leu Ala Asp Val Gly Arg Val Asp Ile Leu Val Asn Asn Ala Gly Ile
 65                  70                  75                  80

Thr Arg Asp Met Ala Phe Lys Lys Met Asp Lys Pro Asn Trp Asp Ala
                    85                  90                  95

Val Met Arg Thr Asn Leu Asp Ser Val Phe Asn Leu Thr Lys Pro Leu
                   100                 105                 110

Cys Glu Gly Met Val Glu Arg Gly Trp Gly Arg Ile Ile Asn Ile Ser
                   115                 120                 125

Ser Val Asn Ala Ser Lys Gly Ala Phe Gly Gln Thr Asn Tyr Ala Ala
 130                 135                 140

Ala Lys Ala Gly Met His Gly Phe Thr Lys Ser Leu Ala Leu Glu Val
145                 150                 155                 160

Ala Arg Lys Gly Val Thr Val Asn Thr Val Ser Pro Gly Tyr Leu Ala
                   165                 170                 175

Thr Lys Met Val Asn Ala Val Pro Lys Glu Ile Met Glu Thr Lys Ile
                   180                 185                 190

Leu Pro Gln Ile Pro Val Gly Arg Val Gly Lys Pro Glu Glu Val Ala
                   195                 200                 205

Ala Leu Ile Ala Tyr Leu Cys Ser Glu Glu Ala Ala Tyr Val Thr Gly
 210                 215                 220

Ser Asn Ile Ala Ile Asn Gly Gly Gln His Met Gln
225                 230                 235

<210> SEQ ID NO 56
<211> LENGTH: 711
<212> TYPE: DNA
<213> ORGANISM: C. necator

<400> SEQUENCE: 56
atgggtgggc tgggagaagc catcagcatc aagctgcacg acgcaggcta tgcggtggtg      60
gtgacgcact cgccgggcaa tgcggccgcc caggactggc ttgccgcgat ggccgccggc     120
ggccgcgaga tacgtgccta cgaggtggat gtatccgact acgatgcctg ccaggcttgc     180
gcggcgcaga tcctggctga cgtaggccgc gtggatatcc tggtgaacaa cgccggcatt     240
acccgcgaca tggccttcaa gaagatggac aagccgaact gggacgccgt gatgcggacc     300
aatctcgact cggtgttcaa tctcaccaag ccgctttgcg aaggcatggt cgaacgcggc     360
tggggacgca tcatcaacat ctcatcggtc aacgcatcca agggcgcctt cggccagacc     420
aactatgccg ccgccaaggc cgggatgcac ggcttcacca gtcgctggc gctggaagtg      480 gcaaggaagg gcgtgaccgt caacaccgtc tctccgggct accttgccac caagatggtc     540

```
aacgccgtgc ccaaggaaat catggagacc aagatcctgc cgcagattcc ggtcggccgc    600
gtcggcaagc cggaagaagt cgcagcgctg attgcctacc tgtgctcgga ggaagcggcc    660
tacgtgaccg ggtccaatat cgccatcaat ggcgggcagc acatgcagta a             711
```

<210> SEQ ID NO 57
<211> LENGTH: 327
<212> TYPE: PRT
<213> ORGANISM: C. necator

<400> SEQUENCE: 57

```
Met Ala Lys Ala Pro Met Arg Val Ala Val Thr Gly Ala Ala Gly Gln
1               5                   10                  15

Ile Gly Tyr Ser Leu Leu Phe Arg Ile Ala Asn Gly Asp Met Leu Gly
            20                  25                  30

Lys Asp Gln Pro Val Ile Leu Gln Leu Leu Asp Leu Pro Gln Ala Gln
        35                  40                  45

Gln Ala Val Lys Gly Val Val Met Glu Leu Glu Asp Cys Ala Phe Pro
    50                  55                  60

Leu Leu Ala Gly Val Val Ile Thr Asp Asp Pro Lys Val Ala Phe Lys
65                  70                  75                  80

Asp Ala Asp Val Ala Leu Leu Val Gly Ala Arg Pro Arg Ser Lys Gly
                85                  90                  95

Met Glu Arg Lys Asp Leu Leu Glu Ala Asn Ala Gln Ile Phe Thr Val
            100                 105                 110

Gln Gly Lys Ala Leu Asp Glu Val Ala Ser Arg Asn Val Lys Val Leu
        115                 120                 125

Val Val Gly Asn Pro Ala Asn Thr Asn Ala Tyr Ile Ala Met Lys Ser
    130                 135                 140

Ala Pro Asn Leu Pro Arg Glu Asn Phe Thr Ala Met Leu Arg Leu Asp
145                 150                 155                 160

His Asn Arg Ala Leu Ser Gln Ile Ala Ala Lys Thr Gly Lys Pro Val
                165                 170                 175

Ser Ser Ile Glu Lys Leu Phe Val Trp Gly Asn His Ser Pro Thr Met
            180                 185                 190

Tyr Ala Asp Tyr Arg Tyr Ala Thr Val Asp Gly Lys Ser Val Lys Asp
        195                 200                 205

Leu Ile Asn Asp Pro Val Trp Asn Asn Asp Val Phe Leu Pro Thr Val
    210                 215                 220

Gly Lys Arg Gly Ala Ala Ile Ile Glu Ala Arg Gly Leu Ser Ser Ala
225                 230                 235                 240

Ala Ser Ala Ala Asn Ala Ala Ile Asp His Val Arg Asp Trp Val Leu
                245                 250                 255

Gly Thr Asn Gly Lys Val Val Thr Met Gly Ile Pro Ser Asn Gly Glu
            260                 265                 270

Tyr Gly Ile Pro Ala Asp Thr Met Phe Gly Tyr Pro Val Thr Thr Ala
        275                 280                 285

Asn Gly Lys Tyr Glu Ile Val Lys Gly Leu Glu Ile Asp Ala Tyr Ser
    290                 295                 300

Gln Glu Lys Ile Asn Ile Thr Leu Asn Glu Leu Glu Glu Glu Lys Ala
305                 310                 315                 320

Gly Val Gln His Leu Leu Gly
                325
```

<210> SEQ ID NO 58

-continued

<211> LENGTH: 984
<212> TYPE: DNA
<213> ORGANISM: C. necator

<400> SEQUENCE: 58

| | | | | | |
|---|---|---|---|---|---|
| atggctaaag | ccccaatgcg | cgtcgcagtg | accggcgccg | ctggccagat | cggctactcc | 60 |
| ctgctgttcc | gcatcgccaa | tggcgacatg | ctgggcaaag | accagccggt | catcctccaa | 120 |
| ctgctcgacc | tcccgcaagc | ccagcaagcc | gtcaagggcg | tggtgatgga | actggaagac | 180 |
| tgcgcgttcc | cgctgctggc | cggcgtggtc | atcaccgacg | accccaaggt | tgccttcaag | 240 |
| gacgccgacg | tggccctgct | ggttggcgcc | cgtccgcgca | gcaagggtat | ggagcgcaag | 300 |
| gacctgctcg | aagccaatgc | ccagatcttc | acggtgcagg | gcaaggcgct | ggacgaagtc | 360 |
| gccagccgca | acgtcaaggt | gctggtggtc | ggcaacccgg | ccaacaccaa | cgcctacatc | 420 |
| gccatgaagt | cggcaccgaa | cctgccgcgc | gagaacttca | ccgcgatgct | gcgcctggac | 480 |
| cacaaccgtg | ccctgtcgca | aatcgccgcc | aagaccggca | agccggtgtc | gtcgatcgag | 540 |
| aagctgttcg | tgtggggcaa | ccacagcccg | accatgtacg | ccgactaccg | ctatgccacc | 600 |
| gtcgacggca | agagcgtcaa | ggacctgatc | aacgacccgg | tgtggaacaa | cgacgtgttc | 660 |
| ctgccgaccg | tcggcaagcg | cggcgccgcc | atcatcgaag | cgcgtggcct | gtcgtcggct | 720 |
| gcttcggccg | ccaacgctgc | catcgaccac | gtgcgcgact | gggtgctggg | caccaacggc | 780 |
| aaggtcgtca | ccatgggcat | cccgtcgaac | ggtgaatacg | gcatcccggc | cgacaccatg | 840 |
| ttcggctacc | cggtgaccac | cgccaacggc | aagtacgaga | tcgtcaaggg | tctggagatc | 900 |
| gacgcctaca | gccaggaaaa | gatcaatatc | accctgaacg | aactggaaga | agaaaaggcc | 960 |
| ggcgtgcagc | acctgctggg | ctga | | | | 984 |

<210> SEQ ID NO 59
<211> LENGTH: 347
<212> TYPE: PRT
<213> ORGANISM: C. necator

<400> SEQUENCE: 59

Met Gln Gln Asp Arg Ile Thr Val Ser Glu Ala Glu Leu Arg Gln Leu
1               5                   10                  15

Gly Val Arg Ala Phe Gln Gly Leu Gly Leu Thr Glu Gly Asp Ala Ile
                20                  25                  30

Asp Val Ile Asp Ile Leu Val Leu Ala Asp Leu Phe Gly Leu Ser Thr
            35                  40                  45

His Gly Leu Ser Arg Ile Glu Ser Tyr Gly Arg Leu Gln Ser Gly
        50                  55                  60

Gly Ile Ser Ala Arg Pro Thr Ile Thr Val Glu Arg Ala Ala Pro Ala
65                  70                  75                  80

Leu Val Lys Val Asp Gly Gly Asn Ala Val Gly Pro Leu Ala Gly Met
                85                  90                  95

Lys Ala Leu Arg Ala Ala Met Glu Val Ala Glu Phe Gly Ile Gly
                100                 105                 110

Met Ala Phe Val Arg Gly Ser Asn His Phe Gly Pro Val Ser Pro Tyr
            115                 120                 125

Ser Tyr Ile Ala Ala Glu Ala Gly Phe Ala Ser Met Ile Gly Ser Asn
        130                 135                 140

Ala Thr Thr Thr Ile Ala Pro Trp Gly Gly Ser Asp Ala Arg Leu Gly
145                 150                 155                 160

Asn Ser Pro Leu Gly Phe Gly Val Pro Gly His Asp Gly Arg His Phe

```
                   165                 170                 175
Leu Leu Asp Met Ala Met Ser Val Ala Ala Arg Ala Lys Ile Arg Asn
                180                 185                 190

Ala Leu Lys Ala Gly Gln Ser Ile Pro Asp Ser Trp Ala Thr Asp Ala
                195                 200                 205

Gln Gly Arg Arg Thr Thr Asp Pro Lys Ala Ala Leu Asp Gly Phe Leu
                210                 215                 220

Leu Pro Ile Gly Gly His Lys Gly Tyr Gly Leu Ala Leu Met Val Asp
225                 230                 235                 240

Leu Phe Ala Gly Leu Leu Ser Asp Ala Ala Tyr Leu Thr His Val Lys
                245                 250                 255

Ser Trp Val Asp Ala Pro Asp Gln Pro Gln Asn Leu Gly His Phe Phe
                260                 265                 270

Ile Leu Val Asp Thr Arg Arg Leu Gly Ser Ala Gln Trp Leu Ala Ala
                275                 280                 285

Arg Met Gln Asp Phe Ala Ala Ile Leu His Gly Ser Ala Pro Ala Glu
                290                 295                 300

Pro Gly Lys Pro Val Ile Val Pro Gly Glu Ile Glu Leu Asp Lys Leu
305                 310                 315                 320

Ala Arg Gln Arg Glu Lys Gly Ile Ala Met Asp Pro Ala Val Lys Ala
                325                 330                 335

Leu Leu Asp Arg His Ala Asn Ala Lys Thr Asn
                340                 345

<210> SEQ ID NO 60
<211> LENGTH: 1044
<212> TYPE: DNA
<213> ORGANISM: C. necator

<400> SEQUENCE: 60
atgcaacaag atcgaatcac tgtatccgaa gccgaactcc gccagctcgg agtgcgcgcg      60
ttccagggcc tgggcctgac cgaaggggac gccatcgatg tcattgacat cctggtactt     120
gcagacctct tcgggctcag cacccatgga ctgtctcgca ttgaatccta tggcgaacgg     180
ctccagtccg gcggtatctc ggcacgcccc accattacag tcgagcgcgc cgcgccagcg     240
ctggtgaagg tcgatggtgg caacgcagtc ggcccgctcg ctggcatgaa ggcgctgcgc     300
gccgccatgg aagtcgccga agaattcggc atcggcatgg ccttcgtccg gggcagcaat     360
catttcgggc agtttcacc gtacagctac attgcggcgg aagcaggatt cgccagcatg     420
attggcagca acgccacgac gaccatcgcg ccatggggtg aagcgacgc acgcctgggc     480 aacagcccgc tgggtttcgg cgtaccgggg catgacggcc gccacttcct gctggacatg     540
gccatgagcg tggccgcacg cgccaagatt cgcaatgcgc tcaaggcagg acaatccatc     600
ccggattcat gggctaccga cgcgcaagga cgacggacca ccgatcccaa ggctgccctc     660
gatggcttcc tgcttccgat tggcgggcac aagggctatg gactggcact gatggtcgat     720
cttttcgcag gactgctgtc ggatgcggcg tacctgactc acgtcaagtc gtgggtcgat     780
gcacccgacc agccccagaa cctgggccat ttctttatcc tggttgatac ccggcgactg     840
ggatcggccc aatggctggc tgcccgcatg caagactttg cggcgatcct ccacggtagc     900
gcacccgcgg agcctggcaa gcctgtcatt gttcccggag agatcgaact cgacaagctg     960
gcgcgtcagc gcgaaaaggg cattgccatg gatccagcgg tgaaggcgct actggatcga    1020
catgccaacg caaagacgaa ctga                                           1044
```

<210> SEQ ID NO 61
<211> LENGTH: 774
<212> TYPE: PRT
<213> ORGANISM: C. necator

<400> SEQUENCE: 61

Met Thr Ser Pro Gln Ser Pro Ser Gln Asp Asp Leu Lys Gln Gln
1               5                   10                  15

Gln Arg Glu Ala Leu Arg Lys Ala Ala Leu Glu Tyr His Glu Phe Pro
            20                  25                  30

Thr Pro Gly Lys Ile Ser Val Thr Pro Thr Lys Pro Leu Ser Asn Gln
        35                  40                  45

Arg Asp Leu Ala Leu Ala Tyr Ser Pro Gly Val Ala Ala Cys Glu
    50                  55                  60

Glu Ile Val Ser Asp Pro Ala Asn Ser Phe Arg Tyr Thr Ala Arg Gly
65                  70                  75                  80

Asn Leu Val Ala Val Ile Thr Asn Gly Thr Ala Val Leu Gly Leu Gly
                85                  90                  95

Asp Ile Gly Ala Ala Ser Lys Pro Val Met Glu Gly Lys Ala Gly
            100                 105                 110

Leu Phe Lys Lys Phe Ala Gly Ile Asp Val Phe Asp Ile Glu Val Asp
        115                 120                 125

Glu Lys Asp Pro Glu Lys Leu Val Gln Ile Ile Ala Ala Leu Glu Pro
    130                 135                 140

Thr Phe Gly Gly Ile Asn Leu Glu Asp Ile Lys Ala Pro Glu Cys Phe
145                 150                 155                 160

Tyr Val Glu Arg Lys Leu Arg Glu Lys Met Lys Ile Pro Val Phe His
                165                 170                 175

Asp Asp Gln His Gly Thr Ala Ile Val Val Ser Ala Ala Ile Ile Asn
            180                 185                 190

Gly Leu Lys Val Val Gly Lys Asp Ile Lys Lys Val Lys Leu Val Ala
        195                 200                 205

Ser Gly Ala Gly Ala Ala Ala Leu Ala Cys Leu Asp Leu Leu Val Asp
    210                 215                 220

Ile Gly Leu Pro Ile Glu Asn Ile Trp Val Thr Asp Leu Ala Gly Val
225                 230                 235                 240

Val Tyr Glu Gly Arg Thr Glu Leu Met Asp Pro Glu Lys Ala Arg Phe
                245                 250                 255

Ser Gln Lys Thr Asp Lys Arg Lys Leu Ala Glu Val Ile Asp Gly Ala
            260                 265                 270

Asp Ile Phe Leu Gly Leu Ser Ala Ala Gly Val Leu Lys Gln Asp Met
        275                 280                 285

Val Gln Arg Met Ala Asp Lys Pro Leu Val Leu Ala Leu Ala Asn Pro
    290                 295                 300

Asn Pro Glu Ile Ala Pro Glu Leu Val Lys Glu Val Arg Pro Asp Ala
305                 310                 315                 320

Val Met Ala Thr Gly Arg Thr Asp Tyr Pro Asn Gln Val Asn Asn Val
                325                 330                 335

Leu Cys Phe Pro Phe Ile Phe Arg Gly Ala Leu Asp Cys Gly Ala Thr
            340                 345                 350

Thr Ile Thr Arg Glu Met Glu Ile Ala Ala Ala Asn Ala Leu Ala Glu
        355                 360                 365

Leu Ala Arg Gln Glu Gln Ser Asp Ile Val Ala Thr Ala Tyr Gly Ile
    370                 375                 380

-continued

```
Gln Asp Leu Ser Phe Gly Pro Glu Tyr Leu Ile Pro Lys Pro Phe Asp
385                 390                 395                 400

Pro Arg Leu Ile Val Lys Val Ala Pro Ala Val Ala Glu Ala Ala Met
            405                 410                 415

Lys Ser Gly Val Ala Ala Arg Pro Ile Glu Asp Met Asp Ala Tyr Arg
        420                 425                 430

Leu Gln Leu Gln Gln Phe Val Tyr His Ser Gly Thr Leu Met Lys Pro
    435                 440                 445

Ile Tyr Ala Ala Ala Arg Lys Val Glu Met Asp Lys Lys Arg Ile Val
450                 455                 460

Phe Ala Glu Gly Glu Gln Glu Arg Val Leu Arg Ala Val Gln Val Ile
465                 470                 475                 480

Val Asp Glu Lys Leu Ala Asn Pro Ile Leu Ile Gly Arg Pro Ala Val
            485                 490                 495

Leu Gln His Arg Ile Glu Arg Phe Gly Leu Arg Leu Arg Ala Gly Val
        500                 505                 510

Asp Phe Thr Val Val Asn Pro Glu His Asp Glu Arg Phe Arg Asp Tyr
    515                 520                 525

Ser Asp Ala Tyr Tyr Arg Met Met Ala Arg Glu Gly Ile Thr Pro Glu
530                 535                 540

Tyr Ala Lys Leu Glu Met Arg Arg Thr Thr Leu Ile Gly Ala Met
545                 550                 555                 560

Leu Val Asn Lys Gly Glu Ala Asp Gly Met Ile Cys Gly Thr Val Ser
            565                 570                 575

Asn Thr Ala Ala His Leu Arg Tyr Ile Asp Gln Val Leu Gly Gly Thr
        580                 585                 590

Ser Lys Val Tyr Ala Ala Met Asn Gly Leu Val Leu Pro Gly Arg Gln
    595                 600                 605

Ile Phe Leu Val Asp Thr His Val Asn Val Asp Pro Ser Ala Glu Glu
610                 615                 620

Leu Ala Gln Ile Thr Leu Met Ala Ala Glu Glu Leu Lys Arg Phe Gly
625                 630                 635                 640

Ile Glu Pro Lys Val Ala Leu Leu Ser His Ser Asn Phe Gly Ser Ser
            645                 650                 655

Glu Ala Pro Ser Ala Arg Lys Met Arg Glu Thr Leu Ala Ile Leu Arg
        660                 665                 670

Asp Arg Ala Pro Asp Leu Glu Ile Asp Gly Glu Met His Gly Asp Ser
    675                 680                 685

Ala Leu Asp Gln Lys Leu Arg Asp Gln Leu Val Pro Asp Gly Ala Leu
690                 695                 700

Lys Gly Glu Ala Asn Leu Leu Val Cys Pro Asn Ile Asp Ala Ala Asn
705                 710                 715                 720

Ile Ser Tyr Asn Leu Leu Lys Val Ala Ala Gly Asn Asn Val Ala Ile
            725                 730                 735

Gly Pro Ile Leu Leu Gly Val Lys Ala Pro Val His Ile Leu Thr Pro
        740                 745                 750

Ser Ala Thr Val Arg Arg Ile Val Asn Met Thr Ser Leu Val Val Val
    755                 760                 765

Asp Ala Ser Ala Lys Arg
    770
```

<210> SEQ ID NO 62
<211> LENGTH: 2325

<212> TYPE: DNA
<213> ORGANISM: C. necator

<400> SEQUENCE: 62

```
atgaccagcc ctcagcagtc cccgtcccaa gacgatctga acagcagca gcgtgaggcg      60
ctgcgcaaag cggcgctcga gtaccacgag tttcccaccc ccggcaagat ctcggtcacg     120
ccgaccaagc cgctgtcgaa ccagcgcgac ctggccctgg cctattcgcc gggcgtggcc     180
gccgcttgtg aagagatcgt ttccgatccg gccaattcct tccgctacac cgcccgcggc     240
aacctggtcg cggtgatcac caacggcacc gccgtgctgg gcctgggcga cattggcgcc     300
gcggcttcca gccggtgat ggaaggcaag gctggcctgt tcaagaagtt tgccggtatc      360
gacgtgttcg atatcgaagt cgatgagaag gacccggaaa agctggtcca gatcatcgcc     420
gcgctggagc ccaccttcgg cggcatcaac ctcgaagaca tcaaggcacc ggagtgcttc     480
tacgtcgagc gcaagctgcg cgagaagatg aagatccccg tcttccacga tgaccagcac     540
ggcaccgcca tcgtggtgtc cgcggccatc atcaacggcc tgaaggtggt cggcaaggac     600
atcaagaagg tcaagctggt ggcctcgggc gccggcgcgg ccgcgctggc ctgcctggac     660
ctgctggtcg acatcggcct gccgatcgag aacatctggg tgacggacct ggccggcgtg     720
gtctatgagg gtcgtaccga gctgatggac ccggaaaagg cgcgcttctc gcaaaagacc     780
gacaagcgca gctggccga agtgatcgac ggtgccgaca tcttcctggg cctgtccgcc     840
gcgggcgtgc tcaagcagga catggtccag cgcatggccg acaagccgct ggtgctggca     900
ctggccaacc ccaaccccga atcgcgccg gagctggtca aggaagtgcg ccccgacgcc     960
gtgatggcca ccggacgcac cgactacccg aaccaggtca caacgtcct gtgcttcccg    1020
ttcatcttcc gcggggcgct ggattgcggc gccaccacca tcacgcgcga gatggaaatc    1080
gccgcggcca atgccctggc cgaactggcg cgccaggagc agagcgacat cgtcgccacc    1140
gcctatggca tccaggacct gtcgttcggc cccgagtacc tgattccgaa gccgttcgac    1200
ccgcgcctga tcgtcaaggt ggcgccggcc gtggccgagg ccgcgatgaa gtccggcgtg    1260
gccgcccgtc cgatcgagga catggacgcc taccgtctgc agctgcagca gttcgtgtac    1320
cactcgggca cgctgatgaa gccgatctac ccgccgcgc gcaaggtcga gatggataag    1380
aagcgcatcg tcttcgccga aggcgagcaa gagcgcgtgc tgcgcgcggt gcaggtgatc    1440
gtcgacgaaa agctggccaa cccgatcctg atcggccgcc cggccgtgct gcagcaccgc    1500
atcgagcgct tcggcctgcg cctgcgcgcc ggcgtggact tcaccgtggt caaccccgag    1560
cacgatgagc gttccgcga ctattccgac gcctattacc gcatgatggc gcgcgagggc    1620
atcacgcccg agtacgccaa gctggaaatg cgccgccgca ccacgctgat cggcgcgatg    1680
ctggtgaaca agggcgaggc cgacggcatg atctgcggca ccgtcagcaa caccgcggcg    1740
cacctgcgct atatcgacca ggtgctgggc ggcaccagca aggtctacgc ggcgatgaat    1800
ggcctggtgc tgccgggccg ccagatcttc ctggtggata cgcacgtcaa cgtcgacccg    1860
agcgccgaag agctggccca gatcacgctg atggccgccg aggaactgaa cgcgcttcggc   1920
atcgagccca aggtcgcgct gctgtcgcac tcgaacttcg gttcgtccga agcgcccttcg   1980
gccccgcaaga tgcgcgaaac cctcgccatc ctgcgcgatc gcgccccgga cctgagatc    2040
gacggcgaaa tgcacggcga cagcgcgctc gaccagaagc tgcgcgacca gctggtgccg    2100
gatgcgcgc tcaagggcga agccaacctg ctggtgtgcc cgaacatcga cgcggccaat    2160
atctcgtaca acctgctcaa ggttgccgcg ggcaacaacg tcgcgatcgg gccgatcctg    2220
```

```
ctgggcgtga aggcgccggt gcacatcctg acgccgtcgg ccacggtgcg ccgcatcgtc    2280
aacatgacct cgctggtcgt ggtggatgcc tctgccaagc gctaa                    2325
```

<210> SEQ ID NO 63
<211> LENGTH: 773
<212> TYPE: PRT
<213> ORGANISM: C. necator

<400> SEQUENCE: 63

```
Met Ser Ser Lys Asn Ser Gly Asp Ala Pro Gln His Ala Pro Asn Ser
1               5                   10                  15

Pro Glu Ala Gln Leu Arg Leu Ala Ala Leu Glu Tyr His Arg Ser Pro
            20                  25                  30

Thr Lys Gly Lys Ile Gln Val Thr Ala Thr Lys Ala Leu Ser Asn Gln
        35                  40                  45

Arg Asp Leu Ser Leu Ala Tyr Ser Pro Gly Val Ala Tyr Ala Cys Glu
    50                  55                  60

Glu Ile Ala Lys Asp Pro Ala Thr Ala Ala Glu Tyr Thr Ser Arg Ala
65                  70                  75                  80

Asn Leu Val Ala Val Val Thr Asn Gly Thr Ala Val Leu Gly Leu Gly
                85                  90                  95

Asp Ile Gly Pro Leu Ala Gly Lys Pro Val Met Glu Gly Lys Gly Cys
            100                 105                 110

Leu Phe Lys Lys Phe Ala Gly Ile Asp Val Phe Asp Ile Glu Leu Asp
        115                 120                 125

Ala Arg Asp Pro Asp Lys Ile Val Glu Ile Val Ala Ala Leu Glu Pro
    130                 135                 140

Thr Leu Gly Gly Val Asn Leu Glu Asp Ile Lys Ala Pro Glu Cys Phe
145                 150                 155                 160

Tyr Ile Glu Gln Lys Leu Arg Glu Arg Met Asn Ile Pro Val Phe His
                165                 170                 175

Asp Asp Gln His Gly Thr Ala Ile Ile Ser Thr Ala Ala Leu Leu Asn
            180                 185                 190

Gly Leu Lys Val Val Gly Lys Asp Val Ala Lys Val Lys Leu Ala Val
        195                 200                 205

Ser Gly Ala Gly Ala Ala Ala Ile Ala Cys Leu Asp Thr Met Val Ser
    210                 215                 220

Leu Gly Val Lys Arg Glu Asn Ile Ser Val Val Asp Ser Lys Gly Val
225                 230                 235                 240

Ile Tyr Val Gly Arg Asp Ala Asn Met Glu Ala Asn Lys Ala Arg Tyr
                245                 250                 255

Ala Gln Asp Thr Ser Ala Arg Thr Leu Ala Asp Ile Val Lys Asp Ala
            260                 265                 270

Asp Val Phe Leu Gly Cys Ser Thr Ala Gly Val Leu Thr Ala Glu Met
        275                 280                 285

Val Lys Thr Met Ala Asp Lys Pro Ile Ile Leu Ala Leu Ala Asn Pro
    290                 295                 300

Glu Pro Glu Ile Arg Pro Glu Val Ala Lys Ala Ala Arg Pro Asp Cys
305                 310                 315                 320

Ile Ile Ala Thr Gly Arg Ser Asp Tyr Pro Asn Gln Val Asn Asn Val
                325                 330                 335

Leu Cys Phe Pro Tyr Ile Phe Arg Gly Ala Leu Asp Cys Gly Ala Thr
            340                 345                 350

Lys Ile Thr Glu Ala Met Lys Leu Ala Cys Val Lys Ala Ile Ala Glu
```

```
            355                 360                 365
Leu Ala Glu Ala Glu Leu Asn Asp Ala Val Ala Ala Tyr Gly Gly
    370                 375                 380
Arg Glu Leu Lys Phe Gly Pro Asp Tyr Ile Ile Pro Thr Pro Phe Asp
385                 390                 395                 400
Gln Arg Leu Ile Glu Lys Ile Ala Pro Ala Val Ala Lys Ala Ala Glu
                    405                 410                 415
Glu Ser Gly Val Ala Thr Arg Pro Ile Lys Asp Leu Glu Ala Tyr Arg
                420                 425                 430
Gln Gln Leu Ser Thr Tyr Val Tyr His Thr Gly Leu Ile Met Lys Pro
            435                 440                 445
Val Phe Ser Ala Ala Lys Ala Ala Pro Lys Arg Val Ala Tyr Ala Glu
    450                 455                 460
Gly Glu Glu Glu Arg Val Leu Arg Ala Val Gln Thr Val Val Asp Glu
465                 470                 475                 480
Gly Leu Ala Arg Pro Thr Leu Ile Gly Arg Pro His Val Ile Gln Met
                    485                 490                 495
Arg Ile Glu Lys Ala Gly Leu Arg Leu Lys Ala Gly Val Asp Phe Asp
                500                 505                 510
Leu Val Asn Pro Glu Glu Asp Pro Arg Tyr Arg Ala Tyr His Glu Ala
            515                 520                 525
Tyr His Ala Leu Arg Gly Arg Asp Gly Val Thr Pro Asp Met Ala Lys
    530                 535                 540
Val Ala Leu Arg Arg Ser Asn Thr Leu Ile Gly Ala Met Leu Met His
545                 550                 555                 560
Met Gly Asp Ala Asp Ala Leu Leu Cys Gly Thr Val Gly Arg Phe Glu
                    565                 570                 575
Ala His Leu Glu His Val Arg Asp Val Ile Gly Leu Ala Pro Gly Ala
                580                 585                 590
Lys Val Phe Ala Ala Met Asn Ala Leu Met Leu Glu Lys His Thr Leu
            595                 600                 605
Phe Ile Thr Asp Thr Phe Val Asn Asp Pro Thr Ala Asp Glu Leu
    610                 615                 620
Ala Ala Ile Thr Gln Leu Ala Ala Glu Glu Ile Ala Arg Phe Gly Leu
625                 630                 635                 640
Val Pro Lys Val Ala Leu Met Ser His Ser Met Phe Gly Ser Ser Thr
                    645                 650                 655
Arg Pro Ser Ala Arg Lys Met Arg Glu Ala Ala Gly Ile Leu Ala Lys
                660                 665                 670
Val Ala Pro His Leu Glu Val Glu Gly Glu Met Gln Gly Asp Ala Ala
            675                 680                 685
Leu Asp Glu Asp Val Arg Arg His Phe Leu Pro Ser Thr Lys Leu Ala
    690                 695                 700
Gly Ser Ala Asn Leu Leu Val Met Pro Thr Leu Asp Ala Ala Asn Ile
705                 710                 715                 720
Ala Phe Asn Leu Leu Lys Ile Thr Gly Gly Gln Gly Val Thr Val Gly
                    725                 730                 735
Pro Ile Leu Leu Gly Ala Ala Lys Pro Val His Ile Leu Asn Pro Gln
                740                 745                 750
Ala Thr Thr Arg Arg Ile Val Asn Met Thr Ala Val Ala Val Ala Glu
            755                 760                 765
Ser Asn Ala Val Arg
    770
```

<210> SEQ ID NO 64
<211> LENGTH: 2321
<212> TYPE: DNA
<213> ORGANISM: C. necator

<400> SEQUENCE: 64

| | | | | | |
|---|---|---|---|---|---|
| atgagcagca | agaatagcgg | tgatgcaccg | caacatgccc | cgaacagtcc | tgaagcgcaa | 60 |
| ttgcgcctcg | ccgcgctgga | ataccatcgc | agccccacca | agggaaagat | ccaggtaacc | 120 |
| gcgaccaagg | cgctgtccaa | ccagcgcgac | ctgtcgctgg | cctattcgcc | gggcgtggcc | 180 |
| tatgcctgcg | aggaaatcgc | caaggatccc | gccactgccg | ccgagtacac | ctcgcgcgcc | 240 |
| aacctggtgg | ccgtggtcac | caacggcacc | gccgtgctgg | gcctgggcga | tatcggcccg | 300 |
| ctggccggca | gccggtgat | ggagggcaag | ggctgcctgt | tcaagaagtt | cgccggcatc | 360 |
| gatgtgttcg | acatcgagct | cgacgcgcgc | gacccggaca | agatcgtcga | gatcgttgcc | 420 |
| gcgctcgagc | ccacgctggg | cggcgtgaac | ctggaagaca | tcaaggcgcc | ggagtgcttc | 480 |
| tacatcgagc | agaagctgcg | cgagcgcatg | aacatccccg | tcttccacga | cgaccagcac | 540 |
| ggcaccgcca | tcatttccac | cgcggcgctg | ctcaatggcc | tgaaggtggt | cggcaaggac | 600 |
| gtggccaagg | tgaagctggc | cgtgtccggc | gccggcgcgg | ctgccattgc | ctgcctggac | 660 |
| accatggtca | gcctcggcgt | gaagcgcgag | aacatctcgg | tggtggactc | caagggcgtg | 720 |
| atctatgttg | gccgcgacgc | caacatggaa | gccaacaagg | cgcgctacgc | gcaggacacc | 780 |
| tcggcgcgca | cgctggctga | catcgtcaag | gacgccgacg | tcttcctggg | ttgctcgacc | 840 |
| gccggcgtgc | tgaccgccga | gatggtcaag | accatggccg | acaagcccat | catcctggcg | 900 |
| ctggccaacc | ccgagccgga | aatccgcccg | gaagtggcca | aggccgcgcg | cccggactgc | 960 |
| atcatcgcca | ctggccgttc | ggactaccgg | aaccaggtca | caacgtgct | gtgcttcccg | 1020 |
| tacatcttcc | gcggcgcgct | ggattgcggc | gcgaccaaga | tcacggaagc | gatgaagctg | 1080 |
| gcctgcgtca | aggccatcgc | cgagctggcc | gaggccgaac | tcaacgacgc | cgttgccgcc | 1140 |
| gcctacggcg | gccgcgagct | gaagttcggc | ccggactaca | tcatcccgac | gccgttcgac | 1200 |
| cagcgcctga | tcgagaagat | cgcgccggcg | gtggccaagg | ccgcggaaga | atccggcgtg | 1260 |
| gccacgcgcc | cgatcaagga | tctcgaggcg | tatcgccagc | agctgtccac | ctatgtctat | 1320 |
| cacaccggcc | tgatcatgaa | gccggtattc | tcggccgcca | aggctgcgcc | caagcgcgtt | 1380 |
| gcctacgccg | agggcgagga | agagcgcgtg | ctgcgtgccg | tgcagaccgt | ggtcgacgaa | 1440 |
| gggctggccc | gccccaccct | gatcggccgc | ccgcacgtga | tccagatgcg | catcgagaag | 1500 |
| gccggcctgc | gcctcaaggc | cggggtggac | ttcgatctgg | tcaatccgga | agaagaccca | 1560 |
| cgctatcgcg | cctaccacga | ggcctaccac | gcgctgcgcg | gcgcgacgg | cgtgacgccg | 1620 |
| gacatggcca | aggtggcact | gcgccgctcc | aacacgctga | tcggcgccat | gctgatgcat | 1680 |
| atgggcgatg | ccgatcgcct | gctgtgcggc | acggtgggcc | gcttcgaggc | cacctcgag | 1740 |
| cacgtgcgcg | acgtgatcgg | cctggcgccg | ggcgccaagg | tgttcgccgc | gatgaacgcg | 1800 |
| ctgatgctgg | aaaagcatac | gctgttcatc | accgacacct | tcgtcaacga | cgatcccacc | 1860 |
| gccgatgaac | tggccgcgat | cacgcaactg | gccgctgagg | aaatcgcgcg | tttcggcctc | 1920 |
| gttcccaagg | tcgcgctgat | gtcgcactcg | atgttcggct | cctctacccg | tccgtcggcg | 1980 |
| cgcaagatgc | gcgaggccgc | ggggatcctt | gccaaggtgg | ctccgcacct | ggaagtggaa | 2040 |
| ggcgagatgc | agggcgacgc | tgccctggac | gaagacgtgc | gccgccactt | cctgccgtcg | 2100 |

```
accaagctgg ccggcagcgc caacctgctg gtgatgccga cgctggacgc cgccaatatc    2160
gccttcaacc tgctcaagat cacgggcggt cagggcgtca cggtgggccc gatcctgctg    2220
ggcgcggcca agccggtgca catcctgaac ccgcaagcca ctacgcgccg catcgtcaac    2280
atgacggccg tggccgtggc ggagagcaac gcggtgcgct g                        2321
```

<210> SEQ ID NO 65
<211> LENGTH: 382
<212> TYPE: PRT
<213> ORGANISM: C. necator

<400> SEQUENCE: 65

```
Met Ala Phe Ile Tyr Tyr Leu Thr His Ile His Leu Asp Phe Gly Ala
1               5                   10                  15

Val Ser Leu Leu Lys Ser Glu Cys Glu Arg Ile Gly Ile Arg Arg Pro
            20                  25                  30

Leu Leu Val Thr Asp Lys Gly Val Ala Ala Gly Val Ala Gln Arg
        35                  40                  45

Ala Ile Asp Ala Met Gln Gly Leu Gln Val Ala Val Phe Asp Glu Thr
    50                  55                  60

Pro Ser Asn Pro Thr Glu Ala Met Val Arg Lys Ala Ala Gln Tyr
65                  70                  75                  80

Arg Glu Ala Gly Cys Asp Gly Leu Val Ala Val Gly Gly Ser Ser
                85                  90                  95

Ile Asp Leu Ala Lys Gly Ile Ala Ile Leu Ala Thr His Glu Gly Glu
            100                 105                 110

Leu Thr Thr Tyr Ala Thr Ile Glu Gly Gly Ser Ala Arg Ile Thr Asp
        115                 120                 125

Lys Ala Ala Pro Leu Ile Ala Val Pro Thr Thr Ser Gly Thr Gly Ser
130                 135                 140

Glu Val Ala Arg Gly Ala Ile Ile Ile Leu Asp Asp Gly Arg Lys Leu
145                 150                 155                 160

Gly Phe His Ser Trp His Leu Leu Pro Lys Ser Ala Val Cys Asp Pro
                165                 170                 175

Glu Leu Thr Leu Gly Leu Pro Ala Gly Leu Thr Ala Ala Thr Gly Met
            180                 185                 190

Asp Ala Ile Ala His Cys Ile Glu Thr Phe Leu Ala Pro Ala Phe Asn
        195                 200                 205

Pro Pro Ala Asp Gly Ile Ala Leu Asp Gly Leu Glu Arg Gly Trp Gly
    210                 215                 220

His Ile Glu Arg Ala Thr Arg Asp Gly Gln Asp Arg Asp Ala Arg Leu
225                 230                 235                 240

Asn Met Met Ser Ala Ser Met Gln Gly Ala Met Ala Phe Gln Lys Gly
                245                 250                 255

Leu Gly Cys Val His Ser Leu Ser His Pro Leu Gly Gly Leu Lys Ile
            260                 265                 270

Asp Gly Arg Thr Gly Leu His His Gly Thr Leu Asn Ala Val Val Met
        275                 280                 285

Pro Ala Val Leu Arg Phe Asn Ala Asp Ala Pro Thr Val Val Arg Asp
    290                 295                 300

Asp Arg Tyr Ala Arg Leu Arg Arg Ala Met His Leu Pro Asp Gly Ala
305                 310                 315                 320

Asp Ile Ala Gln Ala Val His Asp Met Thr Val Arg Leu Gly Leu Pro
                325                 330                 335
```

Thr Gly Leu Arg Gln Met Gly Val Thr Glu Asp Met Phe Asp Lys Val
            340                 345                 350

Ile Ala Gly Ala Leu Val Asp His Cys His Lys Thr Asn Pro Lys Glu
        355                 360                 365

Ala Ser Ala Ala Asp Tyr Arg Arg Met Leu Glu Gln Ser Met
    370                 375                 380

<210> SEQ ID NO 66
<211> LENGTH: 1149
<212> TYPE: DNA
<213> ORGANISM: C. necator

<400> SEQUENCE: 66

```
atggcgttta tctactatct gacccacatc cacctggatt tcggcgcggt aagcctgctc      60
aagtccgaat gcgagcgcat cggcatccgc gcccgttgc tggtgaccga caagggcgtg     120
gtcgccgcgg gagtggcgca gcgtgccatc gatgcaatgc agggcctgca ggttgcggta     180
ttcgatgaaa ccccgtcgaa cccgaccgag gccatggtgc gcaaggccgc cgcacaatac     240
cgcgaggccg gctgcgacgg gctggtggca gtgggcggcg gctcgtcgat cgacctcgcc     300
aagggcatcg ccatcctggc cacgcatgag ggcgagctga ccacctatgc caccatcgaa     360
ggcggcagcg ccaggatcac cgacaaggcg cgccgctga tcgcggtgcc caccacctcg     420
ggcaccggca gcgaggtggc gcgcggcgcc atcatcatcc tggacgacgg ccgcaagctg     480
ggcttccatt cctggcattt gctgcccaag tccgccgtct gcgacccgga actgacgctg     540
gggctgccgg ccgggctgac cgcggccacc ggcatggatg cgatcgcgca ctgcatcgag     600
accttcctgg ccccgccctt caacccgccc gcggacggca ttgcgctgga cgggctggag     660
cgcggctggg gccatatcga acgcgccacc cgcgacggtc aggaccgcga cgcacgcctg     720
aacatgatga gcgcgtcgat gcaggcgca atggcgttcc agaaggggct gggctgcgtg     780
cattcgctgt cgcacccgct gggcgggctg aagatcgacg gccgcaccgg cctgcaccac     840
ggcacgctca cgcggtggt gatgccggcg gtgctgcgct tcaacgccga tgcgcccacg     900
gtggtgcgcg acgaccgcta cgcacgcctg cgccgcgcca tgcacctgcc cgacggcgcc     960
gatatcgcgc aggccgtgca cgacatgacc gtgcgcctgg gcctgcccac cgggctgcgt    1020
cagatgggtg tcaccgagga catgttcgac aaggtgattg ccggtgcgct ggtcgaccat    1080
tgccacaaga ccaacccgaa agaagccagc gccgcggatt atcggcgtat gcttgagcag    1140
tccatgtag                                                            1149
```

<210> SEQ ID NO 67
<211> LENGTH: 433
<212> TYPE: PRT
<213> ORGANISM: C. necator

<400> SEQUENCE: 67

Met Ser Leu Gln Phe Ser Glu Pro Asn Val Leu Leu Arg Arg Met Phe
1               5                   10                  15

Asp Ala Ala Val Ala Ala Gly Gln Pro Ala Arg Thr Leu Ala Arg His
            20                  25                  30

Leu Pro Pro Pro Pro Arg Gly Arg Thr Val Val Ile Gly Ala Gly Lys
        35                  40                  45

Ala Ser Ala Ala Met Ala Ser Ala Leu Glu Ala Ala Trp Pro Gly Pro
    50                  55                  60

Leu Glu Gly Leu Val Val Thr Arg Tyr Gly Tyr Ala Val Pro Cys Ser
65                  70                  75                  80

Arg Ile Glu Ile Val Glu Ala Ala His Pro Val Pro Asp Asp Ala Gly
                    85                  90                  95

Leu Ala Ala Ser Gln Arg Met Leu Ala Met Val Ala Gly Leu Ala Glu
            100                 105                 110

Asp Asp Leu Val Ile Cys Leu Val Ser Gly Gly Ser Ser Leu Leu
        115                 120                 125

Pro Leu Pro Leu Ala Gly Ile Thr Leu Asp Asp Lys Gln Arg Val Asn
    130                 135                 140

Arg Ala Leu Leu Lys Ser Gly Ala Thr Ile Ser Glu Met Asn Cys Val
145                 150                 155                 160

Arg Arg His Leu Ser Ala Ile Lys Gly Gly Arg Leu Ala Ala Ala Cys
                165                 170                 175

Tyr Pro Ala Arg Val Leu Asn Leu Leu Val Ser Asp Val Pro Gly Asp
                180                 185                 190

Asp Pro Ile Asp Ile Ala Ser Gly Pro Thr Val Pro Asp Pro Thr Thr
                195                 200                 205

Arg Ala Asp Ala Leu Ala Ile Val Lys Gln Tyr Ala Ile Asp Leu Pro
    210                 215                 220

Pro Asn Val Met Ala Val Leu Ala Ser Asp Ala Ala Glu Thr Leu Lys
225                 230                 235                 240

Ser Gly Ala Pro Arg Leu Pro Arg Ile Arg Thr Glu Phe Ile Ala Thr
                245                 250                 255

Pro Arg Leu Ala Leu Glu Ala Ala Gln Val Gly Arg Asp Ala Gly
            260                 265                 270

Phe Ala Val His Val Leu Gly Asp Ala Ile Glu Gly Val Ala Arg Asp
                275                 280                 285

Val Gly Lys Val Met Gly Gly Ile Ala Leu Ala Ala Ala Arg His Gly
            290                 295                 300

Gln Leu Phe Ala Ala Pro Cys Val Leu Leu Ser Gly Gly Glu Thr Thr
305                 310                 315                 320

Val Thr Val Arg Gly Ala Gly Arg Gly Gly Arg Asn Val Glu Leu Leu
                325                 330                 335

Leu Ser Leu Ser Leu Thr Leu Arg Gly Glu Pro Gly Ile His Ala Ile
            340                 345                 350

Ala Gly Asp Thr Asp Gly Val Asp Gly Gln Glu Glu Ile Ala Gly Ala
            355                 360                 365

Val Ile Gly Pro Asp Thr Leu Glu Arg Ala Trp Arg Ala Gly Leu Arg
            370                 375                 380

Pro Gln Asp Ala Leu Ala Ala Asn Asp Gly His Gly Phe Phe Glu Ala
385                 390                 395                 400

Leu Gly Asp Ala Val Ile Thr Gly Pro Thr Leu Thr Asn Val Asn Asp
            405                 410                 415

Phe Arg Ala Ile Leu Leu Thr Arg Ala Ser Gly Ala Cys Gly Ala Leu
                420                 425                 430

Pro

<210> SEQ ID NO 68
<211> LENGTH: 1302
<212> TYPE: DNA
<213> ORGANISM: C. necator

<400> SEQUENCE: 68
gtgagcctgc aatttccga gcccaacgtg ttgctgcggc gcatgttcga tgcggcggtc        60

-continued

| | |
|---|---|
| gcagccggcc agccggccag gaccctggcg cggcacctgc cgccgccgcc gcgcggacgc | 120 |
| accgtcgtca ttggcgcggg caaggcctcg gcggcgatgg cgagcgcgct ggaagcggca | 180 |
| tggcccgggc cgcttgaagg cctggtggtt acccgctacg gctatgcggt gccgtgctcg | 240 |
| cgcatcgaga tcgtggaggc cgctcacccc gtgccggacg atgccgggct ggccgcttcg | 300 |
| cagcgcatgc tggcgatggt ggcgggcctg gccgaggacg acctggtgat ctgcctggtc | 360 |
| tccggcggcg gatcgtcgct gctgccgctg ccgcttgccg gcattacgct cgacgacaag | 420 |
| cagcgcgtca atcgcgcgct gctgaagtcc ggcgccacga tttcggagat gaattgcgtg | 480 |
| cgccggcacc tgtccgccat caagggcggc cggctggcag ccgcatgcta tccggcgcgc | 540 |
| gtgctgaacc tgctggtttc cgatgtgccg ggcgatgacc ccatcgatat cgcctctggc | 600 |
| ccgaccgtgc ctgaccccga cacgcgcgcc gatgcgctgg ccatcgtcaa gcagtatgcg | 660 |
| atcgacttc cgcccaatgt gatggcagtg ctggcgtccg acgcggccga dacgctcaag | 720 |
| tccggcgccc cgcgcctgcc gcgcatccgc accgagttca tcgccacgcc ccggctggcg | 780 |
| ctggaagcgg cggcgcaggt gggccgcgac gcaggcttcg ccgtgcacgt gctgggcgac | 840 |
| gccatcgaag gtgaggcccg cgatgtcggc aaggtcatgg cggtatcgc gctggcagcc | 900 |
| gccaggcatg ccagctgtt tgcggcaccg tgcgtgctgc tgtccggcgg cgagaccacg | 960 |
| gtcacagtgc ggggcgcggg caggggcggc aggaacgtgg agttactgct gtcgctgtcg | 1020 |
| ctgacgctgc gcggcgaacc cggcattcat gcgattgcgg cgacaccga cggcgtcgac | 1080 |
| ggccaggaag agatcgcggg tgccgtgatc ggccccgaca cgctggaacg tgcctggcgc | 1140 |
| gccggactgc gtccgcagga tgcgctggcc gccaacgacg ccatggatt tttcgaggcg | 1200 |
| ctgggggatg ccgtcatcac cggccccacg ctgaccaacg tcaacgactt cgcgcgatc | 1260 |
| ttgctgacgc gcgcctctgg agcctgcggt gctctgccat ga | 1302 |

<210> SEQ ID NO 69
<211> LENGTH: 440
<212> TYPE: PRT
<213> ORGANISM: C. necator

<400> SEQUENCE: 69

Met Leu Ala Thr Glu Pro Gln Ala Ala Leu Leu Ser Pro Gln Arg Ala
1               5                   10                  15

Ala Ala His Pro Ala Gln Ser Asp Ala Arg Ala Leu Leu Arg Asp Leu
            20                  25                  30

Phe Asp Thr Ala Val Ala Ser Val Ser Ala Ser His Cys Leu Pro Pro
        35                  40                  45

His Leu Pro Thr Pro Pro Lys Gly Arg Thr Val Val Ile Gly Ala Gly
    50                  55                  60

Lys Ala Ala Ala Met Ala Gln Ala Val Glu Ala His Trp Gln Gly
65                  70                  75                  80

Glu Leu Ser Gly Leu Val Val Thr Arg Tyr Gly His Gly Ala Asp Cys
                85                  90                  95

Gln Arg Ile Glu Val Val Glu Ala Ala His Pro Val Pro Asp Glu Ala
            100                 105                 110

Gly Gln Arg Ala Ala Gln Arg Met Val Glu Leu Val Gln Gly Leu Thr
        115                 120                 125

Ala Asp Asp Leu Val Leu Cys Leu Ile Ser Gly Gly Gly Ser Ala Leu
    130                 135                 140

Leu Ala Ala Pro Ala Pro Gly Leu Thr Leu Ala Asp Lys Gln Ala Val
145                 150                 155                 160

```
Asn Lys Ala Leu Leu Lys Ser Gly Ala Ser Ile Gly Glu Met Asn Cys
            165                 170                 175

Val Arg Lys His Leu Ser Ala Leu Lys Gly Gly Arg Leu Ala Leu His
        180                 185                 190

Cys Ala Pro Ala Arg Val Glu Thr Leu Leu Ile Ser Asp Ile Pro Gly
    195                 200                 205

Asp Asp Pro Thr Leu Ile Ala Ser Gly Pro Thr Leu Pro Asp Ala Thr
210                 215                 220

Thr Cys Ala Asp Ala Leu Ala Val Ile Ala Lys Tyr Gly Ile Glu Val
225                 230                 235                 240

Pro Ala Asn Val Arg Ala His Leu Glu Ser Gly Ala Gly Glu Thr Pro
            245                 250                 255

Lys Pro Gly Asp Ala Arg Phe Glu Gly His Arg Asn Val Thr Leu Ala
        260                 265                 270

Thr Ala Gln Gln Ser Leu Glu Ala Ala Ala Arg Ala Arg Glu Leu
    275                 280                 285

Gly Tyr Glu Ala His Ile Leu Ser Asp Cys Ile Glu Gly Glu Ala Arg
    290                 295                 300

Glu Val Ala Glu Val His Ala Ala Ile Ala Arg Gln Val Ala Gln Arg
305                 310                 315                 320

Gly Gln Pro Phe Ser Lys Pro Cys Val Ile Leu Ser Gly Gly Glu Thr
            325                 330                 335

Thr Val Thr Val Arg Gly Lys Gly Arg Gly Arg Asn Ala Glu Phe
        340                 345                 350

Leu Leu Ala Leu Ala Val Ala Leu Asp Gly Leu Ala Gly Val His Ala
    355                 360                 365

Ile Ala Gly Asp Thr Asp Gly Ile Asp Gly Ser Glu Asp Asn Ala Gly
370                 375                 380

Ala Leu Leu Ser Pro Asp Thr Leu Thr Arg Ala Ala Arg Gly Leu
385                 390                 395                 400

Ser Ala Arg Ala His Leu Asp Asn Asn Asp Gly Tyr Gly Phe Phe Ala
            405                 410                 415

Gly Val Gly Asp Leu Ile Val Thr Gly Pro Thr Arg Thr Asn Val Asn
        420                 425                 430

Asp Phe Arg Ala Ile Leu Ile Val
        435                 440

<210> SEQ ID NO 70
<211> LENGTH: 1323
<212> TYPE: DNA
<213> ORGANISM: C. necator

<400> SEQUENCE: 70
atgctcgcca ccgaacctca agccgccctg ctctcgcccc agcgcgccgc agcgcatccc    60
gcacagtccg acgcgcgcgc gctgttgcgc gacctgttcg acaccgcggt cgcttccgtc   120
agcgctagcc attgcctgcc gccgcacctg cccacgccgc ccaagggccg cacggtggtg   180
atcggcgccg gcaaggccgc tgccgcgatg gcgcaggcgg tcgaggcgca ctggcaaggc   240
gagctgtcgg gcctggtggt gacgcgctac ggccatggcg ccgattgcca gcgcattgaa   300
gtggtcgaag ccgcgcatcc cgttcccgac gaagccggcc agcgcgccgc gcagcgcatg   360
gtggaactgg tgcagggcct gaccgccgac gacctggtgc tgtgcctgat ttccggcggc   420
ggctccgcgc tgctggccgc gcccgcgccg ggcctgacgc tggccgacaa gcaggccgtg   480
```

-continued

```
aacaaggcgc tgctcaagag tggcgcgagc atcggcgaaa tgaactgcgt gcgcaagcac    540
ctgtccgcgc tcaagggcgg acgcctggcg ctgcactgcg ccccggcccg cgtcgagacc    600
ctgctgattt ccgatatccc cggcgatgac ccgaccctga tcgcaagcgg cccgacgctg    660
cccgacgcga ccacctgcgc cgacgcgctg gccgtcatcg ccaagtacgg cattgaagtc    720
cccgccaacg tgcgcgccca cctggagagc ggcgccggcg aaacgcccaa gcccggcgat    780
gcccgcttcg aaggccaccg caacgtgacg ctggccaccg cgcagcaatc gctgaagcc     840
gcggccgcgc gcgcgcgtga actgggctac gaggcccaca tcctgtccga ctgcatcgaa    900
ggcgaagccc gcgaagtggc cgaagtgcac gctgccatcg cgcgccaggt ggcgcagcgc    960
ggccagccct tcagcaagcc ctgcgtaatc ctgtccggcg gcgagaccac cgtgaccgtg   1020
cgcggcaagg gccgcggcgg gcgcaatgcc gagttcctgc tggccctggc ggtgcgctc    1080
gacggcctgg ccggcgtgca cgcaattgcc ggcgacaccg acggcatcga cggctccgag   1140
gacaacgccg gcgcgctgct ctcgcccgac accctgaccc gcgccgccgc gcgcggtctg   1200
tcggcgcgcg cgcacctgga caacaacgac ggctacggct tctttgccgg cgtgggcgac   1260
ctgatcgtca ccggcccgac ccgcaccaat gtgaatgact tccgcgccat cctgattgtg   1320
tag                                                                 1323
```

<210> SEQ ID NO 71
<211> LENGTH: 274
<212> TYPE: PRT
<213> ORGANISM: C. necator

<400> SEQUENCE: 71

```
Met Gly Ala Leu Glu Gly Lys Val Ala Leu Val Thr Gly Ser Gly Arg
1               5                   10                  15

Gly Ile Gly Asn Ala Ile Ala Met Arg Leu Ala Arg Glu Gly Ala Arg
            20                  25                  30

Leu Val Ile Asn Asp Leu Asp Ala Glu Pro Ala Gln Gln Thr Val Glu
        35                  40                  45

Glu Leu Lys Ala Met Gly Val Glu Ala Val Ala Cys Val Gly Asn Val
    50                  55                  60

Ser Ala Pro Asp Phe Ala Asp Arg Phe Ile Asn Thr Ala Met Ser Asn
65                  70                  75                  80

Phe Lys Ser Ile Asp Ile Ile Val Asn Asn Ala Gly Phe Thr Trp Asp
                85                  90                  95

Asp Val Val Gln Lys Met Ser Asp Glu Gln Trp Tyr Ala Ile Leu Asp
            100                 105                 110

Cys His Met Thr Ala Pro Phe Arg Ile Leu Arg Ala Ala Tyr Pro His
        115                 120                 125

Ile Lys Ala Leu Ala Ala Asp Lys Glu Ala Gly Arg Glu Val Tyr
    130                 135                 140

Arg Lys Ile Val Asn Ile Ser Ser Thr Ser Gly Leu Asn Gly Asn Ala
145                 150                 155                 160

Gly Gln Ile Asn Tyr Ser Gly Ala Lys Ala Gly Val Ile Gly Met Thr
                165                 170                 175

Arg Ala Met Ala Arg Glu Trp Gly Arg Phe Asn Val Asn Val Asn Ala
            180                 185                 190

Val Ala Phe Gly Leu Ile His Thr Arg Met Thr Ser Ala Asp Ala Lys
        195                 200                 205

Ala Gly Ala Thr Val Asn Ile Glu Gly Arg Glu Ile Arg Val Gly Leu
    210                 215                 220
```

```
Asn Pro Glu Met Leu Lys Ser His Ala Gln Arg Asn Pro Leu Gly Arg
225                 230                 235                 240

Gly Gly Thr Pro Glu Glu Ala Ala Gly Gly Val Tyr Leu Phe Cys Ser
            245                 250                 255

Pro Asp Ser Asn Tyr Ile Thr Gly Gln Val Ile Ala Val Ala Gly Asn
        260                 265                 270

Val Gln

<210> SEQ ID NO 72
<211> LENGTH: 825
<212> TYPE: DNA
<213> ORGANISM: C. necator

<400> SEQUENCE: 72
atgggagcac ttgaaggcaa ggtggcactg gtcaccggtt cgggccgcgg catcggcaac       60
gccatcgcca tgcggctggc acgcgaaggc gcgcgcctgg tcatcaatga cctggacgcc      120
gagccggcgc aacagaccgt cgaggaactg aaggcaatgg gcgtcgaagc cgtggcctgc      180
gtgggcaacg tgtccgcacc ggactttgcc gaccgcttca tcaacacggc gatgagcaat      240
ttcaagagca tcgacatcat cgtcaacaac gccggcttca cctgggacga cgtggtgcag      300
aagatgagcg acgagcagtg gtacgccatc ctggactgcc acatgaccgc gccgttccgc      360
atcctgcgcg ccgcctaccc gcacatcaag gcactggccg ccgccgacaa ggaagccggc      420
cgcgaggtgt accgcaagat cgtcaatatc tcgtcgacct cgggcctgaa cggcaatgcc      480
ggccagatca actactccgg cgccaaggcc ggcgtgatcg gcatgacccg cgccatggcg      540
cgcgagtggg gccgcttcaa cgtcaacgtg aatgcggtgg cgtttgggct gatccacacc      600
cgcatgacct cggccgacgc caaggccggc gccacggtca acatcgaagg ccgtgaaatc      660
cgcgtcgggc tgaatccgga gatgctgaag tcgcacgccc agcgcaatcc gcttggccgc      720
gggggcaccc cggaagaagc gcggggcggc gtgtacctgt tctgctcgcc ggattccaac      780
tacatcaccg gccaggtgat cgcggtcgcc ggcaacgtgc agtaa                      825

<210> SEQ ID NO 73
<211> LENGTH: 249
<212> TYPE: PRT
<213> ORGANISM: C. necator

<400> SEQUENCE: 73

Met Thr Lys Leu Leu Asp Asn Gln Val Ala Leu Val Thr Gly Ala Ser
1               5                   10                  15

Arg Gly Ile Gly Arg Ala Ile Ala Leu Glu Leu Ala Arg Gln Gly Ala
            20                  25                  30

Thr Val Ile Gly Thr Ala Thr Ser Glu Ala Gly Ala Ala Gly Ile Thr
        35                  40                  45

Asp Tyr Leu Gly Ala Asp Gly Leu Lys Gly Lys Gly Ala Val Leu Asn
    50                  55                  60

Val Asn Asp Ala Ala Ala Cys Asp Ala Leu Ile Asp Glu Ile Val Lys
65                  70                  75                  80

Thr His Gly Gly Ile Gly Val Leu Val Asn Asn Ala Gly Ile Thr Gln
            85                  90                  95

Asp Gln Leu Ala Met Arg Met Lys Asp Glu Asp Trp Leu Ala Val Ile
        100                 105                 110

Gln Thr Asn Leu Thr Ser Val Phe Arg Leu Ser Arg Ala Val Leu Arg
    115                 120                 125
```

```
Pro Met Met Lys Ala Arg Gln Gly Arg Ile Ile Asn Ile Thr Ser Val
    130                 135                 140

Val Gly Ser Val Gly Asn Pro Gly Gln Met Asn Tyr Ser Ala Ala Lys
145                 150                 155                 160

Ala Gly Val Ala Gly Met Thr Arg Ser Leu Ala Glu Ile Gly Ser
                165                 170                 175

Arg Asn Val Thr Val Asn Cys Val Ala Pro Gly Phe Ile Asp Thr Asp
                180                 185                 190

Met Thr Lys Ala Leu Ser Glu Glu Gln His Ala Ser Leu Lys Thr Gln
                195                 200                 205

Ile Pro Leu Gly Arg Leu Gly Gln Pro Glu Asp Ile Ala Asn Ala Val
                210                 215                 220

Ala Phe Leu Ala Gly Pro His Ala Ala Tyr Ile Thr Gly Thr Thr Leu
225                 230                 235                 240

His Val Asn Gly Gly Met Tyr Met Asn
                245
```

<210> SEQ ID NO 74
<211> LENGTH: 750
<212> TYPE: DNA
<213> ORGANISM: C. necator

<400> SEQUENCE: 74

```
atgaccaaac ttctcgacaa ccaggttgcg ctggtcaccg gcgcctcgcg cggcatcggc      60
cgcgccatcg cgctggaact ggcccgccag ggcgccaccg tgatcggcac cgccaccagc     120
gaagccggcg cggccggcat caccgattac ctcggcgccg acggcctgaa gggcaagggc     180
gccgtgctca acgtcaatga cgcggccgct tgcgacgcgc tcatcgacga gattgtcaag     240
acccacggcg gcatcggcgt gctggtcaac aatgccggca tcacgcagga ccagttggcg     300
atgcgcatga aggacgagga ctggctggcc gtgatccaga ccaacctgac ttcggtgttc     360
cgtctgtcgc gcgcggtgct cgcgccgatg atgaaggccc gccagggccg catcatcaat     420
atcacttcgg tggtgggctc ggtcggcaac cccggccaga tgaactactc tgctgccaag     480
gcgggcgtgg cgggcatgac ccgctcgctg gccgcgaaa tcggcagccg caacgtgacc     540
gtgaactgtg tcgcgccggg ctttatcgac accgacatga ccaaggcgct gtccgaagag     600
cagcatgctt cgctcaagac gcagattccg ctgggtcgcc ttggccagcc ggaggatatc     660
gccaacgcag tggccttcct ggctggcccg catgccgctt acattaccgg cactacgctg     720
catgtgaacg gcgggatgta catgaattaa                                       750
```

<210> SEQ ID NO 75
<211> LENGTH: 249
<212> TYPE: PRT
<213> ORGANISM: C. necator

<400> SEQUENCE: 75

```
Met Asp Leu Gly Leu Asn Asp Arg Val Ala Ile Ile Thr Gly Ser Ala
1               5                   10                  15

Arg Gly Ile Gly Ala Glu Thr Ala Arg Met Leu Ala Lys Glu Gly Ala
                20                  25                  30

Ser Val Val Val Thr Asp Leu Asp Leu Asp Ala Ala Ala Glu Asn Ala
            35                  40                  45

Arg Ala Ile Glu Ser Ala Gly Gly Lys Ala Ile Ala Val Ala Cys Asp
        50                  55                  60
```

```
Val Arg Lys Val Glu Gln Val Lys Gln Leu Ala Gly Ala Ala Leu Glu
 65                  70                  75                  80

Ala Tyr Gly Arg Ile Asp Val Leu Val Asn Asn Ala Gly Leu Val Lys
                 85                  90                  95

Asp Arg Thr Ile Leu Lys Met Asp Glu Ser Asp Trp Asp Leu Val Leu
            100                 105                 110

Asp Val Thr Leu Lys Gly Ala Phe His Cys Cys Arg Ala Val Leu Pro
        115                 120                 125

Ala Met His Glu Arg Gly Trp Gly Arg Ile Ile Asn Ile Ser Ser Arg
    130                 135                 140

Ala Leu Phe Gly Asn Pro Gly Gln Ala Asn Tyr Ser Thr Ala Lys Ala
145                 150                 155                 160

Gly Ile Ile Gly Leu Thr Arg Ala Leu Ser Leu Glu Gln Ala Arg Lys
                165                 170                 175

Gly Val Thr Val Asn Ala Ile Ala Pro Gly Tyr Ile Glu Thr Glu Tyr
            180                 185                 190

Ile Lys Ser Leu Pro Asn Tyr Glu Thr Ile Leu Ala Asn Val Met Ala
        195                 200                 205

Lys Asn Ala Val Ser Phe Pro Gly Gln Thr Gly Asp Ile Ala Gly Ala
    210                 215                 220

Val Cys Phe Met Ala Ser Glu His Ala Arg Tyr Ile Thr Gly Thr Thr
225                 230                 235                 240

Leu Phe Val Thr Gly Gly Arg Tyr Gly
                245
```

<210> SEQ ID NO 76
<211> LENGTH: 750
<212> TYPE: DNA
<213> ORGANISM: C. necator

<400> SEQUENCE: 76

```
atggatcttg gattgaacga tcgtgtggcg atcatcaccg gctcggcgcg cggcatcggc    60
gccgagaccg cacgcatgct ggcaaaggaa ggcgcatcgg tcgtcgtgac cgatctcgac   120
cttgacgcag ccgccgaaaa cgcccgcgcc atcgagtccg ccggcggcaa ggccatcgcc   180
gtggcctgcg acgtgcgcaa ggtagaacag gtcaagcagc tcgccggcgc cgcgctggag   240
gcctacggcc gcatcgacgt gctggtgaac aacgccggcc tggtcaagga ccgcaccatc   300
ctgaagatgg acgagtctga ctgggacctc gtgctcgacg tcacgctgaa gggcgcgttc   360
cactgctgcc gcgccgtgct gcccgcgatg cacgagcgcg gctggggccg catcatcaac   420
atcagctcgc gcgccctgtt cggcaaccce ggccaggcca actactcgac cgccaaggcc   480
gggatcatcg gcctgacgcg cgcgctgtcg ctggagcagg cgcgcaaggg cgtgacggtc   540
aatgcgatcg ccccgggcta tatcgagacc gagtacatca agagcctgcc caactacgaa   600
accatcctcg ccaacgtaat ggcgaagaac gcggtctcct tcccggggca gaccggcgac   660
atagccggcg cggtgtgctt catggcgtcc gaacacgcgc gctacatcac gggtaccacc   720
cttttcgtga ccggaggccg ctatggctga                                    750
```

<210> SEQ ID NO 77
<211> LENGTH: 256
<212> TYPE: PRT
<213> ORGANISM: C. necator

<400> SEQUENCE: 77

Met Ser Asp Ile Met Ser Leu Ala Gly Lys Val Ile Ile Val Thr Gly

```
          1               5                  10                  15
        Ala Ala Gln Gly Ile Gly Arg Ala Thr Ala Glu Leu Ala Leu Ser Leu
                         20                  25                  30

Gly Ala Arg Val Cys Val Val Asp Leu Gln Arg Glu Ala Ile Glu Ala
                         35                  40                  45

Phe Ala Ala Glu His Pro Asp His Val Gln Ala Tyr Ala Gly Asn Val
         50                  55                  60

Ala Asp Pro Asp Phe Val Ser Ser Val Glu His Ala Val Ser Arg
         65                  70                  75                  80

Phe Gly Lys Val Asp Gly Leu Val Asn Cys Ala Gly Ile Val Arg Ala
                         85                  90                  95

Ala Met Ile Glu Asn Met Thr Leu Lys Thr Trp His Asp Val Val Asp
                        100                 105                 110

Cys His Leu Thr Gly Ala Phe Leu Trp Leu Gln Ala Val Gly Ser Arg
                        115                 120                 125

Leu Val Glu Arg Ala Lys Ala Gly Glu Lys Val Gln Gly Ser Ile Ile
                        130                 135                 140

Asn Val Ser Ser Asp Ala Gly Arg Arg Gly Ser Val Gly Gln Ile Asn
        145                 150                 155                 160

Tyr Ala Ser Ala Lys Ala Gly Met Leu Gly Met Thr Met Ser Ala Ala
                        165                 170                 175

Arg Glu Trp Gly Lys Phe Gly Val Arg Thr Asn Ser Val Cys Leu Gly
                        180                 185                 190

Met Val Glu Thr Pro Met Thr Glu Thr Ile Arg Gly Glu Arg Phe Arg
                        195                 200                 205

Asp Thr Tyr Leu Ala Met Ile Pro Met Gly Arg Trp Ala Gln Pro Glu
                        210                 215                 220

Glu Ile Ala Ala Pro Ile Cys Phe Leu Leu Ser Asp Ala Ala Gly Tyr
        225                 230                 235                 240

Val Leu Gly Gln His Ile Gly Val Asn Gly Gly Leu His Met Ala Ser
                        245                 250                 255
```

<210> SEQ ID NO 78
<211> LENGTH: 771
<212> TYPE: DNA
<213> ORGANISM: C. necator

<400> SEQUENCE: 78

```
atgtctgaca tcatgtccct ggccggcaag gtcatcatcg ttaccggcgc cgcgcagggc      60
atcggccgcg ccaccgccga actcgcgctg agcctgggcg ccagggtttg cgtggtcgac     120
ctgcagcgcg aagcgatcga ggcgtttgcc gccgagcacc ccgaccatgt ccaggcctat     180
gccggcaacg tggctgatcc cgacttcgtg tcgtcgtccg tcgagcacgc ggtgtcccgc     240
ttcggcaagg tcgatggcct ggtcaactgc gccggcatcg tgcgcgccgc gatgatcgag     300
aacatgacgc tgaagacctg cacgacgtg gtcgactgcc acctgaccgg cgccttcctc      360
tggctgcagg cggtgggctc cgcctcgtc gagcgcgcca aggcgggcga aaggtgcag       420
ggctcgatca tcaacgtctc gtccgatgcc ggccgccgcg gctcggtcgg ccagatcaac     480
tacgcgtcgg ccaaggccgg catgttgggc atgaccatga gcgccgcgcg cgagtggggc     540
aagttcggcg tgcgcacgaa ctcggtctgc ctgggcatgg tggaaacgcc gatgaccgag     600
accatccgcg gcgagcgctt ccgcgacacc tacctggcga tgatcccgat gggccgctgg     660
gcgcagccgg aagaaatcgc cgcgccgatc tgcttcctgc tgtccgacgc cgccggctac     720
```

```
                gtgctgggcc agcacatcgg cgtgaacggc ggcctgcaca tggcgagctg a              771
```

<210> SEQ ID NO 79
<211> LENGTH: 256
<212> TYPE: PRT
<213> ORGANISM: C. necator

<400> SEQUENCE: 79

Met Gly Ala Thr Ala Ser Ala Gln Pro Trp Arg Ala Gly Asp Ala Val
1               5                   10                  15

Ser Asn Phe Tyr Asp Leu Ser Gly Lys Ala Ala Leu Val Thr Gly Gly
            20                  25                  30

Ala Lys Gly Leu Gly Arg Ala Ile Val Ala Gln Leu Ile Asp Ser Gly
        35                  40                  45

Ala Arg Val His Ala Trp Asp Ile Val Pro Phe Gln Met Glu Gly Ala
    50                  55                  60

Ser Thr Glu Val Val Asp Val Ser Asp Ala Gly Gln Val Gly Leu Ala
65                  70                  75                  80

Leu Ala Arg Leu Val Asp Ala Gly Tyr Arg Phe Asp Ile Leu Val Asn
                85                  90                  95

Ala Ala Gly Tyr Leu Gly Pro Met Gln Pro Phe Glu Asn His Glu Ala
            100                 105                 110

Ser Gln Trp His Arg Ile Ile Ala Val Asn Leu Leu Gly Thr Met Tyr
        115                 120                 125

Val Val Gln Ala Met Leu Pro His Met Leu Arg Trp Gly Gly Gly Arg
130                 135                 140

Ile Ile Asn Met Gly Ser Leu Ala Gly Lys Glu Gly Leu Ala Gly Leu
145                 150                 155                 160

Ala Ala Tyr Ser Ala Ala Ser Gly Gly Val Val Val Leu Thr Lys Ala
                165                 170                 175

Ile Gly Arg Glu Leu Val Lys Arg Asn Ile Tyr Val Asn Cys Val Ala
            180                 185                 190

Pro Gly Pro Met Asp Thr Asp Met Ile His Gly Leu Gly Ser His Glu
        195                 200                 205

Val Ala Ala Met Val Ala Asp Ser Pro Ala Gly Arg Leu Gly Asp Pro
    210                 215                 220

Ala Glu Ala Ala His Leu Val Ala Trp Leu Cys Ser Asp Ala Ser Arg
225                 230                 235                 240

Phe Asn Ala Gly Ala Val Phe Asp Met Ser Gly Gly Arg Ala Arg Phe
                245                 250                 255

<210> SEQ ID NO 80
<211> LENGTH: 771
<212> TYPE: DNA
<213> ORGANISM: C. necator

<400> SEQUENCE: 80

```
gtgggcgcta ccgcttctgc gcagccatgg cgcgctgggg atgccgtgtc aaatttctat      60
gatctttcgg ggaaggcagc gctggtgacc ggcggtgcaa aggggctcgg ccgggcgatc     120
gttgcgcaac tgatcgacag tggtgcgcgt gtgcatgctt gggatatcgt gccgttccag     180
atggaaggtg ccagcactga ggtcgtcgat gtctccgatg ccgggcaggt ggggctggcg     240
ctggcgcgac tggtcgatgc gggatatcgc ttcgacatcc tggtcaacgc tgccggctac     300
cttggcccga tgcagccatt cgagaatcac gaggcttcac aatggcatcg catcatcgcc     360
gtgaatctcc tggggaccat gtacgtcgtg caggcgatgt tgccgcacat gttgcgctgg     420
```

```
ggaggcggcc gtatcatcaa tatgggctcg ctggccggca aggagggggct ggccgggctg    480 gctgcatact ccgcggccag cggcggcgtg gtcgttctaa ccaaagcaat cggccgcgaa    540
ctggtgaagc gcaacatcta cgttaattgc gtggcgcccg ggcccatgga taccgacatg    600
attcacgggc tcggcagcca cgaggtggcg gccatggttg ctgatagccc ggccgggcgc    660
ctgggcgatc cggccgaggc tgcgcacctg gtagcgtggc tatgttcgga cgccagccgc    720
tttaatgcag gcgctgtctt tgacatgtcc ggtgggcggg cgcgatttta a             771
```

<210> SEQ ID NO 81
<211> LENGTH: 162
<212> TYPE: PRT
<213> ORGANISM: C. necator

<400> SEQUENCE: 81

```
Met Ala Glu Leu Leu Lys Asp Arg Asp Trp Ile Ala Ala Arg Ile Pro
1               5                   10                  15

His Gln Gly Thr Met Cys Leu Leu Asp Gly Val Leu Ala Trp Asp Pro
            20                  25                  30

Ala Ser Val Arg Cys Thr Ser Ala Thr His Thr Arg Ala Asp Asn Pro
        35                  40                  45

Leu Arg Ala His Gly Arg Leu Ala Ala Leu Ser Gly Ile Glu Tyr Ala
    50                  55                  60

Ala Gln Ala Met Ala Val His Gly Ala Leu Leu Ala Glu Ala Glu Ser
65                  70                  75                  80

Gly Met Gly Ala Gln Arg Pro Arg Ser Gly Tyr Leu Ala Ser Val Arg
                85                  90                  95

Lys Leu Val Leu His Val Glu Arg Leu Asp Asp Ile Asp Ala Pro Leu
            100                 105                 110

Gln Val Glu Ala Gln Arg Ile Ser Gly Glu Gly Ser Ser Val Leu Tyr
        115                 120                 125

Ala Phe Thr Val Ser Ala Lys Gly Gln Ala Leu Leu Ser Gly Arg Ala
    130                 135                 140

Ala Val Ile Leu Asp Ala Ala Ala Val Gly Gln Ser Ala Asp Arg Gly
145                 150                 155                 160

Ala Gly
```

<210> SEQ ID NO 82
<211> LENGTH: 489
<212> TYPE: DNA
<213> ORGANISM: C. necator

<400> SEQUENCE: 82

```
atggctgagc tgctgaaaga ccgcgactgg atcgcggcac gcattccgca ccagggcacg     60
atgtgcctgc tcgacggcgt gctggcctgg gatccggcat cggttcgctg cacgtcagcc    120
acgcatacgc gcgcggacaa cccgctgcgc gcgcacggcc ggctggccgc gctcagcggc    180
attgaatacg cggcacaggc catggccgtg cacggcgcat gctggcgga agcggaatca     240 ggaatgggcg cacagcgccc gcgctcgggc tacctggcca gcgtgcgcaa gctggtgctc    300
catgtggagc ggctcgacga tatcgacgcg ccgctgcagg tcgaggcaca gcgcatcagc    360
ggtgaaggca gcagcgtgct gtatgccttc accgtcagcg ccaagggcca ggcactgctg    420
tcaggccgcg cggcggtcat cctggatgcc gccgcagtcg gccaaagcgc cgaccgcggc    480
gccggctga                                                            489
```

<210> SEQ ID NO 83
<211> LENGTH: 254
<212> TYPE: PRT
<213> ORGANISM: C. necator

<400> SEQUENCE: 83

```
Met Gly Thr Gln Arg Phe Asp Pro Ser His Val Ala Val Val Thr Gly
1               5                   10                  15

Ala Ala Arg Gly Ile Gly Leu Gly Ile Ala Thr Gln Leu Ala Arg Gln
            20                  25                  30

Gly Leu Ala Val Ala Leu Leu Asp Arg Asp Ala Ala Leu Asp Thr
        35                  40                  45

Ala Val Gly Ala Leu Val Ala Glu Gly Phe Asn Ala Phe Gly Ala Ser
    50                  55                  60

Ala Asp Leu Thr Asp Ser Ala Ala Val Asn Asp Ala Phe Ala Gln Ile
65                  70                  75                  80

Gln Ala Arg Thr Gly Arg Val Asp Tyr Leu Val Asn Asn Ala Gly Ala
                85                  90                  95

Val Arg Asp Met Arg Phe Leu Lys Met Thr Asp Asp Trp Asp Leu
            100                 105                 110

Val Ile Asp Thr Asn Leu Arg Ser Gln Phe Leu Cys Cys Arg Ala Ala
        115                 120                 125

Leu Pro Gly Met Val Glu Arg Gly Tyr Gly Arg Val Val Asn Ile Ser
    130                 135                 140

Ser Arg Ala Trp Leu Gly Gly Phe Gly Gln Ala Asn Tyr Ser Ala Ala
145                 150                 155                 160

Lys Gly Gly Val Val Ser Leu Thr Arg Ser Leu Ala Ile Glu Phe Ala
                165                 170                 175

Ser Lys Gly Val Thr Val Asn Ala Val Ala Pro Gly Ile Val Asp Thr
            180                 185                 190

Pro Leu Phe Arg Gly Phe Ala Pro Asp Val Gln Ala Arg Leu Gln Lys
        195                 200                 205

Ser Val Pro Val Gln Arg Ile Gly Thr Ala Asp Ile Ala Asn Ala
    210                 215                 220

Val Ser Phe Phe Leu Asp Pro Gln Ser Ser Tyr Val Thr Gly Gln Val
225                 230                 235                 240

Leu Tyr Val Cys Gly Gly Arg Ser Leu Ser Ser Pro Ser Val
                245                 250
```

<210> SEQ ID NO 84
<211> LENGTH: 765
<212> TYPE: DNA
<213> ORGANISM: C. necator

<400> SEQUENCE: 84

```
atgggcacgc aacgcttcga tccttccat  gtggcggtgg tcaccggcgc agcgcgcggc    60
atcggcctgg gcatcgccac gcaactggcc cgccaggggc tggccgtggc cctgctcgac   120
cgcgacgccg ccgcgctcga taccgccgtc ggtgcgctgg ttgccgaggg cttcaacgcc   180
ttcggcgcca gcgccgacct gaccgactcg gccgccgtca acgatgcctt cgcgcaaatc   240
caggcgcgca ctggccgcgt cgactacctg gtcaacaacg ccggcgccgt gcgcgacatg   300
cgcttcctga agatgaccga cgacgactgg gacctggtca tcgataccaa cctgcgctcg   360
cagttcctgt gctgccgcgc ggcgctgccc ggcatggtcg agcgcggcta cgggcgcgtg   420
gtcaatatct cgtcgcgggc gtggctgggc ggattcggac aggctaacta ctccgcggcc   480
```

-continued

```
aagggcggcg tagtcagcct gacgcgctcg ctggcgatcg agtttgcgag caagggcgtc      540
accgtcaatg cagtggcgcc gggcatcgtc gatacccgc  tgttccgcgg cttcgcgccc      600
gacgtgcagg cccggctgca gaagtcggtc ccggtgcagc gcatcggcac cgccgacgat      660
atcgccaacg cggtcagctt cttcctcgac ccgcagtcgt cctacgtgac cgggcaggtg      720
ctctatgtct gtggcggccg cagcctgtcg tcgccaagcg tgtaa                      765
```

<210> SEQ ID NO 85
<211> LENGTH: 230
<212> TYPE: PRT
<213> ORGANISM: C. necator

<400> SEQUENCE: 85

```
Met Asn Phe Asn Gly Lys Asn Val Leu Ile Thr Gly Ala Arg Gly Asn
1               5                   10                  15

Leu Gly Arg Ala Val Ala Gln Ala Phe Ala Gln Ala Gly Ala Arg Val
            20                  25                  30

Val Leu Leu Asp Arg His Ala Ala Pro Leu Pro Glu Ala Gly Thr Gly
        35                  40                  45

His Leu Thr Leu Gln Ala Asp Leu Leu Asp Ala Ala Lys Leu Ser Glu
    50                  55                  60

Ala Val Ala Gln Ala Val Gln Ser Cys Gly Arg Ile Asp Val Val Cys
65                  70                  75                  80

Asn Leu Ala Gly Gly Phe Ala Met Gly Pro Ser Val His Glu Thr Ser
                85                  90                  95

Ala Glu Ala Trp Asn His Val Phe Asp Met Asn Val Gly Thr Val Leu
            100                 105                 110

Asn Met Ala Arg Ala Val Val Pro His Met Leu Ala Ala Gly Gly Gly
        115                 120                 125

Ala Ile Val Asn Val Gly Ala Asn Ser Ala Ala Arg Gly Leu Ala Gln
    130                 135                 140

Met Ser Ala Tyr Cys Ala Ser Lys Asp Ala Leu Ala Arg Val Thr Glu
145                 150                 155                 160

Ser Met Ser Ala Glu Leu Arg Asp Gln Gly Ile Arg Val Asn Ala Val
                165                 170                 175

Leu Pro Ser Val Leu Asp Thr Pro Glu Asn Arg Gln Ala Met Pro Asp
            180                 185                 190

Ala Asp Ala Ala Arg Trp Val Ser Leu Asp Ala Leu Ala Asp Val Ile
        195                 200                 205

Leu Phe Leu Ala Ser Asp Ala Ala Arg Ala Val Gln Gly Ala Leu Leu
    210                 215                 220

Pro Val Val Asn Arg Ala
225                 230
```

<210> SEQ ID NO 86
<211> LENGTH: 693
<212> TYPE: DNA
<213> ORGANISM: C. necator

<400> SEQUENCE: 86

```
atgaacttca cggcaagaa cgtattgatc accggcgcac gcggcaacct gggccgcgcc      60
gtggcacagg ccttcgcgca ggcaggcgcg cgcgtggtgc tgctggaccg catgcagcg     120 ccgctgcccg aagcgggcac cggccacctc acgctgcagg cggacctgct ggatgccgcc     180
aagctgagcg aggccgtcgc gcaagcggtt cagtcatgcg gccgcatcga cgtggtgtgc     240
```

```
aacctggccg gcggcttcgc catgggccca agcgtgcatg aaaccagcgc cgaggcctgg      300
aaccacgtgt tcgacatgaa cgtgggcacg gtgctgaaca tggcgcgcgc ggtggtgccg      360
cacatgctgg ccgccggcgg cggcgccatc gtcaacgtgg gtgccaactc ggcggcgcgc      420
gggctggcgc agatgagcgc ttattgcgcc tcgaaggacg cgctggcgcg tgtgaccgaa      480
tcgatgtcgg cagagctgcg cgaccagggc atccgcgtca acgcggtgct gcccagcgtg      540
ctggatacgc ccgagaaccg ccaggccatg ccggatgccg atgccgcgcg ctgggtcagc      600
ctggatgcgc tggccgacgt gatcctgttc ctggcctcgg atgcggcgcg cgcggtgcag      660
ggcgcgctgc tgccggtggt caaccgcgcc tga                                  693
```

\<210\> SEQ ID NO 87
\<211\> LENGTH: 243
\<212\> TYPE: PRT
\<213\> ORGANISM: C. necator

\<400\> SEQUENCE: 87

```
Met Thr Asn Pro Thr Val Leu Val Thr Gly Ser Ser Arg Gly Ile Gly
1               5                   10                  15

Arg Ala Ile Ala Leu Arg Leu Ala Arg Asp Gly Tyr Asp Val Val Val
            20                  25                  30

His Cys Arg Ser Arg Arg Asp Glu Ala Asp Ser Val Ala Asp Ala Val
        35                  40                  45

Arg Ala Cys Gly Arg Lys Ala Arg Val Leu Cys Phe Asp Val Ala Arg
    50                  55                  60

Arg Glu Glu Ala Ala Ala Leu Leu Ala Asp Ile Ala His Asp
65                  70                  75                  80

Cys Tyr Tyr Gly Val Val Cys Asn Ala Gly Leu Ala Arg Asp Ala Ala
                85                  90                  95

Phe Pro Ala Met Ser Gly Ala Glu Trp Asp Glu Val Val His Thr Asn
            100                 105                 110

Leu Asp Ala Phe Tyr Asn Val Leu Asn Pro Val Val Met Pro Met Val
        115                 120                 125

Gln Arg Arg Gln Pro Gly Arg Ile Val Thr Leu Ser Ser Val Ser Gly
    130                 135                 140

Leu Val Gly Asn Arg Gly Gln Thr Asn Tyr Ser Ala Ala Lys Ala Gly
145                 150                 155                 160

Ile Ile Gly Ala Thr Lys Ala Leu Ala Ile Glu Leu Ala Lys Arg Ala
                165                 170                 175

Ile Thr Val Asn Cys Val Ala Pro Gly Leu Ile Asp Thr Asp Met Val
            180                 185                 190

Glu Gln His Val Arg Asp Glu Ala Leu Arg Met Ile Pro Ala Arg Arg
        195                 200                 205

Leu Gly Thr Pro Asp Glu Val Ala Ala Thr Val Ala Phe Leu Met Ser
    210                 215                 220

Pro Asp Ala Gly Tyr Ile Thr Arg Gln Val Ile Ser Val Asn Gly Gly
225                 230                 235                 240

Met Phe Gly
```

\<210\> SEQ ID NO 88
\<211\> LENGTH: 732
\<212\> TYPE: DNA
\<213\> ORGANISM: C. necator

\<400\> SEQUENCE: 88

```
atgaccaatc cgaccgtact ggttacggga tcgtcgcgcg gcatcggtcg cgccatcgcc    60
ctgcggctgg cccgcgacgg ctatgacgtg gtggtgcatt gccgctcgcg ccgcgacgaa   120
gccgactccg tcgccgacgc ggtgcgcgct tgcggccgca aggcccgcgt gttgtgcttc   180
gacgtggccc ggcgcgagga agccgctgcc gcgctgctgg ccgatatcgc cgcacatgac   240
tgctactacg gcgtggtgtg caacgccggc ctggcgcgcg acgcggcctt cccggccatg   300
agcggcgcca atgggacga ggtggtgcac accaacctcg acgccttcta caacgtgctc   360
aacccggtgg tgatgccgat ggtgcagcga cgccagcccg gcgcatcgt cacgctgtcg   420
tcggtctcgg gcctggtggg caaccgcggc cagaccaact acagcgcggc caaggccggc   480
atcatcggcg ccaccaaggc gctggcaatc gaacttgcca aacgcgccat cacagtcaac   540
tgcgtggcgc ccggcctgat cgacaccgac atggtcgagc agcacgtgcg cgacgaggcg   600
ctgcgcatga tcccggcgcg gcggctcggc acgcccgacg aagtggccgc gaccgtggcc   660
ttcctgatgt cgcccgacgc tggctatatc acgcgccagg tgatctcggt caacggggc   720
atgttcggat ga                                                      732
```

<210> SEQ ID NO 89
<211> LENGTH: 312
<212> TYPE: PRT
<213> ORGANISM: C. necator

<400> SEQUENCE: 89

```
Met Lys Ile Leu Val Leu Gly Ala Gly Met Gly Gly Tyr Tyr Gly
1               5                   10                  15

Ala Arg Leu Ile Glu Ala Gly Ala Asp Val Thr Phe Met Leu Arg Pro
                20                  25                  30

Gly Arg Ala Arg Ala Leu Glu Arg Val Gly Leu Ala Val Arg Ser Glu
            35                  40                  45

Leu Gly Asp Phe His Arg Pro Val Lys Met Val Leu Ala Gly Gln Val
        50                  55                  60

Gly Ala Gln Phe Asp Val Val Leu Leu Ala Cys Lys Ala Tyr Asp Leu
65                  70                  75                  80

Ala Asp Ala Ile Arg Ala Ile Ser Pro Ala Val Gly Arg Asp Thr Ala
                85                  90                  95

Val Leu Pro Leu Leu Asn Gly Leu Asp Ala Tyr Asp Arg Leu Asp Gln
            100                 105                 110

Cys Phe Gly Arg Gln Arg Val Leu Gly Gly Val Ala Tyr Ile Ala Thr
        115                 120                 125

Thr Leu Ala Ala Asp Gly Thr Val Val His Ala Gly Arg Met Asp Arg
    130                 135                 140

Leu Val Val Gly Pro Arg Ala Ala Gln Gly Ser Ala Leu Ala Ala Asp
145                 150                 155                 160

Phe His Ala Leu Val Ser Arg Ala Ala Gly Thr Arg Glu Leu Ser Gly
                165                 170                 175

Ala Ile Gly Gln Glu Leu Trp Asn Lys Trp Ala Met Ile Ala Ala Gly
            180                 185                 190

Ala Val Met Thr Cys Leu Met Arg Gly Thr Val Ala Asp Ile Met Lys
        195                 200                 205

Thr Gln Asp Gly Arg Arg Leu Met Leu Asp Ala Ile Ala Glu Cys Arg
    210                 215                 220

Thr Val Ala Gln Leu Tyr Gly His Ala Ile Pro Glu Pro Val Val Ala
225                 230                 235                 240
```

Ala Met Gln Ala Arg Leu Leu Asp Glu Ala Ser Thr Trp Ala Ala Ser
            245                 250                 255

Met Met Arg Asp Ile Ala Arg Gly Ala Pro Arg Ile Glu Ala Asp Ala
            260                 265                 270

Ile Val Gly Asp Leu Ile Lys Arg Ala Ala Gly Tyr Gly His Glu Leu
            275                 280                 285

Pro Leu Ser Arg Ala Ala Tyr Cys His Leu Gln Val Tyr Gln Arg Gln
            290                 295                 300

Arg Ala Ala His Gln Thr Ala Gly
305                 310

<210> SEQ ID NO 90
<211> LENGTH: 939
<212> TYPE: DNA
<213> ORGANISM: C. necator

<400> SEQUENCE: 90

```
atgaagattc ttgtactcgg tgccgggggc atgggcggct actatggcgc gcgcctgatc      60
gaggcaggcg cggatgtcac cttcatgttg cggcccggcc gcgcgcgggc gctggaacgg     120
gttggcctgg ccgtgcgtag cgaacttggc gacttccatc gcccggtaaa gatggtcctg     180
gccggtcagg tcggcgcgca gttcgacgtg gtactgctgg catgcaaggc ctacgacctt     240
gccgacgcga tccgggccat cagcccggcc gttggccggg acactgccgt attgcctctg     300
ctcaacggcc ttgacgccta tgaccggctc gaccagtgct ttggcaggca acgcgtgctg     360
ggtggagtcg catacatagc gacaacgctg gcggcggatg aaccgtcgt gcacgccggc     420
cgcatggacc ggctggtagt cggcccgcgc gccgcgcagg ggtcggcatt ggccgcggat     480
ttccatcgcg tggtgtccag gcggccggt acgcgtgagc tatcgggcgc catcgggcag     540
gagctgtgga acaagtgggc catgattgcc gccggcgcag tgatgacatg cctgatgcgc     600
gggaccgtgg cggacatcat gaagacccag gatggccgtc gcctgatgct tgacgcgatt     660
gcggagtgcc gcacggtggc gcaactgtac ggccatgcca tccctgaacc cgttgtcgct     720
gccatgcagg cccgactgct ggacgaagca tcgacctggg ctgcctcgat gatgcgggat     780
atagcgcggg gcgccccacg catagaagcc gacgccatcg tcggcgatct catcaagcgc     840
gcagccgggt acgggcatga gcttccgttg agccgtgcgg catattgcca cctgcaggtc     900
tatcagcgcc agcgcgctgc gcaccagacg gctggttga                           939
```

<210> SEQ ID NO 91
<211> LENGTH: 325
<212> TYPE: PRT
<213> ORGANISM: C. necator

<400> SEQUENCE: 91

Met Lys Val Cys Ile Tyr Gly Ala Gly Ala Ile Gly Gly Tyr Val Gly
1               5                   10                  15

Ala Gln Leu Ala Arg Ala Gly Ala Glu Val Ser Phe Val Ala Arg Gly
            20                  25                  30

Pro His Leu Ala Ala Met Gln Glu His Gly Val Arg Leu Leu Ile Asp
            35                  40                  45

Gly Glu Glu Arg Val Ala Lys Val Arg Cys Thr Ser Asp Pro Arg Glu
        50                  55                  60

Leu Gly His Gln Asp Tyr Val Phe Ile Thr Leu Lys Ala His Ser Val
65                  70                  75                  80

```
Pro Gly Val Val Asp Gln Met Gln Pro Leu Leu Gly Pro Glu Thr Ala
             85                  90                  95

Val Val Thr Gly Val Asn Gly Ile Pro Tyr Trp Tyr Phe Tyr Lys His
        100                 105                 110

Gly Gly Asp Leu Ala Gly Ser Thr Leu Glu Ser Val Asp Pro Gly Gly
            115                 120                 125

Arg Gln Trp Lys Gly Leu Gly Pro Glu Arg Ala Ile Gly Cys Val Val
        130                 135                 140

Tyr Pro Ala Ala Glu Ile Val Ala Pro Gly Val Ile Lys His Val Tyr
145                 150                 155                 160

Gly Lys Lys Phe Pro Leu Gly Glu Pro Asp Gly Ser Arg Ser Ala Arg
                165                 170                 175

Val Thr Arg Leu Ser Glu Met Met Met Ala Ala Asp Leu Asp Ala Pro
            180                 185                 190

Val Arg Asp Asn Ile Arg Asp Glu Ile Trp Leu Lys Leu Trp Gly Asn
        195                 200                 205

Leu Cys Phe Asn Pro Ile Ser Ala Leu Thr His Ala Thr Leu Asp Val
    210                 215                 220

Ile Thr Ala Asp Pro Ala Thr Arg Ala Leu Ser Arg Gln Met Met Val
225                 230                 235                 240

Glu Ala Gln Gly Ile Ala Glu Arg Phe Gly Val Lys Phe Arg Val Asp
                245                 250                 255

Val Glu Arg Arg Ile Asp Gly Ala Gly Ala Val Gly Ala His Lys Thr
            260                 265                 270

Ser Met Leu Gln Asp Leu Glu Ala Gly Arg Ala Met Glu Ile Asp Pro
        275                 280                 285

Leu Leu Thr Val Val Gln Glu Met Gly Arg Leu Val Ala Gln Pro Thr
    290                 295                 300

Pro Met Cys Asp Ala Val Leu Gly Leu Ile Lys Gln Arg Asp Thr Met
305                 310                 315                 320

Ala Lys Leu Ala Ala
                325

<210> SEQ ID NO 92
<211> LENGTH: 978
<212> TYPE: DNA
<213> ORGANISM: C. necator

<400> SEQUENCE: 92
atgaaagtgt gtatctacgg cgcaggcgcg atcggcggct atgtcggggc gcagctggcg      60
cgcgcggggg cggaggtcag cttcgtcgcg cgcggccccc atctcgcggc aatgcaggaa     120
catggtgtca ggctgctgat cgacggcgag gagcgcgtgg ccaaggtgcg ctgcaccagc     180
gatccgcgcg agctcggaca ccaggactat gtgttcatca ccctcaaggc gcattccgtg     240
ccgggcgtgg tggaccagat gcagccgctg ctggggccgg aaaccgcggt cgtcaccggc     300
gtcaacggca ttccgtactg gtatttctac aagcatggcg gcgacttggc cggcagcacg     360
ctggaaagcg tcgatcccgg cgggcgccaa tggaagggcc tggggccgga gcgggcgatc     420
ggctgcgtgg tctatcccgc ggctgagatc gttgcgccgg cgtgatcaa gcacgtctac     480 ggcaagaagt tccgctgggg cgagccggat ggcagccgct cggcgcgcgt gacccggctc     540
agcgaaatga tgatggccgc cgacctggac gccccggtgc gcgacaatat ccgcgacgag     600
atctggctca agctgtgggg caacctgtgc ttcaacccga tcagcgcgct cacgcatgcc     660
acgctcgacg tcatcaccgc cgacccggcc acgcgggcgc tgtcgcgcca gatgatggtt     720
```

```
gaggcgcagg gcatcgccga gcgcttcggg gtgaaattcc gcgtcgacgt ggagcggcgc    780
atcgacggcg ccggtgccgt gggcgcgcac aagacctcga tgctgcagga cctggaggcc    840
gggcgggcca tggaaatcga cccgctgctg accgtggtgc aggaaatggg acgtctggtc    900
gcgcagccca cgccgatgtg cgatgccgtg ctgggtctga tcaagcagcg cgacacgatg    960
gccaagctgg ccgcctga                                                   978
```

<210> SEQ ID NO 93
<211> LENGTH: 312
<212> TYPE: PRT
<213> ORGANISM: C. necator

<400> SEQUENCE: 93

```
Met Lys Ile Leu Val Leu Gly Ala Gly Gly Met Gly Gly Tyr Tyr Gly
1               5                   10                  15

Ala Arg Leu Ile Glu Ala Gly Ala Asp Val Thr Phe Met Leu Arg Pro
                20                  25                  30

Gly Arg Ala Arg Ala Leu Glu Arg Val Gly Leu Ala Val Arg Ser Glu
            35                  40                  45

Leu Gly Asp Phe His Arg Pro Val Lys Met Val Leu Ala Gly Gln Val
50                  55                  60

Gly Ala Gln Phe Asp Val Val Leu Leu Ala Cys Lys Ala Tyr Asp Leu
65                  70                  75                  80

Ala Asp Ala Ile Arg Ala Ile Ser Pro Ala Val Gly Arg Asp Thr Ala
                85                  90                  95

Val Leu Pro Leu Leu Asn Gly Leu Asp Ala Tyr Asp Arg Leu Asp Gln
            100                 105                 110

Cys Phe Gly Arg Gln Arg Val Leu Gly Gly Val Ala Tyr Ile Ala Thr
        115                 120                 125

Thr Leu Ala Ala Asp Gly Thr Val Val His Ala Gly Arg Met Asp Arg
130                 135                 140

Leu Val Val Gly Pro Arg Ala Ala Gln Gly Ser Ala Leu Ala Ala Asp
145                 150                 155                 160

Phe His Ala Leu Val Ser Arg Ala Ala Gly Thr Arg Glu Leu Ser Gly
                165                 170                 175

Ala Ile Gly Gln Glu Leu Trp Asn Lys Trp Ala Met Ile Ala Ala Gly
            180                 185                 190

Ala Val Met Thr Cys Leu Met Arg Gly Thr Val Ala Asp Ile Met Lys
        195                 200                 205

Thr Gln Asp Gly Arg Arg Leu Met Leu Asp Ala Ile Ala Glu Cys Arg
210                 215                 220

Thr Val Ala Gln Leu Tyr Gly His Ala Ile Pro Glu Pro Val Val Ala
225                 230                 235                 240

Ala Met Gln Ala Arg Leu Leu Asp Glu Ala Ser Thr Trp Ala Ala Ser
                245                 250                 255

Met Met Arg Asp Ile Ala Arg Gly Ala Pro Arg Ile Glu Ala Asp Ala
            260                 265                 270

Ile Val Gly Asp Leu Ile Lys Arg Ala Ala Gly Tyr Gly His Glu Leu
        275                 280                 285

Pro Leu Ser Arg Ala Ala Tyr Cys His Leu Gln Val Tyr Glu Arg Gln
290                 295                 300

Arg Ala Ala His Gln Thr Ala Gly
305                 310
```

<210> SEQ ID NO 94
<211> LENGTH: 939
<212> TYPE: DNA
<213> ORGANISM: C. necator

<400> SEQUENCE: 94

| | | | | | |
|---|---|---|---|---|---|
| atgaagattc | ttgtactcgg | tgccgggggc | atgggcggct | actatggcgc | gcgcctgatc | 60 |
| gaggcaggcg | cggatgtcac | cttcatgttg | cggcccggcc | gcgcgcgggc | gctggaacgg | 120 |
| gttggcctgg | ccgtgcgtag | cgaacttggc | gacttccacc | gcccggtaaa | gatggtcctg | 180 |
| gccggtcagg | tcggcgcgca | gttcgacgtg | gtactgctgg | catgcaaggc | ctacgacctt | 240 |
| gccgacgcga | tccgggccat | cagcccggcc | gttggccggg | acactgcggt | attgcctctg | 300 |
| ctcaacggcc | ttgacgccta | tgaccggctc | gaccagtgct | ttggcaggca | acgcgtgctg | 360 |
| ggtggagtcg | catacatagc | gacaacgctg | gcggcggatg | aaccgtcgt | gcacgccggc | 420 |
| cgcatggacc | ggctggtagt | cggcccgcgc | gccgcgcagg | ggtcggcatt | ggccgcggat | 480 |
| ttccatgcgc | tggtgtccag | gcggccggt | acgcgtgagc | tatcgggcgc | catcgggcag | 540 |
| gagctgtgga | acaagtgggc | catgattgcc | gccggcgcag | tgatgacatg | cctgatgcgc | 600 |
| gggaccgtgg | cggacatcat | gaagacccag | gatggccgtc | gcctgatgct | tgacgcgatt | 660 |
| gcggagtgcc | gcacggtggc | gcaactgtac | ggccatgcca | tccctgaacc | cgttgtcgct | 720 |
| gccatgcagg | cccgactgct | ggacgaagca | tcgacctggg | ctgcctcgat | gatgcgggat | 780 |
| atagcgcggg | gcgccccacg | catagaagcc | gacgccatcg | tcggcgatct | catcaagcgc | 840 |
| gcagccgggt | acgggcatga | gcttccgttg | agccgtgcgg | catattgcca | cctgcaggtc | 900 |
| tatgagcgcc | agcgcgctgc | gcaccagacg | gctggctga | | | 939 |

<210> SEQ ID NO 95
<211> LENGTH: 368
<212> TYPE: PRT
<213> ORGANISM: C. necator

<400> SEQUENCE: 95

Met Lys Thr Lys Ala Ala Ile Ala Trp Lys Ala Gly Ala Pro Leu Thr
1               5                   10                  15

Ile Glu Asp Val Asp Leu Asp Gly Pro Arg Ala Gly Glu Val Leu Val
            20                  25                  30

Glu Val Lys Ala Thr Gly Ile Cys His Thr Asp Tyr Tyr Thr Leu Ser
        35                  40                  45

Gly Ala Asp Pro Glu Gly Ile Phe Pro Ala Ile Leu Gly His Glu Gly
    50                  55                  60

Ala Gly Ile Val Thr Asp Val Gly Pro Gly Val Thr Ser Leu Lys Pro
65                  70                  75                  80

Gly Asp His Val Ile Pro Leu Tyr Thr Pro Glu Cys Arg Gln Cys Lys
                85                  90                  95

Phe Cys Leu Ser Arg Lys Thr Asn Leu Cys Gln Ala Ile Arg Ala Thr
            100                 105                 110

Gln Gly Lys Gly Leu Met Pro Asp Gly Thr Ser Arg Phe Ser Ile Asp
        115                 120                 125

Gly Lys Pro Ile Phe His Tyr Met Gly Thr Ser Thr Phe Ala Asn His
    130                 135                 140

Ile Val Val Pro Glu Ile Ala Leu Ala Lys Ile Arg Pro Asp Ala Pro
145                 150                 155                 160

Phe Asp Lys Val Cys Tyr Ile Gly Cys Gly Val Thr Thr Gly Val Gly

```
            165                 170                 175
Ala Val Leu Phe Thr Ala Lys Val Glu Ala Gly Ala Asn Val Val
        180                 185                 190

Phe Gly Leu Gly Gly Ile Gly Leu Asn Val Ile Gln Ala Ala Lys Met
        195                 200                 205

Val Gly Ala Asp Lys Ile Ile Gly Val Asp Leu Asn Pro Gly Arg Glu
        210                 215                 220

Ala Met Ala Arg Lys Phe Gly Met Thr His Phe Ile Asn Pro Lys Asp
225                 230                 235                 240

Val Glu Asn Val Val Asp His Ile Ile Gln Leu Thr Asp Gly Gly Ala
                245                 250                 255

Asp Tyr Ser Phe Glu Cys Ile Gly Asn Thr Gln Val Met Arg Gln Ala
            260                 265                 270

Leu Glu Cys Cys His Lys Gly Trp Gly Lys Ser Ile Ile Ile Gly Val
            275                 280                 285

Ala Glu Ala Gly Ala Glu Ile Ser Thr Arg Pro Phe Gln Leu Val Thr
        290                 295                 300

Gly Arg Glu Trp Lys Gly Ser Ala Phe Gly Gly Ala Arg Gly Arg Thr
305                 310                 315                 320

Asp Val Pro Arg Ile Val Asp Trp Tyr Met Glu Gly Lys Leu Asn Ile
                325                 330                 335

Asp Asp Leu Ile Thr His Thr Leu Pro Leu Arg Ile Asn Glu Gly
            340                 345                 350

Phe Asp Leu Met Lys Arg Gly Glu Ser Ile Arg Ser Val Val Leu Tyr
        355                 360                 365

<210> SEQ ID NO 96
<211> LENGTH: 1107
<212> TYPE: DNA
<213> ORGANISM: C. necator

<400> SEQUENCE: 96
atgaaaacca aagccgccat cgcctggaaa gccggcgccc cgctgaccat tgaagacgtg     60
gacctggacg gcccgcgcgc cggggaagtg ctggtggaag tcaaggccac cggcatctgc    120
cataccgatt actacaccct gtccggcgcc gacccggaag gcatcttccc ggcaatcctg    180
ggccatgagg gcgccggcat cgtcaccgac gttggccccg cgtgacctc gctcaagccc    240 ggcgaccacg tgatcccgct gtacacgccg gaatgccgcc agtgcaagtt ctgcctgtcg    300
cgcaagacca acctgtgcca ggcgatccgc gccacgcagg gcaagggcct gatgccggac    360
ggcacctcgc gcttttccat cgacggcaag ccgatcttcc actacatggg cacctcgacc    420
ttcgccaacc acatcgtggt gccggagatc gcgctggcca agatccgccc ggatgcgccg    480
ttcgacaagg tctgctacat cggctgcggc gtcaccaccg gcgtgggcgc ggtgctgttc    540
accgccaagg tggaagccgg cgccaacgtg gtggtgtttg gcctgggcgg catcggcctg    600
aacgtgatcc aggcggccaa gatggtgggc gccgacaaga tcatcggcgt ggacctgaac    660
ccgggccgcg aagccatggc gcgcaagttc ggcatgaccc acttcatcaa cccgaaggac    720
gtggagaacg tggtcgacca catcatccag ctgaccgacg gcgtgcagac ctattcgttc    780
gaatgcatcg gcaacacgca ggtcatgcgc caggcgctgg agtgctgcca caagggctgg    840
ggcaagtcga tcatcatcgg cgtggccgag gccggcgcgg agatctcgac gcgccgttc    900 cagctggtga ccgggcgcga gtggaagggc tcggcctttg gcggcgcgcg cggggcgcacc    960 gatgtgccca ggatcgtcga ctggtacatg gaaggcaagc tcaatatcga cgacctgatc   1020
```

```
acgcacacgc tgccgctgga gcgcatcaac gagggcttcg acctgatgaa gcgcggcgag    1080
tcgatccgct ccgtggtgct ctactga                                        1107
```

<210> SEQ ID NO 97
<211> LENGTH: 447
<212> TYPE: PRT
<213> ORGANISM: C. necator

<400> SEQUENCE: 97

```
Met Asn Ser Pro Ser Leu Asp Ala Phe Leu Ala Gly Val Ala Arg Arg
1               5                   10                  15

Asp Pro Asn Gln Pro Glu Phe Leu Gln Ala Val Lys Glu Val Met Met
            20                  25                  30

Thr Leu Trp Pro Phe Val Glu Arg Asn Pro Arg Tyr Ala Asp Gln Ala
        35                  40                  45

Leu Leu Glu Arg Leu Val Glu Pro Glu Arg Val Ile Gln Phe Arg Val
    50                  55                  60

Ala Trp Thr Asp Asp Gln Asn Arg Val Gln Val Asn Arg Ala Phe Arg
65                  70                  75                  80

Val Gln His Ser Ser Ala Ile Gly Pro Phe Lys Gly Gly Met Arg Phe
                85                  90                  95

His Pro Thr Val Asn Leu Ser Val Leu Lys Phe Leu Gly Phe Glu Gln
            100                 105                 110

Thr Phe Lys Asn Ala Leu Thr Thr Leu Pro Met Gly Gly Gly Lys Gly
        115                 120                 125

Gly Ser Asp Phe Asp Pro Lys Gly Lys Ser Asp Gly Glu Val Met Arg
    130                 135                 140

Phe Cys Gln Ala Leu Val Thr Glu Leu Phe Arg His Leu Gly Pro Asp
145                 150                 155                 160

Thr Asp Ile Pro Ala Gly Asp Ile Gly Val Gly Ala Arg Glu Val Gly
                165                 170                 175

Phe Met Ala Gly Met Met Lys Lys Leu Ser Asn Gln Ser Ala Cys Val
            180                 185                 190

Phe Thr Gly Lys Gly Leu Ala Tyr Gly Gly Ser Leu Met Arg Pro Glu
        195                 200                 205

Ala Thr Gly Tyr Gly Thr Val Tyr Phe Ala Gln Glu Met Leu His Arg
    210                 215                 220

Arg Gly Arg Ala Phe Asp Gly Leu Arg Val Leu Ile Ser Gly Ser Gly
225                 230                 235                 240

Asn Val Ala Gln Tyr Ala Ala Glu Lys Ala Ile Glu Leu Gly Ala Thr
                245                 250                 255

Val Leu Thr Leu Ser Asp Ser Gly Gly Val Leu His Tyr Pro Gln Gly
            260                 265                 270

Met Thr Thr Glu Gln Leu Ala Glu Val Met Ala Phe Lys Asn Glu Glu
        275                 280                 285

Arg Gly Arg Leu Ser Asp Phe Ala Ala Arg His Gly Met Ala Phe Glu
    290                 295                 300

Ala Gly Arg Thr Pro Trp His Val Pro Ala Asp Val Ala Leu Pro Cys
305                 310                 315                 320

Ala Thr Gln Asn Glu Leu Asp Gly Asn Asp Ala Glu Thr Leu Leu Gly
                325                 330                 335

Asn Gly Val Ile Cys Val Ala Glu Gly Ala Asn Met Pro Ser Thr Leu
            340                 345                 350
```

```
Glu Ala Val Asp Arg Phe Val Asp Ala Lys Ile Leu Tyr Ala Pro Gly
            355                 360                 365

Lys Ala Ser Asn Ala Gly Gly Val Ala Thr Ser Gly Leu Glu Met Ser
        370                 375                 380

Gln Asn Ala Met Arg Leu Ser Trp His His Ala Glu Val Asp Glu Lys
385                 390                 395                 400

Leu His Ala Ile Met Lys Asp Ile His Gln Asn Cys Ile His His Gly
                405                 410                 415

Gln Lys Ala Asp Gly Tyr Ile Asn Tyr Val Glu Gly Ala Asn Ile Ala
            420                 425                 430

Gly Phe Val Lys Val Ala Asp Ala Met Leu Ala Gln Gly Val Ile
        435                 440                 445
```

<210> SEQ ID NO 98
<211> LENGTH: 1344
<212> TYPE: DNA
<213> ORGANISM: C. necator

<400> SEQUENCE: 98

```
gtgaattctc cctcccttga cgcattcctg gcggggggttg cccgccgcga ccccaatcaa     60
cctgaattcc tccaggccgt gaaggaagtg atgatgacgc tctggccctt gtcgagcgc     120
aatccgcgct acgccgacca ggccctgctc gagcggctgg tggagcccga gcgcgtgatc    180
cagttccgcg tggcctggac cgacgaccag aaccgggtgc aggtcaaccg cgccttccgc    240
gtgcagcaca gctcggccat cggcccgttc aagggcggca tgcgcttcca cccgactgtg    300
aacctgtcgg tgctgaagtt cctgggcttc gagcagacct tcaagaacgc gctgaccacg    360
ctgcccatgg gcggcggcaa gggcggctcg gactttgatc ccaagggcaa gtccgatggc    420
gaagtgatgc gtttctgcca ggcgctggtg accgagctgt tccgccacct gggcccggat    480
accgacatcc cggccggcga catcggcgtg gcgcacgtg aagtcggctt tatggccggc    540
atgatgaaga gctttccaa ccagtccgcc tgcgtcttca ccggcaaggg cctgcctac    600
ggcggcagcc tgatgcgccc ggaagcgacc ggctacggca cggtctactt tgcgcaggag    660
atgctgcacc ggcgcgggcg cgcttttcgac ggcctgcgcg tgctgatctc gggctcgggc    720
aacgtggccc agtacgcggc cgagaaggcg atcgagctgg cgccacggt gctgacgctg    780
tccgattcag gcggcgtgct gcactaccg cagggcatga ctaccgagca gctggccgaa    840
gtgatggcct tcaagaatga agagcgcggc cgcctgtctg actttgccgc cgccacggc    900
atggccttcg aagccggccg caccccgtgg cacgtgcccg ccgacgtggc gctgccgtgc    960
gccacccaga acgagctgga cggcaacgac gccgagaccc tgctcggcaa tggcgtgatc    1020
tgcgtggccg aaggcgccaa catgccgtcg acgctggaag ccgtggaccg ctttgtcgat    1080
gcgaagatcc tctacgcccc gggcaaggcc agcaatgccg gcggcgttgc cacttccggc    1140
ctggaaatgt cgcagaacgc catgcgcctg tcctggcacc atgccgaggt cgacgagaag    1200
ctgcacgcga tcatgaagga catccaccag aactgcatcc accacgggca gaaggcggat    1260
ggctatatca actacgtgga aggcgcgaac atcgccggct tcgtcaaggt agccgacgcc    1320
atgctggcgc aaggcgtgat ctga                                           1344
```

<210> SEQ ID NO 99
<211> LENGTH: 312
<212> TYPE: PRT
<213> ORGANISM: C. necator

<400> SEQUENCE: 99

```
Met Asn Ala Lys His Glu Lys Tyr Gln Arg Leu Ile Asp Tyr Cys Lys
1               5                   10                  15

Ala Met Pro Pro Thr Pro Thr Ala Val Ala His Pro Cys Asp Gln Ser
            20                  25                  30

Ser Leu Glu Gly Ala Val Glu Ala Arg Leu Gly Leu Ile Ala Pro
        35                  40                  45

Ile Leu Val Gly Pro Arg Ser Arg Ile Glu Asp Ala Ala Arg Ala Ala
50                  55                  60

Gly Ile Asp Ile Arg Glu Tyr Pro Ile Val Asp Ala Glu His Ser His
65                  70                  75                  80

Ala Ala Ala Ala Ala Val Gln Leu Val Arg Glu Ser Lys Ala Glu
                85                  90                  95

Ala Leu Met Lys Gly Ser Leu His Thr Asp Glu Leu Met Gly Ala Val
            100                 105                 110

Val Ala Gly Asn Ser Gly Leu Arg Thr Gly Arg Arg Ile Ser His Cys
        115                 120                 125

Phe Val Met Asp Val Pro Gly His Glu Asp Ala Leu Ile Ile Thr Asp
130                 135                 140

Ala Ala Val Asn Ile Ala Pro Thr Leu Ala Glu Lys Ala Gly Ile Leu
145                 150                 155                 160

Gln Asn Ala Ile Asp Leu Ala His Ala Leu Gln Val Lys Glu Val Arg
                165                 170                 175

Val Ala Ile Leu Ser Ala Met Glu Thr Val Asn Pro Met Val Pro Ser
            180                 185                 190

Thr Leu Asp Ala Ala Ala Leu Cys Lys Met Val Asp Arg His Gln Ile
        195                 200                 205

Thr Gly Ala Ile Val Asp Gly Pro Leu Ala Leu Asp Asn Ala Ile Asn
210                 215                 220

Leu Asp Ala Ala Arg Ile Lys Lys Ile Asp Ser Pro Val Ala Gly Arg
225                 230                 235                 240

Ala Asn Val Leu Leu Val Pro Asp Leu Asp Ala Gly Asn Met Leu Ala
                245                 250                 255

Lys Ser Leu Thr Phe Leu Ala Gly Ala Asp Ala Ala Gly Ile Val Leu
            260                 265                 270

Gly Ala Arg Val Pro Ile Ile Leu Thr Ser Arg Ala Asp Ser Val Met
        275                 280                 285

Thr Arg Leu Ala Ser Cys Ala Val Ala Leu Val Ala Lys Ala Arg
290                 295                 300

Arg Glu Ser Gly Gln Val Ala Gly
305                 310
```

<210> SEQ ID NO 100
<211> LENGTH: 939
<212> TYPE: DNA
<213> ORGANISM: C. necator

<400> SEQUENCE: 100

```
gtgaacgcca agcatgagaa gtaccagcgc ctgattgatt actgcaaggc catgccgcct      60
acaccgaccg cggtggcgca tccgtgcgac cagtcttcgc tggaaggcgc cgtagaggcc     120
gcccggctgg gcctgatcgc gccgatcctg gttgggccgc gttcccgcat cgaggacgcc     180
gcgcgcgcgg ccggcattga catccgcgag tacccgattg tcgatgccga gcacagccat     240
gcggcggcgg ctgccgcagt gcaactggtg cgcgaaagca aggcagaggc tctgatgaag     300
```

```
ggcagtctgc acaccgatga gctgatggga gccgtggtcg cgggtaacag cggcttgcgc    360
accggccggc gcatcagcca ctgcttcgtg atggatgtgc ccggccacga ggacgctctg    420
atcatcaccg acgctgccgt caatattgcc ccgacgcttg ccgagaaggc cggcatcctg    480
caaaacgcga tcgacctggc ccatgccttg caggtcaagg aggtccgcgt ggcgatcctg    540
tcggcgatgg agaccgtcaa cccgatggtt ccgtccacac tggatgccgc cgcgctgtgc    600
aagatggtcg accgccacca gatcaccggc gcgatcgtcg acggaccgct tgcgctggac    660
aacgcgatca acctggacgc ggcgcggatc aagaagatcg actcaccggt ggccgggcgc    720
gccaatgtcc tgctggtgcc tgacctggac gccggcaaca tgctcgccaa gagcctgacc    780
ttcctggccg gcgccgacgc cgcaggcatc gtgctgggcg cgcgcgtgcc catcatcctg    840
accagccgtg ccgactcggt catgacccgg ctggcgtcgt gcgcggtggc cgcgctggtg    900
gccaaggcac gccgcgagtc cggccaggtg gcggggtga                          939
```

<210> SEQ ID NO 101
<211> LENGTH: 344
<212> TYPE: PRT
<213> ORGANISM: C. necator

<400> SEQUENCE: 101

```
Met Lys Ala Ile Leu Arg Ile Ile Asp Arg Ala Arg Ala Ala Pro Arg
1               5                   10                  15

Arg Ile Val Leu Cys Glu Ala Glu Asp Pro Arg Ile Leu Gln Ala Ala
            20                  25                  30

Gln Arg Ala Ser Gln Glu Gly Ile Ala Arg Ile Val Leu Val Gly Asn
        35                  40                  45

Thr Arg Gln Ile Asn Ala Ala Ala Ala Ile His Gly Ile Gly Leu Asp
    50                  55                  60

Gly Met Thr Leu Val Asp Pro Ser Thr Ser Ala Leu Thr Pro Ser Phe
65                  70                  75                  80

Ala Gln Gln Leu Phe Ala Leu Arg Gln Lys Lys Gly Met Thr Leu Asp
                85                  90                  95

Glu Ala Lys Arg Ala Val Leu Asp Pro Leu Cys Phe Ala Asn Leu Met
            100                 105                 110

Val Arg Leu Gly His Ala Asp Gly Ser Val Ala Gly Ala Asp His Thr
        115                 120                 125

Thr Ala Asp Val Val Arg Asn Ala Ile Gln Leu Ile Gly Leu Ala Pro
    130                 135                 140

Gly Phe Arg Leu Val Ser Ser Phe Phe Leu Met Met Leu Cys Glu Pro
145                 150                 155                 160

Phe His Thr Leu Lys Gly Gly Leu Ile Phe Ser Asp Cys Gly Leu Val
                165                 170                 175

Val Asp Pro Asp Ala Asp Ala Leu Ala Asp Ile Ala Met Ala Ala Ala
            180                 185                 190

Asp Ser Ala Arg Thr Leu Leu Met Glu Glu Pro Arg Val Ala Met Leu
        195                 200                 205

Ser Phe Ser Thr Ser Gly Ser Ala Ser His Ala Ala Val Asp Lys Val
    210                 215                 220

Val Ala Ala Thr Glu Arg Val Arg Ala Gln Pro Asp Leu Ala Ile
225                 230                 235                 240

Asp Gly Asp Val Gln Leu Asp Ala Ala Ile Val Ala Glu Ile Ala Ala
                245                 250                 255

Arg Lys Val Ala His Ser Gln Val Asn Gly His Ala Asn Val Leu Val
```

```
                260                 265                 270
Phe Pro Ser Leu Glu Ala Gly Asn Ile Gly Tyr Lys Leu Ala Glu Arg
            275                 280                 285

Val Gly Gly Ala Lys Ala Ile Gly Pro Met Leu Gln Gly Leu Asn Lys
        290                 295                 300

Pro Ala Asn Asp Leu Ser Arg Gly Cys Ser Ala Asp Asp Val Phe His
305                 310                 315                 320

Val Ile Ala Val Thr Val Gln Ala Gln Thr Ala Glu Gln Ala
                325                 330                 335

Ser Lys Gly Glu Gln Ala Ala Ala
            340
```

<210> SEQ ID NO 102
<211> LENGTH: 1035
<212> TYPE: DNA
<213> ORGANISM: C. necator

<400> SEQUENCE: 102

```
atgaaagcca tcctccgcat catcgaccgc gcccgcgccg cgcctcgccg catcgtgctg     60
tgcgaggccg aagacccgcg catcctgcag gccgcgcagc gcgcgtcgca ggaaggcatc    120
gcgcgcatcg tgctggtcgg caacacgcgc cagatcaacg ccgccgcggc catccacggc    180
atcgggctgg acggcatgac gctggtcgac ccatcgacct cggcgctcac gccctcgttc    240
gcgcagcaac tctttgcgct cgccagaag aagggcatga cgctcgatga agccaagcgc     300
gccgtgctcg atccgctgtg cttcgccaac ctgatggtgc gccttggcca cgccgacggt    360
tcggtggcgg cgccgacca caccaccgcc gacgtggtgc gcaacgcgat ccagctgatc     420
gggctggcac ccggcttccg gctggtgtcg agcttcttcc tgatgatgct gtgcgagcct    480
ttccacacgc tcaagggcgg gctgatcttc tccgactgcg gctggtggt ggatccggat      540
gccgatgcgc ttgccgatat cgccatggcc gcggccgaca cgcacgcac gctgctgatg     600
gaagagccgc gcgtggccat gctgtcgttc tcgaccagtg gcagcgccag ccatgcggca    660
gtggacaagg tggtggccgc caccgagcgc gtgcgcgcgc aacgcccgga cctggccatc    720
gatggcgacg tgcagctcga tgccgccatc gtcgccgaga tcgccgcgcg caaggtcgcg    780
cattcgcagg tgaacggcca cgccaacgtg ctggtgtttc ccagcctgga gccggcaat    840
atcggctaca agctggccga gcgggtcggt ggcgccaagg ccatcgggcc gatgctgcag    900
gggctgaaca gcccgccaa cgacctctcg cgcggctgca gcgcggacga tgtgttccat   960
gtcatcgccg tcaccgtggt ccaggcgcaa gccaccgcgg aacaggccag caagggcgag  1020
caggcggcgg catga                                                  1035
```

<210> SEQ ID NO 103
<211> LENGTH: 387
<212> TYPE: PRT
<213> ORGANISM: E. coli

<400> SEQUENCE: 103

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
```

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
            85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
    195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Gly Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Glu Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 104
<211> LENGTH: 1164
<212> TYPE: DNA
<213> ORGANISM: E. coli

<400> SEQUENCE: 104
atgaacaact ttaatctgca cacccaacc cgcattctgt ttggtaaagg cgcaatcgct      60
ggtttacgcg aacaaattcc tcacgatgct cgcgtattga ttacctacgg tgcggcagc    120 gtgaaaaaa ccggcgttct cgatcaagtt ctggatgccc tgaaaggcat ggacgtgctg    180

```
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat taaaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc tgatcgaaga tggtccgaaa gccctgaaag agccagaaaa ctacgatgtg     720
cgcgccaacg tcatgtgggg ggcgacgcag gcgctgaacg gtttgattgg cgctggcgta     780
ccgcaggact gggcaacgca tatgctgggc acgaactga ctgcgatgca cggtctggat      840
cacgcgcaaa cactggctat cgtcctgcct gcactgtgga atgaaaaacg cgagaccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa aatcatgaca ttacgttgga tgtcagccgc    1140
cgtatatacg aagccgcccg ctaa                                          1164
```

<210> SEQ ID NO 105
<211> LENGTH: 382
<212> TYPE: PRT
<213> ORGANISM: S. cerevisiae

<400> SEQUENCE: 105

```
Met Arg Ala Leu Ala Tyr Phe Lys Lys Gly Asp Ile His Phe Thr Asn
1               5                   10                  15

Asp Ile Pro Arg Pro Glu Ile Gln Thr Asp Glu Val Ile Ile Asp
            20                  25                  30

Val Ser Trp Cys Gly Ile Cys Gly Ser Asp Leu His Glu Tyr Leu Asp
        35                  40                  45

Gly Pro Ile Phe Met Pro Lys Asp Gly Glu Cys His Lys Leu Ser Asn
    50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110

Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140

Gly Phe Ala Glu Gln Val Val Val Ser Gln His His Ile Ile Pro Val
145                 150                 155                 160

Pro Lys Glu Ile Pro Leu Asp Val Ala Leu Val Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
```

```
                195                 200                 205
Leu Lys Gly Met Gly Ala Ser Lys Ile Val Ser Glu Ile Ala Glu
            210                 215                 220
Arg Arg Ile Glu Met Ala Lys Lys Leu Gly Val Glu Val Phe Asn Pro
225                 230                 235                 240
Ser Lys His Gly His Lys Ser Ile Glu Ile Leu Arg Gly Leu Thr Lys
                245                 250                 255
Ser His Asp Gly Phe Asp Tyr Ser Tyr Asp Cys Ser Gly Ile Gln Val
            260                 265                 270
Thr Phe Glu Thr Ser Leu Lys Ala Leu Thr Phe Lys Gly Thr Ala Thr
        275                 280                 285
Asn Ile Ala Val Trp Gly Pro Lys Pro Val Pro Phe Gln Pro Met Asp
        290                 295                 300
Val Thr Leu Gln Glu Lys Val Met Thr Gly Ser Ile Gly Tyr Val Val
305                 310                 315                 320
Glu Asp Phe Glu Glu Val Val Arg Ala Ile His Asn Gly Asp Ile Ala
                325                 330                 335
Met Glu Asp Cys Lys Gln Leu Ile Thr Gly Lys Gln Arg Ile Glu Asp
            340                 345                 350
Gly Trp Glu Lys Gly Phe Gln Glu Leu Met Asp His Lys Glu Ser Asn
        355                 360                 365
Val Lys Ile Leu Leu Thr Pro Asn Asn His Gly Glu Met Lys
    370                 375                 380
```

<210> SEQ ID NO 106
<211> LENGTH: 1149
<212> TYPE: DNA
<213> ORGANISM: S. cerevisiae

<400> SEQUENCE: 106

```
atgagagctt tggcatattt caagaagggt gatattcact tcactaatga tatccctagg    60
ccagaaatcc aaaccgacga tgaggttatt atcgacgtct cttggtgtgg gatttgtggc   120
tcggatcttc acgagtactt ggatggtcca atcttcatgc taaagatgg agagtgccat    180
aaattatcca acgctgcttt acctctggca atgggccatg agatgtcagg aattgtttcc   240
aaggttggtc ctaaagtgac aaaggtgaag gttggcgacc acgtggtcgt tgatgctgcc   300
agcagttgtg cggacctgca ttgctggcca cactccaaat tttacaattc aaaccatgt    360
gatgcttgtc agagggcag tgaaaatcta tgtacccacg ccggttttgt aggactaggt    420
gtgatcagtg gtggctttgc tgaacaagtc gtagtctctc aacatcacat tatcccggtt    480
ccaaaggaaa ttcctctaga tgtggctgct ttagttgagc ctctttctgt cacctggcat    540
gctgttaaga tttctggttt caaaaaaggc agttcagcct tggttcttgg tgcaggtccc    600
attgggttgt gtaccatttt ggtacttaag ggaatggggg ctagtaaaat tgtagtgtct    660
gaaattgcag agagaagaat agaaatggcc aagaaactgg gcgttgaggt gttcaatccc    720
tccaagcacg gtcataaatc tatagagata ctacgtggtt tgaccaagag ccatgatggg    780
tttgattaca gttatgattg ttctggtatt caagttactt tcgaaacctc tttgaaggca    840
ttaacattca aggggacagc caccaacatt gcagtttggg gtccaaaacc tgtcccattc    900
caaccaatgg atgtgactct ccaagagaaa gttatgactg gttcgatcgg ctatgttgtc    960
gaagacttcg aagaagttgt tcgtgccatc cacaacggag acatcgccat ggaagattgt   1020
aagcaactaa tcactggtaa gcaaaggatt gaggacggtt gggaaaaggg attccaagag   1080
```
ttgatggatc acaaggaatc caacgttaag attctattga cgcctaacaa tcacggtgaa   1140
atgaagtaa                                                            1149

<210> SEQ ID NO 107
<211> LENGTH: 367
<212> TYPE: PRT
<213> ORGANISM: E. coli

<400> SEQUENCE: 107

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu

<210> SEQ ID NO 108
<211> LENGTH: 1104
<212> TYPE: DNA
<213> ORGANISM: E. coli

<400> SEQUENCE: 108

```
atggaccgca ttattcaatc accgggtaaa tacatccagg gcgctgatgt gattaatcgt      60
ctgggcgaat acctgaagcc gctggcagaa cgctggttag tggtgggtga caaatttgtt     120
ttaggttttg ctcaatccac tgtcgagaaa agctttaaag atgctggact ggtagtagaa     180
attgcgccgt ttggcggtga atgttcgcaa atgagatcg accgtctgcg tggcatcgcg      240
gagactgcgc agtgtggcgc aattctcggt atcggtggcg aaaaaccct cgatactgcc      300
aaagcactgg cacatttcat gggtgttccg gtagcgatcg caccgactat cgcctctacc     360
gatgcaccgt gcagcgcatt gtctgttatc tacaccgatg agggtgagtt tgaccgctat     420
ctgctgttgc aaataaccc gaatatggtc attgtcgaca ccaaaatcgt cgctggcgca      480
cctgcacgtc tgttagcggc gggtatcggc gatgcgctgg caacctggtt tgaagcgcgt     540
gcctgctctc gtagcggcgc gaccaccatg gcgggcggca gtgcaccca ggctgcgctg      600
gcactggctg aactgtgcta caacaccctg ctggaagaag cgaaaaagc gatgcttgct      660
gccgaacagc atgtagtgac tccggcgctg agcgcgtga ttgaagcgaa cacctatttg      720
agcggtgttg gttttgaaag tggtggtctg gctgcggcgc acgcagtgca taacggcctg     780
accgctatcc cggacgcgca tcactattat cacggtgaaa aagtggcatt cggtacgctg     840
acgcagctgg ttctggaaaa tgcgccggtg gaggaaatcg aaaccgtagc tgcccttagc     900
catgcggtag gtttgccaat aactctcgct caactggata ttaaagaaga tgtcccggcg     960
aaaatgcgaa ttgtggcaga agcggcatgt gcagaaggtg aaaccattca caacatgcct    1020
ggcggcgcga cgccagatca ggtttacgcc gctctgctgg tagccgacca gtacggtcag    1080
cgtttcctgc aagagtggga ataa                                          1104
```

<210> SEQ ID NO 109
<211> LENGTH: 351
<212> TYPE: PRT
<213> ORGANISM: H. sapiens

<400> SEQUENCE: 109

```
Met Ala Ala Ala Pro Leu Lys Val Cys Ile Val Gly Ser Gly Asn Trp
1               5                   10                  15

Gly Ser Ala Val Ala Lys Ile Ile Gly Asn Asn Val Lys Lys Leu Gln
                20                  25                  30

Lys Phe Ala Ser Thr Val Lys Met Trp Val Phe Glu Glu Thr Val Asn
            35                  40                  45

Gly Arg Lys Leu Thr Asp Ile Ile Asn Asn Asp His Glu Asn Val Lys
        50                  55                  60

Tyr Leu Pro Gly His Lys Leu Pro Glu Asn Val Val Ala Met Ser Asn
65                  70                  75                  80

Leu Ser Glu Ala Val Gln Asp Ala Asp Leu Leu Val Phe Val Ile Pro
                85                  90                  95

His Gln Phe Ile His Arg Ile Cys Asp Glu Ile Thr Gly Arg Val Pro
            100                 105                 110

Lys Lys Ala Leu Gly Ile Thr Leu Ile Lys Gly Ile Asp Glu Gly Pro
        115                 120                 125
```

```
Glu Gly Leu Lys Leu Ile Ser Asp Ile Ile Arg Glu Lys Met Gly Ile
    130                 135                 140
Asp Ile Ser Val Leu Met Gly Ala Asn Ile Ala Asn Glu Val Ala Ala
145                 150                 155                 160
Glu Lys Phe Cys Glu Thr Thr Ile Gly Ser Lys Val Met Glu Asn Gly
                165                 170                 175
Leu Leu Phe Lys Glu Leu Leu Gln Thr Pro Asn Phe Arg Ile Thr Val
            180                 185                 190
Val Asp Asp Ala Asp Thr Val Glu Leu Cys Gly Ala Leu Lys Asn Ile
        195                 200                 205
Val Ala Val Gly Ala Gly Phe Cys Asp Gly Leu Arg Cys Gly Asp Asn
    210                 215                 220
Thr Lys Ala Ala Val Ile Arg Leu Gly Leu Met Glu Met Ile Ala Phe
225                 230                 235                 240
Ala Arg Ile Phe Cys Lys Gly Gln Val Ser Thr Ala Thr Phe Leu Glu
                245                 250                 255
Ser Cys Gly Val Ala Asp Leu Ile Thr Thr Cys Tyr Gly Gly Arg Asn
            260                 265                 270
Arg Arg Val Ala Glu Ala Phe Ala Arg Thr Gly Lys Thr Ile Glu Glu
        275                 280                 285
Leu Glu Lys Glu Met Leu Asn Gly Gln Lys Leu Gln Gly Pro Gln Thr
    290                 295                 300
Ser Ala Glu Val Tyr Arg Ile Leu Lys Gln Lys Gly Leu Leu Asp Lys
305                 310                 315                 320
Phe Pro Leu Phe Thr Ala Val Tyr Gln Ile Cys Tyr Glu Ser Arg Pro
                325                 330                 335
Val Gln Glu Met Leu Ser Cys Leu Gln Ser His Pro Glu His Thr
            340                 345                 350
```

<210> SEQ ID NO 110
<211> LENGTH: 1056
<212> TYPE: DNA
<213> ORGANISM: H. sapiens

<400> SEQUENCE: 110

```
atggcagcgg cgcccctgaa agtgtgcatc gtgggctcgg ggaactgggg ttcagctgtt    60
gcaaaaataa ttggtaataa tgtcaagaaa cttcagaaat tgcctccac agtcaagatg    120
tgggtctttg aagaaacagt gaatggcaga aaactgacag acatcataaa taatgaccat    180
gaaaatgtaa aatatcttcc tggacacaag ctgccagaaa atgtggttgc catgtcaaat    240
cttagcgagg ctgtgcagga tgcagacctg ctggtgtttg tcattcccca ccagttcatt    300
cacagaatct gtgatgagat cactgggaga gtgcccaaga aagcgctggg aatcaccctc    360
atcaagggca tagacgaggg ccccgagggg ctgaagctca tttctgacat catccgtgag    420
aagatgggta ttgacatcag tgtgctgatg ggagccaaca ttgccaatga ggtggctgca    480
gagaagttct gtgagaccac catcggcagc aaagtaatgg agaacggcct tctcttcaaa    540
gaacttctgc agactccaaa ttttcgaatt accgtggttg atgatgcaga cactgttgaa    600
ctctgtggtg cgcttaagaa catcgtagct gtgggagctg gttctgcga cggcctccgc    660
tgtggagaca caccaaagc ggccgtcatc cgcctgggac tcatggaaat gattgctttt    720
gccaggatct ctgcaaagg ccaagtgtct acagccacct tcctagagag ctgcggggtg    780
gccgacctga tcaccacctg ttacggaggg cggaaccgca gggtggccga ggccttcgcc    840
```

-continued

```
agaactggga agaccattga agagttggag aaggagatgc tgaatgggca aaagctccaa        900
ggaccgcaga cttctgctga agtgtaccgc atcctcaaac agaagggact actggacaag       960
tttccattgt ttactgcagt gtatcagatc tgctacgaaa gcagaccagt tcaagagatg      1020
ttgtcttgtc ttcagagcca tccagagcat acataa                                1056

<210> SEQ ID NO 111
<211> LENGTH: 350
<212> TYPE: PRT
<213> ORGANISM: S. cerevisiae

<400> SEQUENCE: 111

Met Ser Lys Lys Pro Ile Val Leu Lys Leu Gly Lys Asp Ala Phe Gly
1               5                   10                  15

Asp Gln Ala Trp Gly Glu Leu Glu Lys Ile Ala Asp Val Ile Thr Ile
            20                  25                  30

Pro Glu Ser Thr Thr Arg Glu Gln Phe Leu Arg Glu Val Lys Asp Pro
        35                  40                  45

Gln Asn Lys Leu Ser Gln Val Gln Val Ile Thr Arg Thr Ala Arg Ser
    50                  55                  60

Val Lys Asn Thr Gly Arg Phe Asp Glu Glu Leu Ala Leu Ala Leu Pro
65                  70                  75                  80

Ser Ser Val Val Ala Val Cys His Thr Gly Ala Gly Tyr Asp Gln Ile
                85                  90                  95

Asp Val Glu Pro Phe Lys Lys Arg His Ile Gln Val Ala Asn Val Pro
            100                 105                 110

Asp Leu Val Ser Asn Ala Thr Ala Asp Thr His Val Phe Leu Leu Leu
        115                 120                 125

Gly Ala Leu Arg Asn Phe Gly Ile Gly Asn Arg Arg Leu Ile Glu Gly
    130                 135                 140

Asn Trp Pro Glu Ala Gly Pro Ala Cys Gly Ser Pro Phe Gly Tyr Asp
145                 150                 155                 160

Pro Glu Gly Lys Thr Val Gly Ile Leu Gly Leu Gly Arg Ile Gly Arg
                165                 170                 175

Cys Ile Leu Glu Arg Leu Lys Pro Phe Gly Phe Glu Asn Phe Ile Tyr
            180                 185                 190

His Asn Arg His Gln Leu Pro Ser Glu Glu His Gly Cys Glu Tyr
        195                 200                 205

Val Gly Phe Glu Glu Phe Leu Lys Arg Ser Asp Ile Val Ser Val Asn
    210                 215                 220

Val Pro Leu Asn His Asn Thr His His Leu Ile Asn Ala Glu Thr Ile
225                 230                 235                 240

Glu Lys Met Lys Asp Gly Val Val Ile Val Asn Thr Ala Arg Gly Ala
                245                 250                 255

Val Ile Asp Glu Gln Ala Met Thr Asp Ala Leu Arg Ser Gly Lys Ile
            260                 265                 270

Arg Ser Ala Gly Leu Asp Val Phe Glu Tyr Glu Pro Lys Ile Ser Lys
        275                 280                 285

Glu Leu Leu Ser Met Ser Gln Val Leu Gly Leu Pro His Met Gly Thr
    290                 295                 300

His Ser Val Glu Thr Arg Lys Lys Met Glu Glu Leu Val Val Glu Asn
305                 310                 315                 320

Ala Lys Asn Val Ile Leu Thr Gly Lys Val Leu Thr Ile Val Pro Glu
                325                 330                 335
```

Leu Gln Asn Glu Asp Trp Pro Asn Glu Ser Lys Pro Leu Val
         340                 345                 350

<210> SEQ ID NO 112
<211> LENGTH: 1053
<212> TYPE: DNA
<213> ORGANISM: S. cerevisiae

<400> SEQUENCE: 112

```
atgagtaaga aaccaattgt tttgaaatta ggaaaggatg cctttggtga ccaagcctgg      60
ggggaattgg aaaagattgc ggatgtaatt accatccctg aatccaccac tagagaacag    120
tttttgcggg aggtaaaaga cccacaaaat aagctctccc aagtacaagt cattactaga    180
acagcaagga gtgtgaaaaa caccggtaga tttgatgaag agcttgctct tgctttgccc    240
tcctccgtag tggctgtatg tcatactggt gctggttatg accaaattga tgttgagcca    300
ttcaagaaaa ggcacatcca ggttgccaat gttcctgatt tagttagcaa tgctaccgct    360
gatacgcatg tatttttgct attgggtgcc ctaagaaact tcggtattgg taacagaagg    420
ttgatcgagg gaaactggcc ggaggcagga cccgcatgtg gttctcccct tggatacgac    480
cctgaaggga aaacagttgg tatactgggt ctaggtagga ttggtcgttg tattttagag    540
agattgaagc cgtttgggtt cgagaatttc atatatcata acagacacca gcttccttcc    600
gaagaagagc atggttgtga atatgtagga ttcgaggagt ttttgaagcg ttctgatata    660
gtatctgtaa acgtcccact gaaccacaat actcaccatc taatcaatgc agagactatt    720
gaaaaaatga agatggtgt agttattgtt aacacagcgc gtggtgccgt gatagacgaa    780
caagccatga ctgatgcttt gcgttctgga aagattagaa gtgctggttt ggacgttttc    840
gaatatgagc caaaaatatc caagagtta ttatcgatgt cccaagtctt aggactgcct    900
catatgggca cacatagtgt agaaacaaga aagaaatgg aagaactggt cgttgaaaat    960
gcaaagaatg tgatattgac cgggaaagtc ttgactattg ttccggaatt acaaaatgaa   1020
gactggccca atgaatctaa gccattagtt tga                                1053
```

<210> SEQ ID NO 113
<211> LENGTH: 332
<212> TYPE: PRT
<213> ORGANISM: H. sapiens

<400> SEQUENCE: 113

Met Ala Thr Ile Lys Ser Glu Leu Ile Lys Asn Phe Ala Glu Glu Glu
1               5                   10                  15

Ala Ile His His Asn Lys Ile Ser Ile Val Gly Thr Gly Ser Val Gly
            20                  25                  30

Val Ala Cys Ala Ile Ser Ile Leu Leu Lys Gly Leu Ser Asp Glu Leu
        35                  40                  45

Val Leu Val Asp Val Asp Glu Gly Lys Leu Lys Gly Glu Thr Met Asp
    50                  55                  60

Leu Gln His Gly Ser Pro Phe Met Lys Met Pro Asn Ile Val Ser Ser
65                  70                  75                  80

Lys Asp Tyr Leu Val Thr Ala Asn Ser Asn Leu Val Ile Ile Thr Ala
                85                  90                  95

Gly Ala Arg Gln Lys Lys Gly Glu Thr Arg Leu Asp Leu Val Gln Arg
            100                 105                 110

Asn Val Ser Ile Phe Lys Leu Met Ile Pro Asn Ile Thr Gln Tyr Ser
        115                 120                 125

```
Pro His Cys Lys Leu Leu Ile Val Thr Asn Pro Val Asp Ile Leu Thr
    130                 135                 140

Tyr Val Ala Trp Lys Leu Ser Gly Phe Pro Lys Asn Arg Val Ile Gly
145                 150                 155                 160

Ser Gly Cys Asn Leu Asp Ser Ala Arg Phe Arg Tyr Phe Ile Gly Gln
                165                 170                 175

Arg Leu Gly Ile His Ser Glu Ser Cys His Gly Leu Ile Leu Gly Glu
                180                 185                 190

His Gly Asp Ser Ser Val Pro Val Trp Ser Gly Val Asn Ile Ala Gly
                195                 200                 205

Val Pro Leu Lys Asp Leu Asn Pro Asp Ile Gly Thr Asp Lys Asp Pro
210                 215                 220

Glu Gln Trp Glu Asn Val His Lys Lys Val Ile Ser Ser Gly Tyr Glu
225                 230                 235                 240

Met Val Lys Met Lys Gly Tyr Thr Ser Trp Gly Ile Ser Leu Ser Val
                245                 250                 255

Ala Asp Leu Thr Glu Ser Ile Leu Lys Asn Leu Arg Arg Val His Pro
                260                 265                 270

Val Ser Thr Leu Ser Lys Gly Leu Tyr Gly Ile Asn Glu Asp Ile Phe
                275                 280                 285

Leu Ser Val Pro Cys Ile Leu Gly Glu Asn Gly Ile Thr Asp Leu Ile
                290                 295                 300

Lys Val Lys Leu Thr Leu Glu Glu Glu Ala Cys Leu Gln Lys Ser Ala
305                 310                 315                 320

Glu Thr Leu Trp Glu Ile Gln Lys Glu Leu Lys Leu
                325                 330

<210> SEQ ID NO 114
<211> LENGTH: 999
<212> TYPE: DNA
<213> ORGANISM: H. sapiens

<400> SEQUENCE: 114
atggcaacta tcaagagtga acttattaag aatttcgcgg aagaggaggc cattcatcac      60
aataagatct ccattgtagg aactggatcg gttggtgtgg cttgtgctat cagcatctta     120
ttaaaaggtt tgagtgatga acttgtcctt gtggatgttg atgaaggcaa actgaagggt     180
gagacaatgg atcttcaaca tggcagccct tttatgaaaa tgccaaatat tgtctccagc     240
aaagattacc tggtcactgc aaactccaat ctagtgatta tcacagcagg tgcacgccag     300
aaaaaaggag aaacacgcct tgatttagtc cagcgaaatg tatccatctt taaattaatg     360
attcccaata ttacccagta cagtcctcac tgcaaactgc ttattgttac taatccagtg     420
gatatcttaa cttatgtagc ctggaagttg agtggatttc ccaaaaaccg tgttattgga     480
agtggttgta atctggactc tgctcgtttt cgttacttta ttgggcaaag gcttggcatc     540
cactctgaaa gctgtcatgg gctgatcctg gagagcatg cgactcaag tgttcctgtg     600 tggagtggtg tgaacattgc tggcgtccct ctgaaggatc tgaacccaga tataggaact     660
gataaagatc ctgagcagtg ggaaaatgtc cacaaaaaag tgatttccag tggctatgag     720
atggtcaaaa tgaaaggtta tacttcttgg ggcattagcc tatctgtagc tgatttaaca     780
gaaagtattt tgaagaatct taggagagtg catccagttt ctacccctaag taagggcctc     840 tatggaataa atgaagacat attccttagt gtcccatgta tcctgggaga gaatggtatc     900
acagacctca taaagtaaa actgactctt gaagaggagg cctgcttgca aaagagtgca     960
``` gaaacactttgggaaattcagaaggagctcaagctttaa                                    999

<210> SEQ ID NO 115
<211> LENGTH: 491
<212> TYPE: PRT
<213> ORGANISM: S. cerevisiae

<400> SEQUENCE: 115

Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
    290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335

Ser Leu Thr Asp Lys Asn Ile Glu Lys Thr Phe Val Asn Val Ala Lys
            340                 345                 350

Pro Phe His Lys Glu Arg Val Ala Gln Ser Leu Ile Val Pro Thr Asn
        355                 360                 365

```
Thr Gly Asn Met Tyr Thr Ala Ser Val Tyr Ala Ala Phe Ala Ser Leu
        370                 375                 380

Leu Asn Tyr Val Gly Ser Asp Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
                420                 425                 430

Leu Ala Lys Arg Ile Thr Glu Thr Pro Lys Asp Tyr Glu Ala Ala Ile
                435                 440                 445

Glu Leu Arg Glu Asn Ala His Leu Lys Lys Asn Phe Lys Pro Gln Gly
450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490

<210> SEQ ID NO 116
<211> LENGTH: 1476
<212> TYPE: DNA
<213> ORGANISM: S. cerevisiae

<400> SEQUENCE: 116
```

| | | | | | |
|---|---|---|---|---|---|
| atgaaactct | caactaaact | ttgttggtgt | ggtattaaag | gaagacttag | gccgcaaaag | 60 |
| caacaacaat | tacacaatac | aaacttgcaa | atgactgaac | taaaaaaaca | aaagaccgct | 120 |
| gaacaaaaaa | ccagacctca | aaatgtcggt | attaaaggta | tccaaattta | catcccaact | 180 |
| caatgtgtca | accaatctga | gctagagaaa | tttgatggcg | tttctcaagg | taaatacaca | 240 |
| attggtctgg | gccaaaccaa | catgtctttt | gtcaatgaca | gagaagatat | ctactcgatg | 300 |
| tccctaactg | ttttgtctaa | gttgatcaag | agttacaaca | tcgacaccaa | caaaattggt | 360 |
| agattagaag | tcggtactga | aactctgatt | gacaagtcca | gtctgtcaa | gtctgtcttg | 420 |
| atgcaattgt | ttggtgaaaa | cactgacgtc | gaaggtattg | acacgcttaa | tgcctgttac | 480 |
| ggtggtacca | acgcgttgtt | caactctttg | aactggattg | aatctaacgc | atgggatggt | 540 |
| agagacgcca | ttgtagtttg | cggtgatatt | gccatctacg | ataagggtgc | cgcaagacca | 600 |
| accggtggtg | ccgtactgt | tgctatgtgg | atcggtcctg | atgctccaat | tgtatttgac | 660 |
| tctgtaagag | cttcttacat | ggaacacgcc | tacgattttt | acaagccaga | tttcaccagc | 720 |
| gaatatcctt | acgtcgatgg | tcattttca | ttaacttgtt | acgtcaaggc | tcttgatcaa | 780 |
| gtttacaaga | gttattccaa | gaaggctatt | tctaaagggt | tggttagcga | tcccgctggt | 840 |
| tcggatgctt | tgaacgtttt | gaaatatttc | gactacaacg | ttttccatgt | tccaacctgt | 900 |
| aaattggtca | aaaatcata | cggtagatta | ctatataacg | atttcagagc | caatcctcaa | 960 |
| ttgttcccag | aagttgacgc | cgaattagct | actcgcgatt | atgacgaatc | tttaaccgat | 1020 |
| aagaacattg | aaaaaacttt | tgttaatgtt | gctaagccat | tccacaaaga | gagagttgcc | 1080 |
| caatctttga | ttgttccaac | aaacacaggt | aacatgtaca | ccgcatctgt | ttatgccgcc | 1140 |
| tttgcatctc | tattaaacta | tgttggatct | gacgacttac | aaggcaagcg | tgttggttta | 1200 |
| ttttcttacg | gttccggttt | agctgcatct | ctatattctt | gcaaaattgt | tggtgacgtc | 1260 |
| caacatatta | tcaaggaatt | agatattact | aacaaattag | ccaagagaat | caccgaaact | 1320 |
| ccaaaggatt | acgaagctgc | catcgaattg | agagaaaatg | cccatttgaa | gaagaacttc | 1380 |
| aaacctcaag | gttccattga | gcatttgcaa | agtggtgttt | actacttgac | caacatcgat | 1440 | gacaaattta gaagatctta cgatgttaaa aaataa                1476

<210> SEQ ID NO 117
<211> LENGTH: 390
<212> TYPE: PRT
<213> ORGANISM: M. neglectum

<400> SEQUENCE: 117

Met Arg Asp Phe Tyr Tyr Gly Leu Asn Gln Ile Pro Pro Glu Asp Ile
1               5                   10                  15

Gly Ser Gly Ile Thr Arg Glu Met Glu Arg Arg Trp Arg Val Leu Ser
            20                  25                  30

Gly Leu Gln Asp Arg Asn Glu Thr Leu Phe Tyr Arg Val Leu Val Glu
        35                  40                  45

His Phe Glu Asp Met Ala Pro Ile Val Tyr Thr Pro Thr Val Gly Trp
    50                  55                  60

Glu Asp Val Gln Ala Ile Val Val Thr Asp Gly Ser Arg Ile Leu Gly
65                  70                  75                  80

Leu Gly Asp Leu Gly Ala Asn Gly Leu Gly Ile Pro Ile Gly Lys Leu
                85                  90                  95

Asp Leu Tyr Val Ala Ala Ala Gly Phe Asp Pro Ser Lys Val Leu Pro
            100                 105                 110

Cys Ile Ile Asp Val Gly Thr Asp Asn Glu Arg Leu Leu Gly Asp Pro
        115                 120                 125

Leu Tyr Val Gly Leu Arg Arg Ser Arg Val Arg Gly Asp Glu Tyr Tyr
    130                 135                 140

Ala Leu Val Asp Glu Phe Val Arg Ala Val Thr Arg Arg Trp Pro Asn
145                 150                 155                 160

Ala Val Leu Gln Phe Glu Asp Phe Ser Ile Glu His Ala Arg Pro Leu
                165                 170                 175

Leu Gln Arg Tyr Arg Gln His His Leu Val Phe Asn Asp Ile Gln
            180                 185                 190

Gly Thr Ala Ala Thr Ala Val Ala Gly Leu Tyr Gly Ala Leu Arg Ala
        195                 200                 205

Gln Gly Leu Pro Pro Ala Asp Leu Ala Arg Gln Thr Val Val Cys Leu
    210                 215                 220

Gly Ala Gly Ser Ala Gly Met Gly Val Val Gln Met Ile Cys Asp Ala
225                 230                 235                 240

Met Glu Ala Gln Gly Ala Ala Pro Glu Gln Ala Arg Gly Asn Phe Trp
                245                 250                 255

Val Leu Ser Ser Lys Gly Leu Ile Thr Ala Ala Arg Pro Ala Ile Pro
            260                 265                 270

Cys Asn Val Val Pro Phe Ala Arg Pro Glu Ala Glu Leu Glu Gly Ser
        275                 280                 285

Cys Leu Leu Asp Val Val Arg Arg Ala Arg Pro Thr Val Leu Leu Gly
    290                 295                 300

Leu Ala Gly Ala Gly Arg Leu Phe Ala Pro Asp Val Leu Ala Ala Ala
305                 310                 315                 320

Ala Glu Gly Cys Glu Arg Pro Ile Ile Phe Pro Met Ser Asn Pro Thr
                325                 330                 335

Ile Lys Met Glu Cys Thr Ala Glu Asp Ala Val Leu Ala Thr Gln Gly
            340                 345                 350

Arg Cys Val Phe Ala Ser Gly Ser Pro Gln Pro Pro Leu Asp Tyr Arg
        355                 360                 365

Gly Val Thr Leu Glu Phe Ser Gln Ala Asn Asn Leu Tyr Ile Phe Pro
    370                 375                 380

Ala Ser Asp Pro Ala Ala
385                 390

<210> SEQ ID NO 118
<211> LENGTH: 1173
<212> TYPE: DNA
<213> ORGANISM: M. neglectum

<400> SEQUENCE: 118

| | | | | |
|---|---|---|---|---|
| atgcgcgatt | tctactacgg | cctcaaccag | atcccaccgg | aagacatagg | gtcggggatc | 60 |
| acgcgggaga | tggagaggcg | gtggagggtg | ctatcgggcc | tgcaggaccg | caatgagacg | 120 |
| ctgttctacc | gcgttctggt | ggagcacttt | gaggacatgg | cgccatcgt | gtacaccccg | 180 |
| acagtcggat | gggaggatgt | ccaggcgatc | gtggtgaccg | acggcagccg | catcctcgga | 240 |
| ctgggtgatc | tgggcgccaa | cggcctgggc | atacccatcg | gcaagctgga | tctgtatgtg | 300 |
| gctgcagccg | gattcgaccc | gtccaaggtt | ctgccctgca | tcatcgacgt | gggcaccgac | 360 |
| aacgagcggc | tgctgggtga | ccccctgtac | gtggggctga | ggcgcagccg | cgtcaggggt | 420 |
| gacgagtatt | acgccctcgt | cgacgagttt | gtgcgtgcgg | tgacgcggcg | gtggcccaac | 480 |
| gcggtgctac | agtttgagga | cttcagcatt | gagcacgcgc | ggccgctgct | gcagcgctac | 540 |
| cgccagcacc | acctcgtctt | caacgacgac | atccagggca | ccgccgcaac | ggctgttgcg | 600 |
| gggctgtacg | gcgccctgcg | cgcccagggc | ctgccgcccg | ctgacctggc | gcggcagacg | 660 |
| gtagtctgcc | tgggggccgg | gtcggcgggg | atgggggtgg | tgcagatgat | ctgcgacgct | 720 |
| atggaagcgc | agggcgcggc | gcccgagcag | gcgcgcggca | acttctgggt | gctctcgtcc | 780 |
| aagggcctca | taaccgccgc | caggcccgcc | atccctgca | acgtggtgcc | ttttgcgcgc | 840 |
| cccgaggctg | agctggaggg | aagctgcctg | ctggatgtcg | tgcgcagggc | caggcccacg | 900 |
| gtgctgctcg | ggctcgcggg | cgcggggcgg | ctgttcgcgc | ccgatgtgct | ggcggccgcg | 960 |
| gcggagggct | gcgagcggcc | gatcatattc | ccgatgagca | accccacgat | caagatggag | 1020 |
| tgcacagctg | aggacgccgt | gctcgccacc | caaggccgct | gcgtgttcgc | cagcggcagc | 1080 |
| ccgcagccgc | ccctggacta | ccgcggggtg | actcttgagt | tctcacaggc | caacaacctg | 1140 |
| tatatcttcc | ccgcttcaga | ccccgctgct | tga | | | 1173 |

<210> SEQ ID NO 119
<211> LENGTH: 319
<212> TYPE: PRT
<213> ORGANISM: H. sapiens

<400> SEQUENCE: 119

Met Ala Ser Ser Ala Ala Gly Cys Val Val Ile Val Gly Ser Gly Val
1               5                   10                  15

Ile Gly Arg Ser Trp Ala Met Leu Phe Ala Ser Gly Gly Phe Gln Val
                20                  25                  30

Lys Leu Tyr Asp Ile Glu Gln Gln Gln Ile Arg Asn Ala Leu Glu Asn
        35                  40                  45

Ile Arg Lys Glu Met Lys Leu Leu Glu Gln Ala Gly Ser Leu Lys Gly
    50                  55                  60

Ser Leu Ser Val Glu Glu Gln Leu Ser Leu Ile Ser Gly Cys Pro Asn
65                  70                  75                  80

Ile Gln Glu Ala Val Glu Gly Ala Met His Ile Gln Glu Cys Val Pro 85                  90                  95
Glu Asp Leu Glu Leu Lys Lys Lys Ile Phe Ala Gln Leu Asp Ser Ile
                100                 105                 110

Ile Asp Asp Arg Val Ile Leu Ser Ser Thr Ser Cys Leu Met Pro
            115                 120                 125

Ser Lys Leu Phe Ala Gly Leu Val His Val Lys Gln Cys Ile Val Ala
        130                 135                 140

His Pro Val Asn Pro Pro Tyr Tyr Ile Pro Leu Val Glu Leu Val Pro
145                 150                 155                 160

His Pro Glu Thr Ala Pro Thr Thr Val Asp Arg Thr His Ala Leu Met
                165                 170                 175

Lys Lys Ile Gly Gln Cys Pro Met Arg Val Gln Lys Glu Val Ala Gly
            180                 185                 190

Phe Val Leu Asn Arg Leu Gln Tyr Ala Ile Ile Ser Glu Ala Trp Arg
        195                 200                 205

Leu Val Glu Glu Gly Ile Val Ser Pro Ser Asp Leu Asp Leu Val Met
    210                 215                 220

Ser Glu Gly Leu Gly Met Arg Tyr Ala Phe Ile Gly Pro Leu Glu Thr
225                 230                 235                 240

Met His Leu Asn Ala Glu Gly Met Leu Ser Tyr Cys Asp Arg Tyr Ser
                245                 250                 255

Glu Gly Ile Lys His Val Leu Gln Thr Phe Gly Pro Ile Pro Glu Phe
            260                 265                 270

Ser Arg Ala Thr Ala Glu Lys Val Asn Gln Asp Met Cys Met Lys Val
        275                 280                 285

Pro Asp Asp Pro Glu His Leu Ala Ala Arg Arg Gln Trp Arg Asp Glu
    290                 295                 300

Cys Leu Met Arg Leu Ala Lys Leu Lys Ser Gln Val Gln Pro Gln
305                 310                 315

<210> SEQ ID NO 120
<211> LENGTH: 960
<212> TYPE: DNA
<213> ORGANISM: H. sapiens

<400> SEQUENCE: 120
atggcgtcct ccgcggccgg ctgcgtggtg atcgttggca gtggagtcat tgggcgaagc      60
tgggccatgc tgtttgccag tggaggcttc caggtgaaac tctatgacat tgagcaacag     120
cagataagga cgccctgga aaacatcaga aggagatga agttgctgga gcaggcaggt      180
tctctgaaag gctccctgag tgtggaagag cagctgtcac tcatcagtgg ttgtcccaat     240
atccaagaag cagtagaggg tgccatgcac attcaggaat gtgttccaga agatctagaa     300
ctgaagaaga agattttgc tcagttagat tccatcattg atgatcgagt gatcttaagc     360
agttccactt cttgtctcat gccttccaag ttgtttgctg gcttggtcca tgtgaagcaa     420
tgcatcgtgg ctcatcctgt gaatccgcca tactacatcc cgctggttga gctggtcccc     480
cacccggaga cggcccctac gacagtggac agaacccacg ccctgatgaa gaagattgga     540
cagtgcccca tgcgagtcca gaaggaggtg gccggcttcg ttctgaaccg cctgcaatat     600
gcaatcatca gcgaggcctg gcggctagtg gaggaaggaa tcgtgtctcc tagtgacctg     660
gaccttgtca tgtcagaagg gttgggcatg cggtatgcat tcattggacc cctggaaacc     720
atgcatctca atgcagaagg tatgttaagc tactgcgaca gatacagcga aggcataaaa     780
catgtcctac agactttggg acccattcca gagttttcca gggccactgc tgagaaggtt     840

```
aaccaggaca tgtgcatgaa ggtccctgat gacccggagc acttagctgc caggaggcag    900
tggagggacg agtgcctcat gagactcgcc aagttgaaga gtcaagtgca gccccagtga    960
```

<210> SEQ ID NO 121
<211> LENGTH: 502
<212> TYPE: PRT
<213> ORGANISM: S. cerevisiae

<400> SEQUENCE: 121

| | | | | | | | | | | | | | | |
|---|---|---|---|---|---|---|---|---|---|---|---|---|---|---|
| Met | Thr | Lys | Ser | Asp | Glu | Thr | Thr | Ala | Thr | Ser | Leu | Asn | Ala | Lys | Thr |
| 1 | | | | 5 | | | | | 10 | | | | | 15 | |
| Leu | Lys | Ser | Phe | Glu | Ser | Thr | Leu | Pro | Ile | Pro | Thr | Tyr | Pro | Arg | Glu |
| | | | 20 | | | | | 25 | | | | | 30 | | |
| Gly | Val | Lys | Gln | Gly | Ile | Val | His | Leu | Gly | Val | Gly | Ala | Phe | His | Arg |
| | | | 35 | | | | 40 | | | | | 45 | | | |
| Ser | His | Leu | Ala | Val | Phe | Met | His | Arg | Leu | Met | Gln | Glu | His | His | Leu |
| | 50 | | | | | 55 | | | | | 60 | | | | |
| Lys | Asp | Trp | Ser | Ile | Cys | Gly | Val | Gly | Leu | Met | Lys | Ala | Asp | Ala | Leu |
| 65 | | | | | 70 | | | | | 75 | | | | | 80 |
| Met | Arg | Asp | Ala | Met | Lys | Ala | Gln | Asp | Cys | Leu | Tyr | Thr | Leu | Val | Glu |
| | | | | 85 | | | | | 90 | | | | | 95 | |
| Arg | Gly | Ile | Lys | Asp | Thr | Asn | Ala | Tyr | Ile | Val | Gly | Ser | Ile | Thr | Ala |
| | | | 100 | | | | | 105 | | | | | 110 | | |
| Tyr | Met | Tyr | Ala | Pro | Asp | Asp | Pro | Arg | Ala | Val | Ile | Glu | Lys | Met | Ala |
| | | | 115 | | | | | 120 | | | | | 125 | | |
| Asn | Pro | Asp | Thr | His | Ile | Val | Ser | Leu | Thr | Val | Thr | Glu | Asn | Gly | Tyr |
| | 130 | | | | | 135 | | | | | 140 | | | | |
| Tyr | His | Ser | Glu | Ala | Thr | Asn | Ser | Leu | Met | Thr | Asp | Ala | Pro | Glu | Ile |
| 145 | | | | | 150 | | | | | 155 | | | | | 160 |
| Ile | Asn | Asp | Leu | Asn | His | Pro | Glu | Lys | Pro | Asp | Thr | Leu | Tyr | Gly | Tyr |
| | | | | 165 | | | | | 170 | | | | | 175 | |
| Leu | Tyr | Glu | Ala | Leu | Leu | Leu | Arg | Tyr | Lys | Arg | Gly | Leu | Thr | Pro | Phe |
| | | | 180 | | | | | 185 | | | | | 190 | | |
| Thr | Ile | Met | Ser | Cys | Asp | Asn | Met | Pro | Gln | Asn | Gly | Val | Thr | Val | Lys |
| | | | 195 | | | | | 200 | | | | | 205 | | |
| Thr | Met | Leu | Val | Ala | Phe | Ala | Lys | Leu | Lys | Lys | Asp | Glu | Lys | Phe | Ala |
| | 210 | | | | | 215 | | | | | 220 | | | | |
| Ala | Trp | Ile | Glu | Asp | Lys | Val | Thr | Ser | Pro | Asn | Ser | Met | Val | Asp | Arg |
| 225 | | | | | 230 | | | | | 235 | | | | | 240 |
| Val | Thr | Pro | Arg | Cys | Thr | Asp | Lys | Glu | Arg | Lys | Tyr | Val | Ala | Asp | Thr |
| | | | | 245 | | | | | 250 | | | | | 255 | |
| Trp | Gly | Ile | Lys | Asp | Gln | Cys | Pro | Val | Val | Ala | Glu | Pro | Phe | Ile | Gln |
| | | | 260 | | | | | 265 | | | | | 270 | | |
| Trp | Val | Leu | Glu | Asp | Asn | Phe | Ser | Asp | Gly | Arg | Pro | Pro | Trp | Glu | Leu |
| | | | 275 | | | | | 280 | | | | | 285 | | |
| Val | Gly | Val | Gln | Val | Val | Lys | Asp | Val | Asp | Ser | Tyr | Glu | Leu | Met | Lys |
| | 290 | | | | | 295 | | | | | 300 | | | | |
| Leu | Arg | Leu | Leu | Asn | Gly | Gly | His | Ser | Ala | Met | Gly | Tyr | Leu | Gly | Tyr |
| 305 | | | | | 310 | | | | | 315 | | | | | 320 |
| Leu | Ala | Gly | Tyr | Thr | Tyr | Ile | His | Glu | Val | Val | Asn | Asp | Pro | Thr | Ile |
| | | | | 325 | | | | | 330 | | | | | 335 | |
| Asn | Lys | Tyr | Ile | Arg | Val | Leu | Met | Arg | Glu | Glu | Val | Ile | Pro | Leu | Leu |
| | | | 340 | | | | | 345 | | | | | 350 | | |

```
Pro Lys Val Pro Gly Val Asp Phe Glu Glu Tyr Thr Ala Ser Val Leu
            355                 360                 365

Glu Arg Phe Ser Asn Pro Ala Ile Gln Asp Thr Val Ala Arg Ile Cys
        370                 375                 380

Leu Met Gly Ser Gly Lys Met Pro Lys Tyr Val Leu Pro Ser Ile Tyr
385                 390                 395                 400

Glu Gln Leu Arg Lys Pro Asp Gly Lys Tyr Lys Leu Leu Ala Val Cys
                405                 410                 415

Val Ala Gly Trp Phe Arg Tyr Leu Thr Gly Val Asp Met Asn Gly Lys
            420                 425                 430

Pro Phe Glu Ile Glu Asp Pro Met Ala Pro Thr Leu Lys Ala Ala Ala
        435                 440                 445

Val Lys Gly Gly Lys Asp Pro His Glu Leu Leu Asn Ile Glu Val Leu
450                 455                 460

Phe Ser Pro Glu Ile Arg Asp Asn Lys Glu Phe Val Ala Gln Leu Thr
465                 470                 475                 480

His Ser Leu Glu Thr Val Tyr Asp Lys Gly Pro Ile Ala Ala Ile Lys
                485                 490                 495

Glu Ile Leu Asp Gln Val
            500

<210> SEQ ID NO 122
<211> LENGTH: 1509
<212> TYPE: DNA
<213> ORGANISM: S. cerevisiae

<400> SEQUENCE: 122
atgacaaaat cagacgaaac aacagctacc agcttgaatg ctaaaactct aaagagtttt       60
gaatcaactc ttccaatacc aacttaccca agagaaggtg ttaaacaagg tattgttcat      120
ctgggagtcg gtgcattcca ccgttcccat ttagctgttt tcatgcaccg tctgatgcag      180
gagcaccact aaaggactg gtccatatgt ggtgttggtt aatgaaggc agatgcactt        240 atgcgcgatg ccatgaaggc ccaagattgc ctatacaccc ttgtggagcg tggtatcaag      300
gacactaacg cttatatcgt cggttccatt actgcttaca tgtacgctcc cgatgatcca      360
agagctgtta ttgaaaagat ggccaatcca gacacacaca ttgtttcttt gacggtcaca      420
gaaaacggtt actaccacag tgaagcaaca aactccttaa tgacagatgc tcccgagatt      480
atcaatgatt tgaaccaccc agaaaagcca gatactctgt atgggtacct atatgaagcc      540
ctgttgttgc gttacaagag aggtcttacc ccattcacta ttatgtcatg tgacaacatg      600
ccccaaaatg gtgtcacagt aaagaccatg cttgttgcat ttgccaagtt aaagaaggat      660
gagaaattcg ccgcctggat gaagacaag gttacttctc ctaacagcat ggtgaccgt        720 gtgaccccac gttgtaccga taagagcgt aaatacgttg ctgacacctg gggaatcaaa       780
gatcaatgtc ccgttgtcgc agaaccttc atccaatggg ttcttgaaga caacttctcc       840
gatggccgtc ctccatggga acttgttggt gttcaggtcg tcaaggatgt cgattcctac      900
gaattgatga agttgcgtct acttaacggt ggacattctg ctatgggata tttgggatac      960
ttggcaggct acacctatat acatgaggtt gtcaacgacc caactatcaa caagtatatc     1020
cgtgttttga tgcgtgagga agttatccca ttattgccta agtgccagg tgttgatttc       1080 gaagagtaca ctgcatcagt gttggaaaga ttctccaatc cagcaattca ggacactgtc     1140
gcacgtattt gtttgatggg ctctggtaag atgcctaagt atgttttgcc atcaatttac     1200
gagcagttgc gtaaaccaga tggtaagtac aagttgttgg cagtatgtgt tgctggctgg     1260
```

-continued

```
ttccgttacc tgactggtgt agacatgaat gggaagccat tcgaaatcga ggatcctatg    1320
gcaccaacct tgaaggcagc cgcagttaag ggcggtaaag atcctcacga actgcttaac    1380
attgaggtgc ttttcagtcc tgagattcgt gacaacaaag aattcgttgc acaattgacc    1440
cactccctag aaacagttta cgataaaggg ccaattgccg ctattaagga aattttagac    1500
caagtgtga                                                            1509
```

<210> SEQ ID NO 123
<211> LENGTH: 475
<212> TYPE: PRT
<213> ORGANISM: E. coli

<400> SEQUENCE: 123

```
Met Met Ile Asn Val Gln Thr Val Ala Val Ile Gly Ser Gly Thr Met
1               5                   10                  15

Gly Ala Gly Ile Ala Glu Val Ala Ala Ser His Gly His Gln Val Leu
                20                  25                  30

Leu Tyr Asp Ile Ser Ala Glu Ala Leu Thr Arg Ala Ile Asp Gly Ile
            35                  40                  45

His Ala Arg Leu Asn Ser Arg Val Thr Arg Gly Lys Leu Thr Ala Glu
        50                  55                  60

Thr Cys Glu Arg Thr Leu Lys Arg Leu Ile Pro Val Thr Asp Ile His
65                  70                  75                  80

Ala Leu Ala Ala Ala Asp Leu Val Ile Glu Ala Ala Ser Glu Arg Leu
                85                  90                  95

Glu Val Lys Lys Ala Leu Phe Ala Gln Leu Ala Glu Val Cys Pro Pro
            100                 105                 110

Gln Thr Leu Leu Thr Thr Asn Thr Ser Ser Ile Ser Ile Thr Ala Ile
        115                 120                 125

Ala Ala Glu Ile Lys Asn Pro Glu Arg Val Ala Gly Leu His Phe Phe
    130                 135                 140

Asn Pro Ala Pro Val Met Lys Leu Val Glu Val Val Ser Gly Leu Ala
145                 150                 155                 160

Thr Ala Ala Glu Val Val Glu Gln Leu Cys Glu Leu Thr Leu Ser Trp
                165                 170                 175

Gly Lys Gln Pro Val Arg Cys His Ser Thr Pro Gly Phe Ile Val Asn
            180                 185                 190

Arg Val Ala Arg Pro Tyr Tyr Ser Glu Ala Trp Arg Ala Leu Glu Glu
        195                 200                 205

Gln Val Ala Ala Pro Glu Val Ile Asp Ala Ala Leu Arg Asp Gly Ala
    210                 215                 220

Gly Phe Pro Met Gly Pro Leu Glu Leu Thr Asp Leu Ile Gly Gln Asp
225                 230                 235                 240

Val Asn Phe Ala Val Thr Cys Ser Val Phe Asn Ala Phe Trp Gln Glu
                245                 250                 255

Arg Arg Phe Leu Pro Ser Leu Val Gln Glu Leu Val Ile Gly Gly
            260                 265                 270

Arg Leu Gly Lys Lys Ser Gly Leu Gly Val Tyr Asp Trp Arg Ala Glu
        275                 280                 285

Arg Glu Ala Val Val Gly Leu Glu Ala Val Ser Asp Ser Phe Ser Pro
    290                 295                 300

Met Lys Val Glu Lys Lys Ser Asp Gly Val Thr Glu Ile Asp Asp Val
305                 310                 315                 320
```

```
Leu Leu Ile Glu Thr Gln Gly Glu Thr Ala Gln Ala Leu Ala Ile Arg
            325                 330                 335

Leu Ala Arg Pro Val Val Ile Asp Lys Met Ala Gly Lys Val Val
        340                 345                 350

Thr Ile Ala Ala Ala Val Asn Pro Asp Ser Ala Thr Arg Lys Ala
        355                 360                 365

Ile Tyr Tyr Leu Gln Gln Gly Lys Thr Val Leu Gln Ile Ala Asp
        370                 375                 380

Tyr Pro Gly Met Leu Ile Trp Arg Thr Val Ala Met Ile Ile Asn Glu
385                 390                 395                 400

Ala Leu Asp Ala Leu Gln Lys Gly Val Ala Ser Glu Gln Asp Ile Asp
            405                 410                 415

Thr Ala Met Arg Leu Gly Val Asn Tyr Pro Tyr Gly Pro Leu Ala Trp
            420                 425                 430

Gly Ala Gln Leu Gly Trp Gln Arg Ile Leu Arg Leu Leu Glu Asn Leu
            435                 440                 445

Gln His His Tyr Gly Glu Glu Arg Tyr Arg Pro Cys Ser Leu Leu Arg
        450                 455                 460

Gln Arg Ala Leu Leu Glu Ser Gly Tyr Glu Ser
465                 470                 475

<210> SEQ ID NO 124
<211> LENGTH: 1428
<212> TYPE: DNA
<213> ORGANISM: E. coli

<400> SEQUENCE: 124
atgatgataa atgtgcaaac tgtggcagtg attgggagcg gcaccatggg ggcaggcatt      60
gctgaagttg ctgccagtca tggacaccag gttttactgt atgacatttc tgctgaagcg     120
ctgacccgcg caatcgacgg gatacacgcg cggctaaatt cacgcgtgac gcgggaaaa      180 ctgactgctg aaacctgtga acgcacattg aaacgcctga tcccggtgac cgatattcac     240
gcgctggcag ctgcggacct ggtcattgaa gcggcgtctg aacgtctgga agtcaaaaaa     300
gcgctctttg cacagctggc ggaagtttgc cgccacaaa cgctattgac cactaacact     360
tcgtcaatct ctataaccgc gattgctgcg gagataaaaa atcctgaacg tgttgcgggg     420
ctgcattttt ttaacccggc accggtgatg aagttggtgg aggtggtcag tgggctggca     480
acggcggcgg aagttgttga gcagttgtgt gaactaacgt tgagttgggg taagcagcct     540
gtgcgctgtc attcgactcc tggatttatc gttaaccgtg ttgcgcgtcc ttattattcc     600
gaggcctggc gggcactgga agagcaggtt gctgcaccag aagtgattga cgctgcactt     660
cgcgatggcg ctggtttccc gatggggccg ctggaattaa ccgatctgat tggtcaggac     720
gtcaattttg ctgtcacctg ttcggtgttt aacgctttct ggcaggagcg tcgttttta      780 ccttcgctgg tgcaacagga actggtgatt ggtggacggt tgggcaagaa aagtgggctg     840
ggcgtgtacg actggcgcgc ggaacgtgag gcagttgttg gcctggaagc ggtaagcgac     900
agttttagcc aatgaaagt agaaaagaaa agtgacggtg tcacggaaat tgacgatgtt     960
ttattgattg agacacaagg cgagacggca caggcgctgg caatacgact ggcacgcccg    1020
gtggtagtga tcgataaaat ggcgggcaag gtggtgacca ttgctgctgc agcggtgaac    1080
ccggactcag cgaccgcaa ggccatttat tacctgcaac agcagggcaa aacagtgctg    1140
caaattgcag attacccagg aatgctgatt tggcgaacgg tagcaatgat catcaatgaa    1200
gcccttgatg cgcttcaaaa aggcgtggcc tctgaacagg atatcgatac cgccatgcgt    1260
```

```
cttggggtga attatccata tggcccactt gcctggggag cgcaacttgg ctggcagcga    1320
atattaaggc tccttgaaaa tctacagcat cactatggcg aagaacgcta tcgcccatgt    1380
tcattgctgc gccaacgggc gcttctggag agcggttatg agtcataa                1428
```

<210> SEQ ID NO 125
<211> LENGTH: 387
<212> TYPE: PRT
<213> ORGANISM: C. necator

<400> SEQUENCE: 125

```
Met Thr Val Val Asn Glu Tyr Arg Pro Val Glu Val Phe Phe Gly Glu
1               5                   10                  15

Gly Ala Val Lys Lys Ala Gly Glu Val Gly Arg Arg Phe Gly Phe Lys
            20                  25                  30

Ala Leu Ile Val Thr Gly Arg Lys Ser Thr Lys Glu Ser Gly Ala Leu
        35                  40                  45

Asp Lys Leu Ile Asn Ser Leu Lys Gln Asn Gln Ile Glu Tyr Val Val
    50                  55                  60

Phe Asp Glu Ile Thr Pro Asn Pro Thr Asp Lys Gln Val Asn Lys Gly
65                  70                  75                  80

Ala Glu Ile Ala Val Asn Glu Lys Val Asp Phe Ile Val Gly Ile Gly
                85                  90                  95

Gly Gly Ser Val Leu Asp Ala Ala Lys Ala Ile Ser Ile Val Ser Ser
            100                 105                 110

Asn Glu Gly Tyr Ala Trp Asp Tyr Val Arg Tyr Pro Glu Gly Ser Arg
        115                 120                 125

Leu Ile Pro Phe Leu Asn Arg Pro Val Ile Thr Ile Pro Thr Thr Ala
    130                 135                 140

Gly Thr Gly Ser Glu Val Asn Arg Tyr Ser Val Leu Thr Asn Pro Met
145                 150                 155                 160

Thr Lys Glu Lys Met Val Ile Ser His Ser Leu Asn Tyr Pro Lys Val
                165                 170                 175

Ala Leu Val Asp Pro Glu Leu Thr Tyr Ser Met Pro Pro Arg Leu Thr
            180                 185                 190

Ala Leu Thr Gly Phe Asp Ala Leu Met His Ala Leu Glu Ser Leu Thr
        195                 200                 205

Asn Lys Arg Glu Asn Phe Ile Ala Glu Glu Tyr Ser Val Lys Ala Ile
    210                 215                 220

Glu Leu Ile Arg Lys Trp Leu Pro Val Ala Phe Glu Glu Pro Glu Asn
225                 230                 235                 240

Lys Glu Ala Arg Arg Tyr Met Ser Tyr Ala Ala Met Leu Ala Gly Ile
                245                 250                 255

Ala Ile Asp His Leu Gly Val Ala Leu Ile His Ala Met Glu His Pro
            260                 265                 270

Val Ser Gly His Tyr Pro Glu Val Ala His Ala Glu Gly Leu Ser Ala
        275                 280                 285

Leu Ala Pro Tyr Ile Thr Ala Phe Asn Tyr Arg Gly Asn Pro Glu Lys
    290                 295                 300

Tyr Ala Leu Phe Ala Arg Leu Met Gly Glu Glu Lys Pro His Lys
305                 310                 315                 320

Ala Val Asp Ala Leu Val Lys Phe Ile Glu Arg Phe Ser Leu Pro Lys
                325                 330                 335

Thr Leu Lys Glu Leu Gly Val Glu Lys Glu Lys Leu Pro Arg Leu Ala
```

```
                340             345             350
Glu Asp Val Tyr Met Cys Ala Arg His Ser Phe Ala Val Asn Pro Val
        355                 360                 365

Glu Val Gly Met Glu Glu Val Glu Glu Leu Tyr Glu Arg Ala Tyr Glu
    370                 375                 380

Gly Arg Leu
385

<210> SEQ ID NO 126
<211> LENGTH: 1164
<212> TYPE: DNA
<213> ORGANISM: C. necator

<400> SEQUENCE: 126
atgactgttg taaatgagta cagacccgtt gaagttttct tcggcgaagg agcggtaaaa      60
aaagcgggag aagtagggag acgctttggc ttcaaagccc tgatagttac tggaagaaaa     120
agcacaaagg aaagcggtgc actggataaa ttgataaact ccttaaaaca aaatcaaata     180
gagtacgtgg tatttgacga gataactccc aacccgacgg acaaacaggt aaacaaaggt     240
gcagagatag ccgtaaacga aaagtggac tttatcgtag gtatcggagg aggaagtgtc      300
ttggacgccg cgaaagcaat tccatagta tcttccaacg aaggttacgc ctgggattac      360
gtaaggtatc cggaagggag caggctgatt ccctttctga acagaccgt gataacgata      420 ccgacaacgg cgggaacggg aagcgaggta acaggtatt ccgtactcac aaacccgatg      480
acaaaagaaa aaatggtaat ttcccacagc ctgaactacc cgaaggttgc actcgtggac      540
ccggagctaa cttatagtat gcctcctaga ctcaccgccc tcacaggctt tgatgccctg      600
atgcacgccc ttgagagttt gacgaataaa agagaaaact tcatagctga agagtactcg      660
gtaaaggcga tagagcttat aaggaagtgg cttcccgtag cctttgaaga gccagaaaat      720
aaagaagcaa ggcggtacat gagttacgca gctatgcttg cggggatagc tatagaccac      780
ctcggagttg ccctcataca cgcaatggaa caccccgttt cgggacacta ccccgaggtg      840
gcacatgcgg aaggactttc ggcgctcgct ccttacataa ccgcctttaa ttacagagga      900
aaccctgaga agtacgccct cttttgcaaga ctgatgggag aagaagaaaa acctcacaaa     960
gcggtggacg ctctcgttaa gttcatagaa aggttttctc tcccaaaaac cctgaaggag     1020
cttggagtag aaaaggaaaa actcccgaga cttgccgaag acgtttacat gtgcgcaagg     1080
cactcctttg ccgttaaccc tgtagaagta ggtatggaag aagtagagga actctacgaa     1140
agggcttacg aaggaagatt atga                                            1164

<210> SEQ ID NO 127
<211> LENGTH: 320
<212> TYPE: PRT
<213> ORGANISM: Sulfolobus acidocaldarius

<400> SEQUENCE: 127

Met Arg Gln Val Asn Val Val Ser Ile Val Gly Ala Gly Ile Ile Gly
1               5                   10                  15

Ala Gly Trp Ser Thr Leu Leu Ala Val His Gly Tyr Arg Asn Ile Phe
            20                  25                  30

Tyr Thr Glu Lys Lys Glu Thr Leu Asp Lys Gly Ile Leu Lys Ile Lys
        35                  40                  45

Gly Tyr Leu Gln Val Met His Glu Tyr Lys Leu Ala Asp Lys Ser Pro
    50                  55                  60
```

| | | | | | | | | | | | | | | | |
|---|---|---|---|---|---|---|---|---|---|---|---|---|---|---|---|
|Glu|Glu|Tyr|Met|Lys|Leu|Ile|Thr|Pro|Thr|Thr|Asp|Phe|Asn|Asp|Val|
|65| | | |70| | | |75| | | |80| | | |

Leu Lys Gly Asp Phe Ile Ile Glu Ala Val Ile Glu Asp Tyr Gly Val
              85                  90                  95

Lys Lys Lys Val Phe Gly Glu Leu Asp Glu Arg Leu Asp Lys Asp Val
            100                 105                 110

Ile Ile Ala Ser Ser Thr Ser Gly Leu Leu Ile Ser Glu Ile Gln Lys
            115                 120                 125

Ser Met Ser Arg His Pro Glu Arg Ala Ile Ile His Pro Trp Asn
130                 135                 140

Pro Pro His Leu Leu Pro Leu Val Glu Ile Val Pro Gly Glu Lys Thr
145                 150                 155                 160

Ser Glu Glu Val Ile Gln Ser Thr Arg Glu Phe Met Glu Asp Lys Leu
                165                 170                 175

Lys Arg Val Val Val Leu Lys Lys Glu Val Pro Gly Phe Ile Gly
                180                 185                 190

Asn Arg Leu Ala Phe Ala Leu Phe Arg Glu Ala Val His Leu Ile Asp
            195                 200                 205

Glu Gly Val Ala Thr Val Glu Asp Ile Asp Lys Val Val Thr Ala Ala
210                 215                 220

Ile Gly Leu Arg Trp Val Phe Met Gly Pro Phe Leu Thr Tyr His Leu
225                 230                 235                 240

Gly Gly Gly Glu Gly Leu Glu Tyr Phe Phe Ser Arg Gly Phe Gly
                245                 250                 255

Tyr Gly Ala Asn Glu Trp Met Tyr Thr Leu Ala Lys Tyr Asp Lys Phe
            260                 265                 270

Pro Tyr Thr Gly Val Ile Lys Ala Val Asn Gln Met Lys Glu Tyr Gln
            275                 280                 285

Phe Ile Lys Gly Lys Ser Phe Gln Glu Leu Ser Lys Trp Arg Asp Glu
            290                 295                 300

Asn Leu Ile Asn Val Leu Arg Phe Leu Lys Glu Lys Gly Ala Lys Lys
305                 310                 315                 320

<210> SEQ ID NO 128
<211> LENGTH: 963
<212> TYPE: DNA
<213> ORGANISM: Sulfolobus acidocaldarius

<400> SEQUENCE: 128

```
atgagacaag taaatgtagt ttctattgta ggagcgggaa ttattggagc aggttggagt      60
accttattag ctgtccatgg atatagaaat atctttttaca cggagaagaa ggagacctta    120
gataaaggaa tactcaaaat taagggttat cttcaagtta tgcatgaata taagctggcg    180
gataagagcc agaggagta catgaaattg ataactccta ctaccgattt taatgatgtt     240
ctgaaagggg atttcataat tgaggctgtt attgaagatt atggagttaa gaagaaagtg    300
ttcggtgaat tggatgagag acttgataaa gatgtaatca tagccagtag cacctcaggg    360
ttactaatct ctgagatcca aaagtccatg tcaagacatc cagaaagggc cattattgcg    420
catccttgga cccctcccca tcttctccct cttgtagaaa tagtgcctgg tgaaaagact    480
tcagaggaag tcatacaatc tacgagagaa ttcatggaag acaaactgaa aagggtagtc    540
gtcgttctca agaaagaagt tccaggattt attggaaata ggcttgcatt tgctctattt    600
agagaagctg tgcatcttat tgacgaggga gttgcaactg taggagatat tgataaagtt    660
gtaactgccg ctattggact agatgggta tttatgggac ccttcctaac gtatcactta    720
```

```
ggtggaggag agggtggatt agagtacttt ttcagcagag gatttggtta tggtgcaaat      780
gaatggatgt ataccttgc aaaatacgat aagtttcctt acacaggagt tattaaagct      840
gtaaaccaaa tgaaagagta ccagttcata aaaggtaaaa gctttcagga actatcaaaa     900
tggagagatg aaaacttgat aaatgtctta agatttttaa aggagaaagg agcaaaaaaa     960
tag                                                                   963
```

<210> SEQ ID NO 129
<211> LENGTH: 535
<212> TYPE: PRT
<213> ORGANISM: H. sapiens

<400> SEQUENCE: 129

```
Met Ala Leu Leu Ala Ala Ala Val Arg Ala Arg Ile Leu Gln
1               5                   10                  15

Val Ser Ser Lys Val Lys Ser Ser Pro Thr Trp Tyr Ser Ala Ser Ser
            20                  25                  30

Phe Ser Ser Val Pro Thr Val Lys Leu Phe Ile Gly Gly Lys Phe
        35                  40                  45

Val Glu Ser Lys Ser Asp Lys Trp Ile Asp Ile His Asn Pro Ala Thr
50                  55                  60

Asn Glu Val Ile Gly Arg Val Pro Gln Ala Thr Lys Ala Glu Met Asp
65                  70                  75                  80

Ala Ala Ile Ala Ser Cys Lys Arg Ala Phe Pro Ala Trp Ala Asp Thr
                85                  90                  95

Ser Val Leu Ser Arg Gln Gln Val Leu Leu Arg Tyr Gln Gln Leu Ile
                100                 105                 110

Lys Glu Asn Leu Lys Glu Ile Ala Lys Leu Ile Thr Leu Glu Gln Gly
            115                 120                 125

Lys Thr Leu Ala Asp Ala Glu Gly Asp Val Phe Arg Gly Leu Gln Val
130                 135                 140

Val Glu His Ala Cys Ser Val Thr Ser Leu Met Met Gly Glu Thr Met
145                 150                 155                 160

Pro Ser Ile Thr Lys Asp Met Asp Leu Tyr Ser Tyr Arg Leu Pro Leu
                165                 170                 175

Gly Val Cys Ala Gly Ile Ala Pro Phe Asn Phe Pro Ala Met Ile Pro
                180                 185                 190

Leu Trp Met Phe Pro Met Ala Met Val Cys Gly Asn Thr Phe Leu Met
            195                 200                 205

Lys Pro Ser Glu Arg Val Pro Gly Ala Thr Met Leu Leu Ala Lys Leu
210                 215                 220

Leu Gln Asp Ser Gly Ala Pro Asp Gly Thr Leu Asn Ile Ile His Gly
225                 230                 235                 240

Gln His Glu Ala Val Asn Phe Ile Cys Asp His Pro Asp Ile Lys Ala
                245                 250                 255

Ile Ser Phe Val Gly Ser Asn Lys Ala Gly Glu Tyr Ile Phe Glu Arg
                260                 265                 270

Gly Ser Arg His Gly Lys Arg Val Gln Ala Asn Met Gly Ala Lys Asn
            275                 280                 285

His Gly Val Val Met Pro Asp Ala Asn Lys Glu Asn Thr Leu Asn Gln
290                 295                 300

Leu Val Gly Ala Ala Phe Gly Ala Ala Gly Gln Arg Cys Met Ala Leu
305                 310                 315                 320
```

```
Ser Thr Ala Val Leu Val Gly Glu Ala Lys Lys Trp Leu Pro Glu Leu
            325                 330                 335

Val Glu His Ala Lys Asn Leu Arg Val Asn Ala Gly Asp Gln Pro Gly
        340                 345                 350

Ala Asp Leu Gly Pro Leu Ile Thr Pro Gln Ala Lys Glu Arg Val Cys
            355                 360                 365

Asn Leu Ile Asp Ser Gly Thr Lys Glu Gly Ala Ser Ile Leu Leu Asp
        370                 375                 380

Gly Arg Lys Ile Lys Val Lys Gly Tyr Glu Asn Gly Asn Phe Val Gly
385                 390                 395                 400

Pro Thr Ile Ile Ser Asn Val Lys Pro Asn Met Thr Cys Tyr Lys Glu
            405                 410                 415

Glu Ile Phe Gly Pro Val Leu Val Val Leu Glu Thr Glu Thr Leu Asp
        420                 425                 430

Glu Ala Ile Gln Ile Val Asn Asn Asn Pro Tyr Gly Asn Gly Thr Ala
            435                 440                 445

Ile Phe Thr Thr Asn Gly Ala Thr Ala Arg Lys Tyr Ala His Leu Val
        450                 455                 460

Asp Val Gly Gln Val Gly Val Asn Val Pro Ile Pro Val Pro Leu Pro
465                 470                 475                 480

Met Phe Ser Phe Thr Gly Ser Arg Ser Ser Phe Arg Gly Asp Thr Asn
            485                 490                 495

Phe Tyr Gly Lys Gln Gly Ile Gln Phe Tyr Thr Gln Leu Lys Thr Ile
        500                 505                 510

Thr Ser Gln Trp Lys Glu Glu Asp Ala Thr Leu Ser Ser Pro Ala Val
            515                 520                 525

Val Met Pro Thr Met Gly Arg
530                 535

<210> SEQ ID NO 130
<211> LENGTH: 1608
<212> TYPE: DNA
<213> ORGANISM: H. sapiens

<400> SEQUENCE: 130
atggcggcgc tattggcggc ggcggcagtg cgagcccgga tcctgcaggt ttcttccaag      60
gtgaaatcca gtcccacctg gtattcagca tcttccttct cttcttcagt gccaactgta     120
aagctcttca ttggtgggaa attcgttgaa tccaaaagtg acaaatggat cgatatccac     180
aacccagcca ccaatgaggt cattggtcgg gtccctcagg ccaccaaggc agaaatggat     240
gcagccattg cttcctgcaa acgtgctttt cctgcatggg cagacacttc agtattaagc     300
cgccagcagg tcttgctccg ctatcaacaa cttattaaag aaaacttgaa agaaattgcc     360
aagttaatca cattggaaca agggaagacc ctagctgatg ctgaaggaga tgtatttcga     420
ggccttcagg tggttgagca tgcctgtagt gtgacatccc tcatgatggg agagaccatg     480
ccatccatca ccaaagacat ggacctttat tcctaccgtc tgcctctggg agtgtgtgca     540
ggcattgctc cattcaattt tcctgccatg atccccttt ggatgttcc catggccatg     600 gtgtgtggaa ataccttcct aatgaaacca tctgagcgag tccctggagc aactatgctt     660
cttgctaagt tgctccagga ttctggtgcc cctgatggaa cattaaacat catccatgga     720
cagcatgaag ctgtaaattt tatttgcgat catccggaca tcaaagcaat cagctttgtg     780
ggatccaaca ggcaggaga gtatatcttc gagagaggat caagacatgg caagagggtt     840
caagccaata tgggagccaa gaaccatggg gtagtcatgc cagatgccaa taggaaaat     900
```

```
acctgaacc agctggttgg ggcagcattt ggagctgctg gtcagcgctg catggctctt    960
tcaacagcag tccttgtggg agaagccaag aagtggctgc agagctggt ggagcatgcc   1020 aaaaacctga gagtcaatgc aggagatcag cctggagctg atcttggccc tctgatcact   1080
ccccaggcca aagagcgagt ctgtaatctg attgatagtg aacaaagga gggagcttcc   1140 atccttcttg atggacgaaa aattaaagtg aaaggctatg aaaatggcaa ctttgttgga   1200
ccaaccatca tctcgaatgt caagccaaat atgacctgtt acaaagagga gattttggt    1260 ccagttcttg tggttctgga gacagaaaca ttggatgaag ccatccagat tgtaaataac   1320
aacccatatg gaaatggaac tgccatcttc accaccaatg gagccactgc tcggaaatat   1380
gcccacttgg tggatgttgg acaggtggga gtgaatgtcc ccattccagt gcctttgcca   1440
atgttctcat tcaccggctc tcgatcctcc ttcaggggag acaccaattt ctatggcaaa   1500
cagggcatcc aattctacac tcagttaaag accattactt ctcagtggaa agaagaagat   1560
gctactcttt cctcacctgc tgttgtcatg cctaccatgg ccgttag                1608

<210> SEQ ID NO 131
<211> LENGTH: 339
<212> TYPE: PRT
<213> ORGANISM: Crinalium epipsammum

<400> SEQUENCE: 131

Met Phe Gly Leu Ile Gly His Leu Thr Ser Leu Glu His Ala Gln Ala
1               5                   10                  15

Val Ala Lys Glu Leu Gly Tyr Pro Glu Tyr Ala Asn Gln Asp Leu Asp
            20                  25                  30

Phe Trp Cys Ser Ala Pro Pro Gln Ile Val Asp His Ile Thr Val Thr
        35                  40                  45

Ser Ile Thr Gly Gln Lys Ile Glu Gly Gln Tyr Val Glu Ser Cys Phe
    50                  55                  60

Leu Pro Glu Met Leu Ala Asn Arg Arg Ile Lys Ala Ala Ile Arg Lys
65                  70                  75                  80

Ile Leu Asn Ala Met Ala His Ala Gln Lys His Gly Ile Asn Ile Thr
                85                  90                  95

Ala Leu Gly Gly Phe Ser Ser Ile Ile Phe Glu Glu Phe Asn Leu His
            100                 105                 110

Glu Ser Lys Gln Val Arg Asn Val Lys Leu Glu Phe Asp Arg Phe Thr
        115                 120                 125

Thr Gly Asn Thr His Thr Ala Tyr Ile Leu Cys Arg Gln Val Glu Gln
    130                 135                 140

Ala Ser Gln Lys Leu Gly Ile Asp Leu Ser Lys Ala Thr Val Ala Val
145                 150                 155                 160

Val Gly Ala Thr Gly Asp Ile Gly Ser Ala Val Cys Arg Trp Leu Asp
                165                 170                 175

Ala Arg Thr Asp Val Ala Asp Leu Leu Val Ala Arg Asn Gln Glu
            180                 185                 190

Arg Leu Gln Asn Leu Gln Glu Glu Leu Gly Arg Gly Lys Ile Leu Lys
        195                 200                 205

Leu Glu Glu Ala Leu Pro Leu Ala Asp Ile Ile Val Trp Val Ala Ser
    210                 215                 220

Met Pro Lys Gly Val Glu Ile Asp Pro Ala Thr Leu Lys Gln Pro Cys
225                 230                 235                 240

Leu Leu Ile Asp Gly Gly Tyr Pro Lys Asn Met Ser Thr Lys Val Gln
```

```
                245                 250                 255
His Pro Gly Val Cys Val Leu Asn Gly Gly Ile Val Glu His Ser Leu
            260                 265                 270

Asp Ile Asp Trp Lys Ile Met Lys Ile Val Asn Met Glu Ala Pro Ala
            275                 280                 285

Arg Gln Leu Phe Ala Cys Phe Ala Glu Ala Met Leu Leu Glu Phe Glu
            290                 295                 300

Lys Trp His Thr Asn Phe Ser Trp Gly Arg Asn Gln Ile Thr Val Glu
305                 310                 315                 320

Lys Met Asp Gln Ile Gly Leu Val Ser Val Lys His Gly Phe Arg Pro
                325                 330                 335

Leu Leu Ser

<210> SEQ ID NO 132
<211> LENGTH: 1020
<212> TYPE: DNA
<213> ORGANISM: Crinalium epipsammum

<400> SEQUENCE: 132
atgtttggtc taatcggtca ccttaccagt ttggaacacg ctcaagccgt cgctaaagag      60
ctaggctatc agaatacgc caatcaagat ttggattttt ggtgcagtgc gccaccccaa     120
atcgtcgatc acattactgt cactagcatt actggtcaaa aaattgaagg tcagtatgtt     180
gaatcatgct ttctaccaga aatgcttgct aatcgccgga ttaaggcagc tatccgtaaa     240
atcctaaacg cgatggctca tgctcaaaag catggcatta acattacagc cttgggaggc     300
ttttcttcaa ttatttttga agaatttaac ttgcacgaaa gtaagcaggt tcgcaatgtc     360
aagttagagt ttgatcgttt tactacaggt aatactcata ctgcttacat tctttgtcgt     420
caagtagaac aagcatctca aaaactaggc attgatttgt ctaaggcgac agttgcagta     480
gtcggggcta cgggtgacat tggcagtgct gttttgtcgtt ggctagatgc ccgcactgat     540
gtagcagatt tgttattggt ggcacgcaat caagaacgac tgcaaaacct acaagaggaa     600
ctgggaagag gcaaaatctt aaagctagaa gaagctttgc cttttggctga tattattgtc     660 tgggttgcca gtatgccaaa aggtgtgaa attgatccag ctactttaaa gcaaccttgt     720
ttgctgatag atggcggata tcctaaaaat atgtcaacga agttcagca tccaggtgta     780 tgtgtcctta atggtgggat tgttgagcat tctttggata ttgactggaa aattatgaaa     840
atcgtcaata tggaagcgcc agcacgccag ttgtttgctt gttttgcaga agcaatgcta     900
ttggaatttg agaaatggca tactaacttt cttggggac gaaatcagat tactgttgaa     960
aagatggatc aaattggtct ggtgtctgtt aaacatggtt tccgaccttt attaagctaa    1020

<210> SEQ ID NO 133
<211> LENGTH: 267
<212> TYPE: PRT
<213> ORGANISM: Pseudopedobacter saltans

<400> SEQUENCE: 133

Met Glu Arg Lys Thr Leu Ala Ile Val Gly Cys Gly Lys Leu Ala Ser
1               5                   10                  15

Ile Ile Ala Asp Ala Leu Asn Ala Asn Leu Leu Pro Glu Tyr Gln Leu
            20                  25                  30

Ile Ala Thr Tyr Ser Arg Ser Ile Glu Lys Ala Gln Asn Ile Ala Asn
        35                  40                  45

Lys Val Asn Asn Glu Ser Gln Lys Asp Ser Pro Cys Lys Ala Cys Asn
```

| | | | | | | | | | | |
|---|---|---|---|---|---|---|---|---|---|---|
| | | 50 | | | 55 | | | 60 | | |
| Ser | Leu | Glu | Glu | Leu | Leu | Ala | Ser | Glu | Ala | Asn | Tyr | Ile | Ile | Glu | Ala |
| 65 | | | | 70 | | | | 75 | | | | | | 80 | |

Ser Leu Glu Glu Leu Leu Ala Ser Glu Ala Asn Tyr Ile Ile Glu Ala
65                  70                  75                  80

Ala Ser Pro Asp Ser Met Arg Thr Leu Ala Leu Pro Ala Leu Lys Asn
                85                  90                  95

Gly Ser Ser Ile Val Thr Leu Ser Ile Gly Ala Phe Ala Asp Glu Glu
            100                 105                 110

Phe Tyr Glu Glu Val Lys Arg Thr Ala Leu Ala Asn Asn Ala Arg Val
        115                 120                 125

His Leu Val Ser Gly Ala Ile Gly Gly Phe Asp Val Met Arg Thr Ala
    130                 135                 140

Ala Leu Met Gly Asn Cys Thr Ala Thr Phe Asp Thr Glu Lys Gly Pro
145                 150                 155                 160

Asn Ser Leu Lys Arg Tyr Ser Val Tyr Asp Glu Ser Leu Gln Thr Glu
                165                 170                 175

Lys Arg Lys Val Phe Glu Gly Asn Ala Lys Glu Ala Ile Ala Leu Phe
            180                 185                 190

Pro Asn Ser Val Asn Val Ser Val Ala Ala Ser Leu Ala Ser Val Gly
        195                 200                 205

Pro Glu Lys Met Lys Val Ser Val Thr Ser Thr Pro Gly Tyr Ile Gly
    210                 215                 220

Asp Asn His Arg Ile Glu Val Lys Asn Glu Gln Val His Ala Val Ile
225                 230                 235                 240

Asp Val Tyr Ser Ser Thr Ala Gln Ile Ala Gly Trp Ser Val Val Asn
                245                 250                 255

Thr Leu Arg Asn Ile Val Ser Pro Ile Val Phe
            260                 265

<210> SEQ ID NO 134
<211> LENGTH: 804
<212> TYPE: DNA
<213> ORGANISM: Pseudopedobacter saltans

<400> SEQUENCE: 134

```
atggaaagaa agacacttgc tattgtaggc tgtggtaaac ttgcctcaat aattgccgat      60
gcgttaaatg cgaacttatt accagaatat caacttattg cgacctattc cagaagcata     120
gaaaaagcac agaacatagc caacaaggtt aacaatgaat cccaaaaaga ttcaccttgt     180
aaagcatgca actctctgga agaattgtta gccagcgaag caaactatat tatcgaagct     240
gcatctccgg actctatgag aactttagct ttaccagctt taaaaaacgg ctcttctatc     300
gtaacattat caattggagc ctttgccgac gaagaattct atgaagaagt aaaaagaaca     360
gctttagcta acaatgcccg tgtacatttg gtatccggag ctattggagg attcgatgta     420
atgcgtaccg cagcattaat gggcaattgc acagcaacct tgatacaga aaagggccg       480
aattctttaa aaagatactc ggtatacgat gaatctctac aaacggaaaa agaaaagta      540
tttgaaggga acgcgaaaga agcaatagct ttatttccta acagtgtcaa cgtatctgtg     600
gcagcttctt tagcttctgt tggcccagaa aaatgaagg tttctgtaac ttcaacacct      660
ggatacattg gcgataacca ccgtatagaa gttaagaacg aacaagtaca cgccgtaatt     720
gatgtttaca gctcaactgc acaaatagca ggatggagcg ttgttaatac gcttagaaat     780
atcgtttctc ctatcgtttt ttaa                                            804
```